US007816534B2

(12) United States Patent
Hagmann et al.

(10) Patent No.: US 7,816,534 B2
(45) Date of Patent: Oct. 19, 2010

(54) SUBSTITUTED AMIDES

(75) Inventors: William K. Hagmann, Westfield, NJ (US); Linus S. Lin, Westfield, NJ (US); Shrenik K. Shah, Metuchen, NJ (US); Ravindra N. Guthikonda, Edison, NJ (US); Hongbo Qi, Edison, NJ (US); Linda L. Chang, Wayne, NJ (US); Ping Liu, Edison, NJ (US); Helen M. Armstrong, Westfield, NJ (US); James P. Jewell, Jersey City, NJ (US); Thomas J. Lanza, Jr., Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/386,336

(22) Filed: Apr. 16, 2009

(65) Prior Publication Data

US 2009/0258884 A1 Oct. 15, 2009

Related U.S. Application Data

(62) Division of application No. 12/012,463, filed on Feb. 1, 2008, now Pat. No. 7,550,489, which is a division of application No. 11/109,076, filed on Apr. 19, 2005, now abandoned, which is a division of application No. 10/387,265, filed on Mar. 12, 2003, now Pat. No. 6,972,295.

(60) Provisional application No. 60/363,597, filed on Mar. 12, 2002, provisional application No. 60/428,351, filed on Nov. 22, 2002.

(51) Int. Cl.
*A61K 31/44* (2006.01)
*C07D 213/04* (2006.01)
*C07D 401/02* (2006.01)
*C07D 403/02* (2006.01)
*C07D 239/02* (2006.01)

(52) U.S. Cl. .................. 546/255; 546/266; 546/268.1; 544/238; 514/256; 514/336; 514/340

(58) Field of Classification Search ................ 546/278, 546/255, 266, 268.1; 514/336, 337, 256, 514/340; 544/238
See application file for complete search history.

(56) References Cited

U.S. PATENT DOCUMENTS

| 3,277,165 | A | 10/1966 | Schultz |
| 4,746,680 | A | 5/1988 | Jeffery et al. |
| 4,929,629 | A | 5/1990 | Scheinbaum |
| 4,956,380 | A | 9/1990 | Toda et al. |
| 4,973,587 | A | 11/1990 | Ward et al. |
| 5,013,837 | A | 5/1991 | Ward et al. |
| 5,081,122 | A | 1/1992 | Ward |
| 5,102,667 | A | 4/1992 | Dubroeucq et al. |
| 5,112,820 | A | 5/1992 | Ward |
| 5,278,316 | A | 1/1994 | Horwell et al. |
| 5,292,736 | A | 3/1994 | Kumar et al. |
| 5,436,272 | A | 7/1995 | Scheinbaum |
| 5,488,149 | A | 1/1996 | Nomoto et al. |
| 5,532,237 | A | 7/1996 | Gallant et al. |
| 5,597,797 | A | 1/1997 | Clark |
| 5,624,941 | A | 4/1997 | Barth et al. |
| 5,707,987 | A | 1/1998 | Nakagawa et al. |
| 5,795,895 | A | 8/1998 | Anchors |
| 5,908,830 | A | 6/1999 | Smith et al. |
| 6,011,048 | A | 1/2000 | Mathvink et al. |
| 6,011,174 | A | 1/2000 | Iwasawa et al. |
| 6,028,084 | A | 2/2000 | Barth et al. |
| 6,121,325 | A | 9/2000 | Chen et al. |
| 6,258,837 | B1 | 7/2001 | Fukami et al. |
| 6,335,345 | B1 | 1/2002 | Scheinbaum |
| 6,344,474 | B1 | 2/2002 | Maruani et al. |
| 6,344,481 | B1 | 2/2002 | Cornelius et al. |

(Continued)

FOREIGN PATENT DOCUMENTS

DE 4332738 3/1995

(Continued)

OTHER PUBLICATIONS

Vizi, "Evidence for presynaptic cannabinoid CB1 receptor-mediated inhibition . . . ", Eur. J. Pharmacology (2001), 237-244, vol. 431.
Batkai, "Endocannabinoids activing at vascular CB1 receptors . . . ", Nature Medicine (2001), 827-832, vol. 7.
Schultz, "Maleamic acids that affect plasma cholesterol . . . ", J. Med. Chem. (1967), 717-724, vol. 10.
Pines, "The stereochemistry of 2,3-diphenyl-1-methylpropylamine", J. Med. Chem. (1967), 725-728, vol. 10.
Barth, "Cannabinoid receptor agonists and antagonists", Exp. Opin. Therap. Patents (1998), 301-313, vol. 8.
Petitet, "The therapeutic applications of cannabinoid agonists and antagonists", Emerging Drugs (1998), 39-53, vol. 3.

(Continued)

*Primary Examiner*—Rita J Desai
(74) *Attorney, Agent, or Firm*—Baerbel R. Brown; Kenrick L. Vidale

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, the treatment of obesity or eating disorders, as well as the treatment of asthma, constipation, chronic intestinal pseudo-obstruction, and cirrhosis of the liver.

13 Claims, No Drawings

U.S. PATENT DOCUMENTS

| | | |
|---|---|---|
| 6,355,631 B1 | 3/2002 | Achard et al. |
| 6,359,175 B1 | 3/2002 | Philippe et al. |
| 6,479,479 B2 | 11/2002 | Achard et al. |
| 6,509,367 B1 | 1/2003 | Martin et al. |
| 2002/0006964 A1 | 1/2002 | Young et al. |
| 2002/0010192 A1 | 1/2002 | Coe et al. |
| 2002/0062022 A1 | 5/2002 | Sabb et al. |
| 2002/0091114 A1 | 7/2002 | Piot-Grosjean et al. |
| 2003/0114495 A1 | 6/2003 | Finke et al. |
| 2004/0058820 A1 | 3/2004 | Hagmann et al. |
| 2004/0122033 A1 | 6/2004 | Nargund et al. |
| 2004/0248956 A1 | 12/2004 | Hagmann et al. |
| 2005/0288213 A1 | 12/2005 | MacNeil et al. |
| 2006/0148721 A1 | 7/2006 | Erondu |
| 2006/0160834 A1 | 7/2006 | Fong et al. |
| 2006/0270650 A1 | 11/2006 | MacNeil et al. |
| 2007/0099884 A1 | 5/2007 | Erondu et al. |

FOREIGN PATENT DOCUMENTS

| | | |
|---|---|---|
| EP | 0163607 | 5/1985 |
| EP | 0611749 | 8/1994 |
| EP | 0920864 | 6/1999 |
| EP | 0658546 | 5/2001 |
| EP | 1302461 | 4/2003 |
| JP | 1-156957 | 6/1989 |
| JP | 3-176469 | 7/1991 |
| JP | 08-165276 | 6/1996 |
| JP | 9-505601 | 3/1997 |
| JP | 03-220168 | 7/2009 |
| WO | 95/11880 | 5/1995 |
| WO | 95/23150 | 8/1995 |
| WO | 96/18391 | 6/1996 |
| WO | 96/33159 | 10/1996 |
| WO | 96/40912 | 12/1996 |
| WO | 97/06816 | 2/1997 |
| WO | 97/16189 | 5/1997 |
| WO | 97/17321 | 5/1997 |
| WO | 97/18833 | 5/1997 |
| WO | 97/29078 | 8/1997 |
| WO | 97/29079 | 8/1997 |
| WO | 97/46250 | 12/1997 |
| WO | 98/18481 | 5/1998 |
| WO | 98/28427 | 7/1998 |
| WO | 98/31227 | 7/1998 |
| WO | 98/32441 | 7/1998 |
| WO | 98/33765 | 8/1998 |
| WO | 98/37061 | 8/1998 |
| WO | 98/41519 | 9/1998 |
| WO | 98/43635 | 10/1998 |
| WO | 98/43636 | 10/1998 |
| WO | 98/56754 | 12/1998 |
| WO | 99/02499 | 1/1999 |
| WO | 99/31055 | 6/1999 |
| WO | 99/37667 | 7/1999 |
| WO | 00/10967 | 3/2000 |
| WO | 00/10968 | 3/2000 |
| WO | 00/37462 | 6/2000 |
| WO | 00/66578 | 11/2000 |
| WO | 00/76493 | 12/2000 |
| WO | 01/01969 | 1/2001 |
| WO | 01/09120 | 2/2001 |
| WO | 01/92229 | 6/2001 |
| WO | 01/52825 | 7/2001 |
| WO | 01/58540 | 8/2001 |
| WO | 01/58869 | 8/2001 |
| WO | 01/64632 | 9/2001 |
| WO | 01/64633 | 9/2001 |
| WO | 01/64634 | 9/2001 |
| WO | 01/70700 | 9/2001 |
| WO | 01/85092 | 11/2001 |
| WO | 01/87849 | 11/2001 |
| WO | 02/12168 | 2/2002 |
| WO | 02/19998 | 3/2002 |
| WO | 02/20488 | 3/2002 |
| WO | 02/22592 | 3/2002 |
| WO | 02/28346 | 4/2002 |
| WO | 02/32897 | 4/2002 |
| WO | 02/38551 | 5/2002 |
| WO | 02/49648 | 6/2002 |
| WO | 02/060427 | 8/2002 |
| WO | 02/060428 | 8/2002 |
| WO | 02/068388 | 9/2002 |
| WO | 02/076949 | 10/2002 |
| WO | 03/006007 | 1/2003 |
| WO | 03/007887 | 1/2003 |
| WO | 03/020217 | 3/2003 |
| WO | 03/026647 | 4/2003 |
| WO | 03/026648 | 4/2003 |
| WO | 03/027068 | 4/2003 |
| WO | 03/027069 | 4/2003 |
| WO | 03/027076 | 4/2003 |
| WO | 03/027114 | 4/2003 |
| WO | 03/037332 | 5/2003 |
| WO | 03/040107 | 5/2003 |
| WO | 03/082190 | 10/2003 |
| WO | 03/082191 | 10/2003 |
| WO | 03/086288 | 10/2003 |
| WO | 03/087037 | 10/2003 |
| WO | 2004/012671 | 2/2004 |
| WO | 2004/029204 | 4/2004 |
| WO | 2004/048317 | 6/2004 |
| WO | 2004/058145 | 7/2004 |
| WO | 2004/058741 | 7/2004 |
| WO | 2004/058744 | 7/2004 |
| WO | 2004/060870 | 7/2004 |
| WO | 2005/000809 | 1/2005 |
| WO | 2005/009479 | 2/2005 |
| WO | 2005/027837 | 3/2005 |
| WO | 2006/036770 | 4/2006 |
| WO | 2006/049933 | 5/2006 |

OTHER PUBLICATIONS

Di Marzo, "Endocannabinoids Part I: Molecular basis of endocannabinoid formation, . . . ", Emerging Therap. Targets (2001), 241-265, vol. 5.
Grundy, "The therapeutic potential of the cannabinoids . . . ", Exp. Opin. Investig. Drugs (2002), 1365-1374, vol. 11.
Goya, "Recent advances in cannabinoid receptor agonists and antagonists", Exp. Opin. Ther. Patents (2000), 1529-1538, vol. 10.
Adam, "Recent advances in the cannabinoids", Exp. Opin. Ther. Patents (2002), 1475-1489, vol. 12.
Ishiwata, "Studies on the syntheses of isoquinoine derivatives", Yakugaku Zasshi (1951), 1272-1274, vol. 71.
Ito, "Catalytic hydrogenation of tetrahydro-4H-1,3-oxazin-4-ones . . . ", Chem. Pharm. Bull (1972), 1762-1767, vol. 20.
D'Souza, "(R)-(+)-3-amino-2-(phenyl)propanoic acid: . . . ", J. Chem. Soc. Perkin Trans. (1995), 1-2, vol. 1.
Gutierrez-Garcia, "Enantioselective synthesis of beta-amino acids . . . ", J. Braz. Chem. Soc. (2001), 652-660, vol. 12.
Chung, "A beta-peptide reverse turn that promotes hairpin formation", J. Am. Chem. Soc. (1998), 10555-10556, vol. 120.
Schlesinger, "N-substituted amides", J. Am. Chem. Soc. (1956), 6123-6127, vol. 78.
LaPlante, "Characterization of the human cytomegalovirus protease as an induced-fit . . . ", J. Am. Chem. Soc. (1999), 2974-2986, vol. 121.
Hanessian, "Design of a novel secondary structure . . . ", Tet. Letters (1997), 3155-3158, vol. 38.
Heymans, "Design and modeling of new platelet-activating . . . ", J. Lipid Mediators Cell Signaling (1996), 161-173, vol. 15.
Hanessian, "Hydrogen-bonding as stereocontrolling element . . . ", J. Am. Chem. Soc. (1996), 2507-2508, vol. 118.

Kittaka, "Man-designed bleomycins. Synthesis of dioxygen . . . ", Tetrahedron (1988), 2821-2833, vol. 44.
Otsuka, "Synthetic study towards man-designed bleomycins", Tet. Letters (1986), 3639-3942, vol. 27.
Ghirardelli, "Stereochemistry of the opening of the imine ring . . . ", J. Am. Chem. Soc. (1957), 734-741, vol. 79.
Sibi, "A new methodology for the synthesis of beta-amino acids", J. Chem. Soc., Perkin Trans. (2000), 1461-1466, vol. 1.
Hintermann, "A useful modification of the Evens auxiliary: . . . ", Helv. Chim. Acta. (1998), 2093-2126, vol. 81.
Abele, "(S)-beta3-homolysine- and (S)-beta3-homoserine-containing beta-peptides . . . ", Helv. Chim. Acta. (1998), 2141-2156, vol. 81.
Arvanitis, "Enantioselective synthesis of 2-substituted 3-aminopropanoic acid . . . ", J. Chem. Soc., Perkin Trans. (1998), 521-528, vol. 1.
Rivera, "Syntheses and characterization of 2-hydroxy-N-(2'-hydroxyalkyl)acetamides", Heteroatom Chemistry (1999), p. 153-158, vol. 10.
Lock, "Autoxidation of N-alkyamides . . . ", J. Chem. Soc. (B) (1966), 690-696, vol. ???.
Benoit-Guyod, "Recherches dans la serie dipropylacetique", Chimie Therapeutique (1973), 412-418, No. 4.
Database Beilstein XP002420916, database accession No. 4426431 (BRN), abstract (1987), 1573-1576, vol. 28.
Database Beilstein XP 002420917, database accession No. 125:195419/DN, abstract, RN181144-376, -21-8, JP08165276 A (Dainippon Pharmaceutical Co., Jun. 25, 1996).
Database Beilstein XP002420915, database accession No. 8483956 (BRN), abstract, Tetrahedron: Assymetry (1999), 3571-3592, vol. 10.
Potapov, Database Beilstein XP002420914, database accession No. 95:132135/DN, abtract, RN79011-29-3, -30-6, -65-2, Khimiya Geterotsiklicheskikh Soedinenii (1981), 675-677, vol. 5.
Kienzle, Database Beilstein XP 00240913, database accession No. 6514637 (BRN), abstract, Helv. Chim. Acta. (1986), 1671-1680, vol. 69.
Metayer, Database Beilstein XP 002420912, database accession No. 3276189 (BRN), abstract, Hebd. Seances Acad. Sci. (1948), 500, vol. 226.
Moore, Database Beilstein XP 002420911, database accession No. 112:216389/DN, abstract, RN126063-62-5, J. Org. Chem. (1990), 3374-3377, vol. 55.
Cho, Database Beilstein XP 002420910, database accession No. 131:96957/DN, abstract, RN230648-60-9, Archives of Pharm. Research (1999), 184-188, vol. 22.
Farrigan, "Obesity market overview", Nature Reviews—Drug Discovery (2002), 257-258, vol. 1.
Bray, "Sibutramine produces dose-related weight loss", Obesity Research (1999), 189-198, vol. 7.
Kopelman, "Obesity as a medical problem", Nature (2000), 635-643, vol. 404.
Steinbeck, "Obesity: the science behind the management", Internal Medical Journal (2002), 237-241, vol. 32.
Qu, "A role for melanin-concentrating hormone . . . ", Nature (1996), 243-247, vol. 380.
Davidson, "Weight control and risk factor reduction . . . ", JAMA (1999), 235-242, vol. 281.
Douglas, "Plasma phentermine levels, weight loss . . . ", Int'l J. of Obesity (1983), 591-595, vol. 7.
Guy-Grand, "Therapeutics: International trial of long-term . . ", The Lancet (1989), 1142-1144.
Muccioli, "Neuroendocrine and peripheral activities . . . ", Eur. J. of Phjarmacol. (2002), 235-254, vol. 440.
Chamorro, "Appetite suppression based on selective inhibition . . . ", Int'l J. of Obesity (2002), 281-298, vol. 26.
Balasubramanian, "Clinical potentials of neuropeptide Y . . . ", The American J. of Surgery (2002), 430-434, vol. 183.
Guerciolini, "Mode of action of orlistat", Int'l J. of Oesity (1997), S-12-S23, vol. 21, Suppl. 3.
Sletten, "Weight reduction with chlorphentermine . . . ", Current Therap. Res. (1967), 570-575, vol. 9.
Kolakowska, "An open clinical trial of fenfluramine", Int'l Clinical Psychopharmacol. (1987), 83-88, vol. 2.

Pierson, "Synthesis and biological evaluation . . . ", J. Med. Chem. (1997), 4302-4307, vol. 40.
Bray, "Medical strategies in the treatment of obesity", Nature, (2000), 672-677, vol. 404.
Kushner, "Obesity pharmacology: . . . ", Curr. Opin. in Gastroenterology (2002), 213-220, vol. 18.
MacNeil, "The role of melanocortins . . . ", Eur. J. of Pharmacol. (2002), 141-157, vol. 440.
Kirkham, "Synergistic efects (sic) of opioid . . . ", Psychopharmacology (2001), 267-270, vol. 153.
Boozer, "Synergy of sibutramine and low-dose leptin . . . ", Metabolism (2001), 889-893, vol. 50.
Wadden, "Effects of sibutramine plus orlistat in obese women . . . ", Obesity Research (2000), 431-437, vol. 8.
Zhou, "Attenuation of withdrawal reaction . . . ", Society for Neuroscience Abstracts: 31st annual meeting of the Society for Neuroscience, San Diego, CA (Nov. 10-15, 2001), 599, vol. 27.
Myrick, "New developments in the pharmacotherapy . . . ", The American J. on Addictions, (2001), 3-15, vol. 10.
Angehelescu, "Add-on combination and maintenance . . . ", J. of Clin. Psychopharmacol. (2000), 521-524, vol. 22.
Rowland, "Effects of the cannabinoid receptor . . . ", Psychopharmacology (2001), 111-116, vol. 159.
Sabath Silva, "Leptina", Revista de Investigacion Clinica (2002), 161-165, vol. 54.
Chaki, "Recent advances in feeding suppressing agents . . . ", Exp. Opin. Ther. Patents (2001), 1677-1692, vol. 11.
Pomonis, "Interaction of the hypothalamic paraventricular . . . ", The J. of Neuroscience (1997), 5175-5182, vol. 17.
LaLonda, "Additive effects of leptin and topiramate . . . ", Physiol. & Behavior (2004), 415-420, vol. 80.
Turton, "A role for glucagon-like peptide-1 . . . ", Nature (1996), 69-72, vol. 379.
Erickson, "Sensitivity to leptin and susceptibility . . . ", Nature (1996), 415-416, vol. 381.
Lonnnqvist, "Overexpression of the obese (ob) gene . . . ", Nature Medicine (1995), 950-953, vol. 1.
De Vos, "Induction of ob bene expression . . . ", J. Biol. Chem. (1995), 15958-15961, vol. 270.
Chen, "Synergistic effects of cannabinoid inverse . . . ", Brain Research (2004), 227-230, vol. 999.
Williams, "Reversal of delta9-THC hyperphagia . . . ", Pharmacol. Biochem. & Behavior (2002), 341-348, vol. 71.
Verty, "The cannabinoid receptor antagonist . . . ", Psychopharmacology (2003), 314-323, vol. 168.
Pietras, "Effect of opioid and cannabinoid receptor . . . ", Eur. J. of Pharmacol. (2002), 237-239, vol. 442.
Hjorth, Society for Neuroscience Abstract Viewer and Itinerary Planner, (2002), Abstract No. 775.17, vol. 2002.
Database Beilstein, XP002467521, No. 7284731 (BRN), (1965) 771-780, vol. 298.
Dorwald, Side Reactions in Organic Synthesis (2005), p. IX of preface.
Rowley, "Comparison of the effects of sibutramine . . . ", Synapse (2000), 167-176, vol. 38.
Physician's Desk Reference, 61st edition (2007), 1215-1216, Adipex-P.
Skotter, "Growth responses in a mutant dwarf rat . . . ", Endocrinology (1989), 2519-2526, vol. 124.
Wellman, "Effects of preexposure of dexfenfluramine, . . . ", Pharmacology, Biochemistry and Behavior (2003), 103-114, vol. 75.
Erondu, "NPY5R antagonism does not augment . . . ", presented at NAA_O, Obesity Society annual meeting, Boston, MA (Oct. 2006).
Zhou, 2003:326801 Biosis, Society for Neuroscience, Abstract Viewer and Itinerary Planner (2002), Abstract No. 775.16, vol. 2002.
Bradley, "Bupropion SR with Phentermine for weight reduction", Abstract No. NR587, 1999.
Database Beilstein, XP002467520, EP No. 348050 (BRN), 775 (1959), vol. 79.
Matson, "Cholecystokinin and leptin act synergistically . . . ", Am. J. Physiol. Regulatory Integrative Comp. Physiol. (2000), R882-R890, vol. 278.

Le, "Use of serotonin (5-HT) and opiate-based drugs . . . ", Alcohol & Alcoholism (1996), 27-32, vol. 31.
Chiesi, "Pharmacotherapy of obesity . . . ", Trends in Pharmacological Sciences, 247-254, vol. 22, May 2001.
Atkinson, "Combined drug treatment . . . ", Obesity Research (1995), 497S-500S, vol. 3.
Raffa, "A novel approach to the pharmacology of analgesics", Am. J. Med. (1996), 40S-46S, vol. 101, Suppl. 1A.
Fernandez-Lopez, "Pharmacological approaches for the treatment of obesity", Drugs (2002), 915-944, vol. 62.
Lu, "Leptin resistance in obesity is characterized by decreased sensitivity", Peptides (2000), 1479-1485, vol. 21.
Dunbar, "Leptin-induced increase in sympathetic nervous and cardiovascular . . . ", Brain Research Bulletin (1999), 215-221, vol. 50.
Bickerdike, "The influence of 5-hydroxytryptamine re-uptake blockade . . . ", Eur. J. of Pharmacology (1994), 403-411, vol. 271.
Proietto, "Novel anti-obesity drugs", Drugs (2000), 1317-1326, vol. 9.
Parker, "Neuropeptide Y receptors as targets . . . ", Eur. J. of Pharmacology (2002), 173-187, vol. 440.

SUBSTITUTED AMIDES

CROSS-REFERENCE TO RELATED APPLICATIONS

This application is a divisional application of U.S. application Ser. No. 12/012,463, filed Feb. 1, 2008 now U.S. Pat. No. 7,550,489, which is a divisional application of U.S. application Ser. No. 11/109,076, filed Apr. 19, 2005 now abandoned, which is a divisional application of U.S. application Ser. No. 10/387,265, filed Mar. 12, 2003 now U.S. Pat. No. 6,972,295, which, in turn, claims priority under 35 U.S.C. §119 from U.S. Provisional Application No. 60/363,597, filed Mar. 12, 2002 and U.S. Provisional Application No. 60/428,351, filed Nov. 22, 2002, both now abandoned.

BACKGROUND OF THE INVENTION

Marijuana (*Cannabis sativa* L.) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

The genes for the respective cannabinoid receptors have each been disrupted in mice. The $CB1^{-/-}$ receptor knockout mice appeared normal and fertile. They were resistant to the effects of $\Delta^9$-THC and demonstrated a strong reduction in the reinforcing properties of morphine and the severity of withdrawal syndrome. They also demonstrated reduced motor activity and hypoalgesia. The $CB2^{-/-}$ receptor knockout mice were also healthy and fertile. They were not resistant to the central nervous system mediated effects of administered $\Delta^9$-THC. There were some effects on immune cell activation, reinforcing the role for the CB2 receptor in immune system functions.

Excessive exposure to $\Delta^9$-THC can lead to overeating, psychosis, hypothermia, memory loss, and sedation. Specific synthetic ligands for the cannabinoid receptors have been developed and have aided in the characterization of the cannabinoid receptors: CP55,940 (J. Pharmacol. Exp. Ther. 1988, 247, 1046-1051); WIN55212-2 (J. Pharmacol. Exp. Ther. 1993, 264, 1352-1363); SR141716A (FEBS Lett. 1994, 350, 240-244; Life Sci. 1995, 56, 1941-1947); and SR144528 (J. Pharmacol. Exp. Ther. 1999, 288, 582-589). The pharmacology and therapeutic potential for cannabinoid receptor ligands has been reviewed (Exp. Opin. Ther. Patents 1998, 8, 301-313; Ann. Rep. Med. Chem., A. Doherty, Ed.; Academic Press, NY 1999, Vol. 34, 199-208; Exp. Opin. Ther. Patents 2000, 10, 1529-1538; Trends in Pharma. Sci. 2000, 21, 218-224). There is at least one CB1 modulator characterized as an inverse agonist or an antagonist, N-(1-piperidinyl)-5-(4-chlorophenyl)-1-(2,4-dichlorophenyl)-4-methylpyrazole-3-carboxamide (SR141716A), in clinical trials for treatment of eating disorders at this time. There still remains a need for potent low molecular weight CB1 modulators that have pharmacokinetic and pharmacodynamic properties suitable for use as human pharmaceuticals.

Treatment of asthma with CB1 receptor modulators (such as CB1 inverse agonists) is supported by the finding that presynaptic cannabinoid CB1 receptors mediate the inhibition of noradrenaline release (in the guinea pig lung) (Europ. J. of Pharmacology, 2001, 431 (2), 237-244).

Treatment of cirrhosis of the liver with CB1 receptor modulators is supported by the finding that a CB1 receptor modulator will reverse the low blood pressure observed in rats with carbon tetrachloride-induced liver cirrhosis and will lower the elevated mesenteric blood flow and portal vein pressure (Nature Medicine, 2001, 7 (7), 827-832).

U.S. Pat. No. 5,624,941 and U.S. Pat. No. 6,028,084, PCT Application Nos. WO98/43636 and WO98/43635, and EPO Application No. EP-658546 disclose substituted pyrazoles having activity against the cannabinoid receptors.

PCT Application Nos. WO98/31227 and WO98/41519 also disclose substituted pyrazoles having activity against the cannabinoid receptors.

PCT Application Nos. WO98/37061, WO00/10967, and WO00/10968 disclose diaryl ether sulfonamides having activity against the cannabinoid receptors.

PCT Application Nos. WO97/29079 and WO99/02499 disclose alkoxy-isoindolones and alkoxy-quinolones as having activity against the cannabinoid receptors.

U.S. Pat. No. 5,532,237 discloses N-benzoyl-indole derivatives having activity against the cannabinoid receptors.

U.S. Pat. No. 4,973,587, U.S. Pat. No. 5,013,837, U.S. Pat. No. 5,081,122, and U.S. Pat. No. 5,112,820, U.S. Pat. No. 5,292,736 disclose aminoalkylindole derivatives as having activity against the cannabinoid receptors.

PCT publication WO 01/58869 discloses pyrazoles, pyrroles and imidazole cannabinoid receptor modulators useful for treating respiratory and non-respiratory leukocyte activation-associated disorders.

PCT publications WO 01/64632, 01/64633, and 01/64634 assigned to Aventis are directed to azetidine derivatives as cannabinoid antagonists.

Schultz, E. M, et al. *J. Med. Chem.* 1967, 10, 717 and Pines, S. H. et al. *J. Med. Chem.* 1967, 10, 725 disclose maleamic acids affecting plasma cholesterol and penicillin excretion.

The compounds of the present invention are modulators of the Cannabinoid-1 (CB1) receptor and are useful in the treatment, prevention and suppression of diseases mediated by the Cannabinoid-1 (CB1) receptor. In particular, compounds of the present invention are antagonists or inverse agonists of the CB1 receptor. The invention is concerned with the use of these compounds to modulate the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of eating disorders by inhibiting excessive food intake and the resulting obesity and complications associated therewith. The compounds are also useful for the treatment of constipation and chronic intestinal pseudo-obstruction, as well as for the treatment of asthma, and cirrhosis of the liver.

SUMMARY OF THE INVENTION

The present invention is concerned with novel substituted amides of the general Formula I:

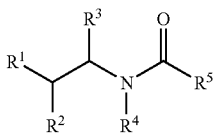

and pharmaceutically acceptable salts thereof which are antagonists and/or inverse agonists of the Cannabinoid-1 (CB1) receptor and are useful in the treatment, prevention and suppression of diseases mediated by the Cannabinoid-1 (CB1) receptor. The invention is concerned with the use of these novel compounds to selectively antagonize the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine, including smoking cessation. The compounds are also useful for the treatment of obesity or eating disorders associated with excessive food intake and complications associated therewith. The compounds are also useful for the treatment of constipation and chronic intestinal pseudo-obstruction. The compounds are also useful for the treatment of cirrhosis of the liver. The compounds are also useful for the treatment of asthma.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with novel compounds of structural formula I.

The invention is also concerned with pharmaceutical formulations comprising one of the compounds as an active ingredient.

The invention is further concerned with processes for preparing the compounds of this invention.

DETAILED DESCRIPTION OF THE INVENTION

The compounds used in the methods of the present invention are represented by the compound of structural formula I:

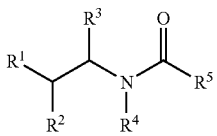

or a pharmaceutically acceptable salt thereof, wherein;
$R^1$ is selected from:
  (1) $C_{1-10}$alkyl,
  (2) $C_{3-10}$cycloalkyl,
  (3) $C_{3-10}$cycloalkyl-$C_{1-4}$alkyl,
  (4) cycloheteroalkyl,
  (5) cycloheteroalkyl-$C_{1-4}$alkyl,
  (6) aryl,
  (7) aryl-$C_{1-4}$alkyl,
  (8) heteroaryl,
  (9) heteroaryl-$C_{1-4}$alkyl,
  (10) $OR^d$,
  (11) —$NR^cR^d$,
  (12) —$NR^cC(O)R^d$,
  (13) —$CO_2R^d$, and
  (14) —$C(O)NR^cR^d$,
  wherein each alkyl is optionally substituted with one to four substituents independently selected from $R^a$, and each cycloalkyl, and cycloheteroalkyl, aryl and heteroaryl are optionally substituted with one to four substituents independently selected from $R^b$;
$R^2$ is selected from:
  (1) $C_{1-10}$alkyl,
  (2) $C_{3-10}$cycloalkyl-$C_{1-4}$alkyl,
  (3) cycloheteroalkyl,
  (4) cycloheteroalkyl-$C_{1-4}$alkyl,
  (5) aryl,
  (6) aryl-$C_{1-14}$alkyl,
  (7) aryloxy,
  (8) arylthio,
  (9) heteroaryl, and
  (10) heteroaryl-$C_{1-4}$-alkyl,
  wherein each alkyl is optionally substituted with one to four substituents independently selected from $R^a$, and each cycloalkyl, cycloheteroalkyl, aryl and heteroaryl is optionally substituted with one to four substituents independently selected from $R^b$;
$R^3$ is selected from:
  (1) hydrogen, and
  (2) $C_{1-14}$alkyl,
  wherein each alkyl is optionally substituted with one to four substituents independently selected from $R^a$;
$R^4$ is selected from:
  (1) hydrogen, and
  (2) $C_{1-4}$alkyl,
  wherein each alkyl is optionally substituted with one to four substituents independently selected from $R^a$;
$R^5$ is selected from:
  (1) $C_{1-10}$alkyl,
  (2) $C_{2-10}$alkenyl,
  (3) $C_{3-10}$cycloalkyl-$C_{1-4}$alkyl,
  (4) cycloheteroalkyl-$C_{1-4}$alkyl,
  (5) aryl-$C_{1-4}$alkyl,
  (6) diaryl-$C_{1-4}$alkyl,
  (7) aryl-$C_{1-4}$alkenyl,
  (8) heteroaryl-$C_{1-4}$alkyl,
  (9) —$OR^d$, and
  (10) —$NR^cR^d$,
  wherein alkyl, alkenyl, cycloalkyl, and cycloheteroalkyl are optionally substituted with one to four substituents independently selected from $R^a$ and cycloalkyl, cycloheteroalkyl, aryl and heteroaryl are optionally substituted with one to four substituents independently selected from $R^b$, provided that $R^5$ is not —CH=CH—COOH;
each $R^a$ is independently selected from:
  (1) —$OR^d$,
  (2) —$NR^cS(O)_mR^d$,
  (3) halogen,
  (4) —$SR^d$,
  (5) —$S(O)_mNR^cR^d$,
  (6) —$NR^cR^d$, (7) —C(O)R$^d$,
(8) —CO$_2$R$^d$,
(9) —CN,
(10) —C(O)NR$^c$R$^d$,
(11) —NR$^c$C(O)R$^d$,
(12) —NR$^c$C(O)OR$^d$,
(13) —NR$^c$C(O)NR$^c$R$^d$,
(14) —CF$_3$,
(15) —OCF$_3$, and
(16) cycloheteroalkyl;
each R$^b$ is independently selected from:
(1) R$^a$,
(2) C$_{1-10}$alkyl,
(3) oxo,
(4) aryl,
(5) arylC$_{1-4}$alkyl,
(6) heteroaryl, and
(7) heteroarylC$_{1-4}$alkyl,
R$^c$ and R$^d$ are independently selected from:
(1) hydrogen,
(2) C$_{1-10}$alkyl,
(3) C$_{2-10}$alkenyl,
(4) cycloalkyl,
(5) cycloalkyl-C$_{1-10}$ alkyl;
(6) cycloheteroalkyl,
(7) cycloheteroalkyl-C$_{1-10}$ alkyl;
(8) aryl,
(9) heteroaryl,
(10) aryl-C$_{1-10}$alkyl, and
(11) heteroaryl-C$_{1-10}$alkyl, or
R$^c$ and R$^d$ together with the atom(s) to which they are attached form a heterocyclic ring of 4 to 7 members containing 0-2 additional heteroatoms independently selected from oxygen, sulfur and N—R$^g$,
each R$^c$ and R$^d$ may be unsubstituted or substituted with one to three substituents selected from R$^h$;
each R$^g$ is independently selected from
(1) C$_{1-10}$alkyl, and
(2) —C(O)R$^c$;
each R$^h$ is independently selected from:
(1) halogen,
(2) C$_{1-10}$ alkyl,
(3) —O—C$_{1-14}$alkyl,
(4) —S—C$_{1-4}$alkyl,
(5) —CN,
(6) —CF$_3$, and
(7) —OCF$_3$, and
m is selected from 1 and 2.

In one embodiment of the present invention, when R$^1$ is unsubstituted phenyl, R$^2$ is unsubstituted benzyl, R$^3$ is unsubstituted methyl, and R$^4$ is hydrogen, then R$^5$ is neither unsubstituted methyl nor unsubstituted phenyl; and when R$^1$ is unsubstituted benzyl, R$^2$ is unsubstituted phenyl, R$^3$ is unsubstituted methyl, and R$^4$ is hydrogen, then R$^5$ is neither unsubstituted methyl nor unsubstituted phenyl; and when R$^1$ is unsubstituted phenyl, R$^2$ is 4-methoxybenzyl, R$^3$ is methyl, R$^4$ is hydrogen, then R$^5$ is not 3,4,5,-trimethoxyphenyl; and when R$^1$ is 4-methoxybenzyl, R$^2$ is unsubstituted phenyl, R$^3$ is methyl, R$^4$ is hydrogen, then R$^5$ is not 3,4,5,-trimethoxyphenyl.

In another embodiment of the present invention, when R$^1$ is unsubstituted phenyl, R$^2$ is unsubstituted benzyl, R$^3$ is unsubstituted methyl, and R$^4$ is hydrogen, then R$^5$ is not unsubstituted methyl; and when R$^1$ is unsubstituted benzyl, R$^2$ is unsubstituted phenyl, R$^3$ is unsubstituted methyl, and R$^4$ is hydrogen, then R$^5$ is not unsubstituted methyl.

In one embodiment of the present invention, R$^1$ is selected from:
(1) C$_{1-10}$alkyl,
(2) C$_{3-10}$cycloalkyl,
(3) C$_{3-10}$cycloalkyl-C$_{1-4}$alkyl,
(4) cycloheteroalkyl,
(5) cycloheteroalkyl-C$_{1-4}$alkyl,
(6) aryl,
(7) aryl-C$_{1-4}$alkyl,
(8) heteroaryl,
(9) heteroaryl-C$_{1-4}$-alkyl,
(10) —OR$^d$,
(11) —NR$^c$R$^d$,
(12) —NR$^c$C(O)R$^d$,
(13) —CO$_2$R$^d$, and
(14) —C(O)NR$^c$R$^d$,
wherein each alkyl is optionally substituted with one to three substituents independently selected from R$^a$, and each cycloalkyl, cycloheteroalkyl, aryl and heteroaryl is optionally substituted with one to three substitutents independently selected from R$^b$.

In one class of this embodiment of the present invention, R$^1$ is selected from:
(1) C$_{1-5}$alkyl,
(2) cycloalkyl,
(3) cycloheteroalkyl,
(4) aryl,
(5) aryl-C$_{1-4}$alkyl,
(6) heteroaryl,
(7) heteroaryl-C$_{1-4}$alkyl,
(8) C$_{1-5}$alkyloxy,
(9) —OR$^d$, and
(10) —CO$_2$R$^d$,
wherein each alkyl is optionally substituted with one to three substituents independently selected from R$^a$, and each aryl and heteroaryl is optionally substituted with one to three substitutents independently selected from R$^b$.

In a subclass of this class of the present invention, R$^1$ is selected from:
(1) C$_{1-5}$alkyl,
(2) cyclobutyl,
(3) cyclopentyl,
(4) cyclohexyl,
(5) pyrrolidinyl,
(6) phenyl,
(7) phenyl-C$_{1-4}$alkyl,
(8) pyridyl, and
(9) pyridyl-C$_{1-4}$alkyl,
wherein each alkyl is optionally substituted with one or two R$^a$ substituents and each phenyl or pyridyl is independently with one to three R$^b$ substituents.

In another subclass of this class of the present invention, R$^1$ is selected from:
(1) C$_{1-5}$alkyl,
(2) cyclobutyl,
(3) cyclopentyl,
(4) cyclohexyl,
(5) pyrrolidinyl,
(6) phenyl,
(7) phenyl-C$_{1-4}$alkyl,
(8) pyridyl, and
(9) pyridyl-C$_{1-4}$alkyl, wherein each phenyl and pyridyl is optionally substituted with one or two substituents selected from halogen, methyl, trifluoromethyl, cyano and methoxy, and each pyridyl is optionally present as the N-oxide.

In yet another subclass of this class of the present invention, $R^1$ is selected from:
(1) ethyl,
(2) isopropyl,
(3) isobutyl,
(4) n-propyl,
(5) n-pentyl,
(6) cyclopentyl,
(7) pyrrolidinyl,
(8) phenyl,
(9) phenyl-$C_{1-4}$alkyl,
(10) pyridyl,
(11) pyridyl-$C_{1-4}$alkyl,
(12) triazolyl,
(13) ethyloxy,
(14) propyloxy,
(15) butyloxy,
(16) n-pentyloxy,
(17) benzyloxylcarbonyl,
(18) cyclopentylmethyloxy, and
(19) cyclobutylmethyloxy, wherein each phenyl and heteroaryl is optionally substituted with one or two substituents selected from halogen, and methoxy, and each pyridyl is optionally present as the N-oxide.

In another embodiment of the present invention, $R^2$ is selected from:
(1) $C_{1-10}$alkyl,
(2) $C_{3-10}$cycloalkyl-$C_{1-4}$alkyl,
(3) cycloheteroalkyl,
(4) cycloheteroalkyl-$C_{1-4}$alkyl,
(5) aryl,
(6) aryl-$C_{1-4}$alkyl,
(7) aryloxy,
(8) arylthio,
(9) heteroaryl, and
(10) heteroaryl-$C_{1-4}$alkyl,
wherein each alkyl is optionally substituted with one to three substituents independently selected from $R^a$, and each cycloalkyl, cycloheteroalkyl, aryl and heteroaryl is optionally substituted with one to three substituents independently selected from $R^b$.

In one class of this embodiment of the present invention, $R^2$ is selected from:
(1) $C_{1-4}$alkyl,
(2) aryl,
(3) aryl-$C_{1-4}$alkyl,
(4) aryloxy,
(5) arylthio,
(6) heteroaryl, and
(7) heteroaryl-$C_{1-4}$alkyl,
wherein each alkyl is optionally substituted with one $R^a$ substituent, and each aryl and heteroaryl is optionally substituted with one to three substituents independently selected from $R^b$.

In a subclass of this class of the present invention, aryl is phenyl and heteroaryl is pyridyl in $R^2$.

In another subclass of this class of the present invention, $R^2$ is selected from:
(1) isopropyl,
(2) isobutyl,
(3) n-propyl,
(4) phenyl,
(5) benzyl,
(6) phenylethyl,
(7) 3-phenylpropyl,
(8) 2-phenylpropyl,
(9) phenoxy,
(10) phenylthio, and
(11) pyridylmethyl, wherein each aryl and heteroaryl is optionally substituted with one or two $R^b$ substituents selected from halogen, trifluoromethyl, cyano, methoxycarbonyl, and methoxy.

In yet another embodiment of the present invention, $R^2$ is selected from:
(1) $C_{1-10}$alkyl,
(2) $C_{3-10}$cycloalkyl-$C_{1-4}$alkyl,
(3) cycloheteroalkyl,
(4) cycloheteroalkyl-$C_{1-4}$alkyl,
(5) aryl,
(6) aryl-$C_{1-4}$alkyl,
(7) aryloxy,
(8) arylthio,
(9) arylamino,
(10) heteroaryl, and
(11) heteroaryl-$C_{1-4}$alkyl,
wherein each alkyl is optionally substituted with one to four substituents independently selected from $R^a$, and each cycloalkyl, cycloheteroalkyl, aryl and heteroaryl is optionally substituted with one to four substituents independently selected from $R^b$.

In another embodiment of the present invention, $R^3$ is selected from:
(1) hydrogen, and
(2) $C_{1-4}$alkyl,
wherein alkyl is optionally substituted with one or two substituents selected from $R^a$.

In one class of this embodiment of the present invention, $R^3$ is selected from:
(1) hydrogen,
(2) methyl,
(3) ethyl, and
(4) isopropyl.

In one subclass of this class of the present invention, $R^3$ is selected from hydrogen, methyl and ethyl.

In another subclass of this class of the present invention, $R^3$ is methyl.

In another embodiment of the present invention, $R^4$ is selected from:
(1) hydrogen, and
(2) $C_{1-4}$alkyl,
wherein alkyl is optionally substituted with one or two substituents selected from $R^a$.

In one class of this embodiment of the present invention, $R^4$ is selected from:
(1) hydrogen, and
(2) methyl.

In one subclass of this class, $R^4$ is hydrogen.

In another embodiment of the present invention, $R^5$ is selected from:
(1) $C_{1-10}$alkyl,
(2) $C_{2-10}$alkenyl,
(3) $C_{3-10}$cycloalkyl-$C_{1-4}$alkyl,
(4) cycloheteroalkyl-$C_{1-4}$alkyl,
(5) aryl-$C_{1-4}$alkyl,
(6) diaryl-$C_{1-4}$alkyl,
(7) aryl-$C_{1-4}$alkenyl,
(8) heteroaryl-$C_{1-4}$alkyl, (9) —OR$^d$, and
(10) —NR$^c$R$^d$, wherein each alkyl or alkenyl is optionally substituted with one or two substituents independently selected from R$^a$, and each cycloalkyl, cycloheteroalkyl, aryl and heteroaryl is each optionally substituted with on to three substituents independently selected from R$^b$, provided that R$^5$ is not —CH=CH—COOH.

In one class of this embodiment of the present invention, R$^5$ is selected from:
(1) C$_{1-8}$alkyl,
(2) C$_{2-8}$alkenyl,
(3) cycloheteroalkyl-C$_{1-14}$alkyl,
(4) aryl-C$_{1-4}$alkyl,
(5) diaryl-C$_{1-4}$alkyl,
(6) aryl-C$_{1-4}$alkenyl,
(7) heteroaryl-C$_{1-4}$alkyl,
(8) —OR$^d$, and
(9) —NR$^c$R$^d$, wherein each alkyl or alkenyl is optionally substituted with one or two substituents independently selected from R$^a$, and each cycloalkyl, cycloheteroalkyl, aryl and heteroaryl is each optionally substituted with on to three substituents independently selected from R$^b$, provided that R$^5$ is not —CH=CH—COOH.

In one subclass of this embodiment of the present invention, R$^5$ is selected from:
(1) C$_{1-8}$alkyl,
(2) C$_{2-8}$alkenyl,
(3) cycloheteroalkyl-C$_{1-4}$alkyl,
(4) aryl-C$_{1-4}$alkyl,
(5) diaryl-C$_{1-4}$alkyl,
(6) aryl-C$_{1-4}$alkenyl,
(7) heteroaryl-C$_{1-4}$alkyl,
(8) —OR$^d$, and
(9) —NR$^c$R$^d$, wherein each alkyl or alkenyl is optionally substituted with one or two substituents independently selected from R$^a$, and each cycloalkyl, cycloheteroalkyl, aryl and heteroaryl is each optionally substituted with one to three substituents independently selected from R$^b$ and wherein cycloheteroalkyl is selected from pyrrolidinyl, 2H-phthalazinyl, azabicyclo[2.2.1]heptanyl, benzoxapinyl, morpholinyl, piperazinyl, dihydroimidazo[2,1-b]thiazolyl, and piperidinyl; aryl is selected from phenyl and naphthyl; and heteroaryl is selected from pyridyl, pyrazolyl, triazolyl, benzothiazolyl, benzoxazolinyl, isoxazolyl, indolyl and thiazolyl, provided that R$^5$ is not —CH=CH—COOH.

In a subclass of this class of the present invention, R$^5$ is selected from:
(1) isopropyl,
(2) isobutyl,
(3) t-butyl,
(4) pentyl,
(5) benzyl,
(6) α-hydroxy-benzyl,
(7) α-methoxy-benzyl,
(8) α-hydroxy-diphenyl-methyl,
(9) 3-(aminosulfonyl)-propyl,
(10) 5-(t-butyloxycarbonylamino)-pentyl,
(11) anilino,
(12) anilino-methyl,
(13) t-butoxy,
(14) phenoxy,
(15) benzyloxy,
(16) 1-naphthyl-methyl,
(17) phenyl-ethyl,
(18) 3-phenyl-propyl,
(19) 3,3-diphenyl-propyl,
(20) 2-phenyl-ethylene,
(21) 1-phenyl-propyl,
(22) methoxymethyl,
(23) 3-benzoyl-propyl,
(24) 7-benzoyl-heptyl,
(25) 2-t-butoxy-ethyl,
(26) phenoxy-methyl,
(27) 1-(phenoxy)-ethyl,
(28) 2-(phenoxy)-isopropyl,
(29) 2-(pyridyloxy)-isopropyl,
(30) 2-(pyrimidinyloxy)-isopropyl,
(31) 2-(pyridazinyloxy)-isopropyl,
(32) cyclopropyl-methyl,
(33) cyclopentyl-methyl,
(34) 2-(cyclohexyloxy)-isopropyl,
(35) (1-indanone)-3-methyl,
(36) (2-thiazolyl)-S-methyl,
(37) (2-benzothiazolyl)-S-methyl,
(38) (2-benzoxazolyl)-S-methyl,
(39) benztriazolyl-methyl,
(40) 2-(benzothiazolyl)-ethyl,
(41) isoxazolyl-methyl,
(42) thiazolyl-methyl,
(43) triazolyl-methyl,
(44) 2-(triazolyl)-ethyl,
(45) pyrazolyl-methyl,
(46) 2-(pyrazolyl)-ethyl, and
(47) (3-(1-oxo-isoindolyl))-methyl;

wherein each alkyl or alkenyl is optionally substituted with one or two substituents independently selected from R$^a$, and each cycloalkyl, cycloheteroalkyl, aryl and heteroaryl is each optionally substituted with on to three substituents independently selected from R$^b$.

In yet another subclass of this class of the invention, R$^5$ is C$_{1-8}$alkyl substituted with —OR$^d$.

In one embodiment of the present invention, each R$^a$ is independently selected from:
(1) —OR$^d$,
(2) —NHS(O)$_m$R$^d$,
(3) halogen,
(4) —SR$^d$,
(5) —S(O)$_m$NHR$^d$,
(6) —NR$^c$R$^d$,
(7) —C(O)R$^d$,
(8) —CO$_2$R$^d$,
(9) —CN,
(10) —C(O)NHR$^d$,
(11) —NHC(O)R$^d$,
(12) —NHC(O)OR$^d$,
(13) —NHC(O)NHR$^d$,
(14) —CF$_3$,
(15) —OCF$_3$, and
(16) cycloheteroalkyl.

In one class of this embodiment of the present invention, each R$^a$ is independently selected from:
(1) —OR$^d$,
(2) —NHS(O)$_2$R$^d$,
(3) halogen,
(4) —SR$^d$,
(5) —S(O)$_2$NH$_2$,
(6) —NHR$^d$,
(7) —N(CH$_2$CH$_3$)R$^d$, (8) —C(O)$R^d$,
(9) —CO$_2$H,
(10) —CN,
(11) —C(O)NH$R^d$,
(12) —NHC(O)$R^d$,
(13) —NHC(O)O$R^d$,
(14) —NHC(O)NH$R^d$,
(15) —CF$_3$,
(16) —OCF$_3$, and
(17) cycloheteroalkyl.

In another embodiment of the present invention, each $R^a$ is independently selected from:
(1) —O$R^d$,
(2) —N$R^c$S(O)$_m R^d$,
(3) halogen,
(4) S(O)$_m R^d$,
(5) —S(O)$_m$N$R^c R^d$,
(6) —N$R^c R^d$,
(7) —C(O)$R^d$,
(8) —CO$_2 R^d$,
(9) —CN,
(10) —C(O)N$R^c R^d$,
(11) —N$R^c$C(O)$R^d$,
(12) —N$R^c$C(O)O$R^d$.
(13) —N$R^c$C(O)N$R^c R^d$,
(14) —CF$_3$,
(15) —OCF$_3$, and
(16) cycloheteroalkyl.

In one embodiment of the present invention, each $R^b$ is independently selected from:
(1) —O$R^d$,
(2) —NHS(O)$_m R^d$,
(3) halogen,
(4) —S$R^d$,
(5) —S(O)$_m$NH$R^d$,
(6) —NH$R^d$,
(7) —C(O)$R^d$,
(8) —CO$_2 R^d$,
(9) —CN,
(10) —C(O)N$R^c R^d$,
(11) —NHC(O)$R^d$,
(12) —NHC(O)O$R^d$,
(13) —NHC(O)N$R^c R^d$,
(14) —CF$_3$,
(15) —OCF$_3$,
(16) cycloheteroalkyl;
(17) C$_{1-10}$alkyl,
(18) oxo,
(19) aryl,
(20) arylC$_{1-4}$alkyl,
(21) heteroaryl, and
(22) heteroarylC$_{1-4}$alkyl.

In one class of this embodiment of the present invention, each $R^b$ is independently selected from:
(1) —O$R^d$,
(2) halogen,
(3) —CN,
(4) —CF$_3$,
(5) —OCF$_3$,
(6) cycloheteroalkyl;
(7) C$_{1-4}$alkyl,
(8) oxo,
(9) phenyl,
(10) benzyl, and
(11) heteroaryl.

In one embodiment of the present invention, each $R^c$ is independently selected from:
(1) hydrogen, and
(2) C$_{1-4}$alkyl, and
each $R^d$ is independently selected from:
(1) hydrogen,
(2) C$_{1-4}$alkyl,
(3) C$_{2-6}$ alkenyl,
(4) cycloalkyl,
(5) cycloalkyl-C$_{1-4}$alkyl,
(6) cycloheteroalkyl,
(7) cycloheteroalkyl-C$_{1-4}$ alkyl,
(8) phenyl,
(9) heteroaryl,
(10) phenyl-C$_{1-4}$alkyl, and
(11) heteroaryl-C$_{1-4}$alkyl, or
$R^c$ and $R^d$ together with the atom(s) to which they are attached form a heterocyclic ring of 4 to 7 members containing 0-2 additional heteroatoms independently selected from oxygen, sulfur and N—$R^g$,
each $R^c$ and $R^d$ may be unsubstituted or substituted with one to three substituents selected from $R^h$.

In one class of this embodiment of the present invention, each $R^c$ is independently selected from:
(1) hydrogen, and
(2) C$_{1-4}$alkyl, and
each $R^d$ is independently selected from:
(1) hydrogen,
(2) C$_{1-15}$alkyl,
(3) —CH$_2$CH=CH$_2$,
(4) cyclohexyl,
(5) cyclopentyl,
(6) cyclopropyl,
(7) cyclobutylmethyl,
(8) cyclopentylmethyl,
(9) cyclohexylmethyl,
(10) pyrrolidinyl,
(11) phenyl,
(12) thiazolyl,
(13) pyridyl,
(14) benzothiazolyl,
(15) benzoxazolyl,
(16) triazolyl,
(17) benzyl, and
(18) pyridyl-methyl-, or
$R^c$ and $R^d$ together with the atom(s) to which they are attached form a piperidinyl ring,
each $R^c$ and $R^d$ may be unsubstituted or substituted with one to three substituents selected from $R^h$.

In one embodiment of the present invention, each $R^g$ is independently selected from:
(1) C$_{1-4}$alkyl, and
(2) —C(O)C$_{1-4}$alkyl.

In one class of this embodiment, each $R^g$ is methyl or methylcarbonyl.

In one subclass of this class, each $R^g$ is methyl.

In one embodiment of the present invention, each $R^h$ is independently selected from:
(1) halogen,
(2) C$_{1-4}$alkyl,
(3) —O—C$_{1-4}$alkyl,
(4) —S—C$_{1-4}$alkyl,
(5) —CN,
(6) —CF$_3$, and
(7) —OCF$_3$.

In one class of this embodiment, each $R^h$ is independently selected from:
(1) halogen,
(2) methyl,
(3) methoxy,
(4) methylthio-,
(5) —CN,
(6) —CF$_3$, and
(7) —OCF$_3$.

In another embodiment of the present invention, each $R^h$ is independently selected from:
(1) halogen,
(2) C$_{1-10}$alkyl,
(3) —O C$_{1-4}$alkyl,
(4) —S(O)$_m$C$_{1-4}$alkyl,
(5) —CN,
(6) —CF$_3$, and
(7) —OCF$_3$.

In a subclass of this embodiment, each $R^h$ is independently selected from:
(1) halogen,
(2) C$_{1-3}$alkyl,
(3) —SO$_2$CH$_3$
(4) —CN, and
(5) —CF$_3$.

In one embodiment of the present invention, m is two.

In another embodiment of the present invention, m is selected from 0, 1, and 2.

Particular novel compounds which may be employed in the methods, uses and compositions of the present invention, include:

(1) N-[2,3-bis(4-chlorophenyl)-1-methyl-propyl]-2-(pyrazol-1-yl)acetamide, trifluoroacetic acid salt;
(2) N-[2,3-bis(4-chlorophenyl)-1-methyl-propyl]-2-(1,2,4-triazol-1-yl)acetamide, trifluoroacetic acid salt;
(3) N-[2,3-bis(4-chlorophenyl)-1-methyl-propyl]-2-(benzothiazole-2-thio)acetamide, trifluoroacetic acid salt;
(4) N-[2,3-bis(4-chlorophenyl)-1-methyl-propyl]-2-(benzoxazole-2-thio)acetamide, trifluoroacetic acid salt;
(5) N-[2,3-bis(4-chlorophenyl)-1-methyl-propyl]-2-(benzoxazolin-2-on-3-yl)acetamide;
(6) N-[2,3-bis(4-chlorophenyl)-1-methyl-propyl]-2-(4-methyl-2H-phthalazin-1-on-2-yl)acetamide;
(7) N-[2,3-bis(4-chlorophenyl)-1-methyl-propyl]-2-(2H-phthalazin-1-on-4-yl)propanamide;
(8) N-[2,3-bis(4-chlorophenyl)-1-methyl-propyl]-2-(3,5-dimethyl-1,2,4-triazol-1-yl)acetamide, trifluoroacetic acid salt;
(9) N-[2,3-bis(4-chlorophenyl)-1-methyl-propyl]-2-(2-methyl-thiazol-4-yl)acetamide, trifluoroacetic acid salt;
(10) N-[2,3-bis(4-chlorophenyl)-1-methyl-propyl]-2-(1-(4-phenyl-pyrrolidin-2-on-1-yl))acetamide;
(11) N-[2,3-bis(4-chlorophenyl)-1-methyl-propyl]-2-(3,5-dimethyl-pyrazol-1-yl)acetamide, trifluoroacetic acid salt;
(12) N-[2,3-bis(4-chlorophenyl)-1-methyl-propyl]-2-(3-methyl-pyrazol-1-yl)acetamide, trifluoroacetic acid salt;
(13) N-[2,3-bis(4-chlorophenyl)-1-methyl-propyl]-2-(isoindolin-1-on-3-yl)acetamide;
(14) N-[2,3-bis(4-chlorophenyl)-1-methyl-propyl]-2-(3,5-dimethyl-isoxazol-4-yl)acetamide, trifluoroacetic acid salt;
(15) N-[2,3-bis(4-chlorophenyl)-1-methyl-propyl]-3-(3,5-dimethyl-pyrazol-1-yl)propanamide, trifluoroacetic acid salt;
(16) N-[2,3-bis(4-chlorophenyl)-1-methyl-propyl]-2-(3-methyl-pyrazol-1-yl)acetamide, trifluoroacetic acid salt;
(17) N-[2,3-bis(4-chlorophenyl)-1-methyl-propyl]-2-(4-(imidazolidin-2-on-1-yl)phenyl)acetamide;
(18) N-[2,3-bis(4-chlorophenyl)-1-methyl-propyl]-2-(5-methyl-1,2,4-triazol-3-yl)acetamide, trifluoroacetic acid salt;
(19) N-[2,3-bis(4-chlorophenyl)-1-methyl-propyl]-5-(2-methyl)phenyl-5-oxo-pentanamide;
(20) N-[2,3-bis(4-chlorophenyl)-1-methyl-propyl]-3-(benzothiazol-2-yl)propanamide, trifluoroacetic acid salt;
(21) N-[2,3-bis(4-chlorophenyl)-1-methyl-propyl]-3-(azabicyclo[2.2.1]heptan-2-yl)propanamide, trifluoroacetic acid salt;
(22) N-[2,3-bis(4-chlorophenyl)-1-methyl-propyl]-2-(5-methoxy-2-oxo-2,3-dihydro-1H-indol-3-yl)acetamide;
(23) N-[2,3-bis(4-chlorophenyl)-1-methyl-propyl]-2-(benzotriazol-2-yl)acetamide, trifluoroacetic acid salt;
(24) N-[2,3-bis(4-chlorophenyl)-1-methyl-propyl]-2-(4-methyl-thiazol-2-yl-thio)acetamide, trifluoroacetic acid salt;
(25) N-[2,3-bis(4-chlorophenyl)-1-methyl-propyl]-2-(4,4-diphenyl)butanamide;
(26) N-[2,3-bis(4-chlorophenyl)-1-methyl-propyl]-3-(1,2,4-triazol-1-yl)propanamide, trifluoroacetic acid salt;
(27) N-[2,3-bis(4-chlorophenyl)-1-methyl-propyl]-2-(imidazo[2,1-b][1,3]thiazol-6-yl)acetamide, trifluoroacetic acid salt;
(28) N-[2,3-bis(4-chlorophenyl)-1-methyl-propyl]-3-(3,5-dichlorophenyl)propanamide;
(29) N-[2,3-bis(4-chlorophenyl)-1-methyl-propyl]-4-(3,5-dichlorophenyl)butanamide;
(30) N-[2,3-bis(4-chlorophenyl)-1-methyl-propyl]-3-(t-butoxy)propanamide;
(31) N-[2,3-bis(4-chlorophenyl)-1-methyl-propyl]-4-(2,3-dihydro-indol-1-yl)butanamide;
(32) N-[2,3-bis(4-chlorophenyl)-1-methyl-propyl]-3-(1-methyl-pyrazol-5-yl)propanamide, trifluoroacetic acid salt;
(33) N-[2,3-bis(4-chlorophenyl)-1-methyl-propyl]-3-(4-t-butoxyphenyl)propanamide;
(34) N-[2,3-bis(4-chlorophenyl)-1-methyl-propyl]-3-(3,5-dimethylphenyl)propanamide;
(35) N-[2,3-bis(4-chlorophenyl)-1-methyl-propyl]-2-(5-methyl-pyrazol-1-yl)acetamide, trifluoroacetic acid salt;
(36) N-[2,3-bis(4-chlorophenyl)-1-methyl-propyl]-2-(4-methyl-1,2,4-triazol-3-yl-thio)acetamide, trifluoroacetic acid salt;
(37) N-[2,3-bis(4-chlorophenyl)-1-methyl-propyl]-2-(2,3,4,5-tetrahydro-1,4-benzoxazepin-4-yl)acetamide, trifluoroacetic acid salt;
(38) N-[2,3-bis(4-chlorophenyl)-1-methyl-propyl]-6-(t-butyloxycarbonylamino)hexanamide;
(39) N-[2,3-bis(4-chlorophenyl)-1-methyl-propyl]-2-(5,6-dihydro-imidazo[2,1-b]thiazol-3-yl)acetamide, trifluoroacetic acid salt;
(40) N-[2,3-bis(4-chlorophenyl)-1-methyl-propyl]-2-(morpholin-4-yl)-2-(3-pyridyl)acetamide, trifluoroacetic acid salt;
(41) N-[2,3-bis(4-chlorophenyl)-1-methyl-propyl]-4-(aminosulfonyl)-butanamide;
(42) N-[2,3-bis(4-chlorophenyl)-1-methyl-propyl]-2-(4-phenyl-piperazin-1-yl)acetamide, trifluoroacetic acid salt;
(43) N-[2,3-bis(4-chlorophenyl)-1-methyl-propyl]-trans-cinnamamide;
(44) N-[2,3-bis(4-chlorophenyl)-1-methyl-propyl]-9-phenyl-9-oxo-nonanamide;
(45) N-[2,3-bis(4-chlorophenyl)-1-methyl-propyl]-2-phenyl-butanamide;
(46) N-[2,3-bis(4-chlorophenyl)-1-methyl-propyl]-2-cyclopropyl-acetamide;

(47) N-[2,3-bis(4-chlorophenyl)-1-methyl-propyl]-2-(1-naphthyl)-acetamide;
(48) N-[2,3-bis(4-chlorophenyl)-1-methyl-propyl]-2-(5-methoxy-1-indanon-3-yl)-acetamide;
(49) N-[2,3-bis(4-chlorophenyl)-1-methyl-propyl]-2-phenoxy-acetamide;
(50) N-[2,3-bis(4-chlorophenyl)-1-methyl-propyl]-3-(4-hydroxyphenyl)-propanamide;
(51) N-[2,3-bis(4-chlorophenyl)-1-methyl-propyl]-hexanamide;
(52) N-[2,3-bis(4-chlorophenyl)-1-methyl-propyl]-2-cyclopentyl-acetamide;
(53) N-[2,3-bis(4-chlorophenyl)-1-methyl-propyl]-2-ethoxy-acetamide;
(54) N-[2,3-bis(4-chlorophenyl)-1-methyl-propyl]-3-methyl-butanamide;
(55) N-[2,3-bis(4-chlorophenyl)-1-methyl-propyl]-3-(1-t-butoxycarbonyl-piperidin-4-yl)-propanamide;
(56) N-[2,3-bis(4-chlorophenyl)-1-methyl-propyl]-2-(3-chlorophenyl)-acetamide;
(57) N-[2,3-bis(4-chlorophenyl)-1-methyl-propyl]-3-(4-chlorophenyl)-propanamide;
(58) N-[2,3-bis(4-chlorophenyl)-1-methyl-propyl]-2-hydroxy-2-phenyl-acetamide;
(59) N-[2,3-bis(4-chlorophenyl)-1-methyl-propyl]-2-hydroxy-2-(4-methoxy-phenyl)-acetamide;
(60) N-[2,3-bis(4-chlorophenyl)-1-methyl-propyl]-2-methoxy-2-phenyl-acetamide;
(61) N-[2,3-bis(4-chlorophenyl)-1-methyl-propyl]-2-hydroxy-2,2-diphenyl-acetamide;
(62) N-[2,3-Bis(4-Chlorophenyl)-1-methylpropyl]-2-(4-chlorophenyloxy)-2-methylpropanamide;
(63) N-[2,3-Bis(4-chlorophenyl)-1-methylpropyl]-2-(4-cyclohexyloxy)-2-methylpropanamide;
(64) N-[2,3-Bis(4-chlorophenyl)-1-methylpropyl]-2-(2-fluorophenyloxy)-2-methylpropanamide;
(65) N-[2,3-Bis(4-chlorophenyl)-1-methylpropyl]-2-(3-fluorophenyloxy)-2-methylpropanamide;
(66) N-[2,3-Bis(4-chlorophenyl)-1-methylpropyl]-2-(3,4-difluorophenyloxy)-2-methylpropanamide;
(67) N-[2,3-Bis(4-chlorophenyl)-1-methylpropyl]-2-(3-chlorophenyloxy)-2-methylpropanamide;
(68) N-[2,3-Bis(4-chlorophenyl)-1-methylpropyl]-2-(2-chlorophenyloxy)-2-methylpropanamide;
(69) N-[2,3-Bis(4-chlorophenyl)-1-methylpropyl]-2-(3,5-difluorophenyloxy)-2-methylpropanamide;
(70) N-[2,3-Bis(4-chlorophenyl)-1-methylpropyl]-2-(3-cyanophenyloxy)-2-methylpropanamide;
(71) N-[3-(4-Chlorophenyl)-2-(2,4-dichlorophenyl)-1-methylpropyl]-2-(4-chlorophenyloxy)-2-methylpropanamide;
(72) N-[2,3-Bis(4-chlorophenyl)-1-methylpropyl]-2-phenyloxy-2-methylpropanamide;
(73) N-[2,3-Bis(4-chlorophenyl)-1-methylpropyl]-2-(4-fluorophenyloxy)-2-methylpropanamide;
(74) N-[2,3-Bis(4-chlorophenyl)-1-methylpropyl]-2,2-dimethylpropanamide;
(75) N-[2,3-Bis(4-chlorophenyl)-1-methylpropyl]-4-chlorophenylcarbamate;
(76) N-[2,3-Bis(4-chlorophenyl)-1-methylpropyl]-N'-(4-chlorophenyl)urea;
(77) N-[2,3-Bis(4-chlorophenyl)-1-methylpropyl]benzyl carbamate;
(78) N-[2,3-Bis(4-chlorophenyl)-1-methylpropyl]-tert-butylcarbamatec;
(79) N-[2,3-Bis(4-chlorophenyl)-1-methylpropyl]-2-(3-pyridyloxy)-2-methylpropanamide;
(80) N-[2,3-Bis(4-chlorophenyl)-1-methylpropyl]-2-(2-pyridylox)-2-methylbutanamide;
(81) N-[2,3-Bis(4-chlorophenyl)-1-methylpropyl]-2-(2-pyridyloxy)-2-methylpropanamide;
(82) N-[2,3-Bis(4-chlorophenyl)-1-methylpropyl]-2-(4-pyridyloxy)-2-methylpropanamide;
(83) N-[3,4-Bis(4-Chlorophenyl)-1-methylpropyl]-2-(2-methoxyphenyloxy)-propenamide;
(84) N-[3,4-Bis(4-Chlorophenyl)-1-methylpropyl]-2-(2-methoxyphenyloxy)-propenamide;
(85) N-[3-(4-Chlorophenyl)-1-methyl-2-phenylpropyl]-2-(2-fluorophenyloxy)-2-methylpropanamide;
(86) N-[3-(4-Chlorophenyl)-1-methyl-2-phenylpropyl]-2-(3-fluorophenyloxy)-2-methylpropanamide;
(87) N-[3-(4-Chlorophenyl)-1-methyl-2-phenylpropyl]-2-(3,4-difluorophenyloxy)-2-methylpropanamide;
(88) N-[3-(4-Chlorophenyl)-1-methyl-2-phenylpropyl]-2-(3-chlorophenyloxy)-2-methylpropanamide;
(89) N-[3-(4-Chlorophenyl)-1-methyl-2-phenylpropyl]-2-(2-chlorophenyloxy)-2-methylpropanamide;
(90) N-[3-(4-Chlorophenyl)-1-methyl-2-phenylpropyl]-2-(3,5-difluorophenyloxy)-2-methylpropanamide;
(91) N-[3-(4-Chlorophenyl)-1-methyl-2-phenylpropyl]-2-cyclohexyloxy)-2-methylpropanamide;
(92) N-[3-(4-Chlorophenyl)-1-methyl-2-phenylpropyl]-2-(4-fluorophenyloxy)-2-methylpropanamide;
(93) N-[3-(4-Chlorophenyl)-2-(2-fluorophenyl)-1-methylpropyl]-2-(4-chlorophenyloxy)-2-methylpropanamide;
(94) N-[3-(4-Chlorophenyl)-2-(3-fluorophenyl)-1-methylpropyl]-2-(4-chlorophenyloxy)-2-methylpropanamide;
(95) N-[3-(4-Chlorophenyl)-1-methyl-2-phenylpropyl)]-2-methyl-2-phenylpropanamide;
(96) N-[3-(4-Chlorophenyl)-2-(3-fluorophenyl)-1-methylpropyl]-2-(2-pyridyloxy)-2-methylpropanamide;
(97) N-[3-(4-Chlorophenyl)-2-(3-fluorophenyl)-1-methylpropyl]-2-(3,5-difluorophenyloxy)-2-methylpropanamide;
(98) N-[3-(4-Chlorophenyl)-1-methyl-2-phenylpropyl]-2-(3-pyridyloxy)-2-methylpropanamide;
(99) N-[3-(4-Chlorophenyl)-1-methyl-2-phenylpropyl]-2-(2-pyridyloxy)-2-methylbutanamide;
(100) N-[3-(4-Chlorophenyl)-1-methyl-2-phenylpropyl]-2-(2-pyridyloxy)-2-methylpropanamide;
(101) N-[3-(4-Chlorophenyl)-1-methyl-2-phenylpropyl]-2-(4-pyridyloxy)-2-methylpropanamide;
(102) N-[2-(4-Chlorophenyl)-1-methyl-3-phenylpropyl]-2-(4-chlorophenyloxy)-2-methylpropanamide;
(103) N-[2-(4-Chlorophenyl)-1-methyl-3-phenylpropyl]-2-(4-fluorophenyloxy)-2-methylpropanamide;
(104) N-[3-(4-Methoxycarbonylphenyl)-1-methyl-2-phenylpropyl]-2-(4-fluorophenyloxy)-2-methylpropanamide;
(105) N-[3-(4-Methoxycarbonylphenyl)-1-methyl-2-phenylpropyl]-2-(4-fluorophenyloxy)-2-methylpropanamide;
(106) N-[3-(4-Methoxycarbonylphenyl)-1-methyl-2-phenylpropyl]-2-(4-Chlorophenyloxy)-2-methylpropanamide;
(107) N-[2-(2-Chlorophenyl)-1-methyl-3-phenylpropyl]-2-(4-fluorophenyloxy)-2-methylpropanamide;
(108) N-[2-(2-Chlorophenyl)-1-methyl-3-phenylpropyl]-2-(4-chlorophenyloxy)-2-methylpropanamide;
(109) N-[2-(2-Chlorophenyl)-1-methyl-3-phenylpropyl]-2-(4-chlorophenyloxy)-2-methylpropanamide;
(110) N-[2-(4-Methoxyphenyl)-1-methyl-3-phenylpropyl]-2-(4-fluorophenyloxy)-2-methylpropanamide;
(111) N-[2-(4-Chlorophenyl)-3-(2,4-dichlorophenyl)-1-methyl-propyl]-2-(4-chlorophenyloxy)-2-methylpropanamide;

(112) N-[2-(4-Chlorophenyl)-3-(2,4-dichlorophenyl)-1-methyl-propyl]-2,2-dimethylpropanamide;
(113) N-[2-(4-Chlorophenyl)-2-(4-chloro-2-fluorophenyl)-1-methyl-propyl]-2-(4-chlorophenyloxy)-2-methylpropanamide;
(114) N-[2-(4-Chlorophenyl)-2-(4-chloro-2-fluorophenyl)-1-methyl-propyl]-2-(4-chlorophenyloxy)-2-methylpropanamide;
(115) N-[2-(4-Chlorophenyl)-2-(4-chloro-2-fluorophenyl)-1-methyl-propyl]-2-(4-fluorophenyloxy)-2-methylpropanamide;
(116) N-[3-(4-Chlorophenyl)-2-(4-fluorophenyl)-1-methyl-propyl]-2-(4-chlorophenyloxy)-2-methylpropanamide;
(117) N-[3-(4-Chlorophenyl)-1-methyl-2-(2-pyridyl)propyl]-tert-butylcarbamate;
(118) N-[3-(4-Chlorophenyl)-1-methyl-2-(2-pyridyl)propyl]-2-(4-chlorophenyloxy)-2-methylpropanamide;
(119) N-[3-(4-Chlorophenyl)-1-methyl-2-(2-pyridyl)propyl]-2-(4-fluorophenyloxy)-2-methylpropanamide;
(120) N-[3-(4-Chlorophenyl)-1-methyl-2-(4-pyridyl)propyl]-2-(4-chlorophenyloxy)-2-methylpropanamide;
(121) N-[3-(4-Cyanophenyl)-1-methyl-2-phenylpropyl]-2-(3-chlorophenyloxy)-2-methylpropanamide;
(122) N-[3-(5-Chloro-2-pyridyl)-1-methyl-2-phenylpropyl]-2-(3,5-difluorophenyloxy)-2-methylpropanamide;
(123) N-[3-(4-Chlorophenyl)-1-methyl-2-(3-pyridyl)propyl]-tert-butylcarbamate;
(124) N-[3-(4-Chlorophenyl)-1-methyl-2-(3-pyridyl)propyl]-2-(4-chlorophenyloxy)-2-methylpropanamide;
(125) N-[3-(4-Chlorophenyl)-1-methyl-2-(3-pyridyl)propyl]-2-(3,5-difluorophenyloxy)-2-methylpropanamide;
(126) N-[3-(4-Chlorophenyl)-1-methyl-2-(3-pyridyl)propyl]-2-(3-fluorophenyloxy)-2-methylpropanamide;
(127) N-[2-(4-Chlorophenoxy)-2-(4-chlorophenyl)ethyl]-2-(4-chlorophenyloxy)-2-methylpropanamide;
(128) N-[2,2-Bis(4-chlorophenyl)ethyl]allylcarbamate;
(129) N-[2,2-Bis(4-chlorophenyl)ethyl]-2-(4-chlorophenyloxy)-2-methylpropanamide;
(130) N-[2-(4-Chlorophenylthio)-2-(4-chlorophenyl)-1-methylpropyl]-2-(4-chlorophenyloxy)-2-methylpropanamide;
(131) N-[2,3-Bis(4-Chlorophenyl)-1-methylpropyl]-2-(4-chlorophenyloxy)-2-methylpropanamide;
(132) N-[2,3-Bis(4-chlorophenyl)-1-methylpropyl]-2-phenyloxy)-2-methylpropanamide;
(133) N-[2,3-Bis(4-chlorophenyl)-1-methylpropyl]-2-phenyloxy-2-methylpropanamide;
(134) N-[2,3-Bis(4-chlorophenyl)-1-methylpropyl]-2-(4-fluorophenyloxy)-2-methylpropanamide;
(135) N-[2,3-Bis(4-chlorophenyl)-1-methylpropyl]-2-(6-methyl-3-pyridyloxy)-2-methylpropanamide;
(136) N-[3-(4-Chlorophenyl)-1-methyl-2-phenylpropyl]-2-(3-fluorophenyloxy)-2-methylpropanamide;
(137) N-[3-(4-Chlorophenyl)-1-methyl-2-phenylpropyl]-2-(3,4-difluorophenyloxy)-2-methylpropanamide;
(138) N-[3-(4-Chlorophenyl)-1-methyl-2-phenylpropyl]-2-(3-chlorophenyloxy)-2-methylpropanamide;
(139) N-[3-(4-Chlorophenyl)-1-methyl-2-phenylpropyl]-2-(3,5-difluorophenyloxy)-2-methylpropanamide;
(140) N-[3-(4-Chlorophenyl)-1-methyl-2-phenylpropyl]-2-(4-fluorophenyloxy)-2-methylpropanamide;
(141) N-[3-(4-Chlorophenyl)-2-(3-fluorophenyl)-1-methyl-propyl]-2-(4-fluorophenyloxy)-2-methylpropanamide;
(142) N-[3-(4-Chlorophenyl)-2-(3-fluorophenyl)-1-methyl-propyl]-2-(3,5-difluorophenyloxy)-2-methylpropanamide;
(143) N-[3-(4-Chlorophenyl)-2-(3-fluorophenyl)-1-methyl-propyl]-2-(2-pyridyloxy)-2-methylpropanamide;
(144) N-[3-(4-Chlorophenyl)-1-methyl-2-phenylpropyl]-2-(2-pyridyloxy)-2-methylpropanamide;
(145) N-[3-(4-Chlorophenyl)-1-methyl-2-(2-pyridyl)propyl]-2-(4-chlorophenyloxy)-2-methylpropanamide;
(146) N-[3-(4-Cyanophenyl)-1-methyl-2-phenylpropyl]-2-(3-chlorophenyloxy)-2-methylpropanamide;
(147) N-[3-(4-Chlorophenyl)-1-methyl-2-(3-pyridyl)propyl]-2-(4-chlorophenyloxy)-2-methylpropanamide;
(148) N-[3-(4-Chlorophenyl)-1-methyl-2-(3-pyridyl)propyl]-2-(3,5-difluorophenyloxy)-2-methylpropanamide;
(149) N-[3-(4-Chlorophenyl)-1-methyl-2-(3-pyridyl)propyl]-2-(3-fluorophenyloxy)-2-methylpropanamide;
(150) N-[2-(4-Chlorophenoxy)-2-(4-chlorophenyl)ethyl]-2-(4-chlorophenyloxy)-2-methylpropanamide;
(151) N-[3-(4-chlorophenyl)-2(S)-phenyl-1(S)-methylpropyl]-2-(3,5-difluorophenyloxy)-2-methylpropanamide;
(152) N-[3-(4-chlorophenyl)-2(S)-phenyl-1(S)-methylpropyl]-2-(3,4,5-trifluorophenyloxy)-2-methylpropanamide;
(153) N-[3-(4-chlorophenyl)-2(S)-phenyl-1(S)-methylpropyl]-2-(3-chloro-4-fluorophenyloxy)-2-methylpropanamide;
(154) N-[3-(4-chlorophenyl)-2(S)-phenyl-1(S)-methylpropyl]-2-(4-chloro-3-fluorophenyloxy)-2-methylpropanamide;
(155) N-[3-(4-chlorophenyl)-2(S)-phenyl-1(S)-methylpropyl]-2-(3,4-dichlorophenyloxy)-2-methylpropanamide;
(156) N-[3-(4-chlorophenyl)-2(S)-phenyl-1(S)-methylpropyl]-2-(3,5-dichlorophenyloxy)-2-methylpropanamide;
(157) N-[2,3-Bis(4-chlorophenyl)-1-methylpropyl]-3-hydroxy-2,2-dimethylpropanamide;
(158) N-[2,3-Bis(4-chlorophenyl)-1-methylpropyl]-3-diethylamino-2,2-dimethylpropanamide;
(159) N-[2,3-Bis(4-chlorophenyl)-1-methylpropyl]-3-cyclopropylamino-2,2-dimethylpropanamide;
(160) N-[2,3-Bis(4-chlorophenyl)-1-methylpropyl]-2,2-dimethyl-3-piperidinylpropanamide;
(161) N-[2,3-Bis(4-chlorophenyl)-1-methylpropyl]-3-tert-butylamino-2,2-dimethylpropanamide;
(162) N-[2,3-Bis(4-chlorophenyl)-1-methylpropyl]-2-(4-chlorophenylamino)-2-methylpropanamide;
(163) N-[3-(4-Chlorophenyl)-1-methyl-2-phenylpropyl]-2-(3-pyridyloxy-N-oxide)-2-methylpropanamide;
(164) N-[3-(4-Chlorophenyl)-1-methyl-2-(3-pyridyl-N-oxide)propyl]-2-(4-chlorophenyloxy)-2-methylpropanamide;
(165) N-[3-(4-Chlorophenyl)-1-methyl-2-(3-pyridyl-N-oxide)propyl]-2-(3,5-difluorophenyloxy)-2-methylpropanamide;
(166) N-[3-(4-Chlorophenyl)-1(S)-methyl-2(S)-phenylpropyl]-2-(4-chloro-3,5-difluorophenyloxy)-2-methylpropanamide;
(167) N-[3(R)-(4-Chlorophenyl)-1(S),3-dimethyl-2(S)-phenylbutyl]-2-(3,5-difluoro-4-methylphenyloxy)-2-methylpropanamide;
(168) N-[3(S)-(4-Chlorophenyl)-1(S),3-dimethyl-2(S)-phenylbutyl]-2-(3,5-difluoro-4-methylphenyloxy)-2-methylpropanamide;
(169) N-[2,3-Bis(4-Chlorophenyl)-1-methylpropyl]-2-(6-methyl-3-pyridyloxy)-2-methylpropanamide;
(170) N-[3-(4-Chlorophenyl)-2-phenyl-1-methylpropyl]-2-(6-methyl-3-pyridyloxy)-2-methylpropanamide;
(171) N-(1,4-dimethyl-2-phenylpentyl)-2-(4-chlorophenoxy)-2-methylpropanamide;
(172) N-(1-methyl-2-phenylpentyl)-2-(4-chlorophenoxy)-acetamide;

(173) N-(1-methyl-2,5-diphenylpentyl)-2-(4-chlorophenoxy)-acetamide;
(174) N-(1,3-dimethyl-2-phenylbutyl)-2-(4-chlorophenoxy)-propanamide;
(175) N-(2,3-Diphenyl-1-methylpropyl)-2-(4-chlorophenoxy)-2-methylpropanamide;
(176) N-(2,3-Diphenyl-1-ethylpropyl)-2-(4-chlorophenoxy)-2-methylpropanamide;
(177) N-(3-(4-chlorophenyl)-2-phenyl-1-methylpropyl)-2-(4-chlorophenoxy)-acetamide;
(178) N-(2,3-diphenyl-1-methylpropyl)-2-(4-chlorophenoxy)-acetamide;
(179) N-(3-(4-chlorophenyl)-2-phenyl-1-methylpropyl)-2-(4-chlorophenoxy)-propanamide;
(180) N-(2,3-diphenyl-1-methylpropyl)-2-(4-chlorophenoxy)-propanamide;
(181) N-(2,3-bis(4-chlorophenyl)-1-methylpropyl)-2-methyl-3-phenyl-propanamide;
(182) N-(2,3-bis(4-chlorophenyl)-1-methylpropyl)-2-methyl-3-(4-chlorophenyl)-propanamide;
(183) N-(3-(4-chlorophenyl)-2-phenyl-1-methylpropyl)-2-(4-chloro-anilino)-acetamide;
(184) N-(2,3-diphenyl-1-methylpropyl)-2-(4-chloro-anilino)-acetamide;
(185) N-(2,3-bis(4-chlorophenyl)-1-methylpropyl)-2,2-dimethyl-3-phenyl-propanamide;
(186) N-(3-(4-chlorophenyl)-2-phenyl-1-methylpropyl)-2-methyl-2-(4-chlorophenoxy)-propanamide;
(187) N-(3-(2-chlorophenyl)-2-phenyl-1-methylpropyl)-2-methyl-2-(4-chlorophenoxy)-propanamide;
(188) N-(3-(4-trifluoromethylphenyl)-2-phenyl-1-methylpropyl)-2-methyl-2-(4-chlorophenoxy)-propanamide;
(189) N-(3-(4-fluorophenyl)-2-phenyl-1-methylpropyl)-2-methyl-2-(4-chlorophenoxy)-propanamide;
(190) N-(3-(4-chlorophenyl)-2-phenyl-1-methylpropyl)-2-methyl-2-phenoxy-propanamide;
(191) N-(3-(4-chlorophenyl)-2-phenyl-1-methylpropyl)-2-methyl-2-(4-fluorophenoxy)-propanamide;
(192) N-(2,3-diphenyl-1-methylpropyl)-2-methyl-2-(4-fluorophenoxy)-propanamide;
(193) N-(3-phenyl-2-benzyl-1-methylpropyl)-2-methyl-2-(4-chlorophenoxy)-propanamide;
(194) N-[3-(4-Chlorophenyl)-2-(3,5-difluorophenyl)-1-methylpropyl]-2-(3,5-difluorophenyloxy)-2-methylpropanamide;
(195) N-[3-(4-Chlorophenyl)-2-(3,5-difluorophenyl)-1-methylpropyl]-2-methyl-2-(3,4,5-trifluorophenyloxy)propanamide;
(196) N-[3-(4-Chlorophenyl)-2-(3,5-difluorophenyl)-1-methylpropyl]-2-methyl-2-(2-pyridyloxy)propanamide;
(197) N-[3-(4-Chlorophenyl)-2-(3,5-difluorophenyl)-1-methylpropyl]-2-(4-chlorophenyloxy)-2-methylpropanamide;
(198) N-[3-(4-Chlorophenyl)-2-(3-pyridyl)-1-methylpropyl]-2-(3,5-dichlorophenyloxy)-2-methylpropanamide;
(199) N-[3-(4-Chlorophenyl)-2-(3-pyridyl)-1-methylpropyl]-2-(3-chlorophenyloxy)-2-methylpropanamide;
(200) N-[3-(4-Chlorophenyl)-2-(3-pyridyl)-1-methylpropyl]-2-(3-chloro-5-fluorophenyloxy)-2-methylpropanamide;
(201) N-[3-(4-Chlorophenyl)-2-(3-pyridyl)-1-methylpropyl]-2-methyl-2-(2-pyridyloxy)propanamide;
(202) N-[3-(4-Chlorophenyl)-2-(3-fluorophenyl)-1-methylpropyl]-2-(3-chloro-5-fluorophenyloxy)-2-methylpropanamide;
(203) N-[3-(4-Chlorophenyl)-2-(3-fluorophenyl)-1-methylpropyl]-2-(3-chlorophenyloxy)-2-methylpropanamide;
(204) N-[3-(4-Chlorophenyl)-2-(3-cyanophenyl)-1-methylpropyl]-2-(3-chlorophenyloxy)-2-methylpropanamide;
(205) N-[3-(4-Chlorophenyl)-2-(3-cyanophenyl)-1-methylpropyl]-2-methyl-2-(2-pyridyloxy)propanamide;
(206) N-[2-(3-Chlorophenyl)-3-(4-chlorophenyl)-1-methylpropyl]-2-methyl-2-(2-pyridyloxy)propanamide;
(207) N-[3-(4-Chlorophenyl)-2-(3,5-difluorophenyl)-1-methylpropyl]-2-(3,5-difluorophenyloxy)-2-methylpropanamide;
(208) N-[3-(4-Chlorophenyl)-2-(3,5-difluorophenyl)-1-methylpropyl]-2-methyl-2-(3,4,5-trifluorophenyloxy)propanamide;
(209) N-[3-(4-Chlorophenyl)-2-(3,5-difluorophenyl)-1-methylpropyl]-2-(4-chlorophenyloxy)-2-methylpropanamide;
(210) N-[3-(4-Chlorophenyl)-2-(3,5-difluorophenyl)-1-methylpropyl]-2-methyl-2-(2-pyridyloxy)propanamide;
(211) N-[3-(4-Chlorophenyl)-2-(3-pyridyl)-1-methylpropyl]-2-(3,5-dichlorophenyloxy)-2-methylpropanamide;
(212) N-[3-(4-Chlorophenyl)-2-(3-pyridyl)-1-methylpropyl]-2-(3-chlorophenyloxy)-2-methylpropanamide;
(213) N-[2-(3-Bromophenyl)-3-(4-chlorophenyl)-1-methylpropyl]-2-methyl-2-(2-pyridyloxy)propanamide;
(214) N-[3-(4-chlorophenyl)-2-(3-iodophenyl)-1-methylpropyl]-2-methyl-2-(2-pyridyloxy)propanamide;
(215) N-[2-(3-Bromophenyl)-3-(4-chlorophenyl)-1-methylpropyl]-2-methyl-2-(2-pyridyloxy)propanamide;
(216) N-[3-(4-chlorophenyl)-2-(3-iodophenyl)-1-methylpropyl]-2-methyl-2-(2-pyridyloxy)propanamide;
(217) N-[2-(3-Bromophenyl)-3-(4-chlorophenyl)-1-methylpropyl]-2-methyl-2-(2-phenyloxy)propanamide;
(218) N-[3-(4-Chlorophenyl)-2-(3-pyridyl)-1-methylpropyl]-2-methyl-2-(2-pyridyloxy)propanamide;
(219) N-[3-(4-Chlorophenyl)-2-(3-fluorophenyl)-1-methylpropyl]-2-(3-chloro-5-fluorophenyloxy)-2-methylpropanamide;
(220) N-[3-(4-Chlorophenyl)-2-(3-fluorophenyl)-1-methylpropyl]-2-(3-chlorophenyloxy)-2-methylpropanamide;
(221) N-[3-(4-Chlorophenyl)-2-(3-cyanophenyl)-1-methylpropyl]-2-(3-chlorophenyloxy)-2-methylpropanamide;
(222) N-[3-(4-Chlorophenyl)-2-(3-cyanophenyl)-1-methylpropyl]-2-methyl-2-(2-pyridyloxy)propanamide;
(223) N-[2-(3-Chlorophenyl)-3-(4-chlorophenyl)-1-methylpropyl]-2-methyl-2-(2-pyridyloxy)propanamide;
(224) N-[(2S,3S)-3-(4-Chlorophenyl)-1-methyl-2-phenylpropyl]-2-(5-chloropyridyloxy)-2-methylpropanamide;
(225) N-[(2S,3S)-3-(4-Chlorophenyl)-1-methyl-2-phenylpropyl]-2-(6-methylpyridyloxy)-2-methylpropanamide;
(226) N-[(2S,3S)-3-(4-Chlorophenyl)-1-methyl-2-phenylpropyl]-2-(3-chloro-5-fluorophenyloxy)-2-methylpropanamide;
(227) N-[(2S,3S)-3-(4-Chlorophenyl)-1-methyl-2-phenylpropyl]-2-(3-pyridazinyloxy)-2-methylpropanamide;
(228) N-[(2S,3S)-3-(4-Chlorophenyl)-1-methyl-2-phenylpropyl]-2-(4-trifluoromethylphenyloxy)-2-methylpropanamide;
(229) N-[(2S,3S)-3-(4-Chlorophenyl)-1-methyl-2-phenylpropyl]-2-(5-trifluoromethylpyridyloxy)-2-methylpropanamide;
(230) N-[(2S,3S)-3-(4-Chlorophenyl)-1-methyl-2-phenylpropyl]-2-(4,6-dimethylpyridyloxy)-2-methylpropanamide;
(231) N-(3-(4-chlorophenyl)-2-cyclopentyl-1-methyl)propyl-2-(3,5-dichlorophenoxy)-2-methylpropanamide;
(232) N-(3-(4-chlorophenyl)-2-cyclopentyl-1-methyl)propyl-2-(3,5-difluorophenoxy)-2-methylpropanamide;

(233) N-(3-(4-chlorophenyl)-2-ethoxy-1-methyl)propyl-2-(3,5-dichlorophenoxy)-2-methylpropanamide;
(234) N-(3-(4-chlorophenyl)-2-isopropyl-1-methyl)propyl-2-(3,5-dichlorophenoxy)-2-methylpropanamide;
(235) N-(3-(4-chlorophenyl)-1-methyl-2-propoxy)propyl-2-(3,5-dichlorophenoxy)-2-methylpropanamide;
(236) N-(3-(4-chlorophenyl)-1-methyl-2-pentoxy)propyl-2-(3,5-dichlorophenoxy)-2-methylpropanamide;
(237) N-(3-(4-chlorophenyl)-2-cyclopentylmethoxy-1-methyl)propyl-2-(3,5-dichlorophenoxy)-2-methylpropanamide;
(238) N-(3-(4-chlorophenyl)-2-cyclobutylmethoxy-1-methyl)propyl-2-(3,5-dichlorophenoxy)-2-methylpropanamide;
(239) N-(3-(4-chlorophenyl)-2-ethyl-1-methyl)propyl-2-(3,5-dichlorophenoxy)-2-methylpropanamide;
(240) N-(3-(4-chlorophenyl)-2-methoxy-1-methyl)propyl-2-(3,5-dichlorophenoxy)-2-methylpropanamide;
(241) N-(3-(4-chlorophenyl)-2-pyrrolidin-N-yl-1-methyl)propyl-2-(3,5-dichlorophenoxy)-2-methylpropanamide;
(242) N-(3-(4-chlorophenyl)-2-benzyloxycarbonyl-1-methyl)propyl-2-(3,5-dichlorophenoxy)-2-methylpropanamide;
(243) N-(2-(1-(1,2,3-triazolyl))-3-(4-chlorophenyl)-1-methylpropyl)-2-(4-chlorophenyloxy)-2-methylpropanamide;
(244) N-(2-(1-(1,2,4-triazolyl))-3-(4-chlorophenyl)-1-methylpropyl)-2-(2-pyridyloxy)-2-methylpropanamide;
(245) N-[3-(5-chloro-2-pyridyl)-2(S)-phenyl-1(S)-methylpropyl]-2-(5-chloro-2-pyridyloxy)-2-methylpropanamide;
(246) N-[3-(4-chlorophenyl)-2(S)-phenyl-1(S)-methylpropyl]-2-(3-trifluoromethylphenyloxy)-2-methylpropanamide;
(247) N-[3-(4-chlorophenyl)-2(S)-phenyl-1(S)-methylpropyl]-2-(6-chloro-2-pyridyloxy)-2-methylpropanamide;
(248) N-[3-(4-chlorophenyl)-2(S)-phenyl-1(S)-methylpropyl]-2-(4-cyanophenyloxy)-2-methylpropanamide;
(249) N-[3-(4-chlorophenyl)-2(S)-phenyl-1(S)-methylpropyl]-2-(3-cyanophenyloxy)-2-mrethylpropanamide;
(250) N-[3-(5-chloro-2-pyridyl)-2(S)-phenyl-1(S)-methylpropyl]-2-(5-trifluoromethyl-2-pyridyloxy)-2-methylpropanamide;
(251) N-[3-(4-chlorophenyl)-2(S)-phenyl-1(S)-methylpropyl]-2-(5-chloro-2-pyrimidyloxy)-2-methylpropanamide;
(252) N-[3-(4-chlorophenyl)-2(S)-phenyl-1(S)-methylpropyl]-2-(2-pyrimidyloxy)-2-methylpropanamide;
(253) N-[3-(4-chlorophenyl)-2(S)-phenyl-1(S)-methylpropyl]-2-(4-trifluoromethyl-2-pyridyloxy)-2-methylpropanamide;
(254) N-[3-(4-chlorophenyl)-2(S)-phenyl-1(S)-methylpropyl]-2-(4-trifluoromethyl-2-pyrimidyloxy)-2-methylpropanamide;
(255) N-[3-(4-chlorophenyl)-2(S)-phenyl-1(S)-methylpropyl]-2-(4-pyrimidyloxy)-2-methylpropanamide;
(256) N-[3-(4-chlorophenyl)-2(S)-phenyl-1(S)-methylpropyl]-2(R)-(4-trifluoromethyl-2-pyridyloxy)propanamide;
(257) N-[3-(4-chlorophenyl)-2(S)-phenyl-1(S)-methylpropyl]-2-(4-trifluoromethyl-4-pyrimidyloxy)-2-methylpropanamide;
(258) N-[3-(4-Chlorophenyl)-2-(3-fluorophenyl)-1-methylpropyl]-2-(5-chloro-2-pyridyloxy)-2-methylpropanamide;
(259) N-[3-(4-Chlorophenyl)-2-(3-fluorophenyl)-1-methylpropyl]-2-(5-trifluoromethyl-2-pyridyloxy)-2-methylpropanamide;
(260) N-[3-(4-Chlorophenyl)-2-(3-fluorophenyl)-1-methylpropyl]-2-(6-trifluoromethyl-4-pyrimidyloxy)-2-methylpropanamide;
(261) N-[3-(4-Chlorophenyl)-2-(3-fluorophenyl)-1-methylpropyl]-2-(4-trifluoromethyl-2-pyridyloxy)-2-methylpropanamide;
(262) N-[2-(3-Bromo-5-fluorophenyl)-3-(4-fluorophenyl)-1-methylpropyl]-2-(5-trifluoromethyl-2-pyridyloxy)-2-methylpropanamide;
(263) N-[2-(3-Bromo-5-fluorophenyl)-3-(4-fluorophenyl)-1-methylpropyl]-2-(6-trifluoromethyl-4-pyrimidyloxy)-2-methylpropanamide;
(264) N-[2-(3-Chlorophenyl)-3-(4-chlorophenyl)-1-methylpropyl]-2-(5-chloro-2-pyridyloxy)-2-methylpropanamide;
(265) N-[2-(3-Chlorophenyl)-3-(5-chloro-2-pyridyl)-1-methylpropyl]-2-(5-trifluoromethyl-2-pyridyloxy)-2-methylpropanamide;
(266) N-[2-(3-Chlorophenyl)-3-(4-chlorophenyl)-1-methylpropyl]-2-(5-trifluoromethyl-2-pyridyloxy)-2-methylpropanamide;
(267) N-[2-(3-Bromopheriyl)-3-(4-chlorophenyl)-1-methylpropyl]-2-(5-trifluoromethyl-2-pyridyloxy)-2-methylpropanamide;
(268) N-[2-(3-Bromophenyl)-3-(5-chloro-2-pyridyl)-1-methylpropyl]-2-(5-trifluoromethyl-2-pyridyloxy)-2-methylpropanamide;
(269) N-[3-(4-Chlorophenyl)-2-(3-trifluoromethylphenyl)-1-methylpropyl]-2-(5-trifluoromethyl-2-pyridyloxy)-2-methylpropanamide;
(270) N-[3-(4-Chlorophenyl)-2-(3-methylphenyl)-1-methylpropyl]-2-(5-trifluoromethyl-2-pyridyloxy)-2-methylpropanamide;
(271) N-[3-(4-Chlorophenyl)-2-(3-cyanophenyl)-1-methylpropyl]-2-(5-chloro-2-pyridyloxy)-2-methylpropanamide;
(272) N-[3-(4-Chlorophenyl)-2-(3-cyanophenyl)-1-methylpropyl]-2-(5-trifluoromethyl-2-pyridyloxy)-2-methylpropanamide;
(273) N-[3-(5-Chloro-2-pyridyl)-2-(3-cyanophenyl)-1-methylpropyl]-2-(5-trifluoromethyl-2-pyridyloxy)-2-methylpropanamide;
(274) N-[3-(4-Chlorophenyl)-2-(3-cyanophenyl)-1-methylpropyl]-2-(6-trifluoromethyl-4-pyrimidyloxy)-2-methylpropanamide;
(275) N-[3-(4-Chlorophenyl)-2-(2-pyridyl)-1-methylpropyl]-2-(5-trifluoromethyl-2-pyridyloxy)-2-methylpropanamide;
(276) N-[3-(4-Chlorophenyl)-2-(3-pyridyl)-1-methylpropyl]-2-(5-trifluoromethyl-2-pyridyloxy)-2-methylpropanamide;
(277) N-[3-(4-Chlorophenyl)-2-(5-fluoro-3-pyridyl)-1-methylpropyl]-2-(5-trifluoromethyl-2-pyridyloxy)-2-methylpropanamide;
(278) N-[3-(4-Chlorophenyl)-2-(5-fluoro-3-pyridyl)-1-methylpropyl]-2-(6-trifluoromethyl-4-pyrimidyloxy)-2-methylpropanamide;
(279) N-[3-(4-Chlorophenyl)-2-(5-chloro-3-pyridyl)-1-methylpropyl]-2-(5-trifluoromethyl-2-pyridyloxy)-2-methylpropanamide;
(280) N-[3-(4-Chlorophenyl)-2-(5-chloro-3-pyridyl)-1-methylpropyl]-2-(4-trifluoromethyl-2-pyrimidyloxy)-2-methylpropanamide;
(281) N-[3-(4-Chlorophenyl)-2-(5-chloro-3-pyridyl)-1-methylpropyl]-2-(6-trifluoromethyl-4-pyrimidyloxy)-2-methylpropanamide;

(282) N-[3-(4-Chlorophenyl)-2-(5-chloro-3-pyridyl)-1-methylpropyl]-2-(6-trifluoromethyl-4-pyridyloxy)-2-methylpropanamide;
(283) N-[2-(5-Chloro-3-pyridyl)-3-cyclobutyl-1-methylpropyl]-2-(6-trifluoromethyl-4-pyridyloxy)-2-methylpropanamide;
(284) N-[2-(5-Chloro-3-pyridyl)-3-cyclobutyl-5-methyl-2-hexyl]-2-(6-trifluoromethyl-4-pyridyloxy)-2-methylpropanamide;
(285) N-[3-(4-Chlorophenyl)-2-(5-cyano-3-pyridyl)-1-methylpropyl]-2-(5-trifluoromethyl-2-pyridyloxy)-2-methylpropanamide;
(286) N-[3-(4-Chlorophenyl)-2-(5-cyano-3-pyridyl)-1-methylpropyl]-2-(6-trifluoromethyl-4-pyrimidyloxy)-2-methylpropanamide;
(287) N-[3-(4-Chlorophenyl)-2-(5-cyano-3-pyridyl)-1-methylpropyl]-2-(4-trifluoromethyl-2-pyridyloxy)-2-methylpropanamide;
(288) N-[2-(5-Bromo-3-pyridyl)-3-(4-chlorophenyl)-1-methylpropyl]-2-(5-trifluoromethyl-2-pyridyloxy)-2-methylpropanamide;
(289) N-[2-(5-Bromo-3-pyridyl)-3-(4-fluorophenyl)-1-methylpropyl]-2-(4-trifluoromethyl-2-pyridyloxy)-2-methylpropanamide;
(290) N-[2-(5-Bromo-3-pyridyl)-3-(4-chlorophenyl)-1-methylpropyl]-2-(4-trifluoromethyl-2-pyridyloxy)-2-methylpropanamide;
(291) N-[2-(5-Bromo-3-pyridyl)-3-(4-fluorophenyl)-1-methylpropyl]-2-(6-trifluoromethyl-4-pyrimidyloxy)-2-methylpropanamide;
(292) N-[2-(5-Bromo-3-pyridyl)-3-(4-chlorophenyl)-1-methylpropyl]-2-(6-trifluoromethyl-4-pyrimidyloxy)-2-methylpropanamide;
(293) N-[3-(4-Chlorophenyl)-2-(5-methyl-3-pyridyl)-1-methylpropyl]-2-(5-trifluoromethyl-2-pyridyloxy)-2-methylpropanamide;
(294) N-[3-(4-Chlorophenyl)-2-(3-fluorophenyl)-1-methylpropyl]-2-(5-chloro-2-pyridyloxy)-2-methylpropanamide;
(295) N-[3-(4-Chlorophenyl)-2-(3-fluorophenyl)-1-methylpropyl]-2-(5-chloro-2-pyridyloxy)-2-methylpropanamide;
(296) N-[3-(4-Chlorophenyl)-2-(3-fluorophenyl)-1-methylpropyl]-2-(5-trifluoromethyl-2-pyridyloxy)-2-methylpropanamide;
(297) N-[3-(4-Chlorophenyl)-2-(3-fluorophenyl)-1-methylpropyl]-2-(6-trifluoromethyl-4-pyrimidyloxy)-2-methylpropanamide;
(298) N-[3-(4-Chlorophenyl)-2-(3-fluorophenyl)-1-methylpropyl]-2-(4-trifluoromethyl-2-pyridyloxy)-2-methylpropanamide;
(299) N-[2-(3-Chlorophenyl)-3-(4-chlorophenyl)-1-methylpropyl]-2-(5-chloro-2-pyridyloxy)-2-methylpropanamide;
(300) N-[2-(3-Chlorophenyl)-3-(5-chloro-2-pyridyl)-1-methylpropyl]-2-(5-trifluoromethyl-2-pyridyloxy)-2-methylpropanamide;
(301) N-[2-(3-Chlorophenyl)-3-(4-chlorophenyl)-1-methylpropyl]-2-(5-trifluoromethyl-2-pyridyloxy)-2-methylpropanamide;
(302) N-[2-(3-Bromophenyl)-3-(4-chlorophenyl)-1-methylpropyl]-2-(5-chloro-2-pyridyloxy)-2-methylpropanamide;
(303) N-[2-(3-Bromophenyl)-3-(5-chloro-2-pyridyl)-1-methylpropyl]-2-(5-trifluoromethyl-2-pyridyloxy)-2-methylpropanamide;
(304) N-[3-(4-chlorophenyl)-2-(3-trifluoromethylphenyl)-1-methylpropyl]-2-(5-trifluoromethyl-2-pyridyloxy)-2-methylpropanamide;
(305) N-[3-(4-chlorophenyl)-2-(3-methylphenyl)-1-methylpropyl]-2-(5-trifluoromethyl-2-pyridyloxy)-2-methylpropanamide;
(306) N-[3-(4-chlorophenyl)-2-(3-cyanophenyl)-1-methylpropyl]-2-(5-chloro-2-pyridyloxy)-2-methylpropanamide;
(307) N-[3-(4-chlorophenyl)-2-(3-cyanophenyl)-1-methylpropyl]-2-(5-trifluoromethyl-2-pyridyloxy)-2-methylpropanamide;
(308) N-[3-(4-Chlorophenyl)-2-(2-pyridyl)-1-methylpropyl]-2-(5-trifluoromethyl-2-pyridyloxy)-2-methylpropanamide;
(309) N-[3-(4-Chlorophenyl)-2-(5-fluoro-3-pyridyl)-1-methylpropyl]-2-(5-trifluoromethyl-2-pyridyloxy)-2-methylpropanamide;
(310) N-[3-(4-Chlorophenyl)-2-(5-fluoro-3-pyridyl)-1-methylpropyl]-2-(6-trifluoromethyl-4-pyrimidyloxy)-2-methylpropanamide;
(311) N-[3-(4-Chlorophenyl)-2-(5-chloro-3-pyridyl)-1-methylpropyl]-2-(5-trifluoromethyl-2-pyridyloxy)-2-methylpropanamide;
(312) N-[3-(4-Chlorophenyl)-2-(5-chloro-3-pyridyl)-1-methylpropyl]-2-(4-trifluoromethyl-2-pyridyloxy)-2-methylpropanamide;
(313) N-[3-(4-Chlorophenyl)-2-(5-chloro-3-pyridyl)-1-methylpropyl]-2-(4-trifluoromethyl-2-pyrimidyloxy)-2-methylpropanamide;
(314) N-[3-(4-Chlorophenyl)-2-(5-chloro-3-pyridyl)-1-methylpropyl]-2-(6-trifluoromethyl-4-pyrimidyloxy)-2-methylpropanamide;
(315) N-[2-(5-chloro-3-pyridyl)-3-(4-fluorophenyl)-1-methylpropyl]-2-(5-trifluoromethyl-4-pyridyloxy)-2-methylpropanamide;
(316) N-[2-(5-chloro-3-pyridyl)-3-cyclobutyl-1-methylpropyl]-2-(5-trifluoromethyl-4-pyridyloxy)-2-methylpropanamide;
(317) N-[2-(5-chloro-3-pyridyl)-3-cyclobutyl-1-methylpropyl]-2-(5-trifluoromethyl-4-pyridyloxy)-2-methylpropanamide;
(318) N-[2-(5-chloro-3-pyridyl)-1,4-dimethylpentyl]-2-(5-trifluoromethyl-4-pyridyloxy)-2-methylpropanamide;
(319) N-[2-(5-chloro-3-pyridyl)-1,4-dimethylpentyl]-2-(5-trifluoromethyl-4-pyridyloxy)-2-methylpropanamide;
(320) N-[3-(4-Chlorophenyl)-2-(5-cyano-3-pyridyl)-1-methylpropyl]-2-(5-trifluoromethyl-2-pyridyloxy)-2-methylpropanamide;
(321) N-[3-(4-Chlorophenyl)-2-(5-cyano-3-pyridyl)-1-methylpropyl]-2-(6-trifluoromethyl-4-pyrimidyloxy)-2-methylpropanamide;
(322) N-[2-(5-cyano-3-pyridyl)-3-(3,4-difluorophenyl)-1-methylpropyl]-2-(6-trifluoromethyl-4-pyrimidyloxy)-2-methylpropanamide;
(323) N-[3-(3-Chlorophenyl)-2-(5-cyano-3-pyridyl)-1-methylpropyl]-2-(5-trifluoromethyl-2-pyridyloxy)-2-methylpropanamide;
(324) N-[2-(5-cyano-3-pyridyl)-3-(4-fluorophenyl)-1-methylpropyl]-2-(5-trifluoromethyl-2-pyridyloxy)-2-methylpropanamide;
(325) N-[2-(5-Bromo-3-pyridyl)-3-(4-chlorophenyl)-1-methylpropyl]-2-(5-trifluoromethyl-2-pyridyloxy)-2-methylpropanamide;
(326) N-[2-(5-Bromo-3-pyridyl)-3-(4-fluorophenyl)-1-methylpropyl]-2-(5-trifluoromethyl-2-pyridyloxy)-2-methylpropanamide;

(327) N-[2-(5-Bromo-3-pyridyl)-3-(4-fluorophenyl)-1-methylpropyl]-2-(6-trifluoromethyl-4-pyrimidyloxy)-2-methylpropanamide;

(328) N-[2-(5-Bromo-3-pyridyl)-3-(4-chlorophenyl)-1-methylpropyl]-2-(6-trifluoromethyl-4-pyrimidyloxy)-2-methylpropanamide;

(329) N-[3-(4-Chlorophenyl)-2-(5-methyl-3-pyridyl)-1-methylpropyl]-2-(5-trifluoromethyl-2-pyridyloxy)-2-methylpropanamide;

(330) N-[2-(3-Bromophenyl)-3-(4-chlorophenyl)-1-methylpropyl]-2-(5-chloro-2-pyridyloxy)-2-methylpropanamide;

(331) N-[3-(4-Chlorophenyl)-2-(3-cyano-5-fluorophenyl)-1-methylpropyl]-2-(5-trifluoromethyl-2-pyridyloxy)-2-methylpropanamide;

(332) N-[2-(3-Cyano-5-fluorophenyl)-3-(4-fluorophenyl)-1-methylpropyl]-2-(5-trifluoromethyl-2-pyridyloxy)-2-methylpropanamide;

(333) N-[2-(3-Cyano-5-fluorophenyl)-3-(4-fluorophenyl)-1-methylpropyl]-2-(6-trifluoromethyl-4-pyrimidyloxy)-2-methylpropanamide;

(334) N-[3-(4-Chlorophenyl)-2-(3-cyano-5-fluorophenyl)-1-methylpropyl]-2-(6-trifluoromethyl-4-pyrimidyloxy)-2-methylpropanamide;

(335) N-[3-(5-Chloro-2-pyridyl)-2-(3-cyanophenyl)-1-methylpropyl]-2-(5-trifluoromethyl-2-pyridyloxy)-2-methylpropanamide;

(336) N-[2-(5-Chloro-3-pyridyl)-3-(4-chloro-3-iodophenyl)-1-methylpropyl]-2-(5-trifluoromethyl-2-pyridyloxy)-2-methylpropanamide;

(337) N-[3-(4-Chloro-3-iodophenyl)-2-(3-cyanophenyl)-1-methylpropyl]-2-(5-trifluoromethyl-2-pyridyloxy)-2-methylpropanamide;

(338) N-(3-(4-chlorophenyl)-2-benzisoxazol-3-yl)-1-methyl)propyl-2-(5-chloro-2-oxypyridine-2-yl)-2-methylpropanamide;

(339) N-(3-(4-chlorophenyl)-2-(benzisoxazol-3-yl)-1-methyl)propyl-2-(3,5-dichlorophenoxy)-2-methylpropanamide;

(340) N-(3-(4-chlorophenyl)-2-(benzisoxazol-3-yl)-1-methyl)propyl-2-(5-trifluoromethyl-2-oxypyridine-2-yl)-2-methylpropanamide;

(341) N-(3-(4-chlorophenyl)-2-(7-azaindol-N-yl)-1-methyl)propyl-2-(5-trifluoromethyl-2-oxypyridine-2-yl)-2-methylpropanamide;

(342) N-(3-(4-chlorophenyl)-2-(N-methyl-N-phenyl)amino-1-methyl)propyl-2-(5-trifluoromethyl-2-oxypyridine-2-yl)-2-methylpropanamide;

(343) N-(3-(4-chlorophenyl)-2-(indol-N-yl)-1-methyl)propyl-2-(5-trifluoromethyl-2-oxypyridine-2-yl)-2-methylpropanamide;

(344) N-(3-(4-chlorophenyl)-2-(indolin-N-yl)-1-methyl)propyl-2(4-trifluoromethyl-2-oxypyridine-2-yl)-2-methylpropanamide;

(345) N-(3-(4-chlorophenyl)-2-(indolin-N-yl)-1-methyl)propyl-2(5-trifluoromethyl-2-oxypyridine-2-yl)-2-methylpropanamide;

(346) 2-Methyl-N-[1-methyl-3-(4-methylphenyl)-2-phenylpropyl]-2-{[5-(trifluoromethyl)pyridin-2-yl]oxy}propanamide;

(347) N-[3-(4-Methoxyphenyl)-1-methyl-2-phenylpropyl]-2-methyl-2-{[5-(trifluoromethyl)pyridin-2-yl]oxy}propanamide;

(348) N-[3-(4-Fluorophenyl)-1-methyl-2-phenylpropyl]-2-methyl-2-{[5-(trifluoromethyl)pyridin-2-yl]oxy}propanamide;

(349) N-[3-(4-Cyanophenyl)-1-methyl-2-phenylpropyl]-2-methyl-2-{[5-(trifluoromethyl)pyridin-2-yl]oxy}propanamide;

(350) N-[2-(3-Cyanophenyl)-3-(4-fluorophenyl)-1-methylpropyl]-2-methyl-2-{[5-(trifluoromethyl)pyridin-2-yl]oxy}propanamide;

(351) N-(2-(1H-1,2,3-Benzotriazol-1-yl)-3-(4-chlorophenyl)-1-methylpropyl)-2-methyl-2-(5-chloropyridin-2-yl)oxy)-2-methylpropanamide;

(352) N-(2-(1H-1,2,3-Benzotriazol-1-yl)-3-(4-chlorophenyl)-1-methylpropyl)-2-methyl-2-(5-trifluoromethylpyridin-2-yl)oxy)-2-methylpropanamide;

(353) N-(2-(1H-1,2,3-Benzotriazol-1-yl)-3-(4-chlorophenyl)-1-methylpropyl)-2-methyl-2-(4-chlorophenoxy)-2-methylpropanamide;

(354) N-(3-(4-chlorophenyl)-1-methyl-2-(1H-indazol-1-yl)propyl)-2-methyl-2-(5-trifluoromethylpyridin-2-yl)oxy)-2-methylpropanamide;

(355) N-(3-(4-chlorophenyl)-1-methyl-2-(1-methyl-1H-indol-3-yl)propyl)-2-methyl-2-(5-chloropyridin-2-yl)oxy)-2-methylpropanamide;

(356) N-(3-(4-chlorophenyl)-1-methyl-2-(1-methyl-1H-indol-3-yl)propyl)-2-methyl-2-(5-trifluoromethylpyridin-2-yl)oxy)-2-methylpropanamide;

(357) N-(3-(4-chlorophenyl)-1-methyl-2-(1-methyl-1H-indol-3-yl)propyl)-2-methyl-2-(4-chlorophenoxy)-2-methylpropanamide;

(358) N-(3-(4-chlorophenyl)-1-methyl-2-(1-methyl-1H-indol-4-yl)propyl)-2-methyl-2-(5-trifluoromethylpyridin-2-yl)oxy)-2-methylpropanamide;

(359) N-(3-(4-chlorophenyl)-1-methyl-2-(thiophen-2-yl)propyl)-2-methyl-2-(5-chloropyridin-2-yl)oxy)-2-methylprpoanamide;

(360) N-(3-(4-chlorophenyl)-1-methyl-2-(thiophen-3-yl)propyl)-2-methyl-2-(5-chloropyridin-2-yl)oxy)-2-methylprpoanamide;

(361) N-(3-(4-chlorophenyl)-1-methyl-2-(pyrimidin-5-yl)propyl)-2-methyl-2-(5-chloropyridin-2-yl)oxy)-2-methylprpoanamide;

(362) N-(3-(4-chlorophenyl)-1-methyl-2-(pyradizin-3-yl)propyl)-2-methyl-2-(5-chloropyridin-2-yl)oxy)-2-methylprpoanamide;

(363) N-(2-(3-cyanophenyl)-3-cyclopropyl-1-methylpropyl)-2-methyl-2((5-(trifluoromethyl)pyridin-2-yl)oxy)-propanamide;

(364) N-(2-(3-cyanophenyl)-1,4-dimethylpentyl)-2-methyl-2((5-(trifluoromethyl)pyridin-2-yl)oxy)-propanamide;

(365) N-(2-(3-cyanophenyl)-3-cyclobutyl-1-methylpropyl)-2-methyl-2((5-(trifluoromethyl)pyridin-2-yl)oxy)-propanamide;

(366) N-(2-(3-cyanophenyl)-3-cyclohexyl-1-methylpropyl)-2-methyl-2((5-(trifluoromethyl)pyridin-2-yl)oxy)-propanamide;

(367) N-(2-(3-cyanophenyl)-3-cyclopentyl-1-methylpropyl)-2-methyl-2((5-(trifluoromethyl)pyridin-2-yl)oxy)-propanamide;

(368) N-(2-(3-cyanophenyl)-3-((1-tertbutyloxycarbonyl)piperidin-4-yl)-1-methylpropyl)-2-methyl-2((5-(trifluoromethyl)pyridin-2-yl)oxy)-propanamide;

(369) N-(2-(2,3-Dihydro-1H-indol-1-yl)-1,4-dimethylpentyl)-2-methyl-2((5-(trifluoromethyl)pyridin-2-yl)oxy)-propanamide;

(370) N-(3-Cyclobutyl-2-(3,4-dihydroquinolin-1(2H)-yl)-1-methylpropyl)-2-methyl-2((5-(trifluoromethyl)pyridin-2-yl)oxy)-propanamide;

(371) N-(2-(3,4-dihydroquinolin-1(2H)-yl)-1,4-dimethylpentyl)-2-methyl-2((5-(trifluoromethyl)pyridin-2-yl)oxy)-propanamide;
(372) N-(2-(3-cyanophenyl)-1,4-dimethylpentyl)-2-methyl-2((5-(trifluoromethyl)pyridin-2-yl)oxy)-propanamide;
(373) N-(2-(3-cyanophenyl)-3-cyclobutyl-1-methylpropyl)-2-methyl-2((5-(trifluoromethyl)pyridin-2-yl)oxy)-propanamide;
(374) N-(2-(3-cyanophenyl)-3-cyclopentyl-1-methylpropyl)-2-methyl-2((5-(trifluoromethyl)pyridin-2-yl)oxy)-propanamide;
(375) N-(2-(3-cyanophenyl)-3-cyclohexyl-1-methylpropyl)-2-methyl-2((5-(trifluoromethyl)pyridin-2-yl)oxy)-propanamide;
(376) N-[3-(4-chlorophenyl)-2-(3-methylthiophenyl)-1-methylpropyl]-2-methyl-2-(5-trifluoromethylpyridin-2-oxy)propanamide;
(377) N-[3-(4-chlorophenyl)-2-(3-methylsulfonylphenyl)-1-methylpropyl]-2-methyl-2-(5-trifluoromethylpyridin-2-oxy)propanamide;
(378) N-[3-(4-chlorophenyl)-2-(3-methylsulfonylphenyl)-1-methylpropyl]-2-methyl-2-(5-trifluoromethylpyridin-2-oxy)propanamide;
(379) N-[3-(4-chlorophenyl)-2-(3-methylsulfonylphenyl)-1-methylpropyl]-2-methyl-2-(5-trifluoromethylpyridin-2-oxy)propanamide;
(380) N-[3-(4-chlorophenyl)-2-(3-cyanophenyl)-1-methylpropyl]-2-methyl-2-(5-methyl sulfonylpyridin-2-oxy)propanamide;
(381) N-[3-(4-chlorophenyl)-2-(3-methylthiophenyl)-1-methylpropyl]-2-methyl-2-(5-trifluoromethylpyridin-2-oxy)propanamide;
(382) N-[3-(4-chlorophenyl)-2-(3-methylthiophenyl)-1-methylpropyl]-2-methyl-2-(5-trifluoromethylpyridin-2-oxy)propanamide;

and pharmaceutically acceptable salts thereof.

In one particular subclass of compounds of the present invention, $R^1$ is selected from:
(1) ethyl,
(2) isopropyl,
(3) isobutyl,
(4) n-propyl,
(5) n-pentyl,
(6) cyclopentyl,
(7) pyrrolidinyl,
(8) phenyl,
(9) phenyl-$C_{1-4}$alkyl,
(10) pyridyl,
(11) pyridyl-$C_{1-4}$alkyl,
(12) triazolyl,
(13) ethyloxy,
(14) propyloxy,
(15) butyloxy,
(16) n-pentyloxy,
(17) benzyloxylcarbonyl,
(18) cyclopentylmethyloxy,
(19) cyclobutylmethyloxy, wherein each phenyl is optionally substituted with one or two substituents selected from halogen, and methoxy, and each pyridyl is optionally present as the N-oxide;
$R^2$ is selected from:
(1) isopropyl,
(2) isobutyl,
(3) n-propyl,
(4) phenyl,
(5) benzyl,
(6) phenylethyl,
(7) 3-phenylpropyl,
(8) 2-phenylpropyl,
(9) phenoxy,
(10) phenylthio, wherein each aryl and heteroaryl is optionally substituted with one or two substituents selected from halogen, trifluoromethyl, cyano, methoxycarbonyl, and methoxy;
$R^3$ is selected from:
(1) hydrogen,
(2) methyl, and
(3) ethyl;
$R^4$ is hydrogen;
$R^5$ is $C_{1-18}$alkyl substituted with —$OR^d$;
$R^d$ is selected from:
(1) hydrogen,
(2) $C_{1-4}$alkyl,
(3) $C_{2-6}$ alkenyl,
(4) cycloalkyl,
(5) cycloalkyl-$C_{1-4}$-alkyl;
(6) cycloheteroalkyl,
(7) cycloheteroalkyl-$C_{1-4}$ alkyl;
(8) phenyl,
(9) heteroaryl,
(10) phenyl-$C_{1-4}$alkyl, and
(11) heteroaryl-$C_{1-4}$alkyl, wherein each $R^d$ may be unsubstituted or substituted with one to three substituents selected from $R^h$;
each $R^h$ is independently selected from:
(1) halogen,
(2) $C_{1-4}$alkyl,
(3) —O—$C_{1-4}$alkyl,
(4) —S—$C_{1-4}$alkyl,
(5) —CN,
(6) —$CF_3$, and
(7) —$OCF_3$;

and pharmaceutically acceptable salts thereof.

Particular compounds of this subclass include:
(1) N-[2,3-bis(4-chlorophenyl)-1-methylpropyl]-2-(4-chlorophenyloxy)-2-methylpropanamide;
(2) N-[2,3-bis(4-chlorophenyl)-1-methylpropyl]-2-(4-cyclohexyloxy)-2-methylpropanamide;
(3) N-[2,3-bis(4-chlorophenyl)-1-methylpropyl]-2-(4-cyclohexyloxy)-2-methylpropanamide;
(4) N-[2,3-bis(4-chlorophenyl)-1-methylpropyl]-2-(2-fluorophenyloxy)-2-methylpropanamide;
(5) N-[2,3-bis(4-chlorophenyl)-1-methylpropyl]-2-(3-fluorophenyloxy)-2-methylpropanamide;
(6) N-[2,3-bis(4-chlorophenyl)-1-methylpropyl]-2-(3,4-difluorophenyloxy)-2-methylpropanamide;
(7) N-[2,3-bis(4-chlorophenyl)-1-methylpropyl]-2-(3-chlorophenyloxy)-2-methylpropanamide;
(8) N-[2,3-bis(4-chlorophenyl)-1-methylpropyl]-2-(2-chlorophenyloxy)-2-methylpropanamide;
(9) N-[2,3-bis(4-chlorophenyl)-1-methylpropyl]-2-(3,5-difluorophenyloxy)-2-methylpropanamide;
(10) N-[2,3-bis(4-chlorophenyl)-1-methylpropyl]-2-(3-cyanophenyloxy)-2-methylpropanamide;
(11) N-[3-(4-chlorophenyl)-2-(2,4-dichlorophenyl)-1-methylpropyl]-2-(4-chlorophenyloxy)-2-methylpropanamide;
(12) N-[3-(4-chlorophenyl)-2-(2,4-dichlorophenyl)-1-methylpropyl]-2-(4-chlorophenyloxy)-2-methylpropanamide;
(13) N-[2,3-bis(4-chlorophenyl)-1-methylpropyl]-2-phenyloxy-2-methylpropanamide;

(14) N-[2,3-bis(4-chlorophenyl)-1-methylpropyl]-2-(4-fluorophenyloxy)-2-methylpropanamide;
(15) N-[2,3-bis(4-chlorophenyl)-1-methylpropyl]-2-(3-pyridyloxy)-2-methylpropanamide;
(16) N-[2,3-bis(4-chlorophenyl)-1-methylpropyl]-2-(2-pyridylox)-2-methylbutanamide;
(17) N-[2,3-bis(4-chlorophenyl)-1-methylpropyl]-2-(2-pyridyloxy)-2-methylpropanamide;
(18) N-[2,3-bis(4-chlorophenyl)-1-methylpropyl]-2-(4-pyridyloxy)-2-methylpropanamide;
(19) N-[3-(4-chlorophenyl)-1-methyl-2-phenylpropyl]-2-(2-fluorophenyloxy)-2-methylpropanamide;
(20) N-[3-(4-chlorophenyl)-1-methyl-2-phenylpropyl]-2-(3-fluorophenyloxy)-2-methylpropanamide;
(21) N-[3-(4-chlorophenyl)-1-methyl-2-phenylpropyl]-2-(3,4-difluorophenyloxy)-2-methylpropanamide;
(22) N-[3-(4-chlorophenyl)-1-methyl-2-phenylpropyl]-2-(3-chlorophenyloxy)-2-methylpropanamide;
(23) N-[3-(4-chlorophenyl)-1-methyl-2-phenylpropyl]-2-(2-chlorophenyloxy)-2-methylpropanamide;
(24) N-[3-(4-chlorophenyl)-1-methyl-2-phenylpropyl]-2-(3,5-difluorophenyloxy)-2-methylpropanamide;
(25) N-[3-(4-chlorophenyl)-1-methyl-2-phenylpropyl]-2-cyclohexyloxy-2-methylpropanamide;
(26) N-[3-(4-chlorophenyl)-1-methyl-2-phenylpropyl]-2-(4-fluorophenyloxy)-2-methylpropanamide;
(27) N-[3-(4-chlorophenyl)-2-(2-fluorophenyl)-1-methylpropyl]-2-(4-chlorophenyloxy)-2-methylpropanamide;
(28) N-[3-(4-chlorophenyl)-2-(3-fluorophenyl)-1-methylpropyl]-2-(4-chlorophenyloxy)-2-methylpropanamide;
(29) N-[3-(4-chlorophenyl)-2-(3-fluorophenyl)-1-methylpropyl]-2-(4-chlorophenyloxy)-2-methylpropanamide;
(30) N-[3-(4-chlorophenyl)-2-(2-fluorophenyl)-1-methylpropyl]-2-(4-chlorophenyloxy)-2-methylpropanamide;
(31) N-[3-(4-chlorophenyl)-1-methyl-2-phenylpropyl)]-2-methyl-2-phenylpropanamide;
(32) N-[3-(4-chlorophenyl)-2-(3-fluorophenyl)-1-methylpropyl]-2-(2-pyridyloxy)-2-methylpropanamide;
(33) N-[3-(4-chlorophenyl)-2-(3-fluorophenyl)-1-methylpropyl]-2-(3,5-difluorophenyloxy)-2-methylpropanamide;
(34) N-[3-(4-chlorophenyl)-2-(3-fluorophenyl)-1-methylpropyl]-2-(3,5-difluorophenyloxy)-2-methylpropanamide;
(35) N-[3-(4-chlorophenyl)-1-methyl-2-phenylpropyl]-2-(3-pyridyloxy)-2-methylpropanamide;
(36) N-[3-(4-chlorophenyl)-1-methyl-2-phenylpropyl]-2-(2-pyridyloxy)-2-methylbutanamide;
(37) N-[3-(4-chlorophenyl)-1-methyl-2-phenylpropyl]-2-(2-pyridyloxy)-2-methylpropanamide;
(38) N-[3-(4-chlorophenyl)-1-methyl-2-phenylpropyl]-2-(4-pyridyloxy)-2-methylpropanamide;
(39) N-[2-(4-chlorophenyl)-1-methyl-3-phenylpropyl]-2-(4-chlorophenyloxy)-2-methylpropanamide;
(40) N-[2-(4-chlorophenyl)-1-methyl-3-phenylpropyl]-2-(4-chlorophenyloxy)-2-methylpropanamide;
(41) N-[2-(4-chlorophenyl)-1-methyl-3-phenylpropyl]-2-(4-fluorophenyloxy)-2-methylpropanamide;
(42) N-[2-(4-chlorophenyl)-1-methyl-3-phenylpropyl]-2-(4-chlorophenyloxy)-2-methylpropanamide;
(43) N-[3-(4-methoxycarbonylphenyl)-1-methyl-2-phenylpropyl]-2-(4-fluorophenyloxy)-2-methylpropanamide;
(44) N-[3-(4-methoxycarbonylphenyl)-1-methyl-2-phenylpropyl]-2-(4-fluorophenyloxy)-2-methylpropanamide;
(45) N-[3-(4-methoxycarbonylphenyl)-1-methyl-2-phenylpropyl]-2-(4-fluorophenyloxy)-2-methylpropanamide;
(46) N-[3-(4-methoxycarbonylphenyl)-1-methyl-2-phenylpropyl]-2-(4-Chlorophenyloxy)-2-methylpropanamide;
(47) N-[2-(2-chlorophenyl)-1-methyl-3-phenylpropyl]-2-(4-fluorophenyloxy)-2-methylpropanamide;
(48) N-[2-(2-chlorophenyl)-1-methyl-3-phenylpropyl]-2-(4-fluorophenyloxy)-2-methylpropanamide;
(49) N-[2-(2-chlorophenyl)-1-methyl-3-phenylpropyl]-2-(4-chlorophenyloxy)-2-methylpropanamide;
(50) N-[2-(2-chlorophenyl)-1-methyl-3-phenylpropyl]-2-(4-chlorophenyloxy)-2-methylpropanamide;
(51) N-[2-(4-methoxyphenyl)-1-methyl-3-phenylpropyl]-2-(4-fluorophenyloxy)-2-methylpropanamide;
(52) N-[2-(4-methoxyphenyl)-1-methyl-3-phenylpropyl]-2-(4-chlorophenyloxy)-2-methylpropanamide;
(53) N-[2-(4-chlorophenyl)-3-(2,4-dichlorophenyl)-1-methyl-propyl]-2-(4-chlorophenyloxy)-2-methylpropanamide;
(54) N-[2-(4-chlorophenyl)-3-(2,4-dichlorophenyl)-1-methyl-propyl]-2-(4-chlorophenyloxy)-2-methylpropanamide;
(55) N-[2-(4-chlorophenyl)-2-(4-chloro-2-fluorophenyl)-1-methyl-propyl]-2-(4-chlorophenyloxy)-2-methylpropanamide;
(56) N-[2-(4-chlorophenyl)-2-(4-chloro-2-fluorophenyl)-1-methyl-propyl]-2-(4-chlorophenyloxy)-2-methylpropanamide;
(57) N-[2-(4-chlorophenyl)-2-(4-chloro-2-fluorophenyl)-1-methyl-propyl]-2-(4-chlorophenyloxy)-2-methylpropanamide;
(58) N-[2-(4-chlorophenyl)-2-(4-chloro-2-fluorophenyl)-1-methyl-propyl]-2-(4-fluorophenyloxy)-2-methylpropanamide;
(59) N-[2-(4-chlorophenyl)-2-(4-chloro-2-fluorophenyl)-1-methyl-propyl]-2-(4-fluorophenyloxy)-2-methylpropanamide;
(60) N-[3-(4-chlorophenyl)-2-(4-fluorophenyl)-1-methylpropyl]-2-(4-chlorophenyloxy)-2-methylpropanamide;
(61) N-[3-(4-chlorophenyl)-2-(4-fluorophenyl)-1-methylpropyl]-2-(4-chlorophenyloxy)-2-methylpropanamide;
(62) N-[3-(4-chlorophenyl)-1-methyl-2-(2-pyridyl)propyl]-tert-butylcarbamate;
(63) N-[3-(4-chlorophenyl)-1-methyl-2-(2-pyridyl)propyl]-2-(4-chlorophenyloxy)-2-methylpropanamide;
(64) N-[3-(4-chlorophenyl)-1-methyl-2-(2-pyridyl)propyl]-2-(4-fluorophenyloxy)-2-methylpropanamide;
(65) N-[3-(4-chlorophenyl)-1-methyl-2-(4-pyridyl)propyl]-2-(4-chlorophenyloxy)-2-methylpropanamide;
(66) N-[3-(4-cyanophenyl)-1-methyl-2-phenylpropyl]-2-(3-chlorophenyloxy)-2-methylpropanamide;
(67) N-[3-(5-chloro-2-pyridyl)-1-methyl-2-phenylpropyl]-2-(3,5-difluorophenyloxy)-2-methylpropanamide;
(68) N-[3-(4-chlorophenyl)-1-methyl-2-(3-pyridyl)propyl]-tert-butylcarbamate;
(69) N-[3-(4-chlorophenyl)-1-methyl-2-(3-pyridyl)propyl]-2-(4-chlorophenyloxy)-2-methylpropanamide;
(70) N-[3-(4-chlorophenyl)-1-methyl-2-(3-pyridyl)propyl]-2-(3,5-difluorophenyloxy)-2-methylpropanamide;
(71) N-[3-(4-chlorophenyl)-1-methyl-2-(3-pyridyl)propyl]-2-(3-fluorophenyloxy)-2-methylpropanamide;
(72) N-[2-(4-chlorophenoxy)-2-(4-chlorophenyl)ethyl]-2-(4-chlorophenyloxy)-2-methylpropanamide;
(73) N-[2,2-bis(4-chlorophenyl)ethyl]-2-(4-chlorophenyloxy)-2-methylpropanamide;
(74) N-[2-(4-chlorophenylthio)-2-(4-chlorophenyl)-1-methylpropyl]-2-(4-chlorophenyloxy)-2-methylpropanamide;
(75) N-[2-(4-chlorophenylthio)-2-(4-chlorophenyl)-1-methylpropyl]-2-(4-chlorophenyloxy)-2-methylpropanamide;

(76) N-[2,3-bis(4-chlorophenyl)-1-methylpropyl]-2-(4-chlorophenyloxy)-2-methylpropanamide;
(77) N-[2,3-bis(4-chlorophenyl)-1-methylpropyl]-2-phenyloxy)-2-methylpropanamide;
(78) N-[2,3-bis(4-chlorophenyl)-1-methylpropyl]-2-phenyloxy-2-methylpropanamide;
(79) N-[2,3-bis(4-chlorophenyl)-1-methylpropyl]-2-(4-fluorophenyloxy)-2-methylpropanamide;
(80) N-[2,3-bis(4-chlorophenyl)-1-methylpropyl]-2-(4-fluorophenyloxy)-2-methylpropanamide;
(81) N-[2,3-bis(4-chlorophenyl)-1-methylpropyl]-2-(6-methyl-3-pyridyloxy)-2-methylpropanamide;
(82) N-[2,3-bis(4-chlorophenyl)-1-methylpropyl]-2-(6-methyl-3-pyridyloxy)-2-methylpropariamide;
(83) N-[3-(4-chlorophenyl)-1-methyl-2-phenylpropyl]-2-(3-fluorophenyloxy)-2-methylpropanamide;
(84) N-[3-(4-chlorophenyl)-1-methyl-2-phenylpropyl]-2-(3-fluorophenyloxy)-2-methylpropanamide;
(85) N-[3-(4-chlorophenyl)-1-methyl-2-phenylpropyl]-2-(3,4-difluorophenyloxy)-2-methylpropanamide;
(86) N-[3-(4-chlorophenyl)-1-methyl-2-phenylpropyl]-2-(3,4-difluorophenyloxy)-2-methylpropanamide;
(87) N-[3-(4-chlorophenyl)-1-methyl-2-phenylpropyl]-2-(3-chlorophenyloxy)-2-methylpropanamide;
(88) N-[3-(4-chlorophenyl)-1-methyl-2-phenylpropyl]-2-(3-chlorophenyloxy)-2-methylpropanamide;
(89) N-[3-(4-chlorophenyl)-1-methyl-2-phenylpropyl]-2-(3,5-difluorophenyloxy)-2-methylpropanamide;
(90) N-[3-(4-chlorophenyl)-1-methyl-2-phenylpropyl]-2-(3,5-difluorophenyloxy)-2-methylpropanamide;
(91) N-[3-(4-chlorophenyl)-1-methyl-2-phenylpropyl]-2-(4-fluorophenyloxy)-2-methylpropanamide;
(92) N-[3-(4-chlorophenyl)-1-methyl-2-phenylpropyl]-2-(4-fluorophenyloxy)-2-methylpropanamide;
(93) N-[3-(4-chlorophenyl)-2-(3-fluorophenyl)-1-methylpropyl]-2-(4-fluorophenyloxy)-2-methylpropanamide;
(94) N-[3-(4-chlorophenyl)-2-(3-fluorophenyl)-1-methylpropyl]-2-(4-fluorophenyloxy)-2-methylpropanamide;
(95) N-[3-(4-chlorophenyl)-2-(3-fluorophenyl)-1-methylpropyl]-2-(3,5-difluorophenyl oxy)-2-methylpropanamide;
(96) N-[3-(4-chlorophenyl)-2-(3-fluorophenyl)-1-methylpropyl]-2-(3,5-difluorophenyloxy)-2-methylpropanamide;
(97) N-[3-(4-chlorophenyl)-2-(3-fluorophenyl)-1-methylpropyl]-2-(2-pyridyloxy)-2-methylpropanamide;
(98) N-[3-(4-chlorophenyl)-2-(3-fluorophenyl)-1-methylpropyl]-2-(2-pyridyloxy)-2-methylpropanamide;
(99) N-[3-(4-chlorophenyl)-1-methyl-2-phenylpropyl]-2-(2-pyridyloxy)-2-methylpropanamide;
(100) N-[3-(4-chlorophenyl)-1-methyl-2-phenylpropyl]-2-(2-pyridyloxy)-2-methylpropanamide;
(101) N-[3-(4-chlorophenyl)-1-methyl-2-(2-pyridyl)propyl]-2-(4-chlorophenyloxy)-2-methylpropanamide;
(102) N-[3-(4-chlorophenyl)-1-methyl-2-(2-pyridyl)propyl]-2-(4-chlorophenyloxy)-2-methylpropanamide;
(103) N-[3-(4-cyanophenyl)-1-methyl-2-phenylpropyl]-2-(3-chlorophenyloxy)-2-methylpropanamide;
(104) N-[3-(4-cyanophenyl)-1-methyl-2-phenylpropyl]-2-(3-chlorophenyloxy)-2-methylpropanamide;
(105) N-[3-(4-chlorophenyl)-1-methyl-2-(3-pyridyl)propyl]-2-(4-chlorophenyloxy)-2-methylpropanamide;
(106) N-[3-(4-chlorophenyl)-1-methyl-2-(3-pyridyl)propyl]-2-(4-chlorophenyloxy)-2-methylpropanamide;
(107) N-[3-(4-chlorophenyl)-1-methyl-2-(3-pyridyl)propyl]-2-(3,5-difluorophenyloxy)-2-methylpropanamide;
(108) N-[3-(4-chlorophenyl)-1-methyl-2-(3-pyridyl)propyl]-2-(3,5-difluorophenyloxy)-2-methylpropanamide;
(109) N-[3-(4-chlorophenyl)-1-methyl-2-(3-pyridyl)propyl]-2-(3-fluorophenyloxy)-2-methylpropanamide;
(110) N-[3-(4-chlorophenyl)-1-methyl-2-(3-pyridyl)propyl]-2-(3-fluorophenyloxy)-2-methylpropanamide;
(111) N-[2-(4-chlorophenoxy)-2-(4-chlorophenyl)ethyl]-2-(4-chlorophenyloxy)-2-methylpropanamide;
(112) N-[2-(4-chlorophenoxy)-2-(4-chlorophenyl)ethyl]-2-(4-chlorophenyloxy)-2-methylpropanamide;
(113) N-[3-(4-chlorophenyl)-2(S)-phenyl-1(S)-methylpropyl]-2-(3,5-difluorophenyloxy)-2-methylpropanamide;
(114) N-[3-(4-chlorophenyl)-2(S)-phenyl-1(S)-methylpropyl]-2-(3,4,5-trifluorophenyloxy)-2-methylpropanamide;
(115) N-[3-(4-chlorophenyl)-2(S)-phenyl-1(S)-methylpropyl]-2-(3-chloro-4-fluorophenyloxy)-2-methylpropanamide;
(116) N-[3-(4-chlorophenyl)-2(S)-phenyl-1(S)-methylpropyl]-2-(4-chloro-3-fluorophenyloxy)-2-methylpropanamide;
(117) N-[3-(4-chlorophenyl)-2(S)-phenyl-1(S)-methylpropyl]-2-(3,4-dichlorophenyloxy)-2-methylpropanamide;
(118) N-[3-(4-chlorophenyl)-2(S)-phenyl-1(S)-methylpropyl]-2-(3,5-dichlorophenyloxy)-2-methylpropanamide;
(119) N-[3-(4-chlorophenyl)-1-methyl-2-phenylpropyl]-2-(3-pyridyloxy-N-oxide)-2-methylpropanamide;
(120) N-[3-(4-chlorophenyl)-1-methyl-2-(3-pyridyl-N-oxide)propyl]-2-(4-chlorophenyloxy)-2-methylpropanamide;
(121) N-[3-(4-chlorophenyl)-1-methyl-2-(3-pyridyl-N-oxide)propyl]-2-(3,5-difluorophenyloxy)-2-methylpropanamide;
(122) N-[3-(4-chlorophenyl)-1(S)-methyl-2(S)-phenylpropyl]-2-(4-chloro-3,5-difluorophenyloxy)-2-methylpropanamide;
(123) N-[3(R,S)-(4-chlorophenyl)-1(S),3-dimethyl-2(S)-phenylbutyl]-2-(3,5-difluoro-4-methylphenyloxy)-2-methylpropanamide;
(124) N-[2,3-bis(4-chlorophenyl)-1-methylpropyl]-2-(6-methyl-3-pyridyloxy)-2-methylpropanamide;
(125) N-[3-(4-chlorophenyl)-2-phenyl-1-methylpropyl]-2-(6-methyl-3-pyridyloxy)-2-methylpropanamide;
(126) N-(1,4-dimethyl-2-phenylpentyl)-2-(4-chlorophenoxy)-2-methylpropanamide;
(127) N-(2,3-diphenyl-1-methylpropyl)-2-(4-chlorophenoxy)-2-methylpropanamide;
(128) N-(2,3-diphenyl-1-ethylpropyl)-2-(4-chlorophenoxy)-2-methylpropanamide;
(129) N-(3-(4-chlorophenyl)-2-phenyl-1-methylpropyl)-2-methyl-2-(4-chlorophenoxy)-propanamide;
(130) N-(3-(2-chlorophenyl)-2-phenyl-1-methylpropyl)-2-methyl-2-(4-chlorophenoxy)-propanamide;
(131) N-(3-(4-trifluoromethylphenyl)-2-phenyl-1-methylpropyl)-2-methyl-2-(4-chlorophenoxy)-propanamide;
(132) N-(3-(4-fluorophenyl)-2-phenyl-1-methylpropyl)-2-methyl-2-(4-chlorophenoxy)-propanamide;
(133) N-(3-(4-chlorophenyl)-2-phenyl-1-methylpropyl)-2-methyl-2-phenoxy-propanamide;
(134) N-(3-(4-chlorophenyl)-2-phenyl-1-methylpropyl)-2-methyl-2-(4-fluorophenoxy)-propanamide;
(135) N-(2,3-diphenyl-1-methylpropyl)-2-methyl-2-(4-fluorophenoxy)-propanamide; and
(136) N-(3-phenyl-2-benzyl-1-methylpropyl)-2-methyl-2-(4-chlorophenoxy)-propanamide;

and pharmaceutically acceptable salts thereof.

In another embodiment of the present invention,
$R^1$ is selected from:
(1) cycloheteroalkyl,
(2) aryl,
(3) heteroaryl, and
(4) —$NR^cR^d$;

wherein aryl and heteroaryl are optionally substituted with one to three substituents independently selected from $R^b$;

$R^2$ is selected from:
(1) $C_{1-10}$alkyl,
(2) $C_{3-10}$cycloalkyl-$C_{1-4}$alkyl,
(3) aryl-$C_{1-4}$alkyl,
(4) heteroaryl-$C_{1-4}$alkyl,
wherein each cycloalkyl, aryl and heteroaryl is optionally substituted with one to three substituents independently selected from $R^b$;

$R^3$ is methyl;
$R^4$ is hydrogen;
$R^5$ is

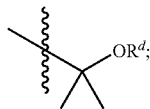

each $R^b$ is independently selected from:
(1) halogen,
(2) cyano,
(3) trifluoromethyl,
(4) trifluoromethoxy,
(5) $C_{1-3}$alkyloxy, and
(6) $C_{1-3}$alkyl;
each $R^c$ is independently selected from:
(1) hydrogen,
(2) methyl, and
(3) trifluoromethyl;
$R^d$ is independently selected from:
(1) hydrogen,
(2) $C_{1-6}$alkyl,
(3) cycloalkyl,
(4) aryl,
(5) heteroaryl,
(6) arylmethyl, and
(7) heteroarylmethyl,
each $R^d$ may be unsubstituted or substituted with one to three substituents selected from $R^h$;
each $R^h$ is independently selected from:
(1) halogen,
(2) $C_{1-3}$alkyl,
(3) —CN, and
(4) —$CF_3$;
wherein when pyridyl groups are present in the molecule unsubstituted on the nitrogen, they are may optionally be present as the N-oxide;

and pharmaceutically acceptable salts thereof.

In one class of this embodiment, $R^1$ is selected from:
(1) phenyl,
(2) pyridyl,
(3) indolyl,
(4) 7-aza-indolyl,
(5) thiophenyl, and
(6)

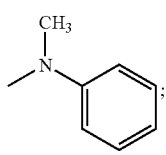

wherein each aryl and heteroaryl is optionally substituted with one or two substitutents independently selected from $R^b$, and each pyridyl is optionally present as the N-oxide.

In one subclass of this class of the present invention, $R^1$ is selected from:
(1) phenyl,
(2) 3-cyanophenyl,
(3) 3-methylphenyl,
(4) 3,5-difluorophenyl,
(5) 3-pyridyl,
(6) 5-chloro-3-pyridyl,
(7) 5-methyl-3-pyridyl,
(8) 5-cyano-3-pyridyl,
(9) 1-oxido-5-cyano-3-pyridyl,
(10) 1-indolyl,
(11) 7-aza-indol-N-yl,
(12) 2-thiophenyl, and
(13)

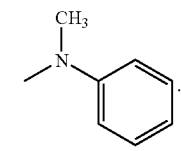

In another subclass of this class of the present invention, $R^1$ is 5-cyano-3-pyridyl.

In another class of this embodiment, $R^2$ is selected from:
(1) $C_{1-6}$alkyl,
(2) $C_{3-6}$cycloalkylmethyl,
(3) phenylmethyl,
(4) heteroarylmethyl, wherein each cycloalkyl, aryl and heteroaryl is optionally substituted with one to three substituents independently selected from $R^b$.

In one subclass of this class of the present invention, $R^2$ is selected from:
(1) $C_{1-6}$alkyl,
(2) $C_{4-6}$cycloalkylmethyl,
(3) phenylmethyl,
(4) pyridyl,
wherein each cycloalkyl, aryl and heteroaryl is optionally substituted with one or two substituents independently selected from $R^b$.

In another subclass of this class of the present invention, $R^2$ is selected from:
(1) 2-methylpropyl,
(2) n-pentyl,
(3) cyclobutylmethyl,
(4) cyclopentylmethyl,
(5) cyclohexylmethyl,
(6) benzyl,
(7) 4-chlorobenzyl,
(8) 4-methylbenzyl,
(9) 4-fluorobenzyl,
(10) 4-methoxybenzyl, and
(11) (5-chloro-2-pyridyl)methyl.

In one class of this embodiment, each $R^b$ is independently selected from:
(1) halogen,
(2) cyano,
(3) $C_{1-3}$alkyloxy and
(4) $C_{1-3}$alkyl.

In one subclass of this class, each $R^b$ is independently selected from:
(1) fluoro,
(2) chloro,
(3) bromo, (4) iodo,
(5) cyano,
(6) methoxy, and
(7) methyl.

In another subclass of this class, each $R^b$ is independently selected from:
(1) fluoro,
(2) chloro,
(3) cyano,
(4) methoxy, and
(5) methyl.

In one class of this embodiment, each $R^c$ is independently selected from:
(1) hydrogen,
(2) methyl, and
(3) trifluoromethyl.

In one subclass, $R^c$ is methyl.

In one class of this embodiment, $R^d$ is selected from:
(1) $C_{4-6}$cycloalkyl,
(2) aryl, and
(3) heteroaryl, wherein $R^d$ may be unsubstituted or substituted with one or two substituents selected from $R^h$.

In one subclass of the present invention, $R^d$ is selected from:
(1) phenyl,
(2) pyridyl, and
(3) pyrimidinyl, wherein $R^d$ may be unsubstituted or substituted with one or two substituents selected from $R^h$.

In another subclass of the present invention, $R^d$ is selected from:
(1) phenyl,
(2) 4-chlorophenyl,
(3) 3-chlorophenyl,
(4) 3,5-difluorophenyl,
(5) 3,5-dichlorophenyl,
(6) 2-pyridyl,
(7) 5-chloro-2-pyridyl,
(8) 6-methyl-2-pyridyl,
(9) 5-trifluoromethyl-2-pyridyl,
(10) 4-trifluoromethyl-2-pyridyl,
(11) 4-trifluoromethyl-2-pyrimidyl, and
(12) 6-trifluoromethyl-4-pyrimidyl.

In yet another subclass of the present invention, $R^d$ is 5-trifluoromethyl-2-pyridyl.

In one class of this embodiment, each $R^h$ is independently selected from:
(1) halogen,
(2) $C_{1-3}$alkyl,
(3) —CN, and
(4) —CF$_3$.

In one subclass of this class, each $R^h$ is independently selected from:
(1) fluoro,
(2) chloro,
(3) methyl,
(4) —CN, and
(5) —CF$_3$.

Particular novel compounds of this embodiment which may be employed in the methods, uses and compositions of the present invention, include:
(1) N-[3-(4-chlorophenyl)-1-methyl-2-phenylpropyl]-2-(4-chlorophenyloxy)-2-methylpropanamide;
(2) N-[3-(4-chlorophenyl)-1-methyl-2-phenylpropyl]-2-(2-pyridyloxy)-2-methylpropanamide;
(3) N-[3-(4-chlorophenyl)-1-methyl-2-(3-pyridyl)propyl]-2-(4-chlorophenyloxy)-2-methylpropanamide;
(4) N-[3-(4-chlorophenyl)-1-methyl-2-phenylpropyl]-2-(3,5-difluorophenyloxy)-2-methylpropanamide;
(5) N-[3-(4-chlorophenyl)-2-phenyl-1-methylpropyl]-2-(3,5-dichlorophenyloxy)-2-methylpropanamide;
(6) N-[3-(4-chlorophenyl)-1-methyl-2-phenylpropyl]-2-(3-chlorophenyloxy)-2-methylpropanamide;
(7) N-[3-(4-chlorophenyl)-2-(3,5-difluorophenyl)-1-methylpropyl]-2-(2-pyridyloxy)-2-methylpropanamide;
(8) N-[3-(4-chlorophenyl)-1-methyl-2-phenyl-propyl]-2-(5-chloro-2-pyridyloxy)-2-methylpropanamide;
(9) N-[3-(4-chlorophenyl)-1-methyl-2-phenylpropyl]-2-(6-methyl-pyridyloxy)-2-methylpropanamide;
(10) N-[3-(4-chlorophenyl)-1-methyl-2-phenylpropyl]-2-(phenyloxy)-2-methylpropanamide;
(11) N-[(3-(4-chlorophenyl)-1-methyl-2-phenylpropyl]-2-(5-trifluoromethylpyridyloxy)-2-methylpropanamide;
(12) N-[3-(4-chlorophenyl)-2-(3-pyridyl)-1-methylpropyl]-2-(5-trifluoromethyl-2-pyridyloxy)-2-methylpropanamide;
(13) N-[3-(4-chlorophenyl)-2-(3-cyanophenyl)-1-methylpropyl]-2-(5-trifluoromethyl-2-pyridyloxy)-2-methylpropanamide;
(14) N-[3-(4-chlorophenyl)-2-(5-chloro-3-pyridyl)-1-methylpropyl]-2-(5-trifluoromethyl-2-pyridyloxy)-2-methylpropanamide;
(15) N-[3-(4-chlorophenyl)-2-(5-methyl-3-pyridyl)-1-methylpropyl]-2-(5-trifluoromethyl-2-pyridyloxy)-2-methylpropanamide;
(16) N-[3-(4-chlorophenyl)-2-(5-cyano-3-pyridyl)-1-methylpropyl]-2-(5-trifluoromethyl-2-pyridyloxy)-2-methylpropanamide;
(17) N-[3-(4-chlorophenyl)-2-(3-methylphenyl)-1-methylpropyl]-2-(5-trifluoromethyl-2-pyridyloxy)-2-methylpropanamide;
(18) N-[3-(4-chlorophenyl)-2-phenyl-1-methylpropyl]-2-(4-trifluoromethyl-2-pyridyloxy)-2-methylpropanamide;
(19) N-[3-(4-chlorophenyl)-2-phenyl-1-methylpropyl]-2-(4-trifluoromethyl-2-pyrimidyloxy)-2-methylpropanamide;
(20) N-[3-(4-chlorophenyl)-1-methyl-2-(thiophen-3-yl)propyl]-2-(5-chloro-2-pyridyloxy)-2-methylpropanamide;
(21) N-[3-(5-chloro-2-pyridyl)-2-phenyl-1-methylpropyl]-2-(5-trifluoromethyl-2-pyridyloxy)-2-methylpropanamide;
(22) N-[3-(4-methyl-phenyl)-1-methyl-2-phenylpropyl]-2-(4-trifluoromethyl-phenyloxy)-2-methylpropanamide;
(23) N-[3-(4-fluoro-phenyl)-2-(3-cyano-phenyl)-1-methylpropyl]-2-(5-trifluoromethyl-2-pyridyloxy)-2-methylpropanamide;
(24) N-[3-(4-chlorophenyl)-2-(1-indolyl)-1-methyl)propyl]-2-(5-trifluoromethyl-2-oxypyridine-2-yl)-2-methylpropanamide;
(25) N-[3-(4-chlorophenyl)-2-(7-azaindol-N-yl)-1-methyl)propyl]-2-(5-trifluoromethyl-2-pyridyloxy)-2-methylpropanamide;
(26) N-[3-(4-chloro-phenyl)-2-(1-indolinyl)-1-methylpropyl]-2-(5-trifluoromethyl-2-pyridyloxy)-2-methylpropanamide;
(27) N-[3-(4-chloro-phenyl)-2-(N-methyl-anilino)-1-methylpropyl]-2-(5-trifluoromethyl-2-pyridyloxy)-2-methylpropanamide;
(28) N-[3-(4-methoxy-phenyl)-2-(3-cyano-phenyl)-1-methylpropyl]-2-(5-trifluoromethyl-2-pyridyloxy)-2-methylpropanamide;

(29) N-[3-(4-chlorophenyl)-2-(3-cyanophenyl)-1-methyl-propyl]-2-(6-trifluoromethyl-4-pyrimidyloxy)-2-methyl-propanamide;

(30) N-[2-(3-cyanophenyl)-1,4-dimethylpentyl]-2-(5-trifluoromethyl-2-pyridyloxy)-2-methylpropanamide;

(31) N-[3-(4-chlorophenyl)-2-(1-oxido-5-cyano-3-pyridyl)-1-methylpropyl]-2-(5-trifluoromethyl-2-pyridyloxy)-2-methylpropanamide;

(32) N-[2-(3-cyanophenyl)-3-cyclobutyl-1-methylpropyl]-2-(5-trifluoromethyl-2-pyridyloxy)-2-methylpropanamide;

(33) N-[2-(3-cyanophenyl)-1-methyl-heptyl]-2-(5-trifluoromethyl-2-pyridyloxy)-2-methylpropanamide;

(34) N-[2-(3-cyanophenyl)-3-cyclopentyl-1-methylpropyl]-2-(5-trifluoromethyl-2-pyridyloxy)-2-methylpropanamide;

(35) N-[2-(3-cyanophenyl)-3-cyclohexyl-1-methylpropyl]-2-(5-trifluoromethyl-2-pyridyloxy)-2-methylpropanamide;

and pharmaceutically acceptable salts thereof.

The present invention is also directed to a compound of strucutral formula I, wherein:
$R^1$ is selected from:
(1) phenyl,
(2) pyridyl,
(3) indolyl,
(4) 7-aza-indolyl,
(5) thiophenyl, and
(6)

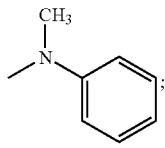

wherein each aryl and heteroaryl is optionally substituted with one or two substitutents independently selected from $R^b$, and each pyridyl may be optionally present as the N-oxide;
$R^2$ is selected from:
(1) $C_{1-6}$alkyl,
(2) $C_{3-6}$cycloalkylmethyl,
(3) phenylmethyl,
(4) heteroarylmethyl, wherein each cycloalkyl, aryl and heteroaryl is optionally substituted with one to three substituents independently selected from $R^b$;
each $R^b$ is independently selected from:
(1) halogen,
(2) cyano,
(3) $C_{1-3}$alkyloxy and
(4) $C_{1-3}$alkyl;
$R^d$ is selected from:
(1) phenyl,
(2) pyridyl, and
(3) pyrimidinyl, wherein $R^d$ may be unsubstituted or substituted with one or two substituents selected from $R^h$;
each $R^h$ is independently selected from:
(1) fluoro,
(2) chloro,
(3) methyl,
(4) —CN, and
(5) —CF$_3$;

and pharmaceutically acceptable salts thereof.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, imidazothiazolyl, and the like. The heteroaryl ring may be substituted on one or more carbon or nitrogen atoms "Cycloheteroalkyl" means mono- or bicyclic or bridged saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "cycloheteroalkyl" include pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl,5,6-dihydroimidazo[2,1-b]thiazolyl, tetrahydrohydroquinolinyl, morpholinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl.

The cycloheteroalkyl ring may be substituted on the ring carbons and/or the ring nitrogens.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

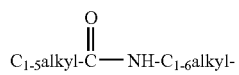

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric

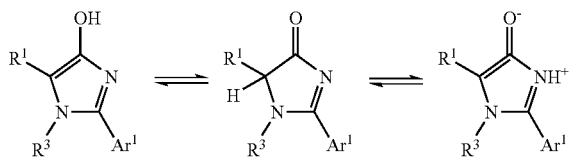

pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxillary followed by separation by chromatography or crystallization, and fractional crystallization of diastereomeric salts.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor, inducing a conformational change in the receptor which, in turn, produces a response such as contraction, relaxation, secretion, change in enzyme activity, etc. similar to that elicited by the physiologically relevant agonist ligand(s) for that receptor. An "antagonist" is a compound which attenuates the effect of an agonist. An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of obesity or eating disorders associated with excessive food intake and complications associated therewith. The compounds are also useful for the treatment of constipation and chronic intestinal pseudo-obstruction.

The compounds are also useful for the treatment of cirrhosis of the liver. The compounds are also useful for the treatment of asthma.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The utilities of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f) reduction in opiate self-administration in mice (Sci. 1999, 283, 401-404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the gunea-pig." Eur. J. Pharmacol., 282, 243 (1995)); h) mediation of the vasodilated state in advanced liver cirrhosis induced by carbon tetrachloride (Nature Medicine, 2001, 7 (7), 827-832); i) amitriptyline-induced constipation in cynomolgus monkeys is beneficial for the evaluation of laxatives (Biol. Pharm. Bulletin (Japan), 2000, 23(5), 657-9); j) neuropathology of paediatric chronic intestinal pseudo-obstruction and animal models related to the neuropathology of paediatric chronic intestinal pseudo-obstruction (Journal of Pathology (England), 2001, 194 (3), 277-88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for preventive use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 1000 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750 or 1000 milligrams of the active ingredient for the symptomatic adjustment of the dosage to the patient to be treated.

For the treatment of diseases of the eye, ophthalmic preparations for ocular administration comprising 0.001-1% by weight solutions or suspensions of the compounds of Formula I in an acceptable ophthalmic formulation may be used.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. In particular, the term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present inveniton include those well known to those of ordinary skill in that art. To be administered in the form of a transdermal delivery system, the dosage administration will, of course, be continuous rather than intermittent throughout the dosage regimen.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, inculidng elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from 0.01 to 1,000 mg, particularly 0.01, 0.05, 0.1, 0.5, 1, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated, and each cachet or capsule contains from about 0.01 to 1,000 mg, particularly 0.01, 0.05, 0.1, 0.5, 1.0, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, axiolytics, anti-Parkinson's agents, anti-epileptics, anorectic agents, and serotonin reuptake inhibitors, and other anti-obesity agents which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention also provides a method for the treatment or prevention of obesity, which method comprises administration to a patient in need of such treatment an amount of a compound of the present invention and an amount of an SSRI, such that together they give effective relief.

Suitable selective serotonin reuptake inhibitors of use in combination with a compound of the present invention include: fluoxetine, fluvoxamine, paroxetine, sertraline, and imipramine, and pharmaceutically acceptable salts thereof.

It will be appreciated that for the treatment or prevention of obesity, the compounds of the present invention may also be used in combination with an opioid antagonist.

The present invention also provides a method for the treatment or prevention of obesity, which method comprises administration to a patient in need of such treatment an amount of a compound of the present invention and an amount of an opioid antagonist, such that together they give effective relief.

Suitable opioid antagonists of use in combination with a compound of the present invention include: naltrexone, 3-methoxynaltrexone, naloxone and nalmefene, and pharmaceutically acceptable salts thereof.

It will be appreciated that for the treatment or prevention of obesity, the compounds of the present invention may also be used in combination with inhibitors of the enzyme 11β-HSD1. Generally, glucocorticoid concentrations are modulated by tissue-specific 11β-hydroxysteroid dehydrogenase enzymes. The 11β-hydroxysteroid dehydrogenase type 1 enzyme (11β-HSD1) is a low affinity enzyme that generally uses NADP+ as a cofactor rather than NAD+ (Agarwal et al., 1989). In vitro studies have shown that 11β-HSD1 is capable of acting as both a reductase and a dehydrogenase. However, 11β-HSD1 in vivo generally acts as a reductase, converting 11-ketoglucocorticoids, such as cortisone, to 11β-hydroxyglucocorticoids such as cortisol.

Excessive levels of cortisol have been associated with obesity, perhaps due to increased hepatic gluconeogenesis. Thus, the administration of an effective amount of an 11β-HSD1 inhibitor in combination with a CB1 antagonist of the present invention may be useful in the treatment or control of obesity. Particular inhibitors of 11β-HSD1 useful in combination with the compounds of the present invention include: 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, and 3-adamantanyl-4,5,6,7,8,9,10,11,12,3a-decahydro-1,2,4-triazolo[4,3-a][11]annulene.

It will be appreciated that for the treatment or prevention of obesity, the compounds of the present invention may also be used in combination with another anti-obesity agent.

The present invention also provides a method for the treatment or prevention of obesity, which method comprises administration to a patient in need of such treatment an amount of a compound of the present invention and an amount of another anti-obesity agent, such that together they give effective relief.

Suitable anti-obesity agents of use in combination with a compound of the present invention, include, but are not limited to: 1) growth hormone secretagogues, such as those disclosed and specifically described in U.S. Pat. No. 5,536,716; 2) growth hormone secretagogue receptor agonists/antagonists, such as NN703, hexarelin, MK-0677, SM-130686, CP-424,391, L-692,429 and L-163,255, and such as those disclosed in U.S. Pat. No. 6,358,951, U.S. Patent Application Nos. 2002/049196 and 2002/022637, and PCT Application Nos. WO 01/56592 and WO 02/32888; 3) melanocortin agonists, such as Melanotan II or those described in WO 99/64002 and WO 00/74679; 4) Mc4r (melanocortin 4 receptor) agonists, such as CHIR86036 (Chiron), ME-10142, and ME-10145 (Melacure), and those disclosed in PCT Application Nos. WO 01/991752, WO 01/74844, WO 02/12166, WO 02/11715, and WO 02/12178; 5) β-3 agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. patent application Nos. 5,705,515, and U.S. Pat. No. 5,451,677 and PCT Patent Publications WO94/18161, WO95/29159, WO97/46556, WO98/04526 and WO98/32753, WO 01/74782, and WO 02/32897; 6) 5HT-2 agonists; 7) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; 8) orexin antagonists, such as SB-334867-A, and those disclosed in PCT Patent Application Nos. WO 01/96302, WO 01/68609, WO 02/51232, and WO 02/51838; 9) melanin concentrating hormone antagonists; 10) melanin-concentrating hormone 1 receptor (MCH1R) antagonists, such as T-226296 (Takeda), and those disclosed in PCT Patent Application Nos. WO 01/82925, WO 01/87834, WO 02/06245, WO 02/04433, and WO 02/51809, and Japanese Patent Application No. JP 13226269; 11) melanin-concentrating hormone 2 receptor (MCH2R) agonist/antagonists; 12) galanin antagonists; 13) CCK agonists; 14) CCK-A (cholecystokinin-A) agonists, such as AR-R 15849, GI 181771, JMV-180, A-71378, A-71623 and SR146131, and those described in U.S. Pat. No. 5,739,106; 15) GLP-1 agonists; 16) corticotropin-releasing hormone agonists; 17) NPY 5 antagonists, such as GW-569180A, GW-594884A, GW-587081x, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,140,354, 6,191,160, 6,313,298, 6,337,332, 6,329,395, 6,326,375, 6,335,345, and 6,340,683, European Patent Nos. EP-01010691, and EP-01044970, and PCT Patent Publication Nos. WO 97/19682, WO 97/20820, WO 97/20821, WO 97/20822, WO 97/20823, WO 98/27063, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; 18) NPY 1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; 19) histamine receptor-3 (H3) modulators; 20) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm.(Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); 21) β-hydroxy steroid dehydrogenase-1 inhibitors (β-HSD-1); 22) PDE (phosphodiesterase) inhibitors, such as theophylline, pentoxifylline, zaprinast, sildenafil, aminone, milrinone, cilostamide, rolipram, and cilomilast; 23) phosphodiesterase-3B (PDE3B) inhibitors; 24) NE (norepinephrine) transport inhibitors, such as GW 320659, despiramine, talsupram, and nomifensine; 25) non-selective serotonin/norepinephrine transport inhibitors, such as sibutramine or fenfluramine; 26) ghrelin antagonists, such as those disclosed in PCT Application Nos. WO 01/87335, and WO 02/08250; 27) leptin, including recombinant human leptin (PEG-OB, Hoffman La Roche) and recombinant methionyl human leptin (Amgen); 28) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; 29) BRS3 (bombesin receptor subtype 3) agonists; 30) CNTF (Ciliary neurotrophic factors), such as GI-181771 (Glaxo-SmithKline), SR146131 (Sanofi Synthelabo), butabindide, PD170,292, and PD 149164 (Pfizer); 31) CNTF derivatives, such as axokine (Regeneron), and those disclosed in PCT Application Nos. WO 94/09134, WO 98/22128, and WO 99/43813; 32) monoamine reuptake inhibitors, such as those disclosed in PCT Application Nos. WO 01/27068, and WO 01/62341; 33) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; 34) thyroid hormone β agonists, such as KB-2611 (KaroBioBMS), and those disclosed in PCT Application No. WO 02/15845, and Japanese Patent Application No. JP 2000256190; 35) FAS (fatty acid synthase) inhibitors, such as Cerulenin and C75; 36) DGAT1 (diacylglycerol acyltransferase 1) inhibitors; 37) DGAT2 (diacylglycerol acyltransferase 2) inhibitors; 38) ACC2 (acetyl-CoA carboxylase-2) inhibitors; 39) glucocorticoid antagonists; 40) acyl-estrogens, such as oleoyl-estrone, disclosed in del Mar-Grasa, M. et al., Obesity Research, 9:202-9 (2001); 41) lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; 42) fatty acid transporter inhibitors; 43) dicarboxylate transporter inhibitors; 44) glucose transporter inhibitors; 45) phosphate transporter inhibitors; 46) serotonin reuptake inhibitors, such as those disclosed in U.S. patent application No. 6,365,633, and PCT Patent Application Nos. WO 01/27060, and WO 01/162341; 47) Metformin (Glucophages); and/or 48) Topiramate (Topimax®).

Specific NPY5 antagonists of use in combination with a compound of the present invention are selected from the group consisting of:
(1) 3-oxo-N-(5-phenyl-2-pyrazinyl)-spiro[isobenzofuran-1 (3H), 4'-piperidine]-1'-carboxamide,
(2) 3-oxo-N-(7-trifluoromethylpyrido[3,2-b]pyridin-2-yl) spiro-[isobenzofuran-1(3H), 4'-piperidine]-1'-carboxamide,
(3) N-[5-(3-fluorophenyl)-2-pyrimidinyl]-3-oxospiro-[isobenzofuran-1(3H), 4'-piperidine]-1'-carboxamide,
(4) trans-3'-oxo-N-(5-phenyl-2-pyrimidinyl)spiro[cyclohexane-1,1' (3' H)-isobenzofuran]-4-carboxamide,
(5) trans-3'-oxo-N-[1-(3-quinolyl)-4-imidazolyl]spiro[cyclohexane-1,1'(3'H)-isobenzofuran]-4-carboxamide,
(6) trans-3-oxo-N-(5-phenyl-2-pyrazinyl)spiro[4-azaisobenzofuran-1(3H), 1'-cyclohexane]-4'-carboxamide,
(7) trans-N-[5-(3-fluorophenyl)-2-pyrimidinyl]-3-oxospiro [5-azaisobenzofuran-1(3H), 1'-cyclohexane]-4'-carboxamide,
(8) trans-N-[5-(2-fluorophenyl)-2-pyrimidinyl]-3-oxospiro [5-azaisobenzofuran-1(3H), 1'-cyclohexane]-4'-carboxamide,
(9) trans-N-[1-(3,5-difluorophenyl)-4-imidazolyl]-3-oxospiro[7-azaisobenzofuran-1(3H), 1'-cyclohexane]-4'-carboxamide,
(10) trans-3-oxo-N-(1-phenyl-4-pyrazolyl)spiro[4-azaisobenzofuran-1(3H), 1'-cyclohexane]-4'-carboxamide,
(11) trans-N-[1-(2-fluorophenyl)-3-pyrazolyl]-3-oxospiro [6-azaisobenzofuran-1(3H), 1'-cyclohexane]-4'-carboxamide,
(12) trans-3-oxo-N-(1-phenyl-3-pyrazolyl)spiro[6-azaisobenzofuran-1(3H), 1'-cyclohexane]-4'-carboxamide,
(13) trans-3-oxo-N-(2-phenyl-1,2,3-triazol-4-yl)spiro[6-azaisobenzofuran-1(3H), 1'-cyclohexane]-4'-carboxamide, and pharmaceutically acceptable salts and esters thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk for obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asian countries, a "subject at risk for obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds or compositions of the present invention to reduce or maintain the body weight of an obese subject. One outcome of treatment may be reducing the body weight of an obese subject relative to that subject's body weight immediately before the administration of the compounds or compositions of the present invention. Another outcome of treatment may be preventing regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds or compositions of the present invention to reduce or maintain the body weight of a subject at risk for obesity. One outcome of prevention may be reducing the body weight of a subject at risk for obesity relative to that subject's body weight immediately before the administration of the compounds or compositions of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk for obesity. Another outcome of prevention may be decreasing the occurrence and/or severity of obesity-related disorders if the treatment is administered prior to the onset of obesity in a subject at risk for obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

Obesity-related disorders are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compositions of the present invention are also useful for reducing the risk of secondary outcomes of obesity, such as reducing the risk of left ventricular hypertrophy.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes. Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds and compositions of the present invention are useful for treating both Type I and Type II diabetes. The compounds and compositions are especially effective for treating Type II diabetes. The compounds and compositions of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable neurokinin-1 receptor antagonists may be peptidal or non-peptidal in nature, however, the use of a non-peptidal neurokinin-1 receptor antagonist is preferred. In a preferred embodiment, the neurokinin-1 receptor antagonist is a CNS-penetrant neurokinin-1 receptor antagonist. In addition, for convenience the use of an orally active neurokinin-1 receptor antagonist is preferred. To facilitate dosing, it is also preferred that the neurokinin-1 receptor antagonist is a long acting neurokinin-1 receptor antagonist. An especially preferred class of neurokinin-1 receptor antagonists of use in the present invention are those compounds which are orally active and long acting.

Neurokinin-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, 97/49710, 98/24438-98/24441, 98/24442-98/24445, 02/16343, and 02/16344; and in British Patent Publication Nos. 2 266 529, 2 268 931, 2 269 170, 2 269 590, 2 271 774, 2 292 144, 2 293 168, 2 293 169, and 2 302 689.

Specific neurokinin-1 receptor antagonists of use in the present invention include:
(±)-(2R3R,2S3S)—N-{[2-cyclopropoxy-5-(trifluoromethoxy)-phenyl]methyl}-2-phenylpiperidin-3-amine;
2-(S)-(3,5-bis(trifluoromethyl)benzyloxy)-3(S)-(4-fluorophenyl)-4-(3-(5-oxo-1H,4H-1,2,4-triazolo)methyl)morpholine;
2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine;
2-(S)-(3,5-bis(trifluoromethyl)benzyloxy)-4-(3-(5-oxo-1H,4H-1,2,4-triazolo)methyl)-3-(S)-phenyl-morpholine;
2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine;
2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine;
2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;
(3S,5R,6S)-3-[2-cyclopropoxy-5-(trifluoromethoxy)phenyl]-6-phenyl-1-oxa-7-aza-spiro[4.5]decane;
(3R,5R,6S)-3-[2-cyclopropoxy-5-(trifluoromethoxy)phenyl]-6-phenyl-1-oxa-7-aza-spiro[4.5]decane;
2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine;
2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;
2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;
2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;
2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;
2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;
2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;

or a pharmaceutically acceptable salt thereof.

Suitable atypical anti-depressants include: bupropion, lithium, nefazodone, trazodone and viloxazine, and pharmaceutically acceptable salts thereof.

Suitable classes of anti-anxiety agents include benzodiazepines and 5-$HT_{1A}$ agonists or antagonists, especially 5-$HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-$HT_{1A}$ receptor agonists or antagonists include, in particular, the 5-$HT_{1A}$ receptor partial agonists buspirone, flesinoxan, gepirone and ipsapirone, and pharmaceutically acceptable salts thereof.

Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient.

It will be appreciated that the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the 5-HT2A receptor antagonists, examples of which include MDL100907 and fananserin. Also of use in combination with a CB1 receptor modulator are the serotonin dopamine antagonists (SDAs) which are believed to combine 5-$HT_{2A}$ and dopamine receptor antagonist activity, examples of which include olanzapine and ziperasidone.

Still further, NK-1 receptor antagonists may be favorably employed with the CB1 receptor modulators of the present invention. Preferred NK-1 receptor antagonists for use in the present invention are selected from the classes of compounds described in European Patent Specification No. 0 577 394, and International Patent Specification Nos. 95/08549, 95/18124, 95/23798, 96/05181, and 98/49710 (Application No. PCT/GB97/01630). The preparation of such compounds is fully described in the aforementioned publications.

Particularly preferred NK-1 receptor antagonists of use in the present invention include: (3S,5R,6S)-3-[2-cyclopropoxy-5-(trifluoromethoxy)phenyl]-6-phenyl-1-oxa-7-aza-spiro[4.5]decane; (3R,5R,6S)-3-[2-cyclopropoxy-5-(trifluoromethoxy)phenyl]-6-phenyl-1-oxa-7-aza-spiro[4.5]decane; (±)-(2R3R,2S3S)—N-{[2-cyclopropoxy-5-(trifluoromethoxy)phenyl]methyl}-2-phenylpiperidin-3-amine; 2-(S)-(3,5-bis(trifluoromethyl)benzyloxy)-3(S)-(4-fluorophenyl)-4-(3-(5-oxo-1H,4H-1,2,4-triazolo)methyl)morpholine; 2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine; 2-(S)-(3,5-bis(trifluoromethyl)benzyloxy)-4-(3-(5-oxo-1H,4H-1,2,4-triazolo)methyl)-3-(S)-phenyl-morpholine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; 2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine; 2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine; 2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine; 2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine; 2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine; 2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine; 2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine; 2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine; 2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine or a pharmaceutically acceptable salt thereof.

It will be appreciated that a combination of a conventional anti-asthmatic drug with a CB1 receptor modulator may provide an enhanced effect in the treatment of asthma.

Thus, according to a further aspect of the present invention there is provided the use of a CB1 receptor modulator and an anti-asthmatic agent for the manufacture of a medicament for the treatment or prevention of asthma.

The present invention also provides a method for the treatment or prevention of asthma, which method comprises administration to a patient in need of such treatment an amount of a compound of the present invention and an amount of an anti-asthmatic agent, such that together they give effective relief.

Suitable anti-asthmatic agents of use in combination with a compound of the present invention include, but are not limited to: (a) VLA-4 antagonists such as natalizumab and the compounds described in U.S. Pat. No. 5,510,332, WO97/03094, WO97/02289, WO96/40781, WO96/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); (f) antagonists of the chemokine receptors, especially CCR-1, CCR-2, and CCk-3; (g) immunosuppressants such as cyclosporin, tacrolimus, rapamycin and other FK-506 type immunosuppressants; (h) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (i) cyclooxygenase-2 (COX-2) inhibitors such as celecoxib; (j) anti-diabetic agents such as insulin, sulfonylureas, biguanides (metformin), a-glucosidase inhibitors (acarbose) and glitazones (troglitazone, pioglitazone, englitazone, MCC-555, BRL49653 and the like); (k) preparations of interferon beta (interferon beta-1a, interferon beta-1b); (l) other compounds such as 5-aminosalicylic acid and prodrugs thereof, and pharmaceutically acceptable salts thereof.

It will be appreciated that a combination of a conventional anti-constipation drug with a CB1 receptor modulator may provide an enhanced effect in the treatment of constipation.

Thus, according to a further aspect of the present invention there is provided the use of a CB1 receptor modulator and an anti-constipation agent for the manufacture of a medicament for the treatment or prevention of constipation.

The present invention also provides a method for the treatment or prevention of constipation, which method comprises administration to a patient in need of such treatment an amount of a compound of the present invention and an amount of an anti-constipation agent, such that together they give effective relief.

It will be appreciated that a combination of a conventional anti-constipation drug with a CB1 receptor modulator may provide an enhanced effect in the treatment of chronic intestinal pseudo-obstruction.

Thus, according to a further aspect of the present invention there is provided the use of a CB1 receptor modulator and an anti-constipation agent for the manufacture of a medicament for the treatment or prevention of chronic intestinal pseudo-obstruction.

The present invention also provides a method for the treatment or prevention of chronic intestinal pseudo-obstruction, which method comprises administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof.

A particularly suitable class of osmotic agents include, but are not limited to sorbitol, lactulose, polyethylene glycol, magnesium, phosphate, and sulfate; and pharmaceutically acceptable salts thereof.

A particularly suitable class of laxatives and detergent laxatives, include, but are not limited to, magnesium, and docusate sodium; and pharmaceutically acceptable salts thereof.

A particularly suitable class of bulking agents include, but are not limited to, psyllium, methylcellulose, and calcium polycarbophil; and pharmaceutically acceptable salts thereof.

A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment of cirrhosis of the liver.

Thus, according to a further aspect of the present invention there is provided the use of a CB1 receptor modulator and an anti-cirrhosis agent for the manufacture of a medicament for the treatment or prevention of cirrhosis of the liver.

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples:
aq.: aqueous
API-ES: atmospheric pressure ionization-electrospray (mass spectrum term)
DEAD: diethyl azodicarboxylate
DMAP: 4-dimethylaminopyridine
DMF: dimethylformamide
DMSO: dimethylsulfoxide
EDC: 1-ethyl-3-(3-dimethylaminopropyl)-carbodiimide hydrochloride
EPA: ethylene polyacrylamide (a plastic)
EtOAc: ethyl acetate
g: gram
h: hours
Hex: hexane
HOBt: 1-hydroxybenzotriazole
HPLC: high pressure liquid chromatography
HPLC/MS: high pressure liquid chromatography/mass spectrum
in vacuo: rotoevaporation
IPAC or IPAc: isopropyl acetate
KHMDS: potassium hexamethyldisilazide
LC: Liquid chromatography
LC/MS, LC-MS: liquid chromatography-mass spectrum
LDA: lithium diisopropyl amide
M: molar
Me: methyl
MeOH: methanol
MHz: megahertz
min: minute
mL: milliliter
mmol: millimole
MS or ms: mass spectrum
N: normal
NaHMDS: sodium hexamethyldisilazide
NMR: nuclear magnetic resonance
PyBOP: (benzotriazol-1-yloxy)tripyrrolidinophosphonium hexafluorophosphate
$R_t$: retention time
rt or RT: room temperature
TFA: trifluoroacetic acid
THF: tetrahydrofuran
TLC: thin layer chromatography Compounds of the present invention may be prepared by procedures illustrated in the accompanying schemes.

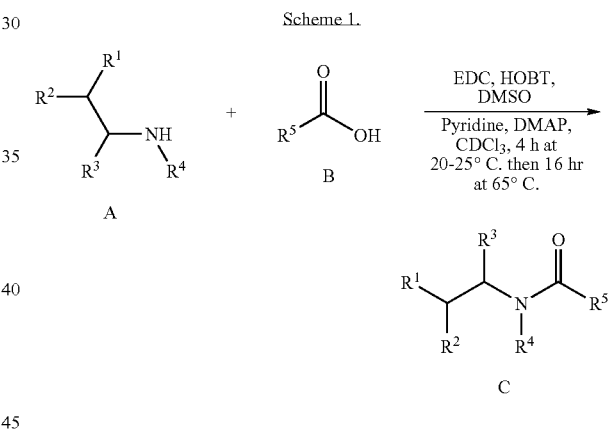

Scheme 1.

In Scheme 1, an appropriately substituted amine A is reacted with a carboxylic acid B under standard amide bond forming conditions to afford the arylamide C. In order to illustrate the invention, the following examples are included. These examples do not limit the invention. They are only meant to suggest a method of reducing the invention to practice. Those skilled in the art may find other methods of practicing the invention which are readily apparent to them. However, those methods are also deemed to be within the scope of this invention.

General Procedures.

The LC/MS analyses were preformed using a MICROMASS ZMD mass spectrometer coupled to an AGILENT 1100 Series HPLC utilizing a YMC ODS-A 4.6×50 mm column eluting at 2.5 mL/min with a solvent gradient of 10 to 95% B over 4.5 min, followed by 0.5 min at 95% B: solvent A=0.06% TFA in water; solvent B=0.05% TFA in acetonitrile. $^1$H-NMR spectra were obtained on a 500 MHz VARIAN Spectrometer in $CDCl_3$ or $CD_3OD$ as indicated and chemical shifts are reported as δ using the solvent peak as reference and coupling constants are reported in hertz (Hz).

Reference Example 1

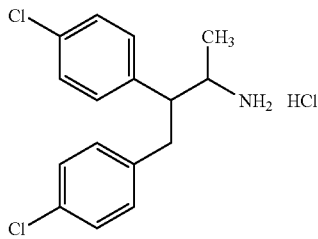

N-[2,3-Bis(4-chlorophenyl)-1-methylpropyl]-amine hydrochloride

The preparation of the two diastereomers (alpha and beta) of N-[2,3-bis(4-chlorophenyl)-1-methylpropyl]-amine hydrochloride salt has been disclosed (Schultz, E. M, et al. *J. Med. Chem.* 1967, 10, 717). Diastereomer α: LC-MS: calculated for $C_{16}H_{17}Cl_2N$ 293, observed m/e 294 $(M+H)^+$ ($R_t$ 2.5 min). Diastereomer β: LC-MS: calculated for $C_{16}H_{17}Cl_2N$ 293, observed m/e 294 $(M+H)^+$ ($R_t$ 2.2 min).

The amines of Reference Examples 2-9 were prepared by the same procedures described in Reference Example 1:

Reference Example 2

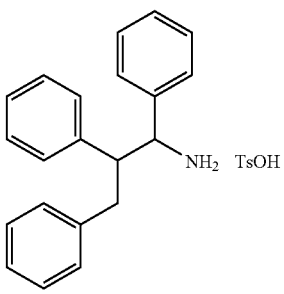

2-Amino-3,4-diphenylbutane hydrochloride salt

Diastereomer α:
LC-MS: calculated for $C_{16}H_{19}N$ 225, observed m/e 226 $(M+H)^+$ (2.0 min).

Diastereomer β:
LC-MS: calculated for $C_{16}H_{19}N$ 225, observed m/e 226 $(M+H)^+$ (1.9 min).

Reference Example 3

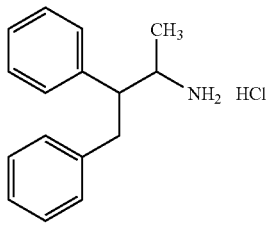

3-Amino-1,2-diphenylpentane hydrochloride salt

Diastereomer α:
LC-MS: calculated for $C_{17}H_{21}N$ 239, observed m/e 240 $(M+H)^+$ (2.1 min).

Diastereomer β:
LC-MS: calculated for $C_{17}H_{21}N$ 239, observed m/e 240 $(M+H)^+$ (2.0 min).

Reference Example 4

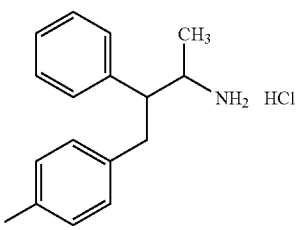

1-Amino-1,2,3-triphenylpropane p-toluenesulfonate salt

Diastereomer α:
LC-MS: calculated for $C_{21}H_{21}N$ 287, observed m/e 288 $(M+H)^+$ (2.3 min).

Diastereomer β:
LC-MS: calculated for $C_{21}H_{21}N$ 287, observed m/e 288 $(M+H)^+$ (2.3 min).

Reference Example 5

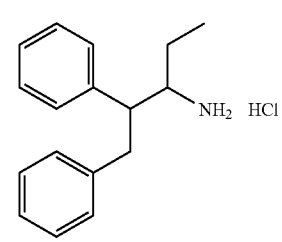

2-Amino-4-(4-chlorophenyl)-3-phenylbutane hydrochloride salt

Diastereomer α:
LC-MS: calculated for $C_{16}H_{18}ClN$ 259, observed m/e 260 $(M+H)^+$ (2.3 min).

Diastereomer β:
LC-MS: calculated for $C_{16}H_{18}ClN$ 259, observed m/e 260 $(M+H)^+$ (2.2 min).

Reference Example 6

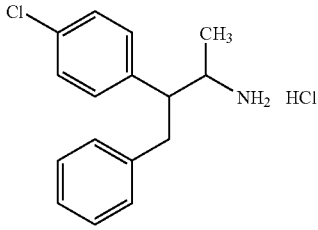

2-Amino-3-(4-chlorophenyl)-4-phenylbutane
hydrochloride salt

Diastereomer α:
LC-MS: calculated for $C_{16}H_{18}ClN$ 259, observed m/e 260 $(M+H)^+$ (2.3 min).

Diastereomer β:
LC-MS: calculated for $C_{16}H_{18}ClN$ 259, observed m/e 260 $(M+H)^+$ (2.1 min).

Reference Example 7

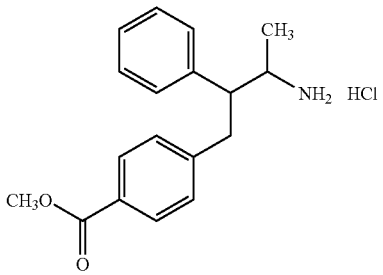

2-Amino-4-(4-methoxycarbonylphenyl)-3-phenylbutane
hydrochloride salt

Diastereomer α:
LC-MS: calculated for $C_{18}H_{21}NO_2$ 283, observed m/e 284 $(M+H)^+$ (2.0 min).

Diastereomer β:
LC-MS: calculated for $C_{18}H_{21}NO_2$ 283, observed m/e 284 $(M+H)^+$ (1.9 min).

Reference Example 8

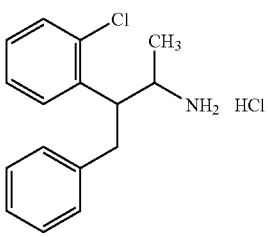

2-Amino-3-(2-Chlorophenyl)-4-phenylbutane
(mixture of diastereomers α/β 1:2)

LC-MS: calculated for $C_{16}H_{18}ClN$ 259, observed m/e 260 $(M+H)^+$ (1.9/2.0 min).

Reference Example 9

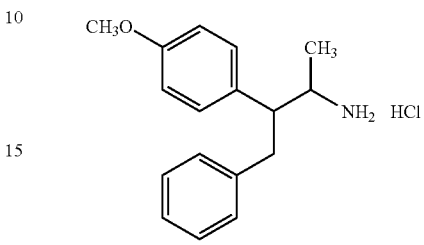

2-Amino-3-(4-methoxyphenyl)-4-phenylbutane
(mixture of diastereomers α/β 2:5)

LC-MS: m/e 256 (M+H)+(1.7 min).

Reference Example 10

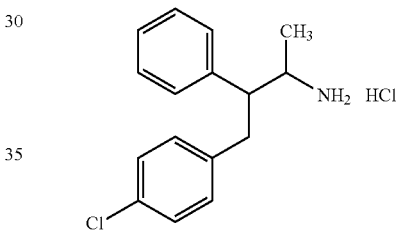

N-[3-(4-Chlorophenyl)-2-phenyl-1-methylpropyl]-
amine hydrochloride (Diastereomer α)

Step A 3-(4-Chlorophenyl)-2-phenylpropanoic acid,
methyl ester

To a solution of methyl phenylacetate (12 g, 80 mmol) and 4-chlorobenzyl bromide (16 g, 80 mmol) in 250 mLanhydrous THF at −78° C. was added sodium hexamethyldisilazide (1 M in THF, 80 mL, 80 mmol) (potassium hexamethyldisilazide in toluene may be used with similar results). The reaction was allowed to warm to room temperature overnight. The volatile materials were removed on a rotary evaporator, and the resulting mixture was partitioned between saturated ammonium chloride (200 mL) and EtOAc (200 mL). The organic layer was separated and the aqueous layer extracted with EtOAc (2×200 mL). The combined organic extracts were dried over anhydrous sodium sulfate, filtered, and concentrated to dryness to give the title compound.
$^1$H NMR (500 MHz, $CD_3OD$): δ 7.36-7.10 (m, 9H), 3.81 (dd, 1H), 3.52 (s, 3H), 3.36 (dd, 1H), 3.02 (dd, 1H).

Step B 3-(4-Chlorophenyl)-2-phenylpropanoic acid

To a mixture of methyl 3-(4-chlorophenyl)-2-phenylpropionate (Step A, 20 g, 74 mmol) in acetonitrile (100 mL) and water (100 mL) was added lithium hydroxide monohydrate (8.8 g, 0.21 mol). After stirring at room temperature for 3 days, the volatile materials were removed by concentrating on a rotary evaporator and the residue was partitioned between water (300 mL) and hexane/ether (1:1, 200 mL). The water layer was separated, acidified to pH=2-3, and extracted with EtOAc (2×200 mL) The combined organic extracts were dried over anhydrous sodium sulfate, filtered, and concentrated to dryness to give the title compound. $^1$H NMR (500 MHz, CD$_3$OD): δ 7.34-7.10 (m, 9H), 3.82 (dd, 1H), 3.36 (dd, 1H), 2.98 (dd, 1H).

Step C N-Methoxy-N-methyl-3-(4-chlorophenyl)-2-phenylpropanamide

To a solution of 3-(4-chlorophenyl)-2-phenylpropionic acid (Step B, 14 g, 55 mmol) in CH$_2$Cl$_2$ (125 mL) at 0° C. was added dimethyl formamide (50 μL) and oxalyl chloride (14 g, 0.11 mol) dropwise. The reaction was allowed to warm to room temperature overnight and concentrated to dryness to give the crude acyl chloride, which was used without further purification. Thus, to a solution of the acyl chloride in CH$_2$Cl$_2$ (250 mL) was added N-methoxy-N-methylamine hydrochloride (11 g, 0.11 mol) and triethyl amine (dried over activated molecular sieves, 30 mL, 0.22 mol) at 0° C. After stirring at room temperature for 4 h, the reaction mixture was diluted with ether (500 mL) and successively washed with water, dilute aqueous sodium hydrogen sulfate and brine, dried over anhydrous MgSO$_4$, filtered and concentrated to dryness to give the crude product, which was used without further purification. $^1$H NMR (500 MHz, CD$_3$OD): δ 7.4-7.1 (m, 9H), 4.38 (br, 1H), 3.48 (s, 3H), 3.35 (dd, 1H), 3.10 (s, 3H), 2.92 (dd, 1H); LC-MS: m/e 304 (3.6 min).

Step D 4-(4-Chlorophenyl)-3-phenyl-2-butanone

To a solution of N-methoxy-N-methyl-3-(4-chlorophenyl)-2-phenylpropanamide (Step C, 16 g, 53 mmol, dried by azeotroping with toluene) in anhydrous THF (200 mL) at 0° C. was added methylmagnesium bromide (3 M in ether, 35 mL, 0.11 mol). After stirring at 0° C. for 2 h, the reaction was quenched with MeOH (5 mL) and 2 M hydrochloric acid (50 mL). The volatile materials were removed by concentrating on a rotary evaporator and the residue partitioned between saturated ammonium chloride (200 mL) and ether (200 mL). The organic layer was separated, and the aqueous layer was extracted with ether (2×200 mL). The combined organic extracts were dried over anhydrous MgSO$_4$, filtered and concentrated to dryness to give the title compound, which was used without further purification. $^1$H NMR (500 MHz, CD$_3$OD): δ 7.45-7.02 (m, 9H), 4.08 (dd, 1H), 3.34 (dd, 1H), 2.90 (dd, 1H), 2.03 (s, 3H).

Step E 4-(4-Chlorophenyl)-3-phenyl-2-butanol

To a solution of 4-(4-chlorophenyl)-3-phenyl-2-butanone (Step D, 13 g, 50 mmol) in MeOH (100 mL) at 0° C. was added sodium borohydride (3.8 g, 100 mmol). After stirring at 0° C. for 30 min, the reaction was quenched by addition of 2 M hydrochloric acid (50 mL). The volatile materials were removed by concentrating on a rotary evaporator and the residue partitioned between water (100 mL) and EtOAc (200 mL). The organic layer was separated and the aqueous layer extracted with EtOAc (2×200 mL). The combined organic extracts were washed with brine, dried over anhydrous sodium sulfate, filtered and concentrated to dryness to give the crude product, which was purified by flash column chromatography on silica gel eluted with 10% EtOAc in hexane to afford the pure faster eluting isomer and a mixture containing both the faster eluting isomer and the slower eluting isomer. Faster eluting isomer: $^1$H NMR (500 MHz, CD$_3$OD): δ 7.25-7.00 (m, 9H), 4.00 (m, 1H), 3.15 (m, 1H), 2.97 (m, 1H), 2.85 (m, 1H), 1.10 (d, 3H).

Step F 4-(4-Chlorophenyl)-2-methanesulfonyloxy-3-phenylbutane

To a solution of 4-(4-chlorophenyl)-3-phenyl-2-butanol (Step E, faster eluting isomer, 9.0 g, 34 mmol) in EtOAc (100 mL) at 0° C. was added triethyl amine (dried over activated molecular sieves, 5.8 mL. 42 mmol) and methanesulfonyl chloride (3.0 mL, 38 mmol). After stirring at 0° C. for 30 min, the reaction was quenched by addition of saturated aqueous sodium bicarbonate (100 mL). After stirring at room temperature for 1 h, the organic layer was separated, dried over anhydrous sodium sulfate, filtered, and concentrated to dryness to give the title compound, which was used without further purification. $^1$H NMR (500 MHz, CD$_3$OD): δ 7.3-7.0 (m, 9H), 5.05 (m, 1H), 3.2-3.0 (m, 3H), 2.80 (s, 3H), 1.40 (d, 3H).

Step G 2-Azido-4-(4-chlorophenyl)-3-phenylbutane

To a solution of 4-(4-chlorophenyl)-2-methanesulfonyloxy-3-phenylbutane (Step F, 12 g, 34 mmol) in DMF (50 mL) was added sodium azide (11 g, 0.17 mol). After stirring at 120° C. for 1 h, the reaction mixture was poured into water (200 mL), and the product was extracted with ether (2×100 mL). The combined organic extracts were washed with water, dried over MgSO$_4$, filtered and concentrated to dryness, and the residue was purified on a silica gel column eluting with hexane to give the title compound.

Step H 2-(N-tert-Butoxycarbonyl)amino-4-(4-chlorophenyl)-3-phenylbutane

To a solution of 2-azido-4-(4-chlorophenyl)-3-phenylbutane (Step G, 7.0 g, 24 mmol) in EtOAc (150 mL) was added di(tert-butyl) dicarbonate (8.0 g, 37 mmol) and platinum dioxide (0.50 g, 2.2 nmol). The mixture was degassed and filled with hydrogen with a balloon. After stirring for 1 day, the reaction mixture was filtered through CELITE diatomaceous earth, and the filtrate was concentrated to give the crude product, which was contaminated with some unreacted di(tert-butyl) dicarbonate. $^1$H NMR (500 MHz, CD$_3$OD): δ 7.25-6.88 (m, 9H), 3.89 (m, 1H), 3.20 (m, 1H), 2.86-2.77 (m, 2H), 1.54 (s, 9H), 0.92 (d, 3H).

Step I N-[3-(4-Chlorophenyl)-2-phenyl-1-methylpropyl]-amine hydrochloride (Diastereomer α)

2-(N-tert-butoxycarbonyl)amino-4-(4-chlorophenyl)-3-phenylbutane (Step H, 7.0 g, 24 mmol) was treated with a saturated solution of hydrogen chloride in EtOAc (100 mL) at room temperature for 30 min (4 M hydrogen chloride in dioxane may be used with similar results). The mixture was concentrated to dryness to give the title compound. $^1$H NMR (500 MHz, CD$_3$OD): δ 7.35-6.98 (m, 9H), 3.62 (m, 1H), 3.20 (dd, 1H), 3.05 (m, 1H), 2.98 (dd, 1H), 1.19 (d, 3H). LC-MS: m/e 260 (M+H)+(2.3 min).

Reference Example 11

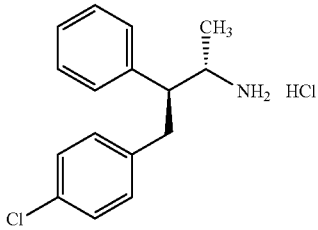

N-[3-(4-Chlorophenyl)-2(S)-phenyl-1(S)-methylpropyl]-amine hydrochloride

Step A 4-(4-Chlorophenyl)-3(S)-phenyl-2(R)-butanol

A sample of magnesium (20 g, 0.82 mol) was activated by stirring under nitrogen for 12 h, and anhydrous ether (100 mL) was added to cover the solid material. The mixture was cooled to 0° C., and was added 4-chlorobenzyl chloride (40 g, 0.25 mmol) in 400 mL anhydrous ether dropwise. After stirring at room temperature for 1 h, a sample of the above solution (32 mL) was added to (1R,2R)-1-phenylpropylene oxide (1.0 g, 7.5 mmol) in 100 mL ether at 0° C. via syringe. After stirring at 0° C. for 2 h, the reaction was quenched by addition of saturated aqueous ammonium chloride (100 mL). The organic layer was separated and the aqueous layer extracted with ether (2×100 mL). The combined organic extracts were washed with brine, dried over anhydrous $MgSO_4$, filtered, and concentrated to dryness, and the residue was purified by flash column chromatography on silica gel eluted with hexane to 15% EtOAc in hexane to afford the title compound. $^1$H NMR (500 MHz, $CD_3OD$): δ 7.28-7.02 (m, 9H), 4.01 (m, 1H), 3.14 (dd, 1H), 2.97 (dd, 1H), 2.85 (m, 1H), 1.12 (d, 3H).

Step B N-[3-(4-chlorophenyl)-2(S)-phenyl-1(S)-methylpropyl]-amine, hydrochloride The product of Step A (4-(4-chlorophenyl)-3(S)-phenyl-2(R)-butanol, 1.8 g, 7.0 mmol) was converted to the title compound following the steps described in Reference Example 10, Steps F-I, except hydrogen chloride in dioxane (4 M) was used in place of hydrogen chloride in EtOAc. $^1$H NMR (500 MHz, $CD_3OD$): δ 7.35-6.98 (m, 9H), 3.62 (m, 1H), 3.20 (dd, 1H), 3.05 (m, 1H), 2.98 (dd, 1H), 1.19 (d, 3H). LC-MS: m/e 260 (M+H)$^+$ (2.3 min).

Reference Example 12

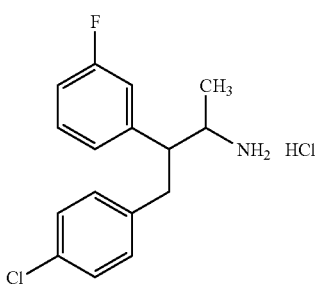

2-Amino-4-(4-chlorophenyl)-3-(3-fluorophenyl) butane hydrochloride salt (mixture of diastereomers α/β 5:1)

Step A Methyl 3-(4-Chlorophenyl)-2-(3-fluorophenyl)propionate

To a solution of 3-fluorophenylacetic acid (5.0 g, 32 mmol) in MeOH (25 mL) and $CH_2Cl_2$ (25 mL) at 0° C. was added trimethylsilyldiazomethane (2 M in hexane, 30 mL, 60 mmol). After stirring at room temperature for 15 min, the reaction mixture was concentrated to dryness, and the residue was azeotroped with toluene to give the crude methyl 3-fluorophenylacetate (5.6 g), which was used without further purification. Thus, the crude methyl 3-fluorophenylacetate obtained above (2.5 g, 15 mmol) was converted to the title compound (purified on silica gel) by reacting with 4-chlorobenzyl bromide (4.6 g, 22 mmol) and sodium hexamethyldisilazide (1 M in THF, 15 mL, 15 mmol) following the procedure described in Reference Example 10, Step A. $^1$H NMR (400 MHz, $CD_3OD$): δ 7.35-6.88 (m, 8H), 3.92 (t, 1H), 3.60 (s, 3H), 3.34 (dd, 1H), 3.00 (dd, 1H). LC-MS: m/e 305 (M+Na)$^+$ (3.9 min).

Step B N-Methoxy-N-methyl-3-(4-chlorophenyl)-2-(3-fluororophenyl) propanamide

To a suspension N-methoxy-N-methylamine hydrochloride (2.0 g, 21 mmol) in 50 mL $CH_2Cl_2$ at 0° C. was added dimethylaluminum chloride (1 M in hexane, 21 mL, 21 mmol). After stirring at room temperature for 1 h, a solution of methyl 3-(4-chlorophenyl)-2-(3-fluorophenyl)propionate (Step A, 2.0 g, 10 mmol) in $CH_2Cl_2$ (10 mL) was added, and the resulting mixture was stirred overnight. The reaction mixture was quenched by addition of MeOH (5 mL), and the resulting mixture was concentrated with silica gel (50 g). The material was loaded onto a silica gel column, which was eluted with 10% EtOAc in hexane to 2% ammonia in MeOH (2 M) in 10% EtOAc/hexane to give the title compound. $^1$H NMR (400 MHz, $CD_3OD$): δ 7.35-6.90 (m, 8H), 4.39 (br, 1H), 3.41 (s, 3H), 3.38-3.30 (m, 1H), 3.08 (s, 3H), 2.92 (dd, 1H). LC-MS: m/e 322 (M+H)$^+$ (3.6 min).

Step C 4-(4-Chlorophenyl)-3-(3-fluorophenyl)-2-butanol

The product of Step B (N-methoxy-N-methyl-3-(4-chlorophenyl)-2-phenylpropionamide) (0.74 g, 2.3 mmol) was converted to the title compound (a 5:1 mixture of diastereomers) following the procedure described in Reference Example 10, Steps D-E. $^1$H NMR (400 MHz, $CD_3OD$): δ 7.22-6.78 (m, 8H), 3.98 (m, 1H), 3.11 (dd, 1H), 2.94 (dd, 1H), 2.85 (m, 1H), 1.08 (d, 3H).

Step D 2-Azido-4-(4-chlorophenyl)-3-(3-fluorophenyl)butane

To a mixture of 4-(4-chlorophenyl)-2-(3-fluorophenyl)-2-butanol (Step C, 0.65 g, 2.3 mmol), triphenylphosphine (1.2 g, 4.7 mmol), imidazole (0.32 g, 4.7 mmol) and zinc azide dipyridine complex (Viaud, M. C.; Rollin, P. *Synthesis* 1990, 130) (0.72 g, 2.3 mmol) in 10 mL $CH_2Cl_2$ was added diethylazodicarboxylate (0.73 mL, 4.7 mmol) at 0° C. After stirring at room temperature for 30 min, the resulting mixture was concentrated with silica gel (20 g) and loaded onto a silica gel column, which was eluted with 2% ether in hexane to 2% ammonia in MeOH (2 M) in 2% ether/hexane to give the title compound. $^1$H NMR (400 MHz, $CD_3OD$): δ 7.25-6.85 (m, 8H), 3.76 (m, 1H), 3.33 (m, 1H), 2.92 (m, 2H), 1.15 (d, 3H).

Step E 2-Amino-4-(4-Chlorophenyl)-3-(3-fluorophenyl)butane hydrochloride salt (mixture of diastereomers α/β 5:1)

The product of Step D (2-azido-4-(4-chlorophenyl)-3-(3-fluorophenyl) butane) (0.49 g, 1.6 mmol) was converted to the title compound following the steps described in Reference Example 10, Steps H-1. $^1$H NMR (400 MHz, CD$_3$OD): δ 7.32-6.90 (m, 7H), 3.61 (m, 1H), 3.20 (dd, 1H), 3.11 (m, 1H), 2.92 (dd, 1H), 1.19 (d, 3H). LC-MS: m/e 278 (M+H)$^+$ (2.4 min).

The amines of Reference Examples 13-16 were prepared according to the procedures described in Reference Example 12:

Reference Example 13

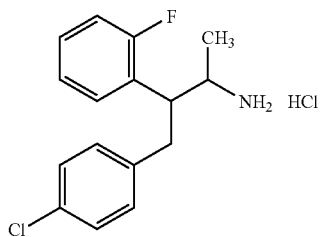

2-Amino-4-(4-chlorophenyl)-3-(2-fluorophenyl) butane hydrochloride salt (mixture of diastereomers α/β 10:1)

LC-MS: m/e 278 (M+H)+(2.3 min).

Reference Example 14

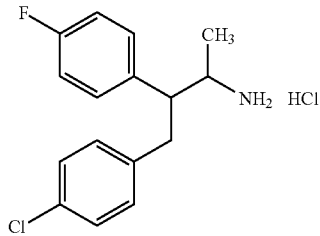

2-Amino-4-(4-chlorophenyl)-3-(4-fluorophenyl) butane hydrochloride salt (mixture of diastereomers α/β 10:1)

LC-MS: m/e 278 (M+H)$^+$ (2.5 min).

Reference Example 15

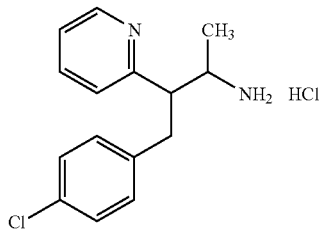

2-Amino-4-(4-chlorophenyl)-3-(2-pyridyl)butane hydrochloride salt (mixture of diastereomers α/β 10:1)
LC-MS: m/e 261 (M+H)$^+$ (1.6 min).

Reference Example 16

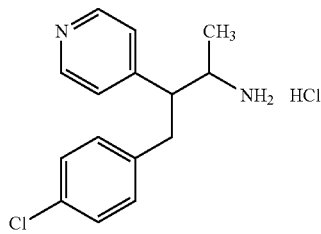

2-Amino-4-(4-chlorophenyl)-3-(4-pyridyl)butane hydrochloride salt (mixture of diastereomers α/β 10:1)

Trimethyl aluminum was used in place of dimethylaluminum chloride at Step B of Reference Example 12. LC-MS: m/e 261 (M+H)$^+$.

Reference Example 17

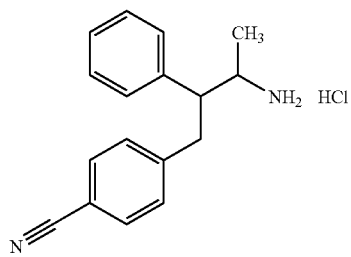

2-Amino-4-(4-cyanophenyl)-3-phenylbutane hydrochloride salt (mixture of diastereomers α/β 10:1)

Step A 4-(4-Cyanophenyl)-3-phenyl-2-butanone

To a solution of phenylacetone (1.2 g, 9.0 mmol) and 4-cyanobenzyl chloride (1.4 g, 9.0 mmol) in 20 mL CH$_2$Cl$_2$ at −78° C. was added cesium hydroxide monohydrate (4.5 g, 27 mmol) and tetrabutyl ammonium iodide (20 mg). The reaction was allowed to warm to room temperature over 6 h, and the resulting mixture partitioned between brine (100 mL) and EtOAc (100 mL). The organic layer was separated and the aqueous layer extracted with EtOAc (2×100 mL). The combined organic extracts were dried over MgSO$_4$, filtered, and concentrated to dryness, and the residue was purified by flash column chromatography on silica gel eluted with 20-50% EtOAc in hexane to give the title compound. $^1$H NMR (500 MHz, CD$_3$OD): δ 7.52 (d, 2H), 7.34-7.16 (m, 7H), 4.12 (dd, 1H), 3.41 (dd, 1H), 3.00 (dd, 1H). LC-MS: m/e 250 (M+H)$^+$ (3.2 min).

Step B 2-Amino-4-(3-cyanophenyl)-3-phenylbutane hydrochloride salt (mixture of diastereomers α/β 10:1).

The product of Step A (4-(4-cyanophenyl)-3-phenyl-2-butanone) (1.0 g, 4.0 mmol) was converted to the title compound following the procedure described in Reference Example 10, Steps E-I. LC-MS: m/e 251 (M+H)$^+$ (1.9 min).

Reference Example 18

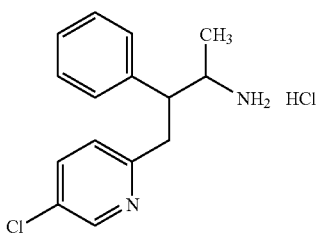

2-Amino-4-(5-chloro-2-pyridyl)-3-phenylbutane hydrochloride salt (mixture of diastereomers α/β 10:1)

5-Chloro-2-choromethylpyridine (Weidmann, K. et al. *J. Med. Chem.* 1992, 35, 438) was used in place of 4-cyanobenzyl bromide in Step A of Reference Example 17. LC-MS: m/e 261 (M+H)$^+$.

Reference Example 19

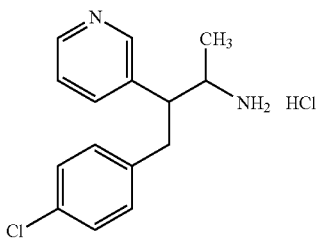

N-[3-(4-chlorophenyl)-2-(3-pyridyl)-1-methylpropyl]-amine, hydrochloride (mixture of diastereomers α/β 10:1)

Step A 4-(4-Chlorophenyl)-3-pyridyl-2-butanone

To a solution of 3-pyridylacetone hydrochloride (Wibaud, van der V. *Recl. Trav. Chim. Pays-Bas.* 1952, 71, 798) (10 g, 58 mmol) and 4-chlorobenzyl chloride (9.1 g, 58 mmol) in 100 mL CH$_2$Cl$_2$ at −78° C. was added cesium hydroxide monohydrate (39 g, 0.23 mol) and tetrabutyl ammonium iodide (1 g). The reaction was allowed to warm to room temperature overnight, and the resulting mixture was partitioned between brine (100 mL) and EtOAc (100 mL). The organic layer was separated and the aqueous layer extracted with EtOAc (2×100 mL). The combined organic extracts were dried over anhydrous MgSO$_4$, filtered, and concentrated to dryness to give the title compound. $^1$H NMR (500 MHz, CD$_3$OD): δ 8.42 (d, 1H), 8.34 (d, 1H), 7.72 (d, 1H), 7.40 (dd, 1H), 7.18 (d, 2H), 7.06 (d, 1H), 4.23 (dd, 1H), 3.38 (dd, 1H), 2.95 (dd, 1H), 2.10 (s, 3H). LC-MS: m/e 260 (M+H)$^+$ (1.9 min).

Step B N-[3-(4-chlorophenyl)-2-(3-pyridyl)-1-methylpropyl]-amine, hydrochloride (mixture of diastereomers α/β 10:1)

The product of Step A (4-(4-chlorophenyl)-3-pyridyl-2-butanone) (14 g, 57 mmol) was converted to the title compound following the procedure described in Reference Example 10, Steps E-I. LC-MS: m/e 261 (M+H)$^+$ (1.2 min).

Reference Example 20

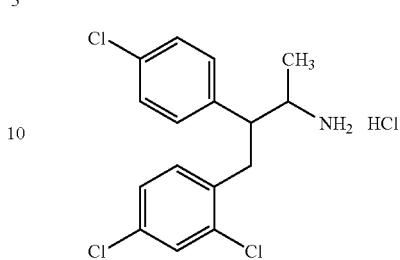

2-Amino-4-(2,4-dichlorophenyl)-3-(4-chlorophenyl) butane hydrochloride salt (3 isomers)

Step A Methyl 3-(2,4-Dichlorophenyl)-2-(4-chlorophenyl)propionate

A sample of 4-chlorophenylacetic acid (4.2 g, 25 mmol) was converted to the title compound (6.5 g) following the procedure in Reference Example 12, Step A substituting 4-chlorophenylacetic acid for 3-fluorophenylacetic acid and 2,4-dichlorobenzyl bromide for 4-chlorobenzyl bromide following the procedures described in Reference Example 10, Step A. $^1$H NMR (500 MHz, CD$_3$OD): δ 7.40 (d, 1H), 7.32-7.22 (m, 4H), 7.15 (dd, 1H), 7.08 (d, 1H), 4.00 (t, 1H), 3.62 (s, 3H), 3.44 (dd, 1H), 3.12 (dd, 1H).

Step B
3-(2,4-Dichlorophenyl)-2-(4-chlorophenyl)propanol

To a solution of methyl 3-(2,4-dichlorophenyl)-2-(4-chorophenyl) propionate (6.4 g, 8.6 mmol) in 50 mL ether at −40° C. was added lithium aluminum hydride (1.4 g, 37 mmol), and the reaction was allowed to warm to room temperature over 2 h. The reaction was quenched by addition of MeOH (3 mL) dropwise at −10° C., and the mixture was partitioned between 100 mL saturated ammonium chloride and EtOAc (100 mL). The organic layer was separated and the aqueous layer extracted with EtOAc (2×100 mL). The combined organic extracts were dried over anhydrous MgSO$_4$, filtered, and concentrated to dryness to give the title compound, which was used without further purification. $^1$H NMR (400 MHz, CD$_3$OD): δ 7.4-6.9 (m, 7H), 3.72 (m, 2H), 3.24 (dd, 1H), 3.16 (m, 1H), 2.85 (dd, 1H).

Step C
3-(2,4-Dichlorophenyl)-2-(4-chorophenyl)propanal

To a solution of 3-(2,4-dichlorophenyl)-2-(4-chorophenyl) propanol (Step B, 0.89 g, 2.8 mmol) in 20 mL CH$_2$Cl$_2$ was added crushed activated molecular sieves (4 g). After stirring at room temperature for 10 min, pyridinium chlorochromate (0.90 g, 4.2 mmol) was added. After stirring at room temperature for 1 h, CELITE diatomaceous earth (4 g) was added followed by 100 mL ether. The resulting mixture was filtered through a silica gel pad, which was washed with ether (2×50 mL). The filtrate was concentrated to dryness and azeotroped with toluene to give the title compound, which was used without further purification.

Step D N-[3-(2,4-Dichlorophenyl)-2-(4-chorophenyl)propylidene]-2-methylpropanesulfinamde To a solution of 3-(2,4-dichlorophenyl)-2-(4-chorophenyl) propanal (Step C, 0.90 g, 2.8 mmol) in 6 mLTHF was added (R)-(+)-2-methyl-2-propane-sulfinamide (0.5 gm, 4.1 mmol) followed by the addition of titanium tetraethoxide (1.5 mL, 8.0 mmol). After stirring at room temperature overnight, the reaction mixture was added to a well-stirred brine solution (50 mL). The resulting mixture was filtered through CELITE diatomaceous earth and washed with EtOAc (20 mL), and the filtrate was extracted with EtOAc (2×50 mL). The combined extracts were dried over anhydrous sodium sulfate, filtered, and concentrated to dryness, and the residue was purified by flash column chromatography on silica gel eluted with 10% ether in hexane to give the title compound as a 1:1 mixture of diastereomers. $^1$H NMR (500 MHz, CD$_3$OD): δ 8.11 (m, 1H), 7.41 (m, 1H), 7.35-7.31 (m, 4H), 7.16-7.06 (m, 2H), 4.26 (m, 1H), 3.78-3.58 (m, 1H), 3.22-3.14 (m, 1H), 1.13/1.12 (s, 9H).

Step E N-[3-(2,4-Dichlorophenyl)-2-(4-chorophenyl)-1-methylpropyl]-2-methylpropanesulfinamide (3 isomers)

To a solution of N-[3-(2,4-dichlorophenyl)-2-(4-chorophenyl)-1-methylpropylidene]-2-methylpropanesulfinamde (Step D, 0.51 g, 1.3 mmol) in 6 mL CH$_2$Cl$_2$ at −60° C. was added methylmagnesium bromide (3 M in ether, 0.90 mL, 2.7 mmol). After stirring at −60° C. for 6 h, the reaction was allowed to warm to room temperature overnight. The resulting mixture was partitioned between saturated aqueous ammonium chloride (50 mL) and EtOAc (50 mL). The organic layer was separated and the aqueous layer extracted with EtOAc (2×50 mL). The combined extracts were dried over anhydrous sodium sulfate, filtered, and concentrated to dryness, and the residue was purified by flash column chromatography on silica gel eluted with 30 to 50% EtOAc in hexane to give the title compound as one pure faster eluting enantiomer and a 1:1 mixture of slower co-eluting diastereomers. The addition of the methyl Grignard reagent was apparently stereoselective for one of the sulfinamide diastereomers.

Faster eluting isomer: $^1$H NMR (500 MHz, CD$_3$OD): δ 7.30 (d, 1H), 7.22 (d, 2H), 7.12 (d, 2H), 7.03 (dd, 1H), 6.94 (d, 1H), 3.62 (m, 1H), 3.56 (dd, 1H), 2.97 (dd, 1H), 1.23 (s, 9H), 1.04 (d, 3H). LC-MS: m/e 432 (M+H)$^+$ (4.2 min).

Slower eluting isomers (1:1): $^1$H NMR (500 MHz, CD$_3$OD): δ 7.33/7.30 (d, 1H), 7.21/7.18 (d, 2H), 7.06/7.04 (d, 2H), 6.99/6.97 (dd, 1H), 6.79/6.75 (d, 1H), 3.70-3.55 (m, 1H), 3.07/2.97 (m, 1H), 2.90/2.80 (dd, 1H), 1.32/0.95 (s, 9H), 1.49/1.10 (d, 3H).

Step F 2-Amino-4-(2,4-dichlorophenyl)-3-(4-chorophenyl)butane hydrochloride (3 isomers)

To a solution of N-[3-(2,4-dichlorophenyl)-2-(4-chorophenyl)-1-methylpropyl]-2-methylpropanesulfinamide (Step F, faster eluting isomer, 50 mg, 0.11 mmol) in 5 mL MeOH was added hydrogen chloride in dioxane (4 M, 2 mL). After stirring at room temperature for 10 min, the reaction mixture was concentrated to dryness to give the title compound as one pure isomer.

Isomer 1: $^1$H NMR (500 MHz, CD$_3$OD): δ 7.35 (d, 1H), 7.29 (d, 2H), 7.15 (d, 2H), 7.06 (dd, 1H), 6.91 (d, 1H), 3.68 (m, 1H), 3.36 (dd, 1H), 3.06 (dd, 1H), 1.18 (d, 3H). LC-MS: m/e 328 (M+H)$^+$ (2.8 min).

The two slower co-eluting isomers were treated in the same fashion to give two other isomers of the title compound. Isomer 2 and 3 (1:1): LC-MS: m/e 328 (M+H)+(2.7/2.8 min).

Reference Example 21

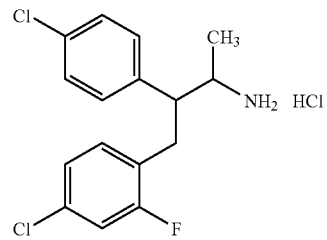

2-Amino-4-(4-chloro-2-fluorophenyl)-3-(4-chlorophenyl)butane hydrochloride salt (Isomers 1, 2 and 3)

The title compound was prepared according to the procedures of Reference Example 20 substituting 2,5-dichlorobenzyl bromide with 4-chloro-2-fluorobenzyl bromide.

Isomer 1: LC-MS: m/e 312 (M+H)$^+$ (2.6 min).

Isomer 2 and 3 (1:1): LC-MS: m/e 312 (M+H)$^+$ (2.5/2.6 min).

Reference Example 22

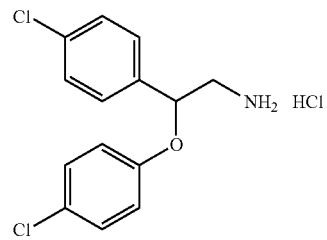

2-(4-Chlorophenyloxy)-2-(4-chlorophenyl)ethylamine hydrochloride salt

Step A 2-(4-Chlorophenyloxy)-2-(4-chlorophenyl)ethanol

To a suspension of 2-(4-chlorophenyloxy)-2-(4-chlorophenyl)acetic acid (Newman et al *J. Amer. Chem. Soc.* 1947, 69, 718) (1.0 g, 3.4 mmol) in 10 mLTHF at 0° C. was added borane (1 M in THF, 6.8 mL, 6.8 mmol). After stirring at room temperature for 2 h, the reaction was quenched by addition of 2 M hydrochloric acid (10 mL). The volatile materials were removed on a rotary evaporator, and the resulting mixture was partitioned between brine (20 mL) and EtOAc (30 mL). The organic layer was separated and the aqueous layer extracted with EtOAc (2×20 mL). The combined extracts were dried over anhydrous sodium sulfate, filtered, and concentrated to dryness to give the title compound, which was used without further purification. LC-MS: m/e 283 (M+H)+ (3.4 min).

Step B
2-(4-Chlorophenyloxy)-2-(4-chlorophenyl)ethyl Azide 2-(4-Chlorophenyloxy)-2-(4-chlorophenyl)ethanol (Step A, 0.45 g, 2.4 mmol) was converted to the title compound (0.29 g) following the procedure described in Reference Example 12, Step D. $^1$H NMR (500 MHz, CD$_3$OD): δ 7.41 (d, 2H), 7.37 (d, 2H), 7.18 (d, 2H), 6.86 (d, 2H), 5.42 (dd, 1H), 3.69 (dd, 1H), 3.45 (dd, 1H). LC-MS: m/e 308 (M+H)+ (4.3 min).

Step C
2-(4-Chlorophenyloxy)-2-(4-chlorophenyl)ethylamine

To a solution of 2-(4-chlorophenoylxy)-2-(4-chlorophenyl)ethyl azide (Step B, 0.23 g, 0.75 mmol) in 4 mLTHF at −20° C. was added trimethylphosphine (0.18 mL, 1.8 mmol), and the reaction was allowed to warm to room temperature over 2 h. Lithium hydroxide monohydrate (61 mg, 1.5 mmol) was added followed by 2 mL water. After stirring at room temperature for 30 min, the reaction was quenched by addition of 2 M hydrochloric acid (final pH=2). The volatile materials were removed on a rotary evaporator, and the resulting mixture was partitioned between brine (20 mL), 5 N aqueous sodium hydroxide (20 mL), ether (20 mL) and toluene (20 mL). The organic layer was separated and the aqueous layer extracted with ether (40 mL). The combined extracts were dried over anhydrous MgSO$_4$, filtered, and concentrated to dryness to give the title compound (0.43 g), which was contaminated with trimethylphosphine oxide and was used without further purification. $^1$H NMR (500 MHz, CD$_3$OD): δ 7.46-7.40 (m, 4H), 7.20 (d, 2H), 6.91 (d, 2H), 5.53 (m, 2H), 3.36 (m, 2H). LC-MS: m/e 282 (M+H)+ (2.5 min).

Reference Example 23

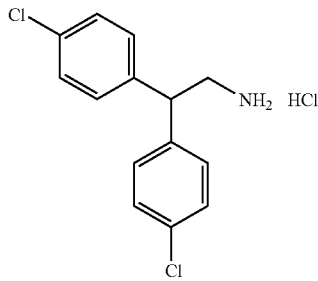

2,2-Bis(4-chlorophenyl)ethylamine hydrochloride salt

Step A Methyl 3,3-Bis(4-chlorophenyl)propenoate

A mixture of di(4-chlorophenyl)ketone (7.5 g, 30 mmol) and methyl (triphenylphosphoranylidene)acetate (10 g, 30 mmol) in 20 mL toluene was heated at 130° C. while allowing the solvent to slowly evaporate overnight. The resulting mixture was dissolved in CH$_2$Cl$_2$ (20 mL) and toluene (20 mL) and was concentrated with 30 g silica gel. The material was loaded onto a silica gel column, which was eluted with 6:3:1 hexane/CH$_2$Cl$_2$/ether to give the title compound.

Step B Methyl 3,3-Bis(4-chlorophenyl)propionate

A suspension of methyl 3,3-bis(4-chlorophenyl)propenoate (Step A, 3.0 g, 14 mmol) and platinum dioxide (0.30 g) in MeOH (20 mL) and 2 M aqueous hydrochloric acid (1 mL) was degassed and filled with hydrogen with a balloon. After stirring at room temperature for 2 h, the reaction mixture was filtered through CELITE diatomaceous earth, and the filtrate was concentrated to dryness. The residue was dissolved in 50 mL ether and was concentrated with 20 g silica gel. The material was loaded onto a silica gel column, which was eluted with 10% ether in hexane to give the title compound. $^1$H NMR (500 MHz, CD$_3$OD): δ 7.29-7.22 (m, 4H), 4.50 (t, 1H), 3.56 (s, 3H), 3.07 (d, 2H). LC-MS: m/e 309 (M+H)+(4.1 min).

Step C 3,3-Bis(4-chlorophenyl)propionic Acid

A mixture of methyl 3,3-bis(4-chlorophenyl)propionate (Step B, 0.78 g, 3.9 mmol), lithium hydroxide monohydrate (0.33 g, 7.8 mmol) in 1:1:1 MeOH/THF/water (15 mL) was stirred at room temperature overnight. The resulting mixture was partitioned between 2 M aqueous hydrochloric acid (50 mL) and ether (50 mL). The organic layer was separated and the aqueous layer extracted with EtOAc (2×50 mL). The combined extracts were dried over anhydrous MgSO$_4$, filtered, and concentrated to dryness to give the title compound. $^1$H NMR (500 MHz, CD$_3$OD): δ 7.29-7.23 (m, 4H), 4.49 (t, 1H), 3.02 (d, 2H).

Step D
N-[2,2-Bis(4-chlorophenyl)ethyl]allylcarbamate

To a solution of 3,3-bis(4-chlorophenyl)propionic acid (Step C, 0.32 g, 1.1 mmol) and triethyl amine (0.60 mL, 4.3 mmol) in 4 mLTHF at 0° C. was added ethyl chloroformate (0.31 mL, 3.3 mmol). After stirring at room temperature for 30 min, the reaction was cooled to 0° C., and was added sodium azide (0.35 g, 5.4 mmol) in 2 mL water. After stirring at room temperature for 1 h, the reaction mixture was partitioned between brine (20 mL) and EtOAc (20 mL). The organic layer was separated and the aqueous layer extracted with EtOAc (2×20 mL). The combined extracts were dried over anhydrous sodium sulfate, filtered, and concentrated to dryness, and the residue was dissolved in allylic alcohol (1 mL) and toluene (1 mL). After stirring at 80° C. overnight, the reaction mixture was concentrated to dryness, and the residue was purified by flash column chromatography on silica gel column eluted with 20% EtOAc in hexane to give the title compound. $^1$H NMR (500 MHz, CD$_3$OD): δ 7.30-7.21 (m, 4H), 5.84 (m, 1H), 5.17 (dd, 1H), 5.10 (dd, 1H), 4.46 (d, 2H), 4.22 (t, 1H), 3.68 (d, 2H). LC-MS: m/e 350 (M+H)+ (3.9 min).

Step E 2,2-Bis(4-chlorophenyl)ethylamine hydrochloride salt

To a solution of N-[2,2-bis(4-chlorophenyl)ethyl]allylcarbamate (Step D, 0.26 g, 0.73 mmol) in 1.5 mLTHF at 0° C. was added tetrakis (triphenylphosphine)palladium (85 mg, 0.073 mmol) and triphenylsilane (0.18 mL, 1.1 mmol). After stirring at 0° C. for 1 h, the reaction mixture was partitioned between ether (20 mL) and 2 M hydrochloric acid (20 mL). The aqueous layer was separated, and was added 5 N aqueous sodium hydroxide (final pH>12). The product was extracted with ether (3×30 mL), and the combined extracts were dried over sodium hydroxide, and filtered through CELITE, diatomaceous earth. After addition of 4 M hydrogen chloride in dioxane (2 mL), the filtrate was concentrated to dryness to give the title compound. $^1$H NMR (500 MHz, CD$_3$OD): δ 7.40-7.34 (m, 4H), 4.28 (m, 1H), 3.62 (d, 2H). LC-MS: m/e 266 (M+H)$^+$ (2.3 min).

Reference Example 24

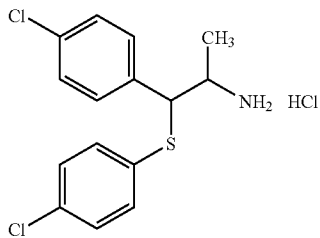

2-Amino-3-(4-chlorophenylthio)-3-(4-chlorophenyl) propane hydrochloride salt (two diastereomers)

Step A Methyl 2-(4-Chlorophenylthio)-2-(4-chlorophenyl)acetate

To a solution of 2-(4-chlorophenylthio)-2-(4-chlorophenyl)acetic acid (Nicolaescu et al *Rev. Roum. Chim.* 1979, 24, 137) (1.0 g, 3.0 mmol) in MeOH (10 mL) and CH$_2$Cl$_2$ (10 mL) at 0° C. was added trimethylsilyldiazomethane (2 M in hexane) until a yellow color persisted. Concentration afforded the title compound, which was used without further purification.

Step B 2-Amino-3-(4-chlorophenylthio)-3-(4-chlorophenyl)propane hydrochloride salt (two diastereomers)

The product of Step A (methyl 2-(4-chlorophenylthio)-2-(4-chlorophenyl)acetate) (1.1 g, 3.0 mmol) was converted to the title compound following the procedures described in Reference Example 12, Steps B-E.
LC-MS: m/e 312 (M+H)$^+$ (2.7 min).

Reference Example 25

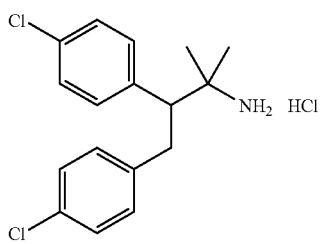

2-Amino-3,4-bis(4-chlorophenyl)-2-methylbutane hydrochloride salt

Step A Methyl 2,3-Bis(4-chlorophenyl)propionate

The title compound was prepared following the procedure described in Reference Example 10, Step A, substituting methyl phenylacetate with methyl 4-chlorophenylacetate. $^1$H NMR (500 MHz, CD$_3$OD): δ 7.30-7.22 (m, 4H), 7.19 (d, 2H), 7.09 (d, 2H), 3.90 (t, 1H), 3.58 (s, 3H), 3.32 (dd, 1H), 2.98 (dd, 1H).

Step B 3,4-Bis(4-chlorophenyl)-2-methyl-2-butanol

To a solution of methyl 2,3-bis(4-chlorophenyl)propionate (2.6 g, 8.4 mmol) in ether (20 mL) was added methylmagnesium bromide (3 M in ether, 8.4 mL, 25 mmol) at −10° C., and the reaction was allowed to warm to room temperature over 2 h. The reaction mixture was poured into saturated aqueous ammonium chloride (100 mL), and the product was extracted with EtOAc (3×100 mL). The combined extracts were dried over anhydrous MgSO$_4$, filtered, and concentrated to dryness to give the title compound, which was used without further purification. $^1$H NMR (500 MHz, CD$_3$OD): δ 7.17 (ABq, 4H), 7.06 (d, 2H), 6.93 (d, 2H), 3.32 (dd, 1H), 2.94 (dd, 1H), 2.84 (dd, 1H), 1.20 (s, 3H), 1.16 (s, 3H).

Step C N-[2,3-Bis(4-chlorophenyl)-1,1-dimethylpropyl]chloroacetamide

To a solution of 3,4-bis(4-chlorophenyl)-2-methyl-2-butanol (Step B, 1.4 g, 4.5 mmol) and chloroacetonitrile (0.57 mL, 9.1 mmol) in acetic acid (0.7 mL) at −10° C. was added concentrated sulfuric acid (0.31 mL, 14 mmol). After stirring at −10° C. for 15 min and room temperature for 2 h, the reaction mixture was poured onto ice (20 g), and the product was extracted with EtOAc (3×20 mL). The combined extracts were washed with brine/saturated aqueous sodium bicarbonate, dried over anhydrous MgSO$_4$, filtered, and concentrated to dryness to give the title compound.
$^1$H NMR (500 MHz, CD$_3$OD): δ 7.19 (ABq, 4H), 7.06 (d, 2H), 6.95 (d, 2H), 3.93 (ABq, 2H), 3.89 (dd, 1H), 3.10 (dd, 1H), 2.99 (dd, 1H), 1.43 (s, 3H), 1.25 (s, 3H). LC-MS: m/e 384 (M+H)$^+$ (3.9 min).

Step D 2-Amino-3,4-bis(4-chlorophenyl)-2-methylbutane hydrochloride

To a solution of N-[2,3-bis(4-chlorophenyl)-1,1-dimethylpropyl] chloroacetamide (Step C, 1.3 g, 3.8 mmol) in ethanol (10 mL) and acetic acid (2 mL) was added thiourea (0.34 g, 4.5 mmol). The reaction was stirred at 80° C. overnight to give a white precipitate. The precipitate was removed by filtration and washed with ethanol (10 mL), and the filtrate was diluted with dilute aqueous sodium hydroxide and extracted with hexane (2×50 mL). The combined extracts were dried over sodium hydroxide, filtered, and concentrated to dryness, and the residue was taken up by hydrogen chloride in dioxane (4 M, 5 mL) and concentrated to dryness to give the title compound. $1_f$ NMR (500 MHz, CD$_3$OD): (free amine) δ 7.22-

7.14 (m, 4H), 7.06 (d, 2H), 6.96 (d, 2H), 3.22 (dd, 1H), 2.95 (dd, 1H), 2.86 (dd, 1H), 1.16 (s, 3H), 1.10 (s, 3H).

Reference Example 26

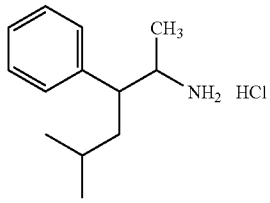

2-Amino-5-methyl-3-phenylhexane hydrochloride salt

Step A 4-Methyl-2-phenylpentanoic acid

A solution of 0.25 g (1.84 mmol) of phenylacetic acid in 3.6 mL dry THF was cooled in ice bath and 4 mL 1 M lithium bis(trimethylsilyl)amide was added. After 15 min, 0.23 mL (2.02 mmol) of isobutyliodide was added and the cold bath was removed. After stirring the reaction overnight, it was quenched with water and extracted once with EtOAc. The aqueous layer was acidified with 1.2 N HCl and extracted with EtOAc. The EtOAc solution was washed with brine, dried and concentrated to furnish the title compound which was used in the next step without purification. $^1$H NMR: (500 MHz, CDCl$_3$): δ 0.92 (d, 6H), 1.51 (m, 1H), 1.72 (m, 1H), 1.98 (m, 1H), 3.67 (m, 1H), 7.0-7.4 (m, 5H).

Step B
N-Methoxy-N-methyl-4-methyl-2-phenylpentanamide

To a solution of 0.234 g (1.22 mmol) of 4-methyl-2-phenylpentanoic acid in 6 mL CH$_2$Cl$_2$ and 2 drops of DMF, 0.12 mL (1.34 mmol) of oxalyl chloride was added. The solution was stirred for 1 h and concentrated. The residue was dissolved in 1 mL CH$_2$Cl$_2$ and added to a mixture of 0.142 g N,O-dimethylhydroxylamine hydrochloride in 4 mL CH$_2$Cl$_2$ and 4 mL saturated NaHCO$_3$. After stirring for 4 h, the layers were separated and the aqueous layer was extracted with CH$_2$Cl$_2$. The combined CH$_2$Cl$_2$ layer was washed with brine, dried and concentrated to give the title compound which was used in the next step without purification. $^1$H NMR: (500 MHz, CDCl$_3$): δ 0.94 and 0.96 (2d, 6H), 1.5 (m, 1H), 1.67 (m, 1H), 2.0 (m, 1H), 3.19 (s, 3H), 3.54 (s, 3H), 4.18 (br, 1H), 7.2-7.4 (m, 5H).

Step C 5-Methyl-3-phenyl-2-hexanone

To a solution of 75 mg (0.317 mmol) N-methoxy-N-methyl-4-methyl-2-phenylpentanamide in 1 mL dry THF, 0.45 mL 1.4 M methylmagnesium bromide was added. The reaction was stirred for 1 h, quenched with 1.2 N HCl and extracted with EtOAc. The EtOAc solution was washed with brine, dried and concentrated leaving the title compound. $^1$H NMR: (500 MHz, CDCl$_3$): δ 0.95 (2d, 6H), 1.42 (m, 1H), 1.67 (m, 1H), 1.9 (m, 1H), 2.06 (s, 3H), 3.73 (m, 1H), 7.0-7.4 (m, 5H).

Step D 5-Methyl-3-phenyl-2-hexanol

A solution of 66 mg (0.345 mmol) of 5-methyl-3-phenyl-2-hexanone in 1 mL MeOH was treated with 16 mg sodium borohydride. After 1.5 h, the reaction was quenched with 1.2 N HCl and concentrated. The residue was partitioned between EtOAc and water. The organic layer was washed with brine, dried and concentrated to yield the crude title compound which was used without purification. $^1$H NMR: (500 MHz, CDCl$_3$): δ 0.88 (2d, 6H), 1.0-1.8 (m, 4H), 1.2 (d, 3H), 2.64 (m, 1H), 3.9 (m, 1H), 7.2-7.4 (m, 5H).

Step E 2-Azido-5-methyl-3-phenylhexane

To a solution of 60 mg 5-methyl-3-phenyl-2-hexanol in 2 mL CH$_2$Cl$_2$, 0.163 g (0.62 mmol) of triphenylphosphine and 96 mg (0.31 mmol) of zinc azide pyridine were added. The reaction mixture was cooled in an ice bath and 98 mL (0.62 mmol) of DEAD was added. The cold bath was removed and the solution was stirred for 3 h. The reaction mixture was filtered through a pad of CELITE diatomaceous earth and the pad was rinsed with CH$_2$Cl$_2$. The filtrate was concentrated and the residue was purified by prep-TLC using 20% EtOAc-hexane to isolate the title compound. $^1$H NMR: (500 MHz, CDCl$_3$): δ 0.88 (2d, 6H), 1.12 (d, 3H), 1.31 (m, 1H), 1.72 (m, 2H), 2.68 (m, 1H), 3.53 (m, 1H), 7.2-7.4 (m, 5H).

Step F 2-Amino-5-methyl-3-phenylhexane

To a solution of 32 mg 2-azido-5-methyl-3-phenylhexane in 1 mL MeOH and 2 drops of 1.2 N HCl, 4 mg PtO$_2$ was added and the solution was stirred under H2 atmosphere for 2 h. The reaction was filtered through a pad of CELITE diatomaceous earth and the pad was rinsed with MeOH. The combined filtrate was concentrated to give the desired product. $^1$H NMR: (500 MHz, CDCl$_3$): δ 0.86 (m, 6H), 0.99 (d, 3H), 1.25 (m, 1H), 1.54 (m, 1H), 1.77 (m, 1H), 2.73 (m, 1H), 3.19 (m, 1H), 7.2-7.4 (m, 5H).

Reference Example 27

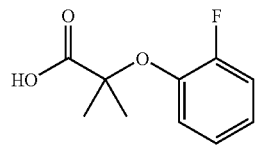

2-(2-Fluorophenyloxy)-2-methylpropionic acid

Step A 2-(2-Fluorophenyloxy)-2-methylpropionic acid

To a solution of 2-fluorophenol (2.0 g, 18 mmol) and 1,1,1-trichloro-2-methyl-2-propanol (7.9 g, 45 mmol) in acetone (100 mL) was added sodium hydroxide (7.1 g, 0.18 mol), and an ice-water bath was periodically applied to maintain a gentle reflux. After the reflux subsided, the reaction was stirred for one additional hour. The volatile materials were removed on a rotary evaporator, and the residue partitioned between ether (100 mL), hexane (100 mL) and water (200 mL). The aqueous layer was separated and acidified with concentrated hydrochloric acid (pH=2), and extracted with ether (3×100 mL). The combined extracts were dried over anhydrous MgSO$_4$, filtered, and concentrated to dryness to give the title compound, which was used without further purification. $^1$H NMR (500 MHz, CD$_3$OD): δ 7.15-7.05 (m, 4H), 1.56 (s, 6H). LC-MS: m/e 199 (M+1)$^+$ (2.3 min).

The acids of Reference Examples 28-38 were prepared following the procedures described for Reference Example 27 substituting 2-fluorophenol with appropriately substituted phenols.

Reference Example 28

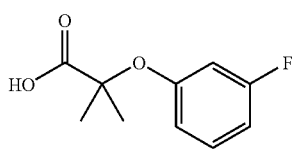

2-(3-Fluorophenyloxy)-2-methylpropionic acid $^1$H NMR (500 MHz, CD$_3$OD): δ 7.26 (ddd, 1H), 6.77-6.70 (m, 2H), 6.64 (dt, 1H), 1.59 (s, 6H). LC-MS: m/e 199 (M+1)$^+$, (2.4 min).

Reference Example 29

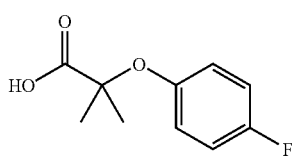

2-(4-Fluorophenyloxy)-2-methylpropionic acid $^1$H NMR (500 MHz, CD$_3$OD): δ 7.02-6.92 (m, 4H), 1.54 (s, 6H).

Reference Example 30

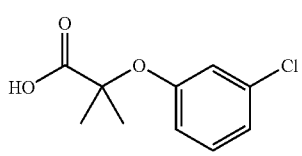

2-(3-Chlorophenyloxy)-2-methylpropionic acid $^1$H NMR (500 MHz, CD$_3$OD): δ 7.23 (t, 1H), 7.00 (dd, 1H), 6.93 (t, 1H), 6.84 (dd, 1H), 1.59 (s, 6H).
LC-MS: m/e 215 (M+1)$^+$, (2.7 min).

Reference Example 31

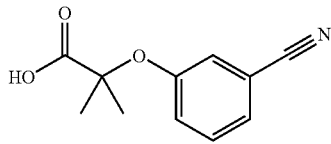

2-(3-Cyanophenyloxy)-2-methylpropionic acid $^1$H NMR (500 MHz, CD$_3$OD): δ 7.44 (dd, 1H), 7.36 (d, 1H), 7.22 (m, 2H), 1.62 (s, 6H).

Reference Example 32

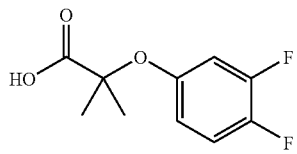

2-(3,4-Difluorophenyloxy)-2-methylpropionic acid $^1$H NMR (500 MHz, CD$_3$OD): δ 7.16 (q, 1H), 6.86 (dddd, 1H), 6.72 (m, 1H), 1.57 (s, 6H). LC-MS: m/e 217 (M+1)$^+$, (2.5 min).

Reference Example 33

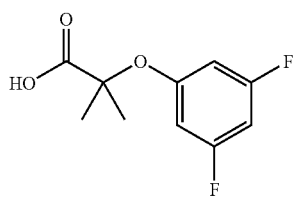

2-(3,5-Difluorophenyloxy)-2-methylpropionic acid $^1$H NMR (500 MHz, CD$_3$OD): δ 6.56 (m, 1H), 6.47 (m, 2H), 1.60 (s, 6H).

Reference Example 34

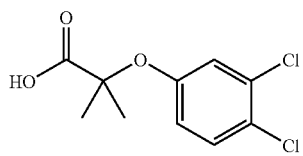

2-(3,4-Dichlorophenyloxy)-2-methylpropionic acid $^1$H NMR (500 MHz, CD$_3$OD): δ 7.40 (dd, 1H), 7.07 (d, 1H), 6.85 (dd, 1H), 1.60 (s, 6H).

Reference Example 35

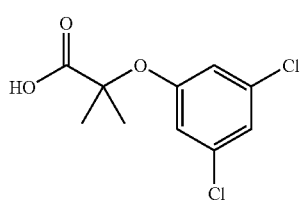

2-(3,5-Dichlorophenyloxy)-2-methylpropionic acid $^1$H NMR (500 MHz, CD$_3$OD): δ 7.05 (t, 1H), 6.84 (d, 2H), 1.60 (s, 6H).

Reference Example 36

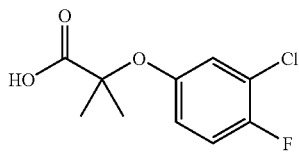

2-(3-Chloro-4-fluorophenyloxy)-2-methylpropionic acid $^1$H NMR (500 MHz, CD$_3$OD): δ 7.16 (t, 1H), 7.05 (dd, 1H), 6.90 (td, 1H), 1.57 (s, 6H).

Reference Example 37

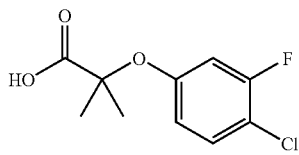

2-(4-Chloro-3-fluorophenyloxy)-2-methylpropionic acid $^1$H NMR (500 MHz, CD$_3$OD): δ 7.36 (t, 1H), 6.80 (dd, 1H), 6.74 (dd, 1H), 1.60 (s, 6H).

Reference Example 38

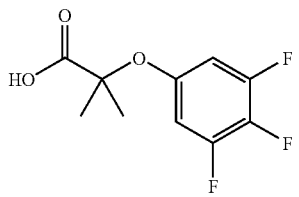

2-(3,4,5-Trifluorophenyloxy)-2-methylpropionic acid $^1$H NMR (500 MHz, CD$_3$OD): δ 6.68 (dd, 2H), 1.60 (s, 6H).

Reference Example 39

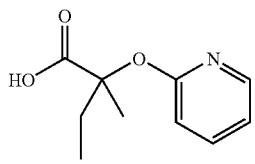

2-(2-Pyridyloxy)-2-methylbutanoic acid

Step A Benzyl 2-(2-Pyridyloxy)propionate

To a mixture of 2-hydroxypyridine (2.9 g, 30 mmol), benzyl lactate (5.0 g, 21 mmol) and triphenylphosphine (12 g, 47 mmol) in 100 mL CH$_2$Cl$_2$ was added diethylazodicarboxylate (7.8 mL, 45 mmol) at 0° C. The reaction was allowed to warm to room temperature for 4 h. The resulting mixture was diluted with hexane (100 mL) and concentrated with 20 g silica gel. The material was loaded onto a silica gel column, which was eluted with 10% EtOAc in hexane to give the title compound.

$^1$H NMR (500 MHz, CD$_3$OD): δ 8.00 (dd, 1H), 7.68 (ddd, 1H), 7.36-7.28 (m, 5H), 6.94 (dd, 1H), 6.84 (dd, 1H), 5.30 (q, 1H), 5.18 (s, 2H), 1.59 (d, 3H). LC-MS: m/e 258 (M+H)$^+$ (3.3 min).

Step B Benzyl 2-(2-Pyridyloxy)-2-methylbutanoate

To a solution of benzyl 2-(2-pyridyloxy)propionate (1.6 g, 6.2 mmol) and ethyl iodide (1.5 mL, 25 mmol) in 10 mL anhydrous THF at −78° C. was added sodium hexamethyldisilazide (1 M in THF, 9.3 mL, 9.3 mmol) (potassium hexamethyldisilazide in toluene may be used with similar results). The reaction was allowed to warm to room temperature over 2 h and was partitioned between saturated ammonium chloride (100 mL) and EtOAc (100 mL). The organic layer was separated and the aqueous layer extracted with EtOAc (2×50 mL). The combined organic extracts were dried over anhydrous sodium sulfate, filtered, and concentrated to dryness, and the residue was purified by flash column chromatography on silica gel eluted with 10% EtOAc in hexane to give the title compound. $^1$H NMR (500 MHz, CD$_3$OD): δ 7.87 (dd, 1H), 7.63 (ddd, 1H), 7.27 (m, 3H), 7.18. (m, 2H), 6.85 (dd, 1H), 6.74 (dd, 1H), 5.08 (ABq, 2H), 2.13 (m, 1H), 1.94 (m, 1H), 1.65 (s, 3H), 0.95 (t, 3H). LC-MS: m/e 286 (M+H)$^+$ (3.8 min).

Step C 2-(2-Pyridyloxy)-2-methylbutanoic Acid

A mixture of benzyl 2-(2-pyridyloxy)-2-methylbutanoate (1.6 g, 5.5 mmol) and 10% palladium on carbon (50 mg) in 50 mL MeOH was degassed and filled with hydrogen using a balloon. After stirring at room temperature overnight, the reaction mixture was filtered through CELITE diatomaceous earth and washed with MeOH (20 mL), and the filtrate was concentrated to dryness to give the title compound. $^1$H NMR (500 MHz, CD$_3$OD): δ 8.03 (dd, 1H), 7.64 (ddd, 1H), 6.89 (dd, 1H), 6.76 (dd, 1H), 2.14 (m, 1H), 1.94 (m, 1H), 1.64 (s, 3H), 0.99 (t, 3H). LC-MS: m/e 196 (M+H)$^+$ (1.8 min).

Reference Example 40

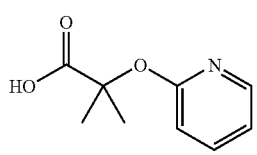

2-(2-Pyridyloxy)-2-methylpropionic Acid

The title compound was prepared following the procedures described for Reference Example 39 substituting ethyl iodide and sodium hexamethyldisilazide with methyl iodide and potassium hexamethyldisilazide respectively at Step B.

¹H NMR (500 MHz, CD₃OD): δ 8.04 (dd, 1H), 7.64 (ddd, 1H), 6.89 (dd, 1H), 6.76 (dd, 1H), 1.66 (s, 6H). LC-MS: m/e 182 (M+H)⁺ (1.5 min).

Reference Example 41

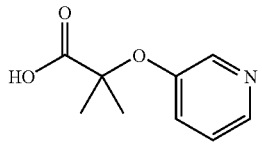

2-(3-Pyridyloxy)-2-methylpropionic Acid

The title compound was prepared following the procedures described for Reference Example 39 substituting 2-hydroxypyridine with 3-hydroxypyridine at Step A and ethyl iodide with methyl iodide at Step B. ¹H NMR (500 MHz, CD₃OD): δ 8.21 (d, 1H), 8.19 (dd, 1H), 7.43-7.35 (m, 2H), 1.62 (s, 6H). LC-MS: m/e 182 (M+H)⁺ (0.3 min).

Reference Example 42

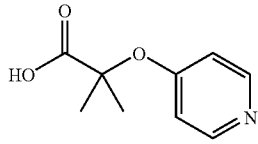

2-(4-Pyridyloxy)-2-methylpropionic Acid

Step A N-Trimethylsilylethoxymethyl-4-pyridone

To a solution of 4-hydroxypyridine (3.0 g, 32 mmol) and trimethylsilylethoxymethyl chloride (5.5 mL, 32 mmol) in 30 mL acetonitrile was added cesium carbonate (11 g, 34 mmol). After stirring at room temperature overnight, the reaction mixture was partitioned between brine (100 mL) and EtOAc (100 mL). The organic layer was separated and aqueous layer extracted with EtOAc (3×100 mL). The combined extracts were dried over anhydrous sodium sulfate, filtered, and concentrated to dryness to give the title compound contaminated with some O-alkylated product. ¹H NMR (500 MHz, CD₃OD): δ 7.92 (d, 2H), 6.49 (d, 2H), 5.28 (s, 2H), 3.62 (t, 2H), 0.96 (t, 2H), 0.024 (s, 9H).

Step B Benzyl 2-(4-Pyridyloxy)propionate

To a solution of benzyl lactate (6.0 g, 33 mmol) and N-methyl morpholine (2.7 mL, 33 mmol) in 100 mL anhydrous CH₂Cl₂ at −20° C. was added trifluoromethanesulfonyl anhydride (5.6 mL, 33 mmol). After stirring at −20° C. for 1 h, the reaction mixture was diluted with 100 mL hexane and washed with dilute aqueous sodium hydrogen sulfate and brine/saturated aqueous sodium bicarbonate. The organic layer was separated, dried over anhydrous MgSO₄, filtered, and concentrated to dryness, and the residue was purified by flash column chromatography on silica gel eluted with 10% ether in hexane to give benzyl 2-trifluoromethanesulfonyloxypropionate (6.4 g), which was used immediately for the ensuing reaction. Thus, a mixture of N-trimethylsilylethoxymethyl-4-pyridone (Step A, 3.4 g, 15 mmol) and benzyl 2-trifluoromethanesulfonyloxypropionate (4.7 g, 15 mmol) was heated at 60° C. overnight. After cooling to room temperature, the reaction mixture was dissolved in CH₂Cl₂ and loaded onto a silica gel column, which was eluted with 5% MeOH in CH₂Cl₂ to give the title compound. ¹H NMR (500 MHz, CD₃OD): δ 8.57 (d, 2H), 7.42 (d, 2H), 7.4-7.3 (m, 5H), 5.44 (q, 1H), 5.24 (ABq, 2H), 1.72 (d, 3H). LC-MS: m/e 258 (M+H)⁺ (1.8 min).

Step C 2-(4-Pyridyloxy)-2-methylpropionic acid

The product of Step B (4.5 g, 18 mmol) was converted to the title compound following the procedure described on Reference Example 39, Steps B-C substituting benzyl 2-(2-pyridyloxy)propionate and ethyl iodide with benzyl 2-(4-pyridyloxy)propionate and methyl iodide at Step B. ¹H NMR (500 MHz, CD₃OD): δ 8.44 (d, 2H), 7.14 (d, 2H), 1.70 (s, 6H). LC-MS: m/e 18(M+H)⁺ (0.28 min).

Reference Example 43

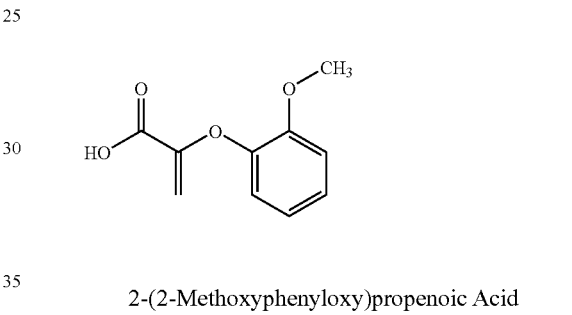

2-(2-Methoxyphenyloxy)propenoic Acid

Step A Methyl 2-(2-Methoxyphenyloxy)propenoate

To a solution of 2,3-dihydro-1,4-benzodioxine-2-carboxylic acid (1.0 g, 5.6 mmol) in CH₂Cl₂ (10 mL) and MeOH (10 mL) at 0° C. was added trimethylsilyldiazomethane (2 M in hexane) until yellow color persisted, and the reaction was stirred at room temperature for 15 min. The reaction mixture was concentrated to dryness and azeotroped with toluene. The residue was dissolved in anhydrous THF (20 mL), and was added methyl iodide (1.8 mL, 28 mmol) and potassium hexamethyldisilazide (0.5 M in toluene, 17 mL, 8.5 mmol) at −78° C. The reaction was allowed to warm to room temperature over 4 h, diluted with EtOAc (100 mL), washed with saturated ammonium chloride (100 mL) and water (100 mL), dried over anhydrous sodium sulfate, filtered, and concentrated to dryness to give the title compound. ¹H NMR (500 MHz, CD₃OD): δ 7.07 (ddd, 1H), 6.97 (dd, 1H), 6.94 (dd, 1H), 6.85 (ddd, 1H), 5.52 (d, 1H), 4.64 (d, 1H), 3.86 (s, 3H), 3.83 (s, 3H). LC-MS: m/e 231 (M+Na)⁺ (2.6 min).

Step B 2-(2-Methoxyphenyloxy)propenoic Acid

To a solution of methyl 2-(2-methoxyphenyloxy)propenoate (0.30 g, 1.4 mmol) in THF (30 mL) and water (30 mL) was added lithium hydroxide monohydrate 0.17 g, 4.0 mmol). After stirring at room temperature overnight, the reaction was quenched by addition of concentrated hydrochloric acid (final pH=2), and the product was extracted with EtOAc (3×100 mL). The combined extracts were dried over anhydrous sodium sulfate, filtered, and concentrated to dryness to give the title compound. $^1$H NMR (500 MHz, CD$_3$OD): δ 7.42 (ddd, 1H), 7.22 (dd, 1H), 7.10 (dd, 1H), 6.97 (ddd, 1H), 5.48 (d, 1H), 4.51 (d, 1H), 3.64 (s, 3H).

Reference Example 44

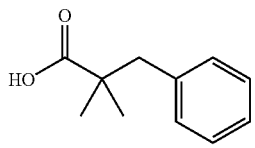

2,2-Dimethyl-3-phenylpropionic acid

Step A 1-Phenyl-2-chloro-2-methylpropane

A mixture of 5.92 g (40 mmoles) of 1-phenyl-2-hydroxy-2-methylpropane and 50 mL conc. hydrochloric acid was stirred at ice bath temperature for 1 h and at RT for 3 h. The reaction mixture was then extracted with ether. The organic layer was dried over MgSO$_4$. Solvent removal gave 1-phenyl-2-chloro-2-methylpropane.

Step B 2,2-Dimethyl-3-phenylpropionic acid

A mixture of 3.36 g (20 mmol) of the above chloride, and 560 mg (23 mmol) of magnesium turnings in 20 mL THF containing 0.01 mL 1,2-dibromoethane was stirred for 4 h at RT Most of the metal was digested. Carbon dioxide from dry ice in a flask connected with a hose was bubbled for 3 h. The reaction mixture was then stirred overnight at RT and quenched with 1N HCl. This was then extracted with EtOAc. The organic phase was dried over MgSO$_4$. Solvent removal gave a residue, which was partitioned between ether and 2N NaOH. The aqueous layer was washed with ether then acidified with 2N HCl and extracted with EtOAc. The EtOAc solution was dried over MgSO$_4$. The solvent was removed in vacuo to give the desired 2,2-dimethyl-3-propionic acid as an oil. NMR: 1.22 (s; 6H), 2.9 (s, 2H), 7.15-7.34 (m, 5H).

Reference Example 45

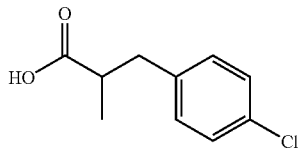

2-Methyl-3-(4-chlorophenyl)propionic acid

A solution of 3-(4-chlorophenyl)propionic acid (1.85 g, 10 mmol) in 10 mL THF was added to 16 mL freshly prepared 1.5 M LDA (24 mmol) at dryice-acetone bath temp. The reaction mixture was stirred 1 hr as it warmed to –30° C. and 1.6 mL (25 mmol) of methyl iodide was added. The resulting mixture was stirred at the same temp. for 0.5 h and the stirring was continued at RT overnight. The reaction was quenched with 1 N HCl, and diluted with ether. The solution was washed with water, 10% sodium thiosulfate and brine. The organic layer was dried over MgSO$_4$. Solvent removal gave a mixture of the desired methylated product and the starting acid. Repetition of the above procedure on this residue gave 1.3 g the desired 2-methyl-3-(4-chlorophenyl) propionic acid contaminated with ~5% of the starting acid as an oil. NMR: 1.5 (d, 3H), 4.78 (q, 1H). 6.84 & 7.26 (2d, 4H).

Reference Example 46

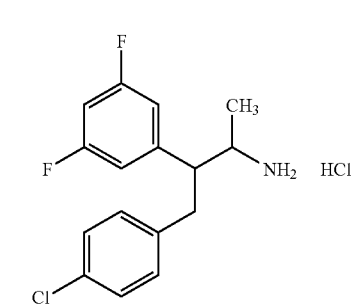

N-[3-(4-Chlorophenyl)-2-(3,5-difluorophenyl)-1-methylpropyl]amine hydrochloride (Diastereomer α)

The title compounds was prepared following the procedures described for Reference Example 10 substituting methyl phenylacetate with methyl 3,5-difluorophenylacetate (prepared from 3,5-difluorophenylacetic acid and trimethylsilyldiazomethane) at Step A and sodium borohydride in MeOH with lithium tri(sec-butylborohydride in THF at Step E. LC-MS: m/e 296 (M+H)$^+$ (2.39 min).

Reference Example 47

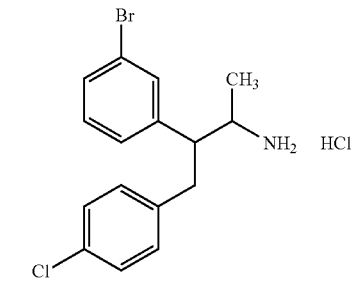

N-[2-(3-Bromophenyl)-3-(4-chlorophenyl)-1-methylpropyl]amine hydrochloride (Diastereomer α)

The title compounds was prepared following the procedures described for Reference Example 10 substituting methyl phenylacetate with methyl 3-bromophenylacetate (prepared from 3-bromophenylacetic acid and trimethylsilyldiazomethane) at Step A and sodium borohydride in MeOH with lithium tri(sec-butylborohydride in THF at Step E. LC-MS: m/e 338 (M+H)$^+$ (2.5 min).

Reference Example 48

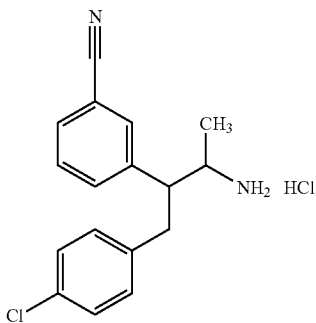

N-[3-(4-Chlorophenyl)-2-(3-cyanophenyl)-1-methyl-propyl]amine hydrochloride (Diastereomer α)

Step A 2-(N-tert-Butoxycarbonyl)amino-4-(4-chlorophenyl)-3-(3-cyanophenyl)butane To a solution of 2-(N-tert-butoxycarbonyl)amino-3-bromophenyl-4-(4-chlorophenyl)butane (Intermediate of Reference Example 471.0 g, 2.3 mmol) in 5 mL DMF was added zinc cyanide (0.16 g, 1.4 mmol), tris(dibenzylidene-acetone)dipalladium chloroform complex (3.0 mg, 2.8 µmol), 1,1'-bis(diphenylphosphino)ferrocene (5.0 mg, 9.0 µmol) and water (0.1 mL). After heating at 120° C. for 6 h under nitrogen, another batch of zinc cyanide (0.16 g, 1.4 mmol), tris(dibenzylideneacetone)dipalladium chloroform complex (5.0 mg, 4.8 µmol), 1,1'-bis(diphenylphosphino)ferrocene (5.0 mg, 9.0 µmol) and water (0.05 mL) was added, and heating was continued for another 18 h. After cooling to room temperature, the resulting mixture was partitioned between water (50 mL) and ether (50 mL). The organic layer was separated and the aqueous layer extracted with ether (2×50 mL). The combined extracts were dried over anhydrous MgSO$_4$, filtered and concentrated, and the residue was purified by flash column chromatography on silica gel eluted with 20% EtOAc in hexane to afford the title compound. $^1$H NMR (400 MHz, CD$_3$OD): δ 7.6-7.3 (m, 4H), 7.10 (d, 2H), 6.92 (d, 2H), 3.88 (m, 1H), 3.20 (m, 1H), 2.97 (m, 1H), 1.82 (m, 1H), 1.45 (s, 9H), 0.94 (d, 3H). LC-MS: m/e 385 (M+H)$^+$ (3.9 min).

Step B N-[3-(4-Chlorophenyl)-2-(3-cyanophenyl)-1-methylpropyl]amine hydrochloride (Diastereomer α)

The title compound was prepared following the procedure described for Reference Example 10, Step I. LC-MS: m/e 285 (M+H)$^+$ (2.2 min).

Reference Example 49

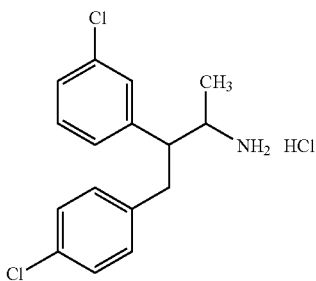

N-[2-(3-Chlorophenyl)-3-(4-chlorophenyl)-1-methylpropyl]amine hydrochloride (Diastereomer α)

Step A 2-(N-tert-Butoxycarbonyl)amino-4-(4-chlorophenyl)-3-(3-trimethylstannylphenyl)butane To a solution of 2-(N-tert-butoxycarbonyl)amino-3-(3-bromophenyl)-4-(4-chlorophenyl)butane (intermediate of Reference Example 47, 1.5 g, 3.4 mmol) in 15 mL anhydrous dioxane was added hexamethylditin (1.6 g, 4.8 mmol), triphenylphosphine (18 mg, 0.068 mmol), lithium chloride (0.16 g, 3.8 mmol) and tetrakis(triphenyl-phosphine)palladium (0.20 g, 0.17 mmol). After heating at 95° C. for 7.5 h under nitrogen, the reaction mixture was cooled to room temperature, diluted with EtOAc (100 mL), washed with 10% aqueous potassium fluoride and brine, dried over anhydrous MgSO$_4$, filtered and concentrated to dryness. The residue was purified by flash column chromatography on silica gel eluted with 20% EtOAc in hexane to afford the title compound. $^1$H NMR (500 MHz, CD$_3$OD): δ 7.3-7.2 (m, 2H), 7.07 (d, J=8.5 Hz, 2H), 7.06-6.99 (m, 2H), 6.86 (d, J=8.5 Hz, 2H), 3.93 (m, 1H), 3.18 (m, 1H), 2.76 (m, 2H), 1.51 (s, 9H), 0.94 (d, J=7.0 Hz, 3H), 0.21 (s, 9H).

Step B 2-(N-tert-Butoxycarbonyl)amino-3-(3-chlorophenyl)-4-(4-chlorophenyl)butane To a solution of 2-(N-tert-butoxycarbonyl)amino-4-(4-chlorophenyl)-3-(3-trimethylstanylphenyl)butane (0.55 g, 1.0 mmol) in 5 mL CH$_2$Cl$_2$ at 0° C. was added tert-butoxychloride (freshly prepared, 0.20 mL, 1.1 mmol). The reaction was allowed to warm to room temperature over 2 h, and the resulting mixture was concentrated with 2 g silica gel. The residue was purified by flash column chromatography on silica gel eluted with 10% ether in hexane to afford the title compound. $^1$H NMR (500 MHz, CD$_3$OD): δ 7.25-7.15 (m, 2H), 7.11 (d, J=8.5 Hz, 2H), 7.09 (m, 1H), 6.99 (d, J=7.5 Hz, 1H), 6.92 (d, J=8.5 Hz, 2H), 3.88 (m, 1H), 3.19 (dd, J=13.0, 3.5 Hz, 1H), 2.90-2.75 (m, 2H), 1.50 (s, 9H), 0.94 (d, J=6.5 Hz).

Step C N-[2-(3-Chlorophenyl)-3-(4-chlorophenyl)-1-methylpropyl]amine hydrochloride (Diastereomer α)

The title compound was prepared following the procedure described for Reference Example 10, Step I. LC-MS: m/e 294 (M+H)$^+$ (2.82 min).

Reference Example 50

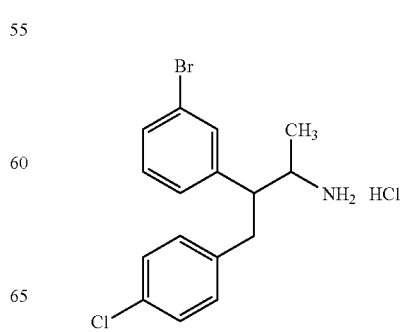

-continued

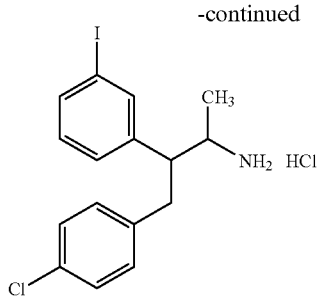

N-[2-(3-Bromophenyl)-3-(4-chlorophenyl)-1-methylpropyl]amine hydrochloride and N-[3-(4-Chlorophenyl)-2-(3-iodophenyl)-1-methylpropyl]amine hydrochloride (1:1 mixture) (Diastereomer α)

Step A 2-(N-tert-Butoxycarbonyl)amino-3-(3-bromophenyl)-4-(4-chlorophenyl)-butane and 2-(N-tert-Butoxycarbonyl)amino-4-(4-chlorophenyl)-3-(3-iodophenyl)butane To a solution of 2-(N-tert-butoxycarbonyl)amino-3-(3-bromophenyl)-4-(4-chlorophenyl)butane (intermediate of Reference Example 47, 2.6 g, 5.9 mmol) in 7 mL anhydrous THF at 0° C. was added methylmagnesium chloride (3 M in THF, 3.9 mL, 12 mmol). After 30 min, the reaction mixture was cooled to −78° C., and was added tert-butyllithium (1.7 M, 10 mL, 17 mmol). After stirring at −78° C. for 2 h, the reaction was allowed to warm to 0° C., and half of the resulting mixture was added to a suspension of iodine (5.0 g, mmol) in 10 mL THF at −40° C. The reaction mixture was allowed to warm to room temperature over 2 h, and was partitioned between ether (100 mL) and saturated aqueous ammonium chloride (100 mL). The organic layer was separated and the aqueous layer extracted with ether (2×50 mL). The combined extracts were washed with dilute aqueous sodium thiosulfate (2×) and brine, dried over anhydrous MgSO$_4$, filtered and concentrated to dryness. The residue was purified by flash column chromatography on silica gel eluted with 10% EtOAc in hexane to afford the title compounds as a 1:1 mixture.

Step B N-[2-(3-Bromophenyl)-3-(4-chlorophenyl)-1-methylpropyl]amine hydrochloride and N-[3-(4-chlorophenyl)-2-(3-iodophenyl)-1-methylpropyl]amine hydrochloride (1:1 mixture) (Diastereomer α)

The title compound was prepared following procedure described for Reference Example 10, Step I. LC-MS: m/e 338/386/(M+H)$^+$ (2.6 min).

Reference Example 51

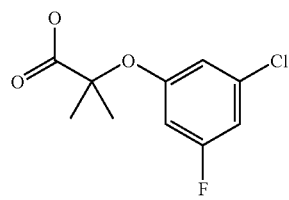

2-Methyl-2-(4-trifluoromethylphenyloxy)propionic acid

The title compound was prepared following the same procedure described for Reference Example 27. $^1$H NMR (500 MHz, CD$_3$OD): δ 7.56 (d, 2H), 7.00 (d, 2H), 1.62 (s, 6H).

Reference Example 52

2-Methyl-2-(3-chloro-5-fluorophenyloxy)propionic acid

Step A 3-Chloro-5-fluorophenol

To a solution of 1-bromo-3-chloro-5-fluorobenzene (16 g, 76 mmol) in 250 mL anhydrous ether at −78° C. was added tert-butyllithium (1.7 M, 100 mL, 170 mmol). After stirring at −78° C. for 1 h, trimethyl borate (20 mL, 176 mmol) was added, and the reaction was allowed to warm to room temperature overnight. The resulting mixture was cooled to −10° C., and was added peracetic acid (32% in acetic acid, 35 mL). After stirring at 0° C. for 30 min, potassium bisulfite (5 g) was added. After stirring at room temperature for 30 min, the aqueous layer was separated and the organic mixture was extracted with 3 M aqueous sodium hydroxide (3×100 mL). The aqueous extracts were acidified with concentrated hydrochloric acid (pH=2), and was extracted with ether (3×150 mL). The combined ether extracts were dried over anhydrous MgSO$_4$, filtered and concentrated to afford the crude phenol, which was azeotroped with heptane (100 mL) to remove traces of acetic acid to give the title compound. $^1$H NMR (500 MHz, CD$_3$OD): δ 7.51 (br s, 1H), 7.35 (br d, 1H), 7.21 (m, 1H).

Step B
2-Methyl-2-(3-chloro-5-fluorophenyloxy)propionic acid

The title compound was prepared following the procedures described for Reference Example 27. $^1$H NMR (500 MHz, CD$_3$OD): δ 7.53 (br s, 1H), 7.36 (br d, 1H), 7.20 (m, 1H), 1.24 (s, 6H).

Reference Example 53

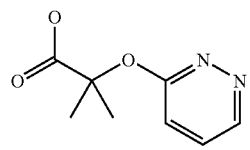

2-Methyl-2-(3-pyridazinyloxy)propionic acid

The title compound was prepared following the procedures described for Reference Example 39 substituting 2-hydroxypyridine with 3-hydroxypyridazine at Step A and ethyl iodide with methyl iodide at Step B. ¹H NMR (500 MHz, CD₃OD): δ 7.98 (dd, 1H), 7.45 (dd, 1H), 6.96 (dd, 1H), 1.70 (s, 6H).

Reference Example 54

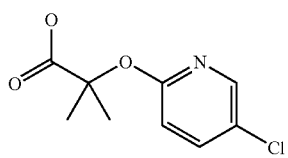

2-Methyl-2-(5-chloro-2-pyridyloxy)propionic acid

Step A Ethyl
2-Methyl-2-(5-chloro-2-pyridyloxy)propionate

A mixture of 5-chloro-2-hydroxypyridine (5.0 g, 39 mmol), ethyl 2-bromoisobutyrate (5.7 mL, 39 mmol) and cesium carbonate (25 g, 77 mmol) in 50 mL acetonitrile was heated at 50° C. overnight. The volatile materials were removed by concentrating on a rotary evaporator, and the residue was partitioned between water (100 mL) and EtOAc (100 mL). The organic layer was separated and the aqueous layer extracted with EtOAc (2×100 mL). The combined organic extracts were dried over anhydrous sodium sulfate, filtered and concentrated to dryness, and the residue was purified by flash column chromatography on silica gel eluted with 5% EtOAc in hexane to give the title compound. ¹H NMR (500 MHz, CD₃OD): δ 7.99 (d, 1H), 7.67 (dd, 1H), 6.68 (d, 1H), 4.13 (q, 2H), 1.64 (s, 6H), 1.14 (t, 3H). LC-MS: m/e 244 (M+H)⁺ (3.41 min).

Step B 2-Methyl-2-(5-chloro-2-pyridyloxy)propionic Acid

A mixture of ethyl 2-methyl-2-(5-chloro-2-pyridyloxy) propionate and sodium hydroxide (0.85 g, 21 mmol) in 15 mL acetonitrile and 15 mL water was heated at 50° C. overnight. The volatile materials were removed by concentrating on a rotary evaporator, and the residue was partitioned between 2 M hydrochloric acid (100 mL) and ether (100 mL). The organic layer was separated and washed with water (2×50 mL), dried over anhydrous MgSO₄, filtered and concentrated to dryness to give the title compound. ¹H NMR (500 MHz, CD₃OD): δ 8.02 (d, 1H), 7.65 (dd, 1H), 6.77 (d, 1H), 1.62 (s, 6H). LC-MS: m/e 216 (M+H)⁺ (2.33 min).

Reference Example 55

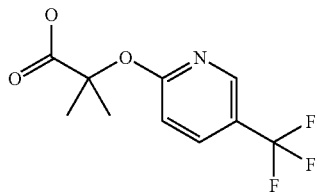

2-Methyl-2-(5-trifluoromethyl-2-pyridyloxy)propionic Acid

The title compound was prepared following the procedures described for Reference Example 54 substituting 5-chloro-2-hydroxypyridine with 5-trifluoromethyl-2-hydroxypyridine at Step A. ¹H NMR (500 MHz, CD₃OD): δ 8.38 (br s, 1H), 7.93 (dd, 1H), 7.13 (d, 1H), 1.70 (s, 6H). LC-MS: m/e 250 (M+H)⁺ (2.6 min).

Reference Example 56

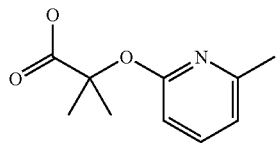

2-Methyl-2-(6-methyl-2-pyridyloxy)propionic Acid

The title compound was prepared following the procedures described for Reference Example 54 substituting 5-chloro-2-hydroxypyridine with 6-methyl-2-hydroxpyridine at Step A. ¹H NMR (500 MHz, CD₃OD): δ 7.51 (t, 1H), 6.74 (d, 1H), 6.53 (d, 1H), 2.34 (s, 3H), 1.64 (s, 6H). LC-MS: m/e 196 (M+H)⁺ (1.3 min).

Reference Example 57

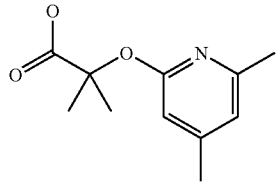

2-Methyl-2-(4,6-dimethyl-2-pyridyloxy)propionic Acid

The title compound was prepared following the procedures described for Reference Example 54 substituting 5-chloro-2-hydroxypyridine with 4,6-dimethyl-2-hydroxpyridine at Step A. LC-MS: m/e 210 (M+H)⁺ (1.17 min).

Reference Example 58

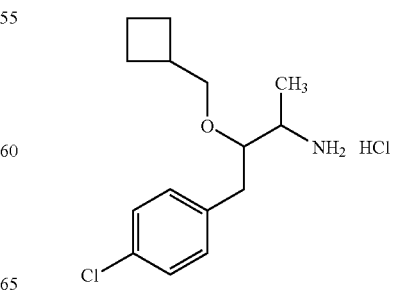

2-Amino-4-(4-chlorophenyl)-3-cyclobutylmethoxybutane

Step A Methyl
2-diazo-3-(4-chlorophenyl)propanoate

DL-4-Chlorophenylalanine methyl ester (5.0 g, 23.36 mmol) was dissolved in 120 mL chloroform and placed into an oven-dried 3-neck flask equipped with a condenser and an addition funnel. Glacial acetic acid (0.267 mL, 4.672 mmol) was added. Finally, isoamylnitrite (3.8 mL, 28 mmol) was added dropwise while slowly bringing the reaction to reflux (73° C.). The reaction was refluxed for 30 minutes and then cooled to 0° C. The reaction mixture was washed with cold 1 N sulfuric acid solution, cold water, cold saturated aqueous sodium bicarbonate solution, and then cold water again. The organic extracts were dried over $MgSO_4$, filtered and concentrated under reduced pressure. The crude mixture was purified by flash chromatography (Biotage 40M cartridge, gradient elution using hexane and EtOAc (100:1 to 50:1) to provide a yellow oil, homogeneous by TLC, $R_f$=0.48 (4:1 hexanes:EtOAc). 500 MHz $^1$H NMR ($CDCl_3$): δ 3.65 (s, 2H); 3.83 (s, 3H); 7.22 (d, J=8.5 Hz, 2H), 7.34 (d, J=8.5, 2H).

Step B Methyl
3-(4-chlorophenyl)-2-cyclobutylmethoxypropanoate

To a solution of 500 mg (2.23 mmol) of methyl-2-diazo-3-(4-chlorophenyl)propanoate (obtained from Step A) and 1.05 mL (5 eq; 11.1 mmol) of cyclobutanemethanol in 5 mL benzene in a pressure tube was added 10 mg (1 mole %) of $Rh_2(OAc)_4$ catalyst. The tube was sealed and heated to 90° C. for 1.5 h. The solvents were evaporated under reduced pressure and the crude material was taken up in $CH_2Cl_2$ and purified by flash chromatography via gradient elution using mixtures of hexane and EtOAc (100:1 to 50:1). This provided the title compound as a clear oil. TLC $R_f$=0.53 (4:1 hexanes: EtOAc). 500 MHz $^1$H NMR ($CDCl_3$): δ 1.68 (m, 2H); 1.85 (m, 1H); 1.88 (m, 1H); 2.01 (m, 2H); 2.53 (sep, 1H); 2.98 (m, 2H); 3.24 (dd, 1H); 3.58 (dd, 1H); 3.76 (s, 3H); 3.98 (dd, 1H); 7.20 (d, 2H); 7.28 (d, 2H).

Step C
4-(4-Chlorophenyl)-3-cyclobutylmethoxybutan-2-one

At 0° C., under anhydrous conditions, to a stirred suspension of N,O-dimethylhydroxylaminehydrochloride (732 mg, 7.50 mmol) in 60 mL $CH_2Cl_2$ was added dimethylaluminum chloride (7.5 mL, 1M solution in hexanes). The solution was allowed to warm to room temperature over a period of one hour. At that point a solution of methyl 2-cyclobutylmethoxy-3-(4-chlorophenyl) propanoate (531 mg, 1.88 mmol, obtained from Step B) in $CH_2Cl_2$ (8 mL) was added dropwise. The reaction was allowed to stir overnight at room temperature when TLC indicated completion of reaction. The reaction was worked up by the addition of pH=8 phospate buffer (25 mL, approx. 3 mL/mmol of $Me_2AlCl$) and allowed to stir at room temperature for 30 minutes, diluted with chloroform (75 mL), and the phases were separated. The organic layer was washed with water and dried over $MgSO_4$. The solvents were evaporated under reduced pressure and the crude product was purified by flash chromatography (gradient elution using hexane and EtOAc, 20:1 to 5:1) to give the Weinreb amide as a clear oil). This purified material (424 mg, 1.36 mmol) was dissolved in 10 mL THF, injected into an oven dried flask, and cooled to 0° C. under nitrogen. Methyl magnesium bromide (1.4 mL 3M solution in ether) was added to the solution dropwise. The reaction was allowed to warm to room temperature. After 4 h the TLC indicated a complete reaction. The reaction was quenched with enough 10% citric acid to bring the pH of the solution to approximately 3. The aqueous layer was extract with ether. The combined organics were washed with water and then dried over $MgSO_4$. The solvents were evaporated under reduced pressure and the crude material was purified by flash chromatography (hexane:EtOAc, 100:1 to 50:1), resulting in 250 mg the title compound as a clear oil. TLC $R_f$=0.55 (4:1 hexanes:EtOAc). 500 MHz $^1$H NMR ($CDCl_3$): δ 1.71 (m, 2H); 1.84 (m, 1H); 1.91 (m, 1H); 2.01 (m, 2H); 2.17 (s, 3H); 2.53 (sep, 1H); 2.90 (m, 2H); 3.28 (dd, 1H); 3.43 (dd, 1H); 3.81 (dd, 1H).

Step D 2-Amino-4-(4-chlorophenyl)-3-cyclobutyl-methoxybutane

A solution of 3-cyclobutylmethoxy-4-(4-chlorophenyl)butan-2-one (247 mg, 0.925 mmol, obtained from Step C) in 0.5 mL $CH_2Cl_2$ was added to a stirred suspension of $NH_4OAc$ (715 mg, 9.25 mmol) and $NaBH_3CN$ (35 mg, 0.555 mmol) at room temperature and allowed to stir overnight. The reaction was quenched by the addition of 2.2 mL conc. HCl allowed to stir for 30 minutes. The solvents were evaporated under reduced pressure and the residue was partitioned between ether and water. The aqueous layer was washed two more times with ether. The combined organics were dried over $Na_2SO_4$. The crude product mixture obtained after filtration and removal of volatiles was purified by flash chromatography, eluting using mixtures of mixtures of $CH_2Cl_2$ and MeOH (100% $CH_2Cl_2$, to 5% MeOH in $CH_2Cl_2$) to provide the title compound as a yellow oil, homogeneous by TLC $R_f$0.12 (5% MeOH in $CH_2Cl_2$). 500 MHz $^1$H NMR ($CDCl_3$): δ 1.16 (t, 3H); 1.67 (m, 2H); 1.85 (m, 3H); 2.01 (m, 2H); 2.48 (m, 1H); 2.74 (m, 2H); 2.90 (dd, 1H); 3.15 (d quint, 2H); 3.37 (m, 2H).

2-Amino-4-(4-chlorophenyl)-3-methoxy-butane, 2-amino-4-(4-chlorophenyl)-3-ethoxy-butane, 2-amino-4-(4-chlorophenyl)-3-n-propyloxy-butane, 2-amino-4-(4-chlorophenyl)-3-n-pentyloxy-butane, and 2-amino-4-(4-chlorophenyl)-3-cyclopentylmethoxy-butane were prepared according to the procedures described in Reference Example 58 substituting an appropriate alcohol for cyclobutylmethanol in Step B.

Reference Example 59

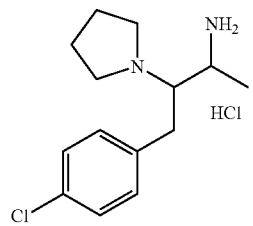

2-Amino-4-(4-chlorophenyl)-3-(1-pyrrolidinyl)-butane hydrochloride

Step A Ethyl
3-(4-chlorophenyl)-2-pyrrolidin-N-yl-propanoate

While stirring rapidly, to a mixture of DL-4-chlorophenylalanine methyl ester hydrochloride (2.5 g, 10 mmole), 40 mL ethanol and sodium carbonate (3.18 g, 30 mmole) was added dropwise a solution of 1,4-dibromobutane (2.16 g, 10 mmol) dissolved in 20 mL ethanol. The mixture was refluxed overnight. The volatiles were removed under reduced pressure, and the residue was partitioned between water and EtOAc. The aqueous layer was re-extracted with EtOAc thrice. The organic layers were combined and washed the water and brine and dried over anhydrous $MgSO_4$. The crude product obtained after filtration and removal of volatiles was purified via flash chromatography using mixtures of $CH_2Cl_2$ and MeOH to provide the titled compound as an oil, homogeneous by TLC, $R_f$=0.55 in 95:5 $CH_2Cl_2$: MeOH. LC/MS m/e=282.1 (M+1). 400 MHz $^1$H NMR ($CDCl_3$) δ 1.12 (t, J=7.2 Hz, 3H), 1.72 (m, 4H), 2.67 (m, 1H), 2.76 (m, 1H), 3.05 (m, 4H), 3.43 (m, 1H), 4.05 (m, 2H), 7.13 (d, J=8.2 Hz, 2H), 7.24 (d, J=8.2 Hz, 2H)

Step B 4-(4-Chlorophenyl)-3-(1-pyrrolidinyl)-butan-2-one

The title compound was prepared according to the procedure of Reference Example 10, Step C except that ethyl 3-(4-chlorophenyl)-2-(1-pyrrolidinyl)-propanoate (from Step A) was the ester used (two steps). TLC $R_f$=0.7 (95:5 $CH_2Cl_2$: MeOH). LC/MS m/e=252 (M+1). 500 MHz $^1$H NMR ($CDCl_3$) δ 1.86 (br s, 4H), 2.03 (s, 3H), 2.66 (m, 2H), 2.78 (m, 2H), 2.98 (dd, J=2.9, 10.3 Hz, 1H), 3.08 (m, 1H), 3.43 (m, 1H), 7.12 (d, J=8.3 Hz, 2H), 7.26 (d, J=8.3 Hz, 2H)

Step C 4-(4-Chlorophenyl)-3-pyrrolidin-N-yl-butan-2-one oxime

To a solution of 4-(4-chlorophenyl)-3-pyrrolidin-N-yl-butan-2-one (200 mg, 0.79 mmol, from Step B) dissolved in ethanol (2 mL), was added pyridine (63 mg, 0.79 mmol), and hydroxylamine hydrochloride (78 mg, 1.12 mmol). The mixture was refluxed for 24 h when LC/MS indicated disappearance of all starting material. The mixture was cooled to room temperature, concentrated under reduced pressure, treated with 33% aqueous potassium carbonated, and extracted with chloroform 5 times. The organic layers were combined and filtered over glass wool and dried over potassium carbonate. The filtrated obtained after passing through sintered glass was concentrated to give the oxime, homogeneous by TLC, $R_f$=0.3 in 95:5 $CH_2Cl_2$: MeOH. LC/MS m/e=267 (M+1). 500 MHz $^1$H NMR ($CDCl_3$) δ 1.73 (m, 4H), 1.76 (s, 3H), 2.40 (m, 2H), 2.60 (m, 2H), 2.72 (dd, J=2.7, 10.8 Hz, 1H), 2.94 (dd, J=4.3, 8.8 Hz, 1H), 3.03 (dd, J=4.4, 13.3 Hz, 1H), 3.8 (s, 1H), 6.96 (d, J=8.3 Hz, 2H), 7.11 (d, J=8.3 Hz, 2H)

Step D 2-Amino-4-(4-chlorophenyl)-3-pyrrolidin-N-yl-butane hydrochloride

At room temperature, to a solution of 4-(4-chlorophenyl)-3-pyrrolidin-N-yl-butan-2-one oxime (173 mg, 0.648 mmol, from Step C) in 1.8 mL anhydrous THF was added dropwise a 1M solution of lithium aluminum hydride in THF (0.778 mmole). The mixture was refluxed for 20 h. The reaction was quenched by addition of saturated aqueous sodium sulfate (0.1 mL), and stirred overnight. This mixture was filtered over a pad of CELITE diatomaceous earth, and the filtrate was concentrated to dryness. The mass spectrum of this material looked very messy, so the HCl salt was prepared (by addition of a HCl(g) in ether solution) in attempt to clean up the mess. By NMR, the reductive amination provided a ~1:1 mixture of the two diastereomeric pairs of amines. This HCl salt was rather sticky and difficult to work with and therefore was used in the ensuing coupling experiment without further purification. LC/MS m/e=253 (M+1). 500 MHz $^1$H NMR ($CD_3OD$) δ 1.56, 1.59 (2 d, J=7.2 Hz, 3H), 2.03 (m, 6H), 2.08 (m, 2H), 3.20-4.00 (m, 3H), 7.43 (m, 4H)

Reference Example 60

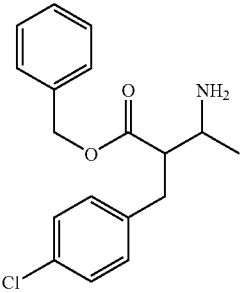

Benzyl 3-amino-2-(4-chlorobenzyl)butyrate

Step A Benzyl 2-(4-chlorobenzyl)-3-ketobutyrate

Benzyl acetoacetate (1.92 g, 10 mmole) and 4-chlorobenzylbromide (2.05 g, 10 mmole) were dissolved in 40 mL anhydrous THF and cooled to −10° C. To this mixture was added dropwise slowly a solution of solution of sodium hexamethyl disilazide (0.5M solution in THF). Monoalkylation occurred almost exclusively of bisalkylation between −10 and 5° C. After quenching with water, the organics were extracted with EtOAc three times. The combined organic layer was washed with brine and dried over anhydrous $MgSO_4$. The crude product obtained after filtration and removal of volatiles was purified via flash chromatography using gradient elution (mixtures of hexane and EtOAc) to provide of the title compound as a clear yellow liquid, homogeneous by TLC, $R_f$=0.4 in 4:1 hexane:EtOAc. By NMR, this compound, this compound exists in a ~4:1 ratio of the keto: enol forms. 400 MHz $^1$H NMR ($CDCl_3$) δ 2.08, 2.18 (2 s, 3H), 3.15 (m, 2H), 3.80 (t, J=7.5 Hz, 0.8H), 5.14, 5.17 (2 s, 2H), 7.05-7.39 (m, 9H).

Step B Benzyl 3-amino-2-(4-chlorobenzyl)butyrate

Benzyl 2-(4-chlorobenzyl)-3-ketobutyrate (317 mg, 1 mmole, obtained from Step A) was added to a cooled mixture of 7M ammonia in MeOH (2.42 mL) and glacial acetic acid (1.6 mL). To this solution, at 10° C., was added sodium cyanoborohydride (101 mg, 1.75 mmol) in small portions. This mixture was stirred at room temperature for 40 h. The excess sodium cyanoborohydride was destroyed by the addition of 6M HCl (to pH 1). The residue obtained after removal of volatiles was taken up in a minimal amount of water and extracted with ether. The aqueous layer was basified to pH 10 using solid KOH. This layer was then saturated with sodium chloride and then extracted with EtOAc. Further analyses of the ether and the EtOAc layers suggest that the desired product resides the EtOAc layer. This material was used in the ensuing coupling reaction without further purification. Proton NMR spectrum show that the two pairs of diastereomers are obtained in ~1:1 ratio, homogeneous by TLC, $R_f$=0.4 in 95:5 $CH_2Cl_2$: MeOH. LC/MS m/e=318 (M+1). 400 MHz $^1$H NMR ($CDCl_3$) δ 1.27, 1.29 (2 d, J=7 Hz, 3H), 2.85 (m, 1H), 3.03 (m, 1H), 3.15 (m, 1H), 3.55 (m, 1H), 4.85 (br, 2H), 5.00-5.18 (m, 2H), 7.0-7.2 (m, 9H).

Reference Example 61

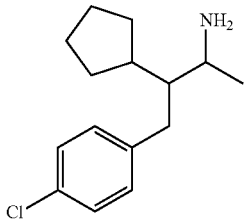

2-Amino-4-(4-chlorophenyl)-3-cyclopentylbutane

Step A Methyl 3-(4-chlorophenyl)-2-cyclolentylpropanoate

A mixture of methyl cyclopentylacetate (3.52 g, 25 mmol) and 4-chlorobenzyl bromide (4.75 g, 23 mmol) was dissolved in 100 mL THF in an oven-dried flask. The solution was cooled to −40° C. and 23 mL 1M NaHMDS solution in hexanes was added slowly over an hour while maintaining the temperature at −40° C. The solution was then stirred for an additional 3 h at −40° C. The reaction was quenched at −40° C. with enough 10% citric acid solution to bring the pH to 3.5. The aqueous layer was extracted with ether three times. The combined organics were washed with water and dried over MgSO$_4$. The solvents were evaporated under reduced pressure and the crude material was purified by flash chromatography [Biotage 40 M, gradient elution using mixtures of hexane and EtOAc (from 0-1% EtOAc)]. This provided a light brown oil, which is a 3:1 ratio of the title compound: methyl cyclopentylacetate based on the methyl ester peak integrations. TLC of the desired product: $R_f$=0.34 in 20:1 hexane:EtOAc. The complete separation of the title compound from the starting material was not practical in this case, as they had overlapping $R_f$'s on the TLC. Therefore, this mixture was carried on to the next step.

Step B 3-(4-Chlorophenyl)-2-cyclopentylpropanioc acid

The mixture of methyl esters from Step A (3.41 g, 14.48 mmol of methyl 3-(4-chlorophenyl)-2-cyclopentylpropanoate—assuming 3:1 mixture obtained in Step A.) was dissolved in 10 mL DMSO and 4 mL distilled water. Then powdered KOH (3.25 g, 57.92 mmol) was added and the solution was stirred overnight at room temperature. The next day the pH was brought to 2 with 2 N HCl. The aqueous layer was extracted 3 times with ether. The combined organic extracts were dried over anhydrous sodium sulfate. Filtration and evaporation of volatiles provided the mixture of acids as an oil. 500 MHz $^1$H NMR (CDCl$_3$): δ 1.28 (m, 2H), 1.64 (m, 6H), 2.06 (m, 1H), 2.47 (m, 1H), 2.86 (t, 2H).

Step C 3-(4-Chlorophenyl)-2-cyclopentyl —N,O-dimethyl-propanamide

The mixture of acids obtained in Step B (3.21 g, 14.48 mmol of the desired acid—based on assumption of 3:1 mixture from Step B) was dissolved in 75 mL CH$_2$Cl$_2$. While being stirred rigorously, N,O-dimethylhydroxylamine hydrochloride (1.56 g, 15.95 mmol), 1-ethyl-3-(3-dimethylaminopropyl)carbodiimide (3.06 g, 16.0 mmol), diisopropylethylamine (5.56 mL, 31.90 mmol), and a catalytic amount of 4-(dimethylaminopyridine) were added sequentially. Stirring was continued overnight at room temperature. The next day the reaction mixture was diluted with EtOAc, treated with water, and the phases were separated. The aqueous layer was re-extracted with EtOAc twice. The combined organic layers were washed with water three times and then with saturated brine. The organic layer was dried over MgSO$_4$, filtered, and the solvents were removed under reduced pressure. The crude material was purified by flash chromatography [Biotage 40 M column, gradient elution using mixtures or hexanes and EtOAc (100:1 to 20:1] to provide the title compound cleanly as an oil. TLC $R_f$=0.31 (4:1 hexanes:EtOAc). LC/MS m/e 295.9 (M+1). 500 MHz $^1$H NMR (CDCl$_3$): δ 1.27 (m, 2H), 1.64 (m, 6H), 1.97 (m, 1H), 2.13 (q, 1H), 2.81 (d, 1H), 2.97 (d, 1H), 3.07 (s, 3H), 3.17 (s, 3H). LC/MS m/e 295.9 (M+1).

Step D 4-(4-Chlorophenyl)-3-cyclopentylbutan-2-one 3-(4-Chlorophenyl)-2-cyclopentyl —N,O-dimethyl-propanamide (514 mg, 1.737 mmol, obtained from Step C) was dissolved in 15 mL anhydrous THF and injected into an oven dried flask under nitrogen. The solution was cooled to 0° C. and CH$_3$MgBr (1 M in ether) was added dropwise. The ice bath was removed and the reaction was allowed to warm to room temperature and stirred for a total of 4 h. TLC indicated a nearly complete reaction. The reaction was quenched with enough 10% citric acid to bring the pH of the solution to 3. The aqueous layer was extracted 3 times with ether and the extracts were dried over anhydrous MgSO$_4$. The solution was filtered and the solvents were removed under reduced pressure. The crude material was purified by flash chromatography (30 mL silica; 100:1 to 50:1 hexanes: EtOAc) to provide 351 mg the title compound as an oil. TLC $R_f$ 0.49 (4:1 hexanes: EtOAc). 500 MHz $^1$H NMR (CDCl$_3$): δ1.23 (m, 3H), 1.58 (m, 1H), 1.71 (m, 3H), 1.91 (s, 3H), 1.93 (m, 1H), 2.05 (m, 1H), 2.68 (m, 1H), 2.84 (m, 2H).

Step E 2-Amino-4-(4-chlorophenyl)-3-cyclopentylbutane

The title compound was prepared according to the procedure of Reference Example 45, Step D, except that 4-(4-chlorophenyl)-3-cyclopentylbutan-2-one (obtained form Step D) was used as the starting material. LC/MS m/e 251.9 (M+1); 500 MHz $^1$H NMR (CDCl$_3$): δ 0.93 (m, 1H), 1.29 (q, 3H), 1.29 (m, 2H), 1.61 (m, 4H), 1.87 (m, 3H), 2.62 (m, 1H), 2.80 (m, 1H), 3.26 and 3.48 (m, 1H).

2-Amino-4-(4-chlorophenyl)-3-ethyl-butane and 2-amino-4-(4-chlorophenyl)-3-isopropyl-butane were also prepared according to the procedures described in Reference Example 61 substituting the appropriate ester for methyl cyclopentylacetate in Step A.

Reference Example 62

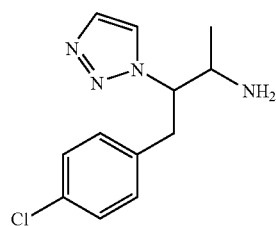

2-Amino-3-(1-(1,2,3-triazolyl))-4-(4-chlorophenyl)butane

Step A Benzyl 2-(1-(1,2,3-triazolyl))acetate

A mixture of 1,2,3-triazole (2.07 g, 30 mmol), benzyl bromoacetate (6.9 g, 30 mmol), and diisopropylethylamine (5.1 mL, 30 mmol) in 40 mL $CH_2Cl_2$ was stirred overnight at room temperature. This mixture was then diluted with ether until no further precipitate formed. The solid was filtered and washed with ether. The filtrate was concentrated and the residue was purified on silica gel using 10% hexane in $CH_2Cl_2$ to give the title compound's isomer, benzyl 2-(2-(1,2,3-triazolyl)acetate as amorphous solid. Further elution with a solvent mixture containing equal amounts of ether and $CH_2Cl_2$ gave the title compound as amorphous solid. $^1H$ NMR (400 MHz, $CDCl_3$): δ 2.251 (s, 2H0, 7.267-7.390 (m, 5H), 7.723 (s, 1H), 7.785 (s, 1H)

Step B 2-(1-(1,2,3-triazolyl))acetic acid

Palladium hydroxide (20% on carbon, 800 mg) was added to a solution of benzyl 2-(1-(1,2,3-triazolyl))acetate (Step A, 8.68 g, 39.9 mmol) in 150 mL MeOH and the mixture was hydrogenated overnight on a Parr shaker under an atmosphere of hydrogen at room temperature and 45 psi. The catalyst was filtered through a bed of CELITE diatomaceous earth and washed with MeOH. The filtrate was concentrated to give a solid, which was dried in vacuo at 50° C. for 36 h resulting in the title compound. $^1H$ NMR (400 MHz, $CD_3OD$): δ 5.3 (s, 2H), 7.75 (s, 1H0, 8.016 (s, 1H).

Step C N-Methoxy-N-methyl-2-(1-(1,2,3-triazolyl))acetamide

Oxalyl chloride (0.95 mL, 11 mmol) was added dropwise to a suspension of 2-(1-1,2,3-triazolyl))acetic acid (Step B, 1.27 g, 10 mmol) in 10 mL $CH_2Cl_2$ containing 0.05 mL DMF. Vigorous effervescence was observed. This mixture was stirred at room temperature for 4 h and cooled to –78° C. A solution of N.O-dimethylhydroxylamine hydrochloride (1.2 g, 13 mmol) and diisopropylethyl amine (6.0 mL, 35 mmol) in 10 mL $CH_2Cl_2$ was added slowly over 3 min. The mixture was then allowed to warm to room temperature and stirred overnight. The reaction mixture was then diluted with ether until no additional precipitate appeared. The solid was filtered and washed with ether. The filtrate was concentrated and the residue was purified on silica gel using EtOAc as solvent to provide the title compound as amorphous solid. $^1H$ NMR (400 MHz, $CDCl_3$): δ 3.252 (s, 3H0, 3.812 (s, 3H), 5.379 (s, 2H), 7.753 & 7.761 (s's, 2H).

Step D N-Methoxy-N-methyl-3-(4-chlorophenyl)-2-(1-(1,2,3-triazolyl)) propionamide Lithium hexamethyldisilazide (1 molar in THF, 8.4 mL, 8.4 mmol) was added dropwise to a solution of N-methoxy-N-methyl-2-(1-(1,2,3-triazolyl))acetamide (Step C, 1.19 g, 7 mmol) in 15 mL THF at –78° C. After additional 30 min stirring, a solution of 4-chlorobenzyl bromide (1.65 g, 8 mmol) in 5 mL THF was added dropwise. The mixture was allowed to warm to room temperature and stirred 5.5 h. This mixture was purified on silica gel using 40% EtOAc in hexane to give the title compound. $^1H$ NMR (400 MHz, $CDCl_3$): δ 3.186 (s, 3H), 3.234-3.267 (m, 1H), 3.453-3.506 (m, 1H), 3.582 (s, 3H), 6.145-6.188 (m, 1H), 7.048-7.279 (m, 4H), 7.726 (s, 1H), 7.954 (s, 1H).

Step E 2-Azido-3-(1-(1,2,3-triazolyl))-4-(4-chlorophenyl)butane

The product of Step D, N-methoxy-N-methyl-3-(4-chlorophenyl)-2-(1-(1,2,3-triazolyl)propionamide was converted to the title compound following the procedures described in Reference Example 10, Step D-E and Reference Example 12, Step D. $^1H$ NMR (400 MHz, $CDCl_3$): δ 1.219-1.246 (d's 3H), 3.253-4.754 (m, 4H0, 6.866-7.299 (d's, 4H), 7.313, 7.618, 7.63, & 7.706 (s's, 2H).

Step F 2-Amino-3-(1-(1,2,3-triazolyl))-4-(4-chlorophenyl)butane

Platinum oxide (14 mg) was added to a solution of 2-azido-3-(1-(1,2,3-triazolyl))-4-(4-chlorophenyl)butane (Step E, 138 mg, 0.5 mmol) in 4 mL MeOH. This mixture was hydrogenated in an atmosphere of hydrogen using a hydrogen filled balloon for 3 h at room temperature. The catalyst was filtered through a bed of CELITE diatomaceous earth and washed with MeOH. The filtrate was concentrated to give the title compound as oil. $^1H$ NMR (400 MHz, $CDCl_3$): δ 1.085-1.174 (d's 3H), 3.220-3.361 (m, 2H), 3.517-3.563 (m, 1H), 4.379-4.431 (m, 1H), 6.679-7.179 (d's, 4H), 7.297, 7.40, 7.592 & 7.607 (s's, 2H).

Reference Example 63

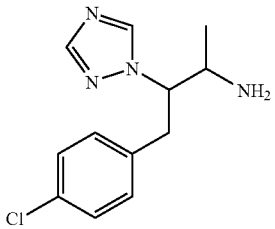

2-Amino-3-(1-(1,2,4-triazolyl)-4-(4-chlorophenyl)butane

The title compound was prepared according to the procedures described in Reference Example 62 substituting 1,2,4-triazole for 1,2,3-triazole in Step A. The azide was separated by column chromatography on silica gel eluted with 20% hexane in EtOAc.

Reference Example 64

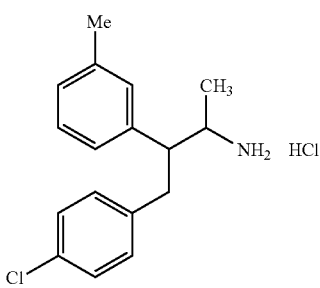

N-[3-(4-Chlorophenyl)-2-(3-methylphenyl)-1-methylpropyl]amine hydrochloride (Diastereomer α)

Step A 2-(N-tert-Butoxycarbonyl)amino-4-(4-chlorophenyl)-3-(3-methylphenyl)butane A mixture of 2-(N-tert-butoxycarbonyl)amino-3-(3-bromophenyl)-4-(4-chlorophenyl)butane (intermediate of Reference Example 47, 0.50 g, 1.1 mmol), tetramethyltin (0.41 g, 2.3 mmol), triphenylphosphine (0.12 g, 0.46 mmol), lithium chloride (0.38 g, 9.1 mmol) and dichlorobis(triphenylphosphine)palladium (0.12 g, 0.17 mmol) in 20 mL anhydrous DMF was heated at 100° C. under nitrogen for 18 h. The reaction mixture was cooled to room temperature, and was partitioned between water (100 mL) and ether (100 mL). The organic layer was separated and the aqueous layer was extracted with ether (100 mL). The combined extracts were dried over anhydrous MgSO$_4$, filtered and concentrated to dryness, and the residue was purified by flash column chromatography on silica gel eluted with 10% EtOAc in hexane to afford the title compound. $^1$H NMR (400 MHz, CD$_3$OD): δ 7.2-6.8 (m, 8H), 3.84 (m, 1H), 3.16 (m, 1H), 2.80-2.68 (m, 2H), 2.24 (s, 3H), 1.45 (s, 9H), 0.86 (d, 3H). LC-MS: m/e 396 (M+Na)$^+$ (4.4 min).

Step B N-[3-(4-Chlorophenyl)-2-(3-methylphenyl)-1-methylpropyl]amine hydrochloride (Diastereomer α)

The title compound was prepared following the procedure described for Reference Example 10, Step I. LC-MS: m/e 274 (M+H)$^+$ (2.5 min).

Reference Example 65

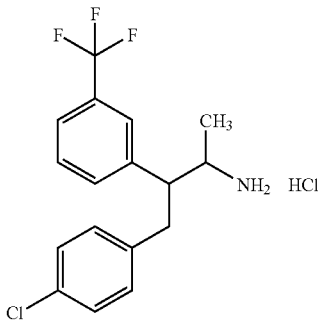

N-[3-(4-Chlorophenyl)-2-(3-trifluoromethylphenyl)-1-methylpropyl]amine hydrochloride (Diastereomer α)

The title compound was prepared following the procedure described in Reference Example 12 substituting fluorophenylacetic acid with 3-trifluoromethylphenylacetic acid at Step A. LC-MS: m/e 328 (M+H)$^+$ (2.6 min).

Reference Example 66

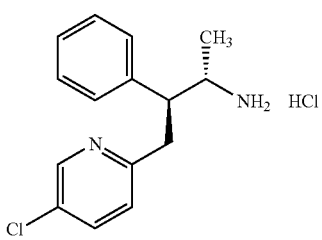

N-[3-(5-Chloro-2-pyridyl)-2(S)-phenyl-1(S)-methylpropyl]amine hydrochloride (Diastereomer α)

Step A 5-Chloro-2-methylpyridine

A mixture of 2,5-dichloropyridine (15 g, 0.10 mol), tetramethyltin (15 mL, 0.11 mol), and dichlorobis(triphenylphosphine)palladium (2.0 g, 2.8 mmol) in 200 mL anhydrous DMF was heated at 110° C. under nitrogen for 72 h. The reaction mixture was cooled to room temperature, and was poured into a saturated solution of potassium fluoride (200 mL). The resulting mixture was partitioned between water (500 mL) and ether (500 mL). The organic layer was separated and the aqueous layer was extracted with ether (200 mL). The combined extracts were dried over anhydrous MgSO$_4$, filtered and concentrated to dryness, and the residue was purified by flash column chromatography on silica gel eluted with 2 to 10% ether in hexane to afford the title compound. $^1$H NMR (500 MHz, CD$_3$OD): δ 8.41 (d, 1H), 7.75 (dd, 1H), 7.30 (d, 1H), 2.53 (s, 3H).

Step B 4-(5-Chloro-2-pyridyl)-3(S)-phenyl-2(R)-butanol

To a solution of 5-chloro-2-methylpyridine (Step A, 1.1 g, 8.7 mmol) in 15 mL anhydrous ether was added phenyl lithium (1.8 M in cyclohexane/ether, 7.2 mL, 13 mmol) at 0° C., and the reaction was stirred at room temperature for 30 min. The resulting mixture was cooled back to 0° C., and was added (1R,2R)-1-phenylpropylene oxide (2.3 g, 17 mmol), and the reaction was allowed to warm to room temperature overnight. The reaction mixture was partitioned between EtOAc (100 mL) and water (100 mL). The organic layer was separated and the aqueous layer extracted with EtOAc (2×100 mL). The combined organic extracts were dried over anhydrous MgSO$_4$, filtered, and concentrated to dryness, and the residue was purified by flash column chromatography on silica gel eluted with 10 to 40% EtOAc in hexane to afford the title compound. $^1$H NMR (500 MHz, CD$_3$OD): δ 8.28 (d, 1H), 7.59 (dd, 1H), 7.25-7.12 (m, 5H), 7.05 (d, 1H), 4.03 (m, 1H), 3.29 (dd, 1H), 3.19 (dd, 1H), 3.12 (m, 1H), 1.12 (d, 3H).

Step C 2(S)-Azido-4-(5-chloro-2-pyridyl)-3(S)-phenylbutane

To a mixture of 4-(5-chloro-2-pyridyl)-3-phenyl-2-butanol (Step B, 0.24 g, 0.92 mmol), triphenylphosphine (1.5 g, 1.4 mmol) and diphenylphosphoryl azide (0.30 mL, 1.4 mmol) in 5 mL anhydrous THF was added diethylazodicarboxylate (0.24 mL, 1.4 mmol). After stirring at room temperature overnight, the resulting mixture was concentrated with silica gel (10 g) and the residue was loaded onto a silica gel column. Elution with 5 to 15% EtOAc in hexane afforded the title compound. $^1$H NMR (500 MHz, CD$_3$OD): δ 8.35 (d, 1H), 7.52 (dd, 1H), 7.25-7.05 (m, 5H), 6.95 (d, 1H), 3.81 (m, 1H), 3.48 (m, 1H), 3.15-3.05 (m, 2H), 1.14 (d, 3H).

Step D N-[3-(5-Chloro-2-pyridyl)-2(S)-phenyl-1(S)-methylpropyl]amine, hydrochloride The product of Step C (0.20 g, 0.70 mmol) was converted to the title compound following the procedure described in Reference Example 10, Steps H-I, except hydrogen chloride in dioxane (4 M) was used in place of hydrogen chloride in EtOAc. $^1$H NMR (500 MHz, CD$_3$OD): δ 8.75 (d, 1H), 8.19

(dd, 1H), 7.55 (d, 1H), 7.4-7.2 (m, 5H), 3.78 (m, 1H), 3.62 (dd, 1H), 3.48 (m, 1H), 3.43 (dd, 1H), 1.22 (d, 3H). LC-MS: m/e 261 (M+H)$^+$ (2.2 min).

Reference Example 67

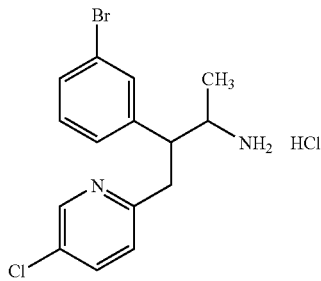

N-[2-(3-Bromophenyl)-3-(5-chloro-2-pyridyl)-1-methylpropyl]amine hydrochloride (Diastereomer α)

Step A 3-Bromophenylacetone

To a solution of N-methoxy-N-methylacetamide (10 g, 100 mmol) in 100 mL anhydrous ether at 0° C. was added 3-bromobenzylmagnesium bromide (0.25 M in ether, 200 mL, 50 mmol). The reaction was allowed to warm to room temperature overnight and was quenched by the addition of saturated ammonium chloride (100 mL). The organic layer was separated and the aqueous layer was extracted with hexane (100 mL). The combined extracts were dried over anhydrous MgSO$_4$, filtered and concentrated to dryness to afford the title compound. $^1$H NMR (500 MHz, CD$_3$OD): δ 7.45-7.40 (m, 2H), 7.26 (t, 1H), 7.19 (d, 1H), 2.20 (s, 3H).

Step B 3-(3-Bromophenyl)-4-(5-chloro-2-pyridyl)-2-butanone

A suspension of 5-chloro-2-methylpyridine (Reference Example 66, Step A, 6.4 g, 50 mmol) and N-bromosuccinimide (12.5 g, 70 mmol) in 100 mL carbon tetrachloride was heated to gentle reflux (bath temperature 90° C.), and 2,2'-azobisisobutyronitrile (0.74 g) was added in several portions over 30 min. After stirring at this temperature for 5 h, the reaction mixture was concentrated. The resulting slurry was diluted with EtOAc (100 mL) and was washed with water (100 mL), saturated aqueous sodium bicarbonate/saturated aqueous sodium thiosulfate, and brine. The organic solution was dried over anhydrous sodium sulfate, filtered, and concentrated to dryness, and the residue was purified by flash column chromatography on silica gel eluted with 2 to 15% ether in CH$_2$Cl$_2$/hexane (1:1) to afford 2-bromomethyl-5-chloropyridine (6.0 g, 60%), which was used immediately for the ensuing reaction. Thus, to a vigorously stirred solution of 2-bromomethyl-5-chloropyridine (6.0 g, 29 mmol) and 3-bromophenyl acetone (Step A, 6.0 g, 28 mmol) and tetrabutylammonium iodide (20 mg) in 30 mL CH$_2$Cl$_2$ at -78° C. was added cesium hydroxide monohydrate (10 g, 60 mmol), and the reaction was allowed to slowly warm to room temperate overnight. The reaction mixture was partitioned between EtOAc (100 mL) and water (100 mL). The organic layer was separated and the aqueous layer extracted with EtOAc (2×100 mL). The combined organic extracts were dried over anhydrous sodium sulfate, filtered, and concentrated to dryness, and the residue was purified by flash column chromatography on silica gel eluted with 5 to 40% EtOAc in hexane to afford the title compound. $^1$H NMR (500 MHz, CD$_3$OD): δ 8.44 (d, 1H), 7.66 (dd, 1H), 7.46-7.41 (m, 2H), 7.24 (t, 1H), 7.22 (d, 1H), 7.15 (d, 1 h), 4.42 (dd, 1H), 3.54 (dd, 1H), 3.07 (dd, 1H), 2.12 (s, 3H). LC-MS: m/e 338 (M+H)$^+$ (3.0 min).

Step C 3-(3-Bromophenyl)-4-(5-chloro-2-pyridyl)-2-butanol

To a solution of 3-(3-bromophenyl)-4-(5-chloro-2-pyridyl)-2-butanone (Step B, 6.7 g, 20 mmol) in 50 mL anhydrous THF at -78° C. was added lithium tri(sec-butyl)borohydride (1.0 M in THF, 30 mL, 30 mmol), and the reaction was allowed to warm to room temperature overnight. The reaction was cooled to 0° C., and was carefully added 2 M hydrochloric acid (50 mL), and the resulting mixture was partitioned between hexane (200 mL) and water (200 mL). The aqueous layer was separated and the organic layer extracted with 2 M hydrochloric acid (2×100 mL). The combined aqueous extracts were neutralized with 5 N aqueous sodium hydroxide (pH>12), and was extracted with EtOAc (2×200 mL). The combined extracts were dried over anhydrous sodium sulfate, filtered, and concentrated to dryness to afford the title compound.

Step D N-[2-(3-Bromophenyl)-3-(5-chloro-2-pyridyl)-1-methylpropyl]amine hydrochloride The product of Step C (5.9 g, 17 mmol) was converted to the title compound following the procedure described in Reference Example 66, Steps C-D. LC-MS: m/e 338 (M+H)$^+$ (2.3 min).

Reference Example 68

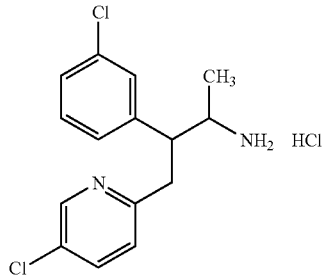

N-[3-(5-Chloro-2-pyridyl)-2-(3-chlorophenyl)-1-methylpropyl]amine hydrochloride (Diastereomer α)

The title compound was prepared following the procedure described in Reference Example 49 substituting 2-(N-tert-butoxycarbonyl)amino-3-bromophenyl-4-(4-chlorophenyl)butane with 2-(N-tert-butoxycarbonyl)amino-3-bromophenyl-4-(5-chloro-2-pyridyl)butane (intermediate of Reference Example 67, Step D) at Step A. LC-MS: m/e 295 (M+H)$^+$ (2.0 min).

107

Reference Example 69

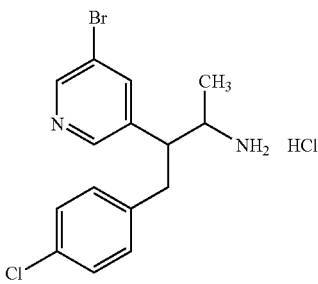

N-[2-(5-Bromo-2-pyridyl)-3-(4-chlorophenyl)-1-methylpropyl]amine hydrochloride (Diastereomer α)

Step A 5-Bromo-3-pyridylacetone

A mixture of 3,5-dibromopyridine (50 g, 0.21 mol), isopropenyl acetate (26 mL, 0.23 mmol), tris(dibenzylideneacetone)dipalladium (1.0 g, 1.1 mmol) and 2-(diphenylphosphino)-2'(N,N-dimethylamino)biphenyl (1.6 g, 4.2 mmol) in 400 mL toluene was heated at 100° C. under nitrogen for 2 h. The reaction mixture was cooled to room temperature, and was concentrated to about 100 mL. The resulting mixture was loaded onto a silica gel column, which was eluted with 0 to 60% EtOAc in hexane to afford the title compound. $^1$H NMR (500 MHz, CD$_3$OD): δ 8.54 (br s, 1H), 8.33 (br s, 1H), 7.88 (br s, 1H), 3.90 (s, 2H), 2.25 (s, 3H).

Step B 3-(5-Bromo-3-pyridyl)-4-(4-chlorophenyl)-2-butanol

The title compound was prepared following the procedure described in Reference Example 67, Step B-C, substituting 2-bromomethyl-5-chloropyridine with 4-chlorobenzyl chloride and 3-bromophenylaceatone with 5-bromo-3-pyridylacetone (Step A). $^1$H NMR (500 MHz, CD$_3$OD): δ 8.43 (d, 1H), 8.24 (d, 1H), 7.98 (dd, 1H), 7.17 (d, 2H), 7.07 (d, 2H), 4.04 (m, 1H), 3.16 (dd, 1H), 3.0-2.9 (m, 2H), 1.04 (d, 3H).

Step C N-[2-(5-Bromo-3-pyridyl)-3-(4-chlorophenyl)-1-methylpropyl]amine hydrochloride (Diastereomer α)

The title compound was prepared following the procedure described for Reference Example 11, Step B. LC-MS: m/e 339 (M+H)$^+$ (2.5 min).

Reference Example 70

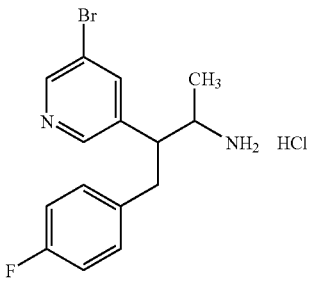

108

N-[2-(5-Bromo-3-pyridyl)-3-(4-fluorophenyl)-1-methylpropyl]amine hydrochloride (Diastereomer α)

The title compound was prepared following the procedure described for Reference Example 69 substituting 4-chlorobenzyl chloride with 4-fluorobenzyl chloride at Step B. LC-MS: m/e 323 (M+H)$^+$ (2.3 min).

Reference Example 71

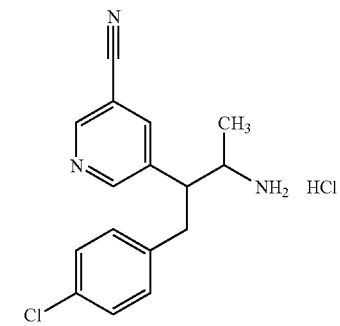

N-[3-(4-Chlorophenyl)-2-(5-cyano-3-pyridyl)-1-methylpropyl]amine hydrochloride (Diastereomer α)

Step A 5-Cyano-3-pyridylacetone

The title compound was prepared following the procedure described for Reference Example 69 substituting 3,5-dibromopyridine with 5-bromonicotinonitrile (5-bromo-3-cyanopyridine) at Step A. $^1$H NMR (400 MHz, CD$_3$OD): δ 8.89 (d, 1H), 8.60 (d, 1H), 8.02 (t, 1H), 3.98 (s, 2H), 2.24 (s, 3H).

Step B N-[3-(4-Chlorophenyl)-2-(5-cyano-2-pyridyl)-1-methylpropyl]amine hydrochloride (Diastereomer α/β 5:1)

The title compound was prepared following the procedure described for Reference Example 19 substituting 3-pyridylacetone with 5-cyano-3-pyridylacetone (Step A). LC-MS: m/e 286 (M+H)$^+$ (1.9 min).

Reference Example 72

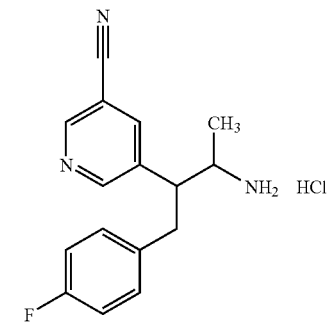

N-[2-(5-Cyano-3-pyridyl)-3-(4-fluorophenyl)-1-methylpropyl]amine hydrochloride (Diastereomer α)

The title compound was prepared following the procedure described for Reference Example 71 substituting 4-chlorobenzyl chloride with 4-fluorobenzyl chloride at Step B. LC-MS: m/e 270 (M+H)$^+$ (2.2 min).

Reference Example 73

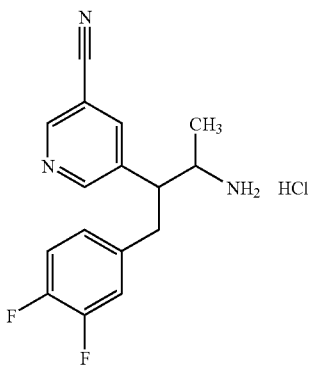

N-[2-(5-Cyano-3-pyridyl)-3-(3,4-difluorophenyl)-1-methylpropyl]amine hydrochloride (Diastereomer α)

The title compound was prepared following the procedure described for Reference Example 72 substituting 4-fluorobenzyl chloride with 3,4-difluorobenzyl chloride at Step B. LC-MS: m/e 288 (M+H)⁺ (2.3 min).

Reference Example 74

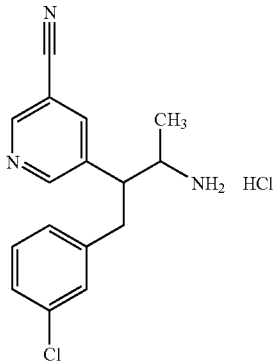

N-[3-(3-Chlorophenyl)-2-(5-cyano-3-pyridyl)-1-methylpropyl]amine hydrochloride (Diastereomer α)

The title compound was prepared following the procedure described for Reference Example 72 substituting 4-fluorobenzyl chloride with 3-chlorobenzyl chloride at Step B. LC-MS: m/e 286 (M+H)⁺ (2.4 min).

Reference Example 75

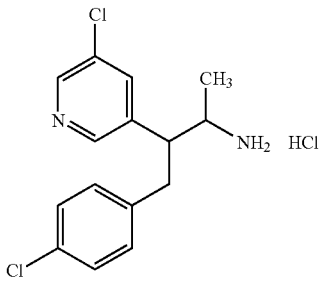

N-[3-(4-Chlorophenyl)-2-(5-chloro-3-pyridyl)-1-methylpropyl]amine hydrochloride (Diastereomer α)

Step A 5-Chloro-3-pyridylacetone

The title compound was prepared following the procedure described for Reference Example 69 substituting 3,5-dibromopyridine with 3,5-dichloropyrdine and 2-(diphenylphosphino)-2'(N,N-dimethylamino)biphenyl with 2-(di-t-butylphosphino) biphenyl at Step A. ¹H NMR (500 MHz, CD₃OD): δ 8.42 (d, 1H), 8.27 (d, 1H), 7.73 (dd, 1H), 3.90 (s, 2H), 2.25 (s, 3H).

Step B N-[3-(4-Chlorophenyl)-2-(5-chloro-3-pyridyl)-1-methylpropyl]amine hydrochloride (Diastereomer α)

The title compound was prepared following the procedure described for Reference Example 69, Step B-C substituting 5-bromo-3-pyridylacetone with 5-chloro-3-pyridylacetone at Step B. LC-MS: m/e 295 (M+H)⁺ (1.9 min).

Reference Example 76

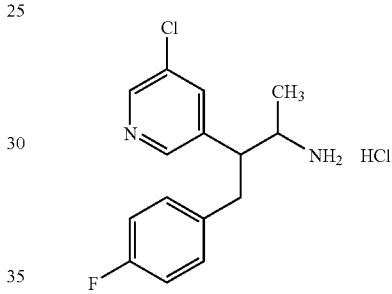

N-[2-(5-Chloro-3-pyridyl)-3-(4-fluorophenyl)-1-methylpropyl]amine hydrochloride (Diastereomer α)

The title compound was prepared following the procedure described for Reference Example 75 substituting 4-chlorobenzyl chloride with 4-fluorobenzyl chloride at Step B. LC-MS: m/e 279 (M+H)⁺ (2.3 min).

Reference Example 77

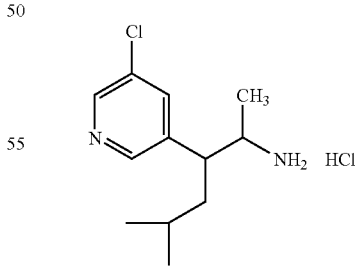

2-Amino-3-(5-chloro-3-pyridyl)-5-methylhane, Hydrochloride Salt (Diastereomer α/β 6:1)

The title compound was prepared following the procedure described for Reference Example 75 substituting 4-chlorobenzyl chloride with 1-iodo-2-methylpropane at Step B. LC-MS: m/e 227 (M+H)+ (2.2 min).

Reference Example 78

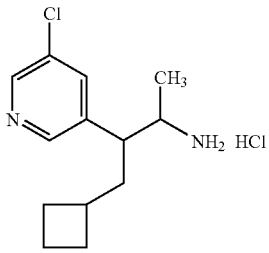

N-[2-(5-Chloro-3-pyridyl)-3-cyclobutyl-1-methyl-propyl]amine hydrochloride (Diastereomer α/β 6:1)

The title compound was prepared following the procedure described for Reference Example 75 substituting 4-chlorobenzyl chloride with (bromomethyl)cyclobutane at Step B. LC-MS: m/e 239 (M+H)+ (2.3 min).

Reference Example 79

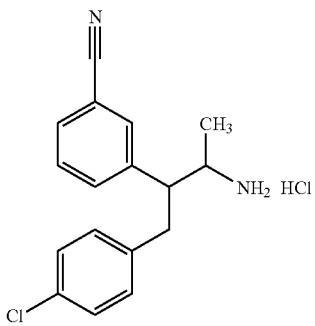

N-[3-(4-Chlorophenyl)-2-(3-cyanophenyl)-1-methyl-propyl]amine hydrochloride (Diastereomer α)

Step A 3-Cyanophenylacetone

The title compound was prepared following the procedure described for Reference Example 69 substituting 3,5-dibromopyridine with 3-bromobenzonitrile and 2-(diphenylphosphino)-2'-(N,N-dimethylamino)biphenyl with 2-(dicyclohexylphosphino)-2'-(N,N-dimethylamino)biphenyl at Step A. 1H NMR (500 MHz, CD3OD): δ 7.6 (m, 1H), 7.56 (br s, 1H), 7.50-7.48 (m, 2H), 3.88 (s, 2H), 2.21 (s, 3H).

Step B N-[3-(4-Chlorophenyl)-2-(3-cyanophenyl)-1-methylpropyl]amine hydrochloride (Diastereomer α)

The title compound was prepared following the procedure described for Reference Example 69 substituting 5-bromo-3-pyridylacetone with 3-canophenylacetone at Step B. LC-MS: m/e 285 (M+H)+ (2.2 min).

Reference Example 80

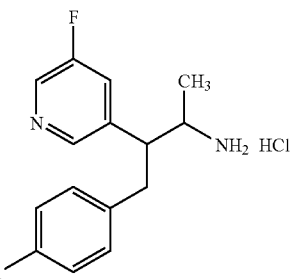

N-[3-(4-Chlorophenyl)-2-(5-fluoro-3-pyridyl)-1-methylpropyl]amine hydrochloride (Diastereomer α)

Step A 5-fluoro-3-pyridylacetone

The title compound was prepared following the procedure described for Reference Example 69 substituting 3,5-dibromopyridine with 3-fluoro-5-trifluoromethanesulfonyloxy-pyridine (prepared form 3-fluoro-5-hydroxypyrdine and triflic anhydride) and 2-(diphenylphosphino)-2'(N,N-dimethylamino)biphenyl with 2-(dicyclohexylphosphino)-2' (N,N-dimethylamino)biphenyl at Step A. 1H NMR (500 MHz, CD3OD): δ 8.34 (d, 1H), 8.22 (br s, 1H), 7.50 (ddd, 1H), 3.93 (s, 2H), 2.25 (s, 3H).

Step B N-[3-(4-Chlorophenyl)-2-(5-chloro-3-pyridyl)-1-methylpropyl]amine hydrochloride (Diastereomer α)

The title compound was prepared following the procedure described for Reference Example 69, Step B-C substituting 5-bromo-3-pyridylacetone with 5-fluoro-3-pyridylacetone at Step B. LC-MS: m/e 279 (M+H)+ (2.4 min).

Reference Example 81

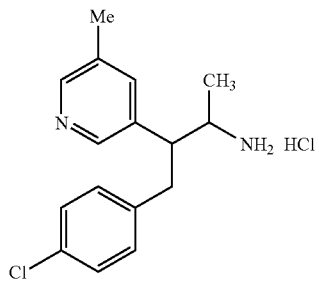

N-[3-(4-Chlorophenyl)-2-(5-methyl-3-pyridyl)-1-methylpropyl]amine hydrochloride (Diastereomer α)

The title compound was prepared following the procedure described for Reference Example 64 substituting 2-(N-tert-butoxycarbonyl)amino-3-(3-bromophenyl)-4-(4-chlorophenyl)butane with 2-(N-tert-butoxycarbonyl)amino-3-(5-bromo-3-pyridyl)-4-(4-chlorophenyl)butane (intermediate to Reference Example 69, Step B) at Step A. LC-MS: m/e 275 (M+H)+ (1.3 min).

Reference Example 82

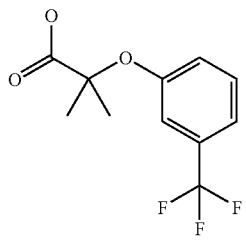

2-Methyl-2-(3-trifluoromethylphenyloxy)propionic acid

The title compound was prepared following the same procedure described for Reference Example 27. $^1$H NMR (500 MHz, CD$_3$OD): δ 7.45 (t, 1H), 7.28 (d, 1H), 7.16 (s, 1H), 7.13 (d, 1H), 1.62 (s, 6H).

Reference Example 83

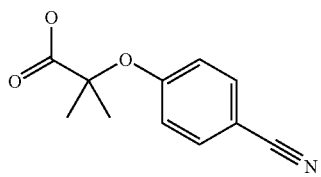

2-Methyl-2-(3-cyanophenyloxy)propionic acid

The title compound was prepared following the same procedure described for Reference Example 27. $^1$H NMR (500 MHz, CD$_3$OD): δ 7.63 (d, 2H), 6.97 (d, 2H), 1.65 (s, 6H).

Reference Example 84

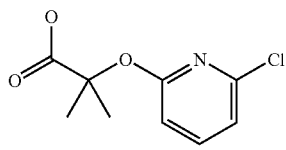

2-Methyl-2-(6-chloromethyl-2-pyridyloxy)propionic Acid

The title compound was prepared following the procedures described for Reference Example 54 substituting 5-chloro-2-hydroxypyridine with 6-chloro-2-hydroxypyridine at Step A. $^1$H NMR (500 MHz, CD$_3$OD): δ 7.64 (t, 1H), 6.95 (d, 1H), 6.72 (d, 1H), 1.65 (s, 6H). LC-MS: m/e 216 (M+H)$^+$ (2.4 min).

Reference Example 85

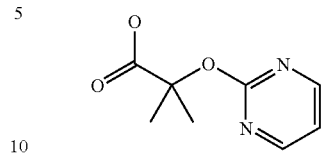

2-Methyl-2-(2-pyrimidyloxy)proipionic Acid

The title compound was prepared following the procedures described for Reference Example 54 substituting 5-chloro-2-hydroxypyridine with 2-hydroxypyrimidine at Step A. $^1$H NMR (500 MHz, CD$_3$OD): δ 8.53 (d, 2H), 7.09 (t, 1H), 1.74 (s, 6H).

Reference Example 86

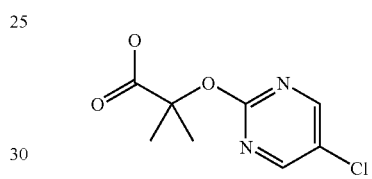

2-Methyl-2-(5-chloro-2-pyrimidyloxy)propionic Acid

The title compound was prepared following the procedures described for Reference Example 54 substituting 5-chloro-2-hydroxypyridine with 5-chloro-2-hydroxypyrimidine at Step A. $^1$H NMR (500 MHz, CD$_3$OD): δ 8.55 (s, 2H), 1.73 (s, 6H).

Reference Example 87

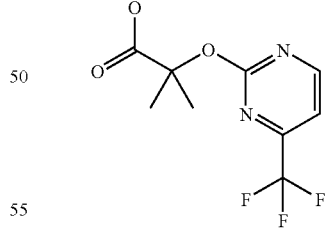

2-Methyl-2-(4-trifluoromethyl-2-pyrimidyloxy)propionic Acid

The title compound was prepared following the procedures described for Reference Example 54 substituting 5-chloro-2-hydroxypyridine with 4-trifluoromethyl-2-hydroxpyrimidine at Step A. $^1$H NMR (500 MHz, CD$_3$OD): δ 8.85 (d, 1H), 7.48 (d, 1H), 1.76 (s, 6H).

Reference Example 88

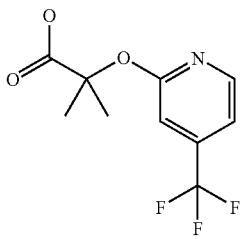

2-Methyl-2-(4-trifluoromethyl-2-pyridyloxy)propionic Acid

The title compound was prepared following the procedures described for Reference Example 54 substituting 5-chloro-2-hydroxpyridine with 4-trifluoromethyl-2-hydroxpyridine at Step A. $^1$H NMR (500 MHz, CD$_3$OD): δ 8.30 (d, 1H), 7.18 (d, 1H), 7.05 (s, 1H), 1.71 (s, 6H).

Reference Example 89

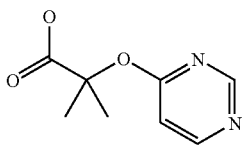

2-Methyl-2-(4-pyrimidyloxy)propionic Acid

The title compound was prepared following the procedures described for Reference Example 54 substituting 5-chloro-2-hydroxpyridine with 4-hydroxpyrimidine at Step A. $^1$H NMR (500 MHz, CD$_3$OD): δ 8.67 (s, 1H), 8.47 (d, 1H), 6.91 (d, 1H), 1.73 (s, 6H).

Reference Example 90

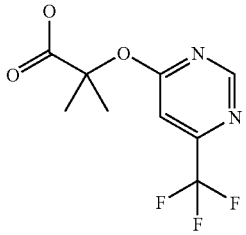

2-Methyl-2-(6-trifluoromethyl-4-pyrimidyloxy)propionic Acid

The title compound was prepared following the procedures described for Reference Example 54 substituting 5-chloro-2-hydroxpyridine with 6-trifluoromethyl-4-hydroxpyrimidine at Step A. $^1$H NMR (500 MHz, CD$_3$OD): δ 8.81 (s, 1H), 7.28 (s, 1H), 1.75 (s, 6H). LC-MS: m/e 251 (M+H)$^+$ (2.1 min).

Reference Example 91

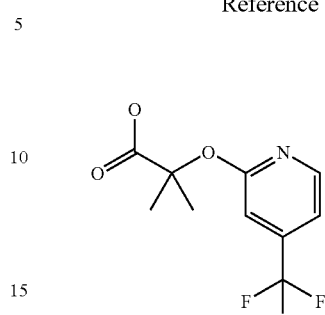

2-Methyl-2-(4-trifluoromethyl-2-pyridyloxy)propionic Acid Step A 2-(4-Trifluoromethyl-2-pyridyloxy)propionic acid To a suspension of lithium lactate (7.8 g, 81 mmol) in 100 mL anhydrous DMF was added sodium hydride (60% dispersion in mineral oil, 3.2 g, 80 mmol). After stirring at room temperature for 30 min, 2-chloro-4-trifluoromethylpyridine (10 g, 55 mmol) was added, and the mixture was heated at 100° C. overnight. The reaction was cooled to room temperature, poured into 500 mL water, and was washed with hexane (200 mL). The aqueous solution was acidified with concentrated hydrochloric acid (pH>2), and was extracted with ether (2×500 mL). The combined extracts were washed with water and brine, dried over anhydrous sodium sulfate, filtered and concentrated to dryness to give the title compound.

Step B Methyl 2-Methyl-2-(4-trifluoromethyl-2-pyridyloxy)propionate

To a solution of 2-(4-trifluoromethyl-2-pyridyloxy)propionic acid (Step A, 15 g, 55 mol) in 100 mL CH$_2$Cl$_2$ and 100 mL MeOH at 0° C. was added trimethylsilydiazomethane (2 M solution in hexane) until a yellow color persisted. After stirring at room temperature for 15 min, the reaction mixture was concentrated to dryness, and the residue was purified by flash chromatography on silica gel eluted with 0 to 10% EtOAc in hexane to give methyl 2-(4-trifluoromethyl-2-pyridyloxy)propionate (10 g), which was used immediately for methylation following the procedure described in Reference Example 39, Step B substituting ethyl iodide with methyl iodide. $^1$H NMR (500 MHz, CD$_3$OD): δ 8.25 (d, 1H), 7.18 (d, 1H), 7.15 (s, 1H), 3.65 (s, 3H), 1.65 (s, 6H).

Step C 2-Methyl-2-(4-trifluoromethyl-2-pyridyloxy)propionic Acid

To a solution of methyl 2-methyl-2-(4-trifluoromethyl-2-pyridyloxy)propionate (Step B, 7.5 g, 29 mol) in 50 mL MeOH, 50 mL THF and 50 mL water was added sodium hydroxide (2.3 g, 57 mmol). After stirring at 50° C. for 5 h, the reaction mixture was partially concentrated, and was added 2 M hydrochloric acid to pH>2. The resulting mixture was extracted with EtOAc (2×200 mL), and the combined extracts were dried over anhydrous sodium sulfate, filtered, and concentrated to dryness to afford the title compound. ¹H NMR (500 MHz, CD₃OD): δ 8.28 (d, 1H), 7.17 (d, 1H), 7.05 (s, 1H), 1.70 (s, 6H).

Reference Example 92

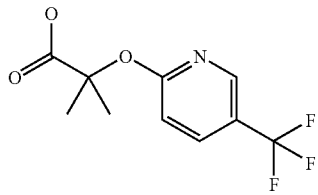

2-Methyl-2-(5-trifluoromethyl-2-pyridyloxy)propionic Acid

The title compound was prepared following the procedure described in Reference Example 91, Step A with 1.5 extra equivalent of sodium hydride substituting lithium lactate with hydroxyisobutyric acid and 2-chloro-4-trifluoromethylpyridine 2-chloro-5-trifluoromethylpyridine. ¹H NMR (500 MHz, CD₃OD): δ 8.38 (br, 1H), 7.94 (dd, 1H), 6.93 (d, 1H), 1.69 (s, 6H).

Reference Example 93

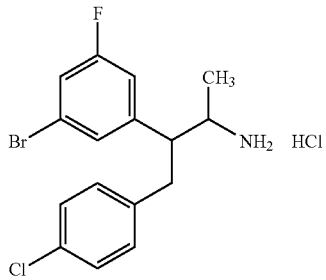

N-[2-(3-Bromo-5-fluorophenyl)-3-(4-Chlorophenyl)-1-methylpropyl]amine hydrochloride (Diastereomer α)

Step A 3-Bromo-5-fluorophenylacetone

The title compound was prepared following the procedure described for Reference Example 69 substituting 3,5-dibromopyridine with 1,3-dibromo-5-fluorobenzene and 2-(diphenylphosphino)-2'-(N,N-dimethylamino)biphenyl with 1,1'-bis(diphenylphosphino)ferrocene at Step A. ¹H NMR (500 MHz, CD₃OD): δ 7.23 (d, 1H), 7.22 (s, 1H), 6.96 (d, 1H), 3.81 (s, 2H), 2.20 (s, 3H).

Step B N-[2-(3-Bromo-5-fluorophenyl)-3-(4-chlorophenyl)-1-methylpropyl]amine hydrochloride (Diastereomer α)

The title compound was prepared following the procedure described for Reference Example 69, Step B substituting 5-bromo-3-pyridylacetone with 3-bromo-5-fluorophenylacetone (Step A). LC-MS: m/e 356 (M+H)⁺ (2.9 min).

Reference Example 94

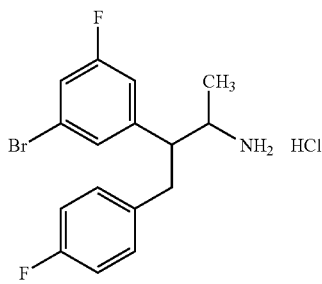

N-[2-(3-Bromo-5-fluorophenyl)-3-(4-fluorophenyl)-1-methylpropyl]amine hydrochloride (Diastereomer α)

The title compound was prepared following the procedure described for Reference Example 93 substituting 4-chlorobenzyl chloride with 4-fluorobenzyl chloride at Step B. LC-MS: m/e 340 (M+H)⁺ (2.8 min).

Reference Example 95

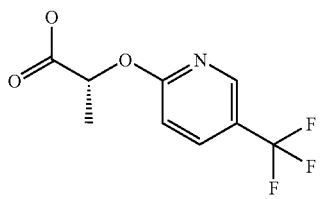

2(R)-(5-Trifluoromethyl-2-pyridyloxy)propionic Acid

Step A
2(R)-(5-trifluoromethyl-2-pyridyloxy)propionate

The title compound was prepared following the procedure described in Reference Example 39, Step A substituting 2-hydroxypyridine with 5-trifluoromethyl-2-hydroxypyridine and benzyl lactate with benzyl (S)-lactate. LC-MS: m/e 326 (M+H)⁺ (3.1 min).

Step B
2(R)-(5-trifluoromethyl-2-pyridyloxy)propionic Acid

The title compound was prepared following the procedure described in Reference Example 39, Step C substituting benzyl 2-(2-pyridyloxy)-2-methylbutanoate with 2(R)-(5-trifluoromethyl-2-pyridyloxy)propionate (Step A). ¹H NMR (500 MHz, CD₃OD): δ 8.70 (s, 1H), 7.67 (d, 1H), 6.63 (d, 1H), 5.30 (q, 1H), 1.67 (d, 3H).

Reference Example 96

2-Methyl-2-(5-trifluoromethyl-2-pyridyloxy)propionic Acid

Two nitrogen flushed, 12 L 3-necked round bottom flasks, each fitted with a thermometer and a reflux condenser were charged with KHMDS in THF (0.91 M, 3.52 L each, 3.205 mol, 1.5 eq). The solutions were cooled to −70° C. and stirred magnetically. Ethyl-2-hydroxyisobutyrate (98%) (463 mL, 447 g, 3.38 mol) was added to each flask over 30 min, keeping the reaction temperature below −62° C. After 10 min 2-chloro-5-trifluormethylpyridine (388 g, 2.14 mol) was added to each flask in one portion. The cooling bath was removed and the reactions were allowed to warm to 20° C. overnight (ca 16 hr.). The reactions were monitored by TLC (silica, 90/10 Hex/EtOAc) and HPLC:

Sodium hydroxide (1.36 L, 5N) was added to each reaction flask and the reactions were refluxed overnight (ca 22 hr). The reactions were concentrated together on a rotary evaporator to remove the THF. To the concentrate was added water (4 L) and the solution extracted with n-heptane (2×4 L). The aqueous layer was added over 10 min to 2N HCl (9 L, 18 mol) with stirring. The resulting suspension was aged for 30 min (temperature 30° C.) then filtered. The cake was washed with water (3×2 L), and air-dried to a damp tan solid.

The material was dissolved in n-heptane (4 L) at 65° C. IPAc (1 L) and DARCO KB (40 g, 100 mesh) were added. The mixture was stirrer for 15 min, filtered through CELITE diatomaceous earth, and the cake washed with 4:1 heptane/IPAc (3×500 mL). The filtrate was concentrated to ca. 2 L affording a white suspension. The slurry was flushed with heptane (2×3 L) and concentrated to ca. 3 L. The resulting white suspension was cooled to 0° C. and aged 1 hr. The product was filtered and the cake washed with cold heptane (1 L) to provide the title compound as white crystalline material. HPLC Column: YMC Combiscreen Pro C18, 50×4.6 mm; Mobile phase: A 0.1% TFA in $H_2O$; B $CH_3CN$. Gradient: 90/10 A/B to 10/90 A/B in 4 min. Flow rate: 4 mL/min. Detection: 254 nm. $R_t$ 2-chloro-5-trifluormethylpyridine 2.1 min. $R_t$ 2-ethoxy-5-trifluoromethylpyridine 2.9 min. $R_t$ Product Ester 3.1 min. $R_t$ Final Acid 2.05 min Reference Example 97

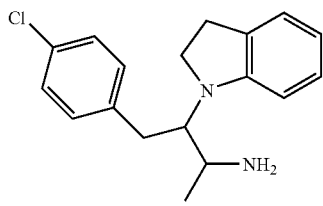

2-Amino-3-indolin-N-yl-4(4-chloro)phenylbutane

Step A. Ethyl
3-(4-chlorophenyl)-2-indolin-N-ylpropanoate

In an oven-dried flask under an atmosphere of nitrogen, 1.1 g $LiOH \cdot H_2O$ (26.25 mmol) in DMF (20 mL) was added to a stirring suspension of 4 angstrom molecular sieves. After 30 minutes of stirring at room temperature 2.8 mL (25 mmol) indoline was added dropwise. After one hour at room temperature 2.9 mL (26.25 mmol) Ethyl bromoacetate was added dropwise. After 1.5 h the solid material was filtered and the residue was washed with copious amounts of EtOAc. The organics were washed 3 times with water and the organic material was dried over $MgSO_4$. The solvents were evaporated under reduced pressure. The crude material was then dissolved in 75 mL anhydrous THF, charged into an oven dried round bottom under an atmosphere of nitrogen, cooled to −78° C., and then treated with 26.25 mL a 1M solution of NaHMDS. The solution was allowed to stir for 30 minutes at −78° C. after which the enolate was quenched with 5.4 g (26.25 mmol) of parachlorobenzyl bromide (solution in 25 mL anhydrous THF). The reaction was allowed to warm to room temperature overnight. The next day the reaction was quenched with water. The aqueous layer was extracted with 3 large portions of EtOAc. The combined organics were dried over $MgSO_4$. The solvents were removed under reduced pressure and the residue was purified by flash chromatography which yielded the title compound as a yellow oil. LC/MS m/e=331 (M+1). TLC $R_f$=0.22 (20:1 hexanes:EtOAc). $^1H$ NMR (500 MHz, $CDCl_3$): δ 1.11 (t, J=3.55 Hz, 3H), 2.96 (m, 2H), 3.06 (m, 1H), 3.25 (m, 1H), 3.60 (t, 2H), 4.07 (m, 2H), 4.36 (t, J=3.75 Hz, 1H).

Step B. N,O-dimethyl-3-(4-chlorophenyl)-2-indolin-N-ylpropanamide

In an oven-dried flask under an atmosphere of nitrogen, 11.75 mL 1 M solution of $(CH_3)_2AlCl$ in $CH_2Cl_2$ was added via addition funnel to a stirring suspension of 1.15 g (11.75 mmol) N,O-dimethylhydroxylamine hydrochloride at 0° C. After warming to room temperature a solution of 970 mg (2.94 mmol) of Ethyl 3-(4-chlorophenyl)-2-indolinylpropanoate in 10 mL was added via addition funnel. After stirring at room temperature for 5 h, 35 mL pH=8 phospate buffer solution was added and the resulting solution was stirred vigorously for 30 minutes. The phases were separated and the aqueous layer was extracted 2 times with chloroform. The combined organics were washed with water and then dried over $MgSO_4$. A brown oil was collected. The crude material was carried on to the next step.). TLC $R_f$=0.12 (10:1 hexanes:EtOAc). $^1H$ NMR (500 MHz, $CDCl_3$): δ 2.83 (m, 1H), 2.97 (m, 2H), 3.13 (s, 3H), 3.34 (m, 1H), 3.45 (s, 3H), 3.61 (m, 2H), 4.87 (b, 1H), 6.54 (d, 1H), 6.66 (t, J=7.1 Hz, 1H), 7.07 (t, J=7.1 Hz, 2H), 7.18 (d, J=8.5 Hz, 2H), 7.24 (d, J=8.5 Hz, 2H)

Step C.
4-(4-chlorophenyl)-3-indolin-N-ylbutan-2-one

In an oven dried flask under an atmosphere of nitrogen, 2.8 mL 1 M solution of $CH_3MgBr$ in THF was added dropwise to a stirring solution of N,O-dimethyl-3-(4-chlorophenyl)-2-indolinylpropanamide (965 mg) in 25 mL anhydrous THF. The solution was stirred for 4 h while being allowed to warm to room temperature. Then approximately 20 mL water were added. The solution was extract three times with 50 mL ether. The combined extracts were dried over $MgSO_4$. The solvents were removed under reduced pressure yielding a brown oil which was carried on to the next step without purification. LC/MS m/e=301 (M+1). TLC $R^f$=0.5 (4:1 hexanes:EtOAc). $^1H$ NMR (500 MHz, $CDCl_3$): δ 2.14 (s, 3H), 2.81 (dd, J=14.6, 6.6 Hz, 1H), 2.97 (t, J=8.5 Hz, 2H), 3.26 (m, 2H), 3.5 (m, 1H), 4.21 (dd, J=6.6, 6.6 Hz), 6.39 (d, J=8 Hz, 1H), 6.66 (dd, J=7, 7 Hz, 1H), 7.07 (m, 2H), 7.13 (d, J=8.5 Hz), 7.22 (d, J=8.3 Hz).

Step D.
4-(4-chlorophenyl)-3-indolin-N-ylbutan-2-one
methoxime

A solution of 472 mg (1.573 mmol) of the product of Step C and 263 mg (3.147 mmol) of methoxyl amine hydrochloride in anhydrous ethanol was treated with 255 μL (3.147 mmol) of pyridine. The solution was stirred for 2 h at room temperature. Solvent was removed under reduced pressure and the residue was partitioned between water and ether. The water was extracted with ether again. The extracts were then combined and dried over MgSO$_4$, filtered and concentrate to obtain crude material obtained. Both the E and Z isomers were carried onto the next step. LC/MS m/e=330 (M+1). TLC R$_f$=0.77 and 0.65 (4:1 hexanes:EtOAc). $^1$H NMR (500 MHz, CDCl$_3$): δ 1.78 (2s, 1H), 2.88 (dd, J=6.2, 13.8 Hz, 1H), 2.95 (m, 2H), 3.30 (m, 2H), 3.45 (m, 1H), 3.75 and 3.89 (2s, 3H), 4.21 (dd, J=6.9, 7.8 Hz, 1H), 6.28 and 6.47 (2d, J=8.1, 1H), 6.61 (m, 1H), 7.02 (m, 2H), 7.22 (m, 4H).

Step E.
2-Amino-3-indolin-N-yl-4(4-chloro)phenylbutane

In an oven-dried flask equipped with a water condenser under an atmosphere of nitrogen, a solution of 301 mg (0.914 mmol) 4-(4-chlorophenyl)-3-indolinylbutan-2-one methoxime in 1.5 mL anhydrous THF was treated with 3.7 mL (3.7 mmol) of 1M BH$_3$.THF at room temperature. The solution was then heated to 75° C. for 2 days. The solution was then cooled to 0° C. and treated with chips of ice until bubbling subsided. 500 µL of 20% KOH were then added and the solution was heated at 45° C. for 2 h. The solution was then cooled to room temperature and extracted with ether 3×. The combined extracts were dried over MgSO$_4$, filtered, and concentrated to afford crude amine which was used in the next experiment without further purification. LC/MS m/e=302 (M+1). $^1$H NMR (500 MHz, CDCl$_3$): δ 1.13, 1.14 (2d, J=6.5 Hz, 1H), 1.55-1.60 (m, 2H), 2.80-3.10 (m, 4H), 3.30-3.60 (m, 2H), 6.348 and 6.38 (2d, J=7.9 Hz, 1H), 6.50-6.78 (m, 2H), 6.95-7.24 (m, 5H)

Reference Example 98

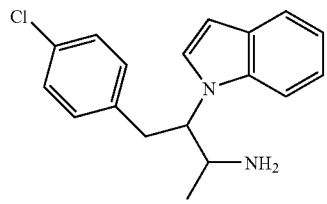

2-Amino-3-indol-N-yl-4(4-chloro)phenylbutane

This compound was prepared in an analogous manner to Reference Example 97 except that during Step A, sodium hydride was used as the base instead of the lithium hydroxide monohydrate/molecular sieves combination. LC/MS: calculated for C$_{18}$H$_{19}$ClN$_2$ 299, observed m/e 300 (M+H)$^+$ (2.4 min).

Reference Example 99

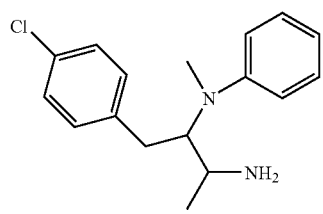

2-Amino-3-(N-methyl N-phenyl)amino-4(4-chloro)phenylbutane

This compound was prepared in an analogous manner to Reference Example 97. LC/MS: calculated for C$_{17}$H$_{21}$ClN$_2$ 289, observed m/e 290 (M+H)$^+$ (2.4 min).

Reference Example 100

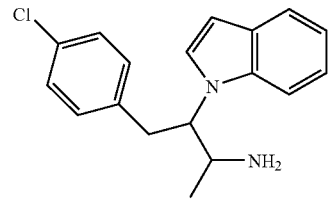

2-Amino-3-(7-azaindol-N-yl)-4(4-chloro)phenylbutane

This compound was prepared in an analogous manner to Reference Example 97. LC/MS: calculated for C$_{17}$H$_{18}$ClN$_3$ 300, observed m/e 301 (M+H)$^+$ (2.7 min).

Reference Example 101

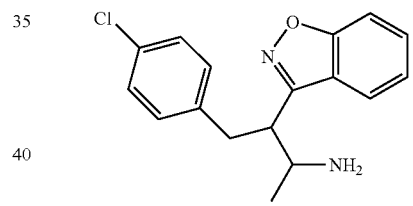

2-Amino-3-(benzisoxazol-3-yl)-4(4-chloro)phenylbutane

This compound was prepared in an analogous manner to Reference Example 97 except starting with ethyl (benzisoxazol-3-yl)acetate. LC/MS: calculated for C$_{17}$H$_{17}$ClN$_2$O 300, observed m/e 301 (M+H)$^+$ (2.2 min).

Reference Example 102

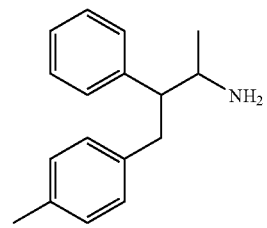

4-(4-Methylphenyl)-3-phenylbutan-2-amine (mixture of 4 isomers)

Step A 1-Phenylacetone

To a solution of N-methyl-N-methoxyacetamide (9.9 mL. 97 mmol) in ether (300 mL) at 0° C. was added benzylmagnesium chloride (97 mL a 1M solution in ether). The cloudy, white reaction mixture was warmed to room temperature for 2 h and then quenched by careful addition of 1N hydrochloric acid (100 mL). The organic phase was separated, washed with brine, dried over $MgSO_4$ and concentrated. The crude material was purified by column chromatography on silica gel eluting from 0-10% EtOAc/hexane to give the title compound. $^1H$ NMR (500 MHz, $CDCl_3$): δ 7.36 (t, J=7.1 Hz, 2H), 7.30 (t, J=7.3 Hz, 1H), 7.24 (d, J=7.3 Hz, 2H), 3.72 (s, 2H), 2.18 (s, 3H). LC-MS: m/e 135 $(M+H)^+$ (1.95 min).

Step B 4-(4-Methylphenyl)-3-phenylbutan-2-one

1-Phenylacetone (200 mg, 1.49 mmol) was mixed with powdered potassium hydroxide (167 mg, 2.98 mmol) and tetra-n-butylammonium bromide (1 mol %, 5 mg) in a flask without solvent. This mixture was stirred at room temperature for 90 min. before the addition of 1-(chloromethyl)-4-methylbenzene (198 μl, 1.49 mmol). The reaction mixture was then stirred overnight before diluting with water and $CH_2Cl_2$. The aqueous layer was separated and neutralized to pH 7 with 2N hydrochloric acid and extracted again into $CH_2Cl_2$. The combined organic washes were dried with $MgSO_4$ and concentrated. The crude material was purified by column chromatography on silica gel eluting from 0-10% EtOAc/hexane to give the title compound. $^1H$ NMR (500 MHz, $CDCl_3$): δ 7.35 (t, J=7.0 Hz, 2H), 7.29 (t, J=7.4 Hz, 1H), 7.23 (d, J=7.1 Hz, 2H), 7.05 (d, 7.8 Hz, 2H), 6.98 (d, J=7.8 Hz, 2H), 3.94 (t, J=7.3 Hz, 1H), 3.43 (dd, J=13.9, 7.5 Hz, 1H), 2.91 (dd, J=14, 7.1 Hz, 1H), 2.32 (s, 3H), 2.08 (s, 3H). LC-MS: m/e 239 $(M+H)^+$ (3.61 min).

Step C 4-(4-Methylphenyl)-3-phenylbutan-2-amine

To a solution of the 4-(4-methylphenyl)-3-phenylbutan-2-one (308 mg, 1.29 mmol) in 7M ammonia in MeOH (5 mL) and acetic acid (3 mL) was added sodium cyanoborohydride (130 mg, 2.06 mmol) and the reaction stirred at room temperature overnight. The reaction was quenched by pouring into 2M sodium carbonate solution and extracted into EtOAc. The aqueous layer was salted and re-extracted. The combined organic extracts were dried over $MgSO_4$ and concentrated to give the title compound as a mixture of 4 isomers which was used without further purification. LC-MS: m/e 240 $(M+H)^+$ (2.22 min).

Reference Example 103

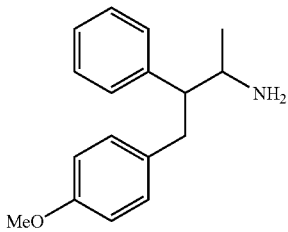

4-(4-Methoxyphenyl)-3-phenylbutan-2-amine

Prepared using the procedures described in Example 102, Steps A through C using 1-(chloromethyl)-4-methoxybenzene as the alkylating agent in Step B. LC-MS: m/e 256 $(M+H)^+$ (1.90 and 2.03 min).

Reference Example 104

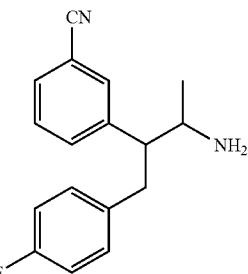

3-[2-Amino-1-(4-fluorobenzyl)propyl]benzonitrile

Prepared using the procedures described in Example 79 using 3-(2-oxopropyl)benzonitrile and 1-(chloromethyl)-4-fluorobenzene as the reactants in Step B. LC-MS: m/e 269 $(M+H)^+$ (2.87 min).

Reference Example 105

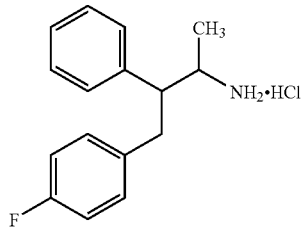

N-[2-Phenyl-3-(4-fluorophenyl)-1-methylpropyl] amine hydrochloride (Diastereomer α)

The title compound was obtained by the method described in Reference Example 26, substituting 4-fluorobenzyl bromide for isobutyl iodide. LC-MS, $R_t$=2.2 min, m/e=244.

Reference Example 106

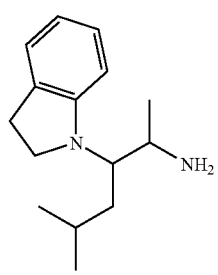

2-(2,3-Dihydro-1-H-indol-1-yl)-1,4-dimethylpentylamine

Step A Ethyl (2-(2,3-dihydro-1H-indol-1-yl)-4-methylpentanoate

A solution of 0.53 g (3.3 mmol) of ethyl (S)-2-hydroxyisocaproate in 8 mL dry $CH_2Cl_2$ was cooled in a −78° C. bath and 0.73 mL (4.34 mmol) of triflic anhydride and 0.6 mL (5.36 mmol) of 2,6 lutidine were added. After 15 min 2 mL (11.5 mmol) of diisopropylethylamine was added and stirred for 10 min. To this solution 0.36 mL (3.21 mmol) of 2,3-dihydroindoline was added and stirred overnight as it slowly warmed to room temperature. The reaction was quenched with saturated $NaHCO_3$ solution and extracted with ether. The combined organic layer was washed with water, brine, dried and concentrated. The residue was purified on a flash column using a gradient of 5-10% EtOAc/hexane to isolate the title compound. $^1H$ NMR: (500 MHz, $CDCl_3$): δ 0.99 (d, 3H), 1.03 (d, 3H), 1.22 (t, 3H), 1.81 (m, 3H), 3.04 (m, 2H), 3.57 (m, 1H), 3.66 (m, 1H), 4.14 (q, 2H), 4.24 (t, 1H), 6.4-7.1 (m, 4H).

Step B 3-(2,3-Dihydro-1H-indol-1-yl)-5-methylhexan-2-one

To a solution of 0.54 g (2.07 mmol) of ethyl (2-(2,3-dihydro-1H-indol-1-yl)-4-methylpentanoate in 10 mL $CH_2Cl_2$, 1.98 g (10 mmol) of N,O-dimethylhydroxylamine hydrochloride and 1.4 mL triethylamine were added. The mixture was cooled in an ice bath and 10 mL (10 mmol) 1 M diethylaluminium chloride in toluene was added. The reaction was stirred overnight as it warmed to room temperature then carefully quenched by pouring into 1.2 N HCl. The solution was extracted with $CH_2Cl_2$. The organic layer was washed with brine, dried and concentrated leaving amide which was used without purification. This amide was dissolved in 5 mL THF and 2.5 mL (3.5 mmol) of 1.4 M methylmagnesium bromide was added. After 1 h, the solution was quenched with 1.2 NHCl and extraced with EtOAc. The EtOAc layer was washed with brine, dried and concentrated. The residue was chromatographed using a gradient of 5-10% EtOAc-hexane to isolate the title compound. $^1H$ NMR: (500 MHz, $CDCl_3$): δ 0.96 (d, 3H), 0.99 (d, 3H), 1.7 (m, 3H), 2.17 (s, 3H), 3.06 (m, 2H), 3.04 (q, 1H), 3.52 (m, 1H), 4.11 (m, 1H) 6.4-7.1 (m, 4H).

Step C 2-(2,3-Dihydro-1-H-indol-1-yl)-1,4-dimethylpentylamine

To a solution of 0.185 g (0.8 mmol) of 3-(2,3-dihydro-1H-indol-1-yl)-5-methylhexan-2-one in 2 mL ethanol, 0.135 g O-methylhydroxylamine hydrochloride and 0.13 mL (1.6 mmol) of pyridine were added. After stirring for 2 h, the solution was concentrated and the residue was partitioned between water and EtOAc. The organic layer was washed with brine, dried and concentrated to give 0.2 g O-methyloxime as a mixture of isomers. This mixture was dissolved in 2 mLTHF and 1.5 mL 1 M $BH_3$ in THF was added. After gas evolution ceased, the reaction was heated in a 50° C. bath. After 2 h another 1.5 mL1 M $BH_3$ in THF was added and heating was continued overnight. The reaction mixture was cooled and quenched with MeOH and concentrated. The residue was dissolved in 6 mL $CH_2Cl_2$ and 2 mL1 N NaOH was added. After stirring for 15 min the layers were separated and the aqueous layer was extracted with $CH_2Cl_2$. The combined organic layer was washed with water, brine dried and concentrated to isolate title compound as a mixture of diastereomers which was used without purification. LC-MS, $R_t$=2.24 min, m/e=233.

The following amines were synthesized by the method of Reference Example 106.

Reference Example 107

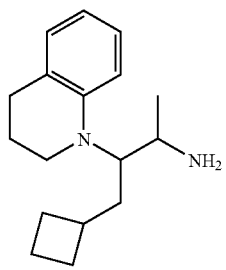

3-Cyclobutyl-2-(3,4-dihydroquinoline-1(2H)-yl)-1-methylpropylamine

LC-MS, $R_t$=2.8 min, m/e=259.

Reference Example 108

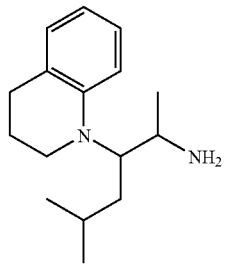

2-(3,4-Dihydroquinoline-1(2H)-yl)-1,4-dimethylpentylamine

LC-MS, $R_t$=2.74 min, m/e=248.

Reference Example 109

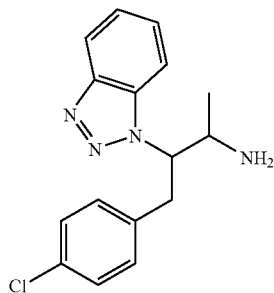

2-(1H-1,2,3-Benzotriazol-1-yl)-3-(4-chlorophenyl)-1-methylpropylamine

Step A 2-(1H-1,2,3-Benzotriazol-1-yl)-N-methoxy-N-methylacetamide

A mixture of 1.77 g (10 mmol) of 2-(1H-1,2,3-benzotriazol-1-yl)acetic acid, 1.07 g (11 mmoles) of N,O-dimethylhydroxylamine hydrochloride, 5.8 g (11 mmol) of PyBOP, and 3.4 mL (24.2 mmol) of diisopropylethylamine in 50 mL $CH_2Cl_2$ was stirred overnight at RT. This mixture was partitioned between EtOAc and water. The organic layer was washed with brine and dried over anhydrous $MgSO_4$. Solvent removal afforded a crude product which was purified on silica gel using 60% EtOAC in hexane as solvent to give 2.01 g the desired amide as a solid.

$^1$H NMR: ($CDCl_3$): δ 3.26 (s, 3H), 3.84 (s, 3H), 5.63 (s, 2H), 7.35-8.2 (m, 4H).

Step B 2-(1H-1,2,3-Benzotriazol-1-yl)-3-(4-chlorophenyl)-N-methoxy-N-methyl-propanamide To a solution of 2.0 g (9 mmol) of 2-(1H-1,2,3-benzotriazol-1-yl)-N-methoxy-N-methylacetamide in 15 mL anhydrous THF at −78° C., 10 mL (10 mmol) of 1M lithium bis(trimethylsilyl)amide was added dropwise. After stirring for 25 min, a solution of 2.06 g (10 mmol) of 4-chlorobenzyl bromide in 2 mL anhydrous THF was added. The resulting reaction mixture was allowed to warm to RT and stirred for 6 h. This reaction was quenched, diluted with 75 mL EtOAc and washed 3 times with 10 mL each of brine, After drying the organic phase solvent removal afforded a crude product which was purified on silica gel using 40% EtOAc in hexane as solvent to afford the desired product as a solid. $^1$H NMR: ($CDCl_3$): δ 3.2 (s, 3H), 3.34 (s, 3H), 3.52 (m, 1H), 3.7 (m, 1H), 6.32 (t, 1H), 6.9-8.2 (m, 8H).

Step C 2-(1H-1,2,3-Benzotriazol-1-yl)-3-(4-chlorophenyl)-butan-2-one

To a solution of 1.73 g (5 mmol) of 2-(1H-1,2,3-benzotriazol-1-yl)-3-(4-chlorophenyl)-N-methoxy-N-methyl-propanamide in 10 mL anhydrous THF at 0° C., 4 mL (10 mmol) of 2.5M methyl magnesium bromide in ether was added. The reaction mixture was stirred for 4 h as it warmed to RT. The reaction was quenched by adding 10 mL 1N HCl and the resulting mixture was partitioned between EtOAc and water. The organic phase was washed with brine and dried over anhydrous $MgSO_4$. Solvent removal gave a crude ketone, which was purified on silica gel using 40% EtOAc in hexane to provide the desired ketone.

Step D 2-(1H-1,2,3-Benzotriazol-1-yl)-3-(4-chlorophenyl)-1-methyl propylamine To a solution of 1.18 g (4 mmol) of 2-(1H-1,2,3-benzotriazol-1-yl)-3-(4-chlorophenyl)-butan-2-one in 8.5 mL (60 mmol) of 7N ammonia in MeOH at 0° C., 4 mL (964 mmol) of glacial acetic acid was added followed by 410 mg (6.5 mmol) of sodium cyanoborohydride. The reaction mixture was allowed to warm to RT and stirred overnight. The reaction was partitioned between EtOAc and saturated $NaHCO_3$ solution. The organic phase was dried over anhydrous $MgSO_4$. The solvent was removed in vacuo and the residue was purified on silica gel using a mixture of 5% 2N methanolic ammonia solution and 95% $CH_2Cl_2$ to give the desired amine as a mixture of diastereomers. LC-MS, $R_f$=2.0 min, m/e=301.

Reference Example 110

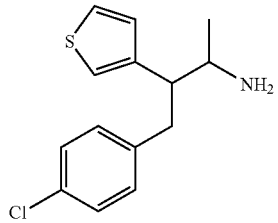

3-(4-Chlorophenyl)-2-(thiophene-3-yl)-1-methylpropylamine

The title amine was prepared by the method described in Reference Example 109, substituting thiophene-3-acetic acid for 2-(1H-1,2,3-benzotriazol-1-yl)acetic acid in Step A. LC-MS, $R_f$=2.19 min, m/e=266.

Reference Example 111

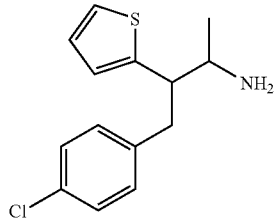

3-(4-Chlorophenyl)-2-(thiophene-2-yl)-1-methylpropylamine

Step A 3-(4-Chlorophenyl)-2-(thiophen-2-yl)-butan-2-one

The title compound was obtained from 2-thiopheneacetic acid according to the procedure described in Reference Example 26, Steps A-C.

Step B 3-(4-Chlorophenyl)-2-(thiophene-2-yl)-1-methylpropylamine

This amine was synthesized by the method of Reference Example 109,

Step D. LC-MS, $R_f$=2.18 min, m/e=266.

Reference Example 112

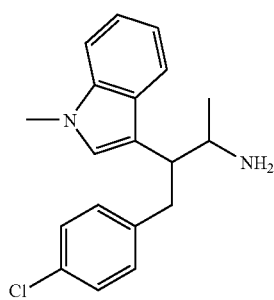

3-(4-Chlorophenyl)-1-methyl-2-(1-methyl-1H-indol-3-yl)propylamine

The title compound was prepared according to the method described in Reference Example 111. LC-MS: $R_t$=2.5 min, m/e=313.

Reference Example 113

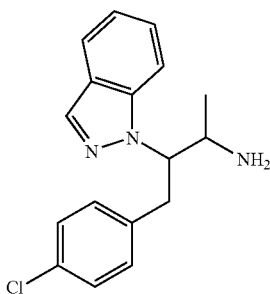

3-(4-Chlorophenyl)-1-methyl-2-(1H-indazol-1-yl)propylamine

Step A 3-(4-Chlorophenyl)-2-(1H-indazol-1-yl)-butan-2-one

The title compound was obtained from indazol-1-yl-acetic acid by following the procedure of Reference Example 10, Steps A-D.

Step B 3-(4-Chlorophenyl)-1-methyl-2-(1H-indazol-1-yl)propylamine

The title amine was prepared according to the procedure of Reference Example 106, Step C. LC-MS: $R_t$=2.24 min, m/e=300.

Reference Example 114

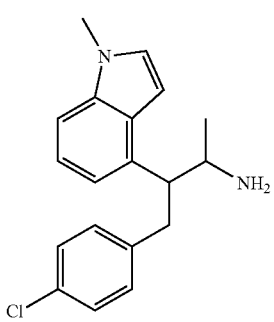

3-(4-Chlorophenyl)-1-methyl-2-(1-methyl-1H-indol-4-yl)propylamine

Step A 4-Chloro-1-methylindole

In a 100 mL flask, 0.3 g (7.5 mmol) sodium hydride was washed twice with dry hexane. The solid was suspended in 15 mL dry THF and 1 g (6.6 mmol) 4-chloroindole was drop wise added. After 15 min, 0.5 mL (7.9 mmol) methyl iodide was added and the solution was stirred overnight. The reaction was quenched with 1.2 N HCl and partitioned between ether and water. The organic layer was washed with brine, dried and concentrated keeping the bath temperature below 30° C. The residue was purified on a flash column using a gradient of 5-10% EtOAc/hexane to isolate the desired product. $^1$H NMR: (500 MHz, CDCl$_3$): δ 3.84 (s, 3H), 6.63 (d, 1H), 7-7.3 (m, 4H).

Step B 1-(1-Methyl-1H-indol-4-yl)acetone

To a solution of 0.852 g (5.14 mmol) of 4-chloro-1-methylindole in 15 mL dry toluene, 0.85 mL (7.73 mmol) isopropenyl acetate and 2.3 mL (8 mmol) tributyltin methoxide were added. The solution was heated to 100° C. After 15 min, 0.24 g (0.61 mmol) 2-dicyclohexylphospino-2'-(N,N-dimethylamino) biphenyl and 0.14 g (0.153 mmol) tris (dibenzylidineacetone)dipalladium were added and heating was continued. After 2 h the solution was cooled, filtered through a pad of CELITE diatomaceous earth and the filtrate was concentrated to ca. 5 mL. This solution was purified on a silica column using a gradient of 5-20% EtOAc/hexane to obtain the title compound. $^1$H NMR: (500 MHz, CDCl$_3$): δ 2.14 (s, 3H), 3.84 (s, 3H), 3.97 (s, 2H), 6.51 (d, 1H), 7-7.3 (m, 4H).

Step C 4-(4-Chlorophenyl)-3-(1-methyl-1H-indol-4-yl)-butan-2-one

To a suspension of 135 mg (3.38 mmol) of sodium hydride in 8 mL dry THF, a solution of 605 mg (3.23 mmol) 1-(1-methyl-1H-indol-4-yl)acetone in 2 mL THF was added. The mixture was stirred for 45 min during which time the sodium hydride dissolved and a yellow orange solution resulted. The reaction was cooled in ice bath and 660 mg (3.24 mmol) 4-chlorobenzyl bromide in 1 mL THF was added. The cold bath was removed and the solution was stirred for 1.5 h. The reaction was quenched with 1.2 N HCl and extracted with EtOAc. The organic layer was washed with brine, dried and concentrated. The residue was chromatographed using a gradient of 10-20% EtOAc/hexane to isolate the desired product. $^1$H NMR: (500 MHz, CDCl$_3$): δ 2.03 (s, 3H), 3.07 (m, 1H), 3.58 (m, 1H), 3.84 (s, 3H), 4.23 (t, 1H), 6.52 (d, 1H), 6.9-7.3 (m, 8H).

Step D 3-(4-Chlorophenyl)-1-methyl-2-(1-methyl-1H-indol-4-yl)propylamine

The title compound was prepared from 4-(4-chlorophenyl)-3-(1-methyl-1H-indol-4-yl)-butan-2-one by following the procedure of Reference Example 106, Step C. LC-MS, $R_t$=2.4 min, m/e=313.

Reference Example 115

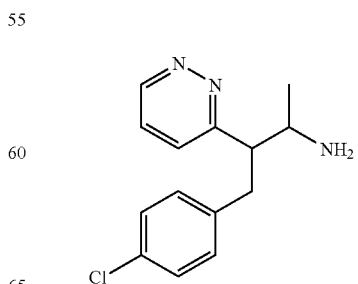

3-(4-Chlorophenyl)-1-methyl-2-(pyridazin-3-yl)propylamine

Step A 4-(4-Chlorophenyl)-3-(pyridazin-3-yl)-butan-2-one

This compound was synthesized from 3-iodopyridazine by the procedure of Reference Example 114, Steps B-C.

Step B N-2,4-Dimethoxybenzyl-N(3-(4-chlorophenyl)-1-methyl-2-(pyridazin-3-yl)propyl)amine A solution of 300 mg (1.15 mmol) 4-(4-chlorophenyl)-3-(pyridazin-3-yl)-butan-2-one in 4 mL dichloroethane was treated with 234 mg (1.15 mmol) 2,4-dimethoxybenzyl amine hydrochloride, 0.16 mL (1.15 mmol) triethylamine and 488 mg (2.3 mmol) sodium triacetoxyborohydride. After stirring the reaction overnight, it was partitioned between water and $CH_2Cl_2$. The organic layer was washed with brine, dried and concentrated and the residue was purified on a flash column using 3% $MeOH—CH_2Cl_2$ to isolate the desired amine.

Step C 3-(4-Chlorophenyl)-1-methyl-2-(pyridazin-3-yl)propylamine

A solution of 300 mg N-2,4-dimethoxybenzyl-N(3-(4-chlorophenyl)-1-methyl-2-(pyridazin-3-yl)propyl)amine in 5 mL trifluoroacetic acid was heated in a 70° C. bath over night followed by 6 h in a 100° C. bath. The reaction was cooled, concentrated and the residue was diluted with EtOAc. This solution was quenched (to pH 10) with 1N NaOH and the layers were separated. The organic layer was washed with brine, dried and concentrated. The residue was purified on a prepTLC using 10% $MeOH/CH_2Cl_2$ with 1% $NH_4OH$ to isolate the title compound (mixture of diastereomers), starting material was also recovered. LC-MS, Rt=1.63 min, m/e=262.

Reference Example 116

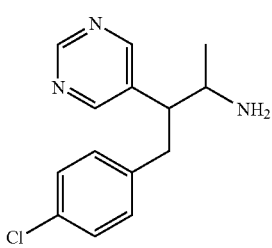

3-(4-Chlorophenyl)-1-methyl-2-(pyrimidin-5-yl)propylamine

Step A 4-(4-Chlorophenyl)-3-(pyrimidin-5-yl)-butan-2-one

The title compound was obtained from 5-bromopyrimidine following the method of Reference Example 114, Steps B-C except that 2-(di-t-butylphosphino)biphenyl was used in place of dicyclohexylphospino-2'-(N,N-dimethylamino)biphenyl in Step B.

Step B 3-(4-Chlorophenyl)-1-methyl-2-(pyrimidin-5-yl)propylamine

The title compound was prepared by the procedure described in Reference Example 10, Steps E-I. LC-MS, Rt=1.57 min, m/e=262.

Reference Example 117

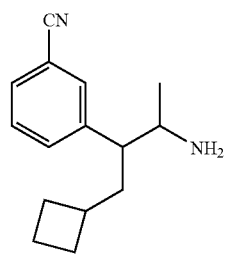

2-(3-Cyanophenyl)-3-cyclobutyl-1-methylpropylamine

Step A 1-(3-Cyanophenyl)acetone

The title compound was prepared from 3-bromobenzonitrile and isopropenyl acetate by the procedure of Reference Example 114, Step B.

Step B 3-(3-Cyanophenyl)-4-cyclobutyl-butan-2-one

To a solution of 1.45 g (9.07 mmol) of 1-(3-cyanophenyl)acetone in 18 mL acetonitrile, 1.1 mL (9.5 mmol) cyclobutyl bromide and 5.91 g (18.1 mmol) cesium carbonate were added. After heating the solution in a 60° C. bath overnight, it was cooled and filtered. The filtrate was partitioned between water and EtOAc and the aqueous layer was extracted with EtOAc. The combined organic layer was washed with brine, dried and concentrated. The residue was purified on a flash column using a gradient of 5-10% EtOAc/hexane to isolate the title compound. $^1H$ NMR: (500 MHz, $CDCl_3$): δ 1.5-2.2 (m, 9H), 2.13 (s, 3H), 3.64 (m, 1H), 7.4-7.7 (m, 4H).

Step C 2-(3-Cyanophenyl)-3-cyclobutyl-1-methylpropylamine

This amine was prepared by following the method of Reference Example 10, Steps E-I. LC-MS, Rt=2.48 min, m/e=229.

The compounds of Reference Examples 118-120 were obtained by procedures described in Reference Example 117.

Reference Example 118

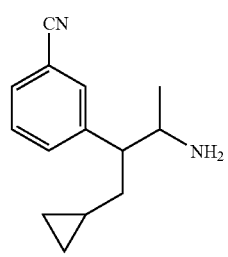

2-(3-Cyanophenyl)-3-cyclopropyl-1-methylpropylamine

LC-MS, Rt=1.8 min, m/e=215.

Reference Example 119

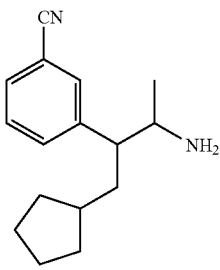

2-(3-Cyanophenyl)-3-cyclopentyl-1-methylpropylamine

LC-MS, Rt=2.7 min, m/e=243.

Reference Example 120

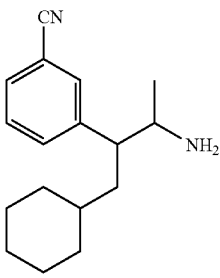

2-(3-Cyanophenyl)-3-cyclohexyl-1-methylpropylamine

LC-MS, Rt=2.8 min, m/e=257.

Reference Example 121

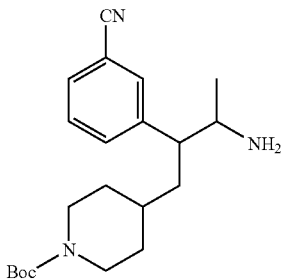

2-(3-Cyanophenyl)-3-(1-tert-butyloxycarbonyl-piperidin-4-yl)-1-methylpropylamine Step A 3-(3-Cyanophenyl)-4-(1-tert-butyloxycarbonyl-piperidin-4-yl)-butan-2-one The title compound was synthesized by the method of Reference Example 117, Steps A-B.

Step B 2-(3-Cyanophenyl)-3-(1-tert-butyloxycarbonyl-piperidin-4-yl)-1-methylpropylamine The title amine was obtained by the method of Reference Example 10, steps E-G except that di-tert-butyl dicarbonate was not added in Step G. LC-MS, Rt=2.72 min, m/e=258 (M-99).

Reference Example 121

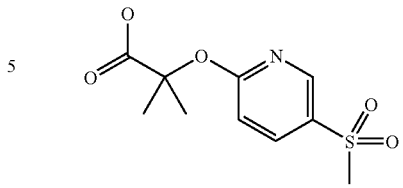

2-Methyl-2-(5-methylsulfonyl-2-pyridyloxy)propionic Acid

Step A Ethyl 2-(5-Methylsulfonyl-2-pyridyloxy)propionate

A mixture of ethyl 2-hydroxyisobutyrate (0.41 mL, 3.0 mmol), 2,5-bis(methyl sulfonyl)pyridine (*J. Heterocycl. Chem.* 1985, 22, 1583) (0.70 g, 3.0 mmol) and sodium hydride (60% dispersion in mineral oil, 0.14 g, 3.6 mmol) in 30 mL of anhydrous DMF was heated at 80° C. overnight. The reaction mixture was cooled to room temperature, and was partitioned between saturated aqueous ammonium chloride (200 mL) and ether (200 mL). The organic layer was separated and was washed with water and brine, dried over anhydrous sodium sulfate, filtered and concentrated to dryness, and the residue was purified by flash column chromatography on silica gel eluting with 0 to 80% ethyl acetate in hexane to give the title compound as a 1:1 mixture with 2-ethoxy-5-methylsulfonylpyridine. LC-MS: m/e 288 (M+H)$^+$ (0.70 min).

Step B 2-Methyl-2-(5-methylsulfonyl-2-pyridyloxy) propionic Acid

To a solution of ethyl 2-methyl-2-(5-methylsulfonyl-2-pyridyloxy)propionate (Step A, 0.45 g, 1.6 mol) in 5 mL MeOH, 10 mL THF and 10 mL water was added sodium hydroxide (0.19 g, 4.7 mmol). After stirring at room temperature for 3 days, the reaction mixture was partially concentrated, and was added 2 M hydrochloric acid to pH>2. The resulting mixture was extracted with EtOAc (2×20 mL), and the combined extracts were dried over anhydrous sodium sulfate, filtered, and concentrated to dryness to afford the title compound. $^1$H NMR (500 MHz, CD$_3$OD): δ 8.60 (d, 1H), 8.16 (dd, 1H), 7.17 (d, 1H), 3.15 (s, 3H), 1.71 (s, 6H).

Reference Example 122

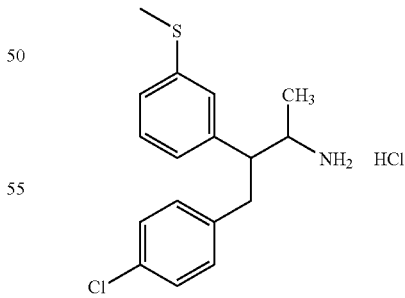

N-[3-(4-Chlorophenyl)-2-(3-methylthiophenyl)-1-methylpropyl]amine hydrochloride (Diastereomer α)

The title compound was prepared following the same procedure as described in Example 69 substituting 3,5-dibromopyridine with 3-bromothioanisole at Step A. LC-MS: m/e 306 (M+H)$^+$ (2.68 min).

Example 1

Automated Synthesis of a One Dimensional Amide Library

The following synthesis of a 1-dimensional, single, pure compound library was performed on a MYRIAD CORE System. All reaction vessels were dried under a stream of nitrogen at 120° C. for 12 h prior to use. All solvents were dried over sieves for at least 12 h prior to use. An appropriate stock solution of N-[2,3-bis(4-chlorophenyl)-1-methylpropyl]-amine hydrochloride (alpha isomer) was prepared immediately prior to use in pyridine with 0.05 equivalents (relative to N-[2,3-bis(4-chlorophenyl)-1-methylpropyl]-amine hydrochloride (alpha isomer)) of dimethylaminopyridine added; the diverse carboxylic acids available from commercial sources were dissolved immediately prior to use in DMSO. The relative amounts of reactants and coupling reagents are listed in Table 1. Compounds of the present invention that were prepared by this method of automated synthesis are listed in Table 2.

TABLE 1

| Substance | Amount per reaction vessel | MW | Concentration | mmols | Equivs. |
|---|---|---|---|---|---|
| Acid in DMSO | 1 mL | N/A | 0.2 M | 0.2 | 1.67 |
| EDC/HOBt Cocktail in Deuterated Chloroform | 0.8 mL | EDC: 191.71 HOBt: 135.13 | 0.25 M each | 0.2 each | 1.67 each |
| Amine in Pyridine with catalytic dimethylaminopyridine (~0.05 eq.) | 0.6 mL | 294.227 | 0.2M | 0.12 | 1.0 |

Procedure

To vessel one of a total of 192 dry, 10 mL fritted MYRIAD reaction vessels under nitrogen was added the appropriate diverse acid subunit (1.0 mL, 0.2 mmoles, 0.2 M in DMSO); this was repeated for the remaining 191 reactions until the diversity acids had been enumerated to all 192 reaction vessels. To each of 192 reaction vessels under nitrogen was then added the EDC/HOBt cocktail (0.8 mL, 0.2 mmoles, 0.25 M each in deuterated chloroform). Finally, to each of the 192 reaction vessels was added N-[2,3-bis(4-chlorophenyl)-1-methylpropyl]-amine hydrochloride (alpha isomer) (0.6 mL, 0.12 mmoles, 0.2M in pyridine). The reactions were then aged for 4 h at room temperature (20-25° C.) followed by 16 h at 65° C. with nitrogen sparging agitation (1s pulse of nitrogen every 30 minutes). The crude reactions were analyzed by HPLC-MS Method 1.

Analytical LC Method 1:

| | |
|---|---|
| Column: | MetaChem Polaris C-18A, 30 mm × 4.6 mm, 5.0 µm |
| Eluent A: | 0.1% TFA in Water |
| Eluent B: | 0.1% TFA in Acetonitrile |
| Gradient: | 5% B to 95% B in 3.3 minutes, ramp back to 5% B in 0.3 min |
| Flow: | 2.5 mL/min. |
| Column Temp.: | 50° C. |
| Injection amount: | 5 uL of undiluted crude reaction mixture. |
| Detection: | UV at 220 and 254 nm. |

MS: API-ES ionization mode, mass scan range (100-700)
ELSD: Light Scattering Detector All 192 crude reactions were purified by preparative HPLC using UV based detection (Preparative method 2). The collected fractions were then analyzed for purity by LC-MS (Analytical method 3); fractions found to be greater than 90% purity were pooled into tared 40 mL EPA vials and lyophilized.

Preparative LC Method 2:

| | |
|---|---|
| Column: | MetaChem Polaris C-18A, 100 mm × 21.2 mm, 10 µm |
| Eluent A: | 0.1% TFA in Water |
| Eluent B: | 0.1% TFA in Acetonitrile |
| Pre-inject Equilibration: | 1.0 min |
| Post-Inject Hold: | 0.0 min |
| Gradient: | 10% B to 100% B in 6.0 minutes, hold at 100% B for an additional 2.0 minutes, ramp back from 100% B to 10% B in 1.5 minutes. |
| Flow: | 25 mL/min. |
| Column Temp.: | ambient |
| Injection amount: | 1.5 mL undiluted crude reaction mixture. |
| Detection: | UV at 220 and 254 nm. |

Analytical LC Method 3:

| | |
|---|---|
| Column: | MetaChem Polaris C-18A, 30 mm × 2.0 mm, 3.0 µm |
| Eluent A: | 0.1% TFA in Water |
| Eluent B: | 0.1% TFA in Acetonitrile |
| Gradient: | 5% B to 95% B in 2.0 minutes, ramp back to 5% B in 0.1 min |
| Flow: | 1.75 mL/min. |
| Column Temp.: | 60° C. |
| Injection amount: | 5 uL of undiluted fraction. |
| Detection: | UV at 220 and 254 nm. |

MS: API-ES ionization mode, mass scan range (100-700)
ELSD: Light Scattering Detector

Lyophilization Parameters

Initial Freeze Setpoint: 1 h at −70° C.

Drying Phase Condenser Setpoint: −50° C.

Drying Phase Table:

| Shelf Temperature (C.) | Duration (minutes) | Vacuum Setpoint (mTorr) |
|---|---|---|
| −60° | 240 | 25 |
| −40° | 240 | 25 |
| 5° | 480 | 25 |
| 20° | 1000 | 25 |

TABLE 2

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 1. | N-[2,3-bis(4-chlorophenyl)-1-methyl-propyl]-2-(pyrazol-1-yl)acetamide, trifluoroacetic acid salt | 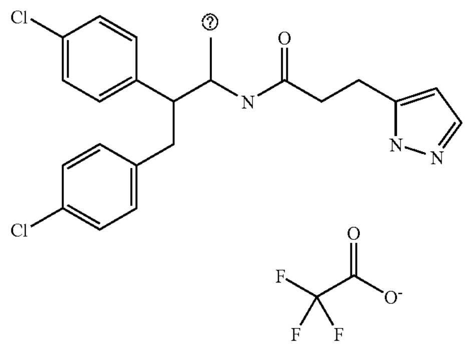 | 1.33 | 402.2 |
| 2. | N-[2,3-bis(4-chlorophenyl)-1-methyl-propyl]-2-(1,2,4-triazol-1-yl)acetamide, trifluoroacetic acid salt | 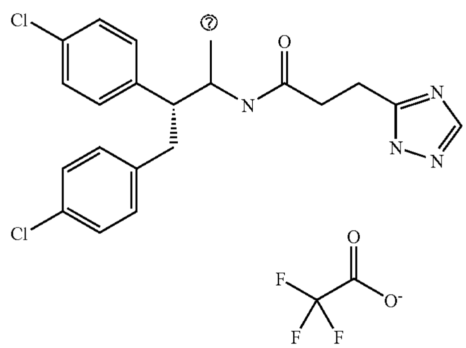 | 1.190 | 403.05 |
| 3. | N-[2,3-bis(4-chlorophenyl)-1-methyl-propyl]-2-(benzothiazole-2-thio)acetamide, trifluoroacetic acid salt | 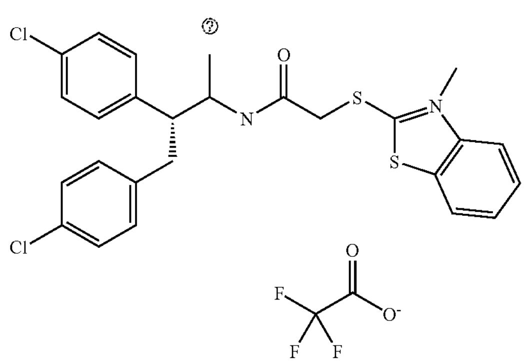 | 1.54 | 501.2 |
| 4. | N-[2,3-bis(4-chlorophenyl)-1-methyl-propyl]-2-(benzoxazole-2-thio)acetamide, trifluoroacetic acid salt | 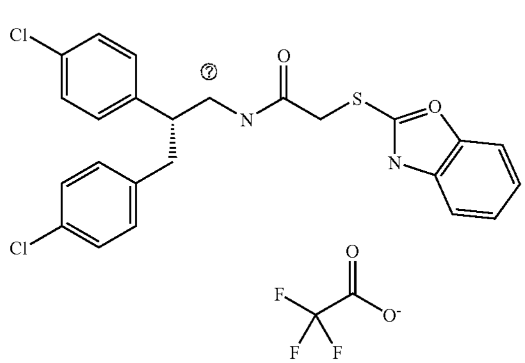 | 1.50 | 485.2 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 5. | N-[2,3-bis(4-chlorophenyl)-1-methyl-propyl]-2-(benzoxazolin-2-on-3-yl)acetamide | 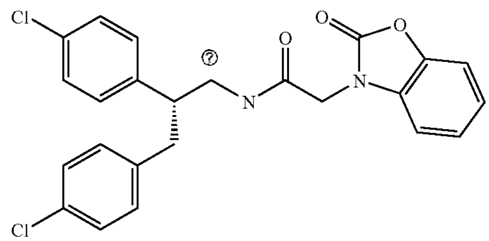 | 1.365 | 469.05 |
| 6. | N-[2,3-bis(4-chlorophenyl)-1-methyl-propyl]-2-(4-methyl-2H-phthalazin-1-on-2-yl)acetamide | 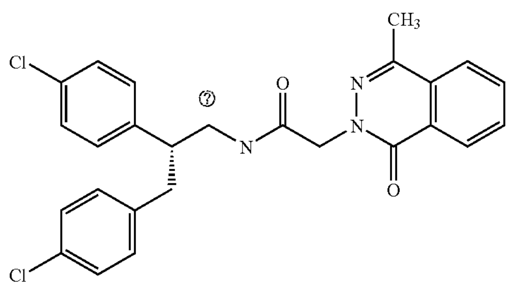 | 1.353 | 494.10 |
| 7. | N-[2,3-bis(4-chlorophenyl)-1-methyl-propyl]-2-(2H-phthalazin-1-on-4-yl)propanamide | 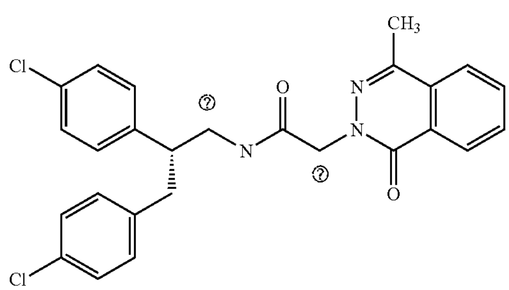 | 1.34 | 494.3 |
| 8. | N-[2,3-bis(4-chlorophenyl)-1-methyl-propyl]-2-(3,5-dimethyl-1,2,4-triazol-1-yl)acetamide, trifluoroacetic acid salt | 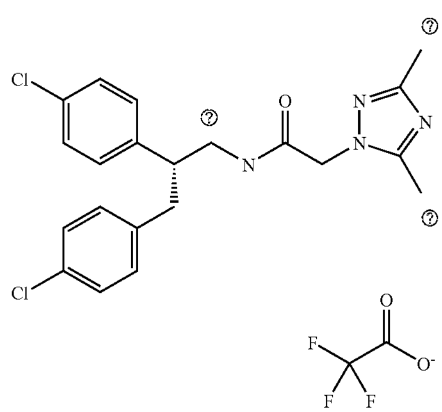 | 1.2 | 431.3 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 9. | N-[2,3-bis(4-chlorophenyl)-1-methyl-propyl]-2-(2-methyl-thiazol-4-yl)acetamide, trifluoroacetic acid salt | 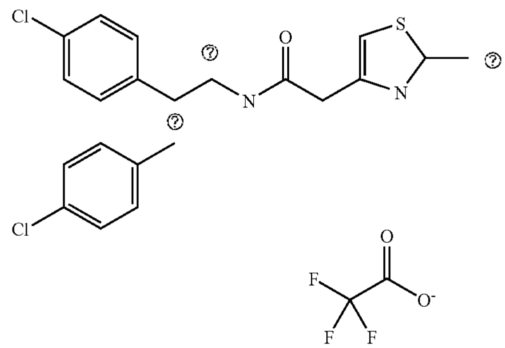 | 1.33 | 433.2 |
| 10. | N-[2,3-bis(4-chlorophenyl)-1-methyl-propyl]-2-(1-(4-phenyl-pyrrolidin-2-on-1-yl))acetamide | 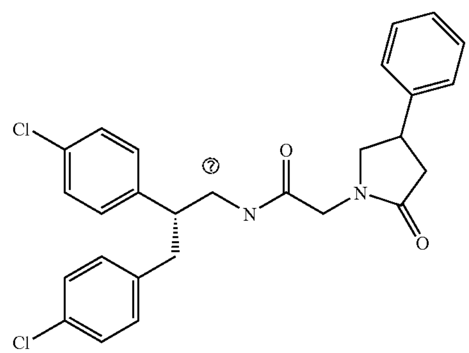 | 1.42 | 495.3 |
| 11. | N-[2,3-bis(4-chlorophenyl)-1-methyl-propyl]-2-(3,5-dimethyl-pyrazol-1-yl)acetamide, trifluoroacetic acid salt | 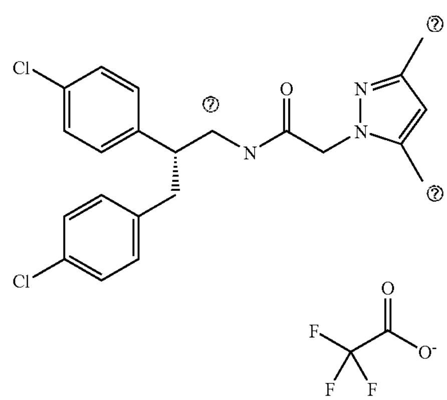 | 1.285 | 430.2 |
| 12. | N-[2,3-bis(4-chlorophenyl)-1-methyl-propyl]-2-(3-methyl-pyrazol-1-yl)acetamide, trifluoroacetic acid salt | 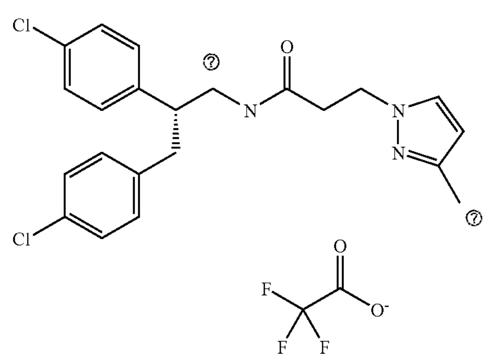 | 1.33 | 430.3 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 13. | N-[2,3-bis(4-chlorophenyl)-1-methyl-propyl]-2-(isoindolin-1-on-3-yl)acetamide | 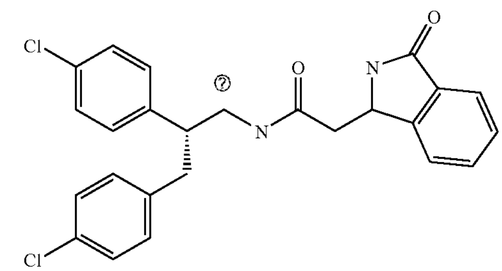 | 1.276 | 467.10 |
| 14. | N-[2,3-bis(4-chlorophenyl)-1-methyl-propyl]-2-(3,5-dimethyl-isoxazol-4-yl)acetamide, trifluoroacetic acid salt | 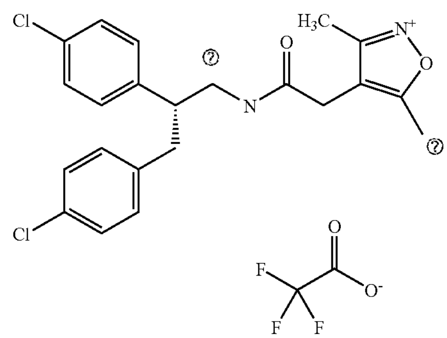 | 1.316 | 431.1 |
| 15. | N-[2,3-bis(4-chlorophenyl)-1-methyl-propyl]-3-(3,5-dimethyl-pyrazol-1-yl)propanamide, trifluoroacetic acid salt | 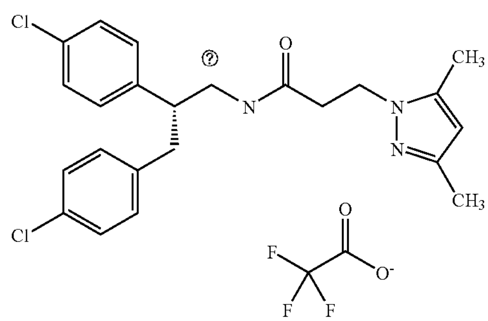 | 1.29 | 444.3 |
| 16. | N-[2,3-bis(4-chlorophenyl)-1-methyl-propyl]-2-(3-methyl-pyrazol-1-yl)acetamide, trifluoroacetic acid salt | 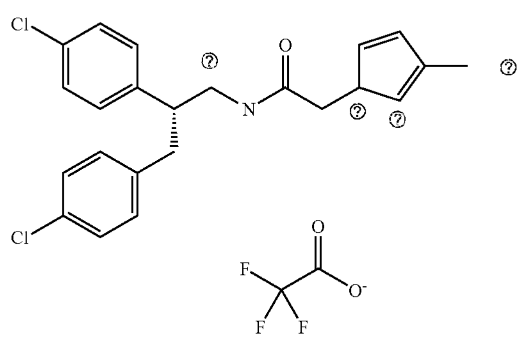 | 1.303 | 416.10 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 17. | N-[2,3-bis(4-chlorophenyl)-1-methyl-propyl]-2-(4-(imidazolidin-2-on-1-yl)phenyl)acetamide | 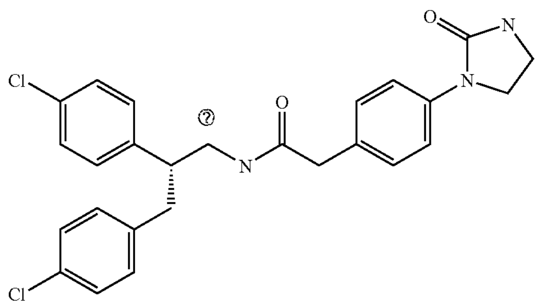 | 1.258 | 496.2 |
| 18. | N-[2,3-bis(4-chlorophenyl)-1-methyl-propyl]-2-(5-methyl-1,2,4-triazol-3-yl)acetamide, trifluoroacetic acid salt | 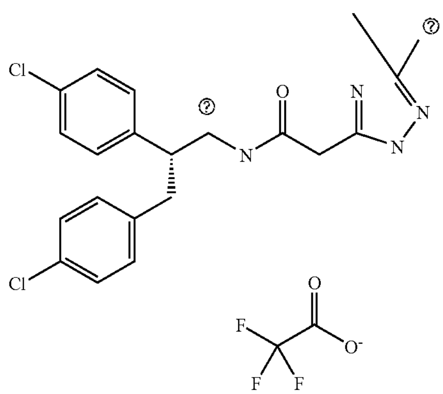 | 1.17 | 417.2 |
| 19. | N-[2,3-bis(4-chlorophenyl)-1-methyl-propyl]-5-(2-methyl)phenyl-5-oxo-pentanamide | 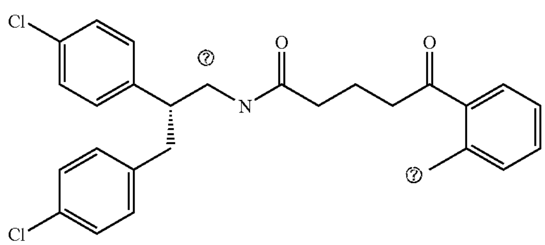 | 1.436 | 482.1 |
| 20. | N-[2,3-bis(4-chlorophenyl)-1-methyl-propyl]-3-(benzothiazol-2-yl)propanamide, trifluoroacetic acid salt | 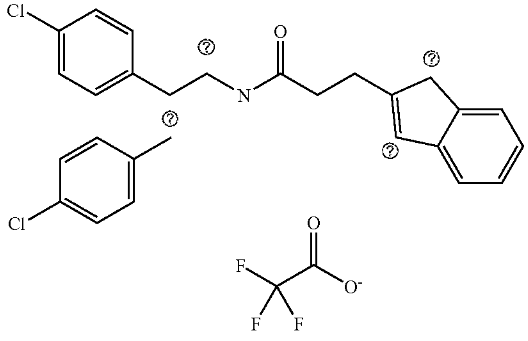 | 1.46 | 483.2 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 21. | N-[2,3-bis(4-chlorophenyl)-1-methyl-propyl]-3-(aza-bicyclo[2.2.1]heptan-2-yl)propanamide, trifluoroacetic acid salt | 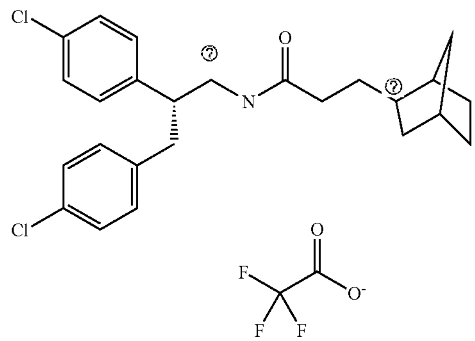 | 1.154 | 445.2 |
| 22. | N-[2,3-bis(4-chlorophenyl)-1-methyl-propyl]-2-(5-methoxy-2-oxo-2,3-dihydro-1H-indol-3-yl)acetamide | 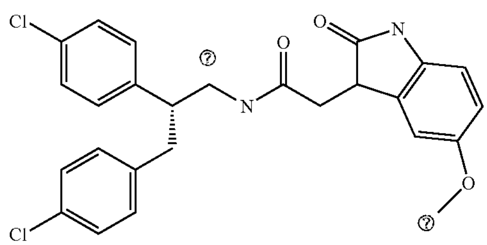 | 1.270 | 497.1 |
| 23. | N-[2,3-bis(4-chlorophenyl)-1-methyl-propyl]-2-(benzotriazol-2-yl)acetamide, trifluoroacetic acid salt | 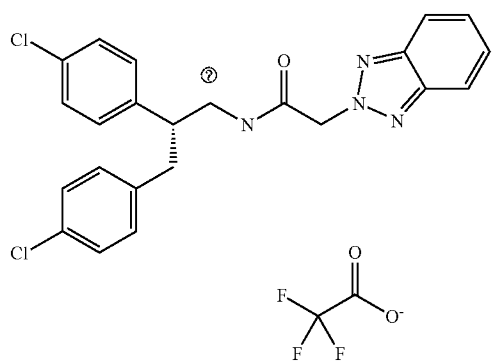 | 1.44 | 453.2 |
| 24. | N-[2,3-bis(4-chlorophenyl)-1-methyl-propyl]-2-(4-methyl-thiazol-2-yl-thio)acetamide, trifluoroacetic acid salt | 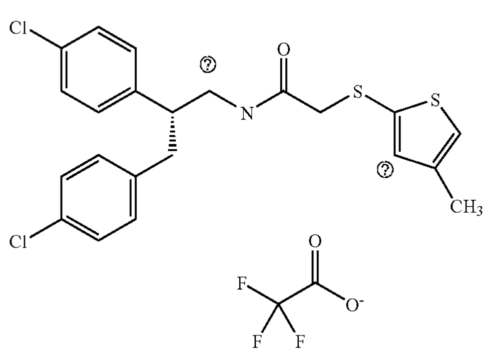 | 1.404 | 465.0 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 25. | N-[2,3-bis(4-chlorophenyl)-1-methyl-propyl]-2-(4,4-diphenyl)butanamide | 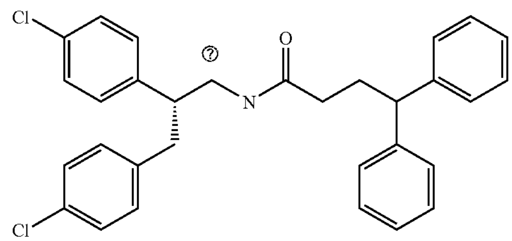 | 1.543 | 516.15 |
| 26. | N-[2,3-bis(4-chlorophenyl)-1-methyl-propyl]-3-(1,2,4-triazol-1-yl)propanamide, trifluoroacetic acid salt | 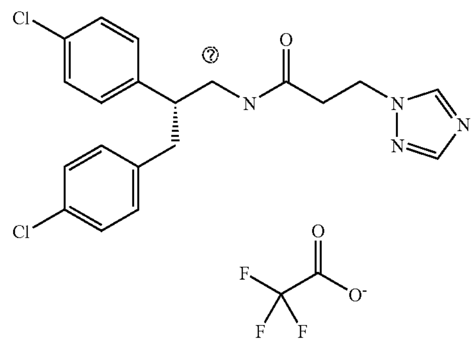 | 1.180 | 417.15 |
| 27. | N-[2,3-bis(4-chlorophenyl)-1-methyl-propyl]-2-(imidazo[2,1-b][1,3]thiazo-6-yl)acetamide, trifluoroacetic acid salt | 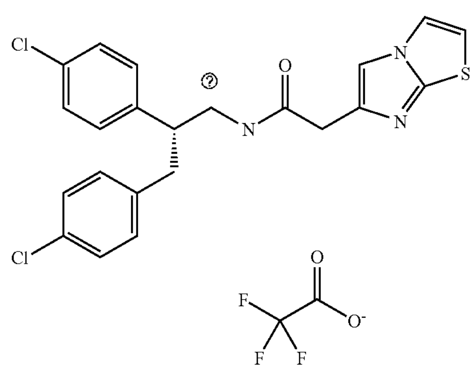 | 1.16 | 458.1 |
| 28. | N-[2,3-bis(4-chlorophenyl)-1-methyl-propyl]-3-(3,5-dichlorophenyl)propanamide | 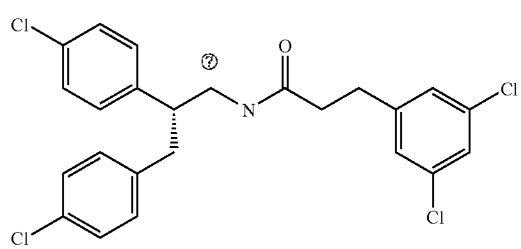 | 1.533 | 496.0 |
| 29. | N-[2,3-bis(4-chlorophenyl)-1-methyl-propyl]-4-(3,5-dichlorophenyl)butanamide | 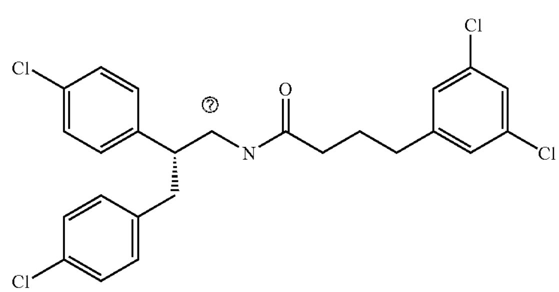 | 1.575 | 510.0 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 30. | N-[2,3-bis(4-chlorophenyl)-1-methyl-propyl]-3-(t-butoxy)propanamide | 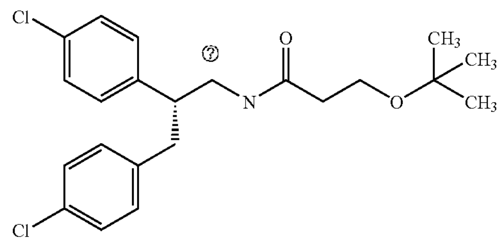 | 1.397 | 422.1 |
| 31. | N-[2,3-bis(4-chlorophenyl)-1-methyl-propyl]-4-(2,3-dihydro-indol-1-yl)butanamide | 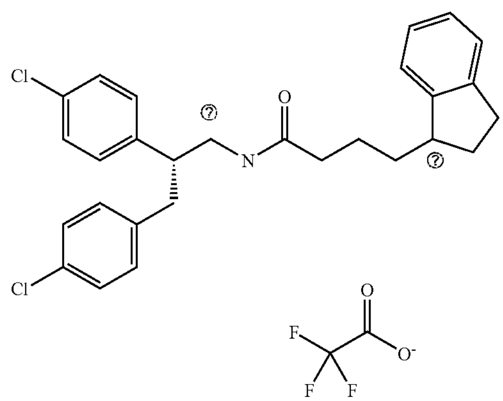 | 1.195 | 481.2 |
| 32. | N-[2,3-bis(4-chlorophenyl)-1-methyl-propyl]-3-(1-methyl-pyrazol-5-yl)propanamide, trifluoroacetic acid salt | 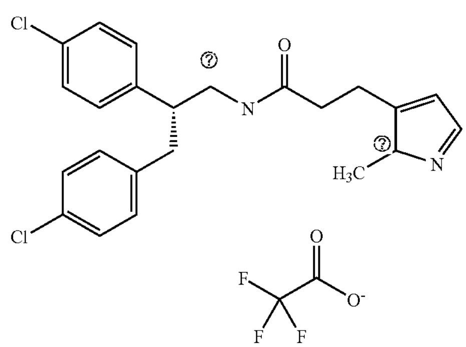 | 1.230 | 430.2 |
| 33. | N-[2,3-bis(4-chlorophenyl)-1-methyl-propyl]-3-(4-t-butoxyphenyl)-propanamide | 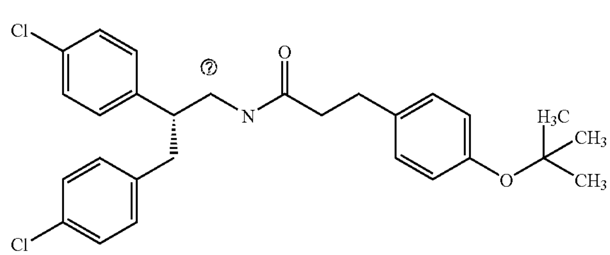 | 1.498 | 498.1 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 34. | N-[2,3-bis(4-chlorophenyl)-1-methyl-propyl]-3-(3,5-dimethylphenyl)propanamide | 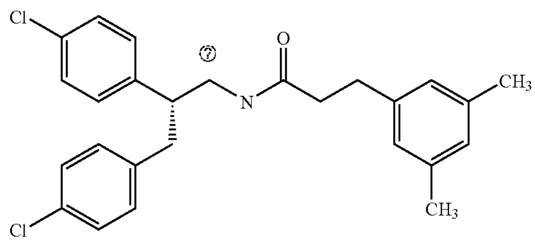 | 1.499 | 454.2 |
| 35. | N-[2,3-bis(4-chlorophenyl)-1-methyl-propyl]-2-(5-methyl-pyrazol-1-yl)acetamide, trifluoroacetic acid salt | 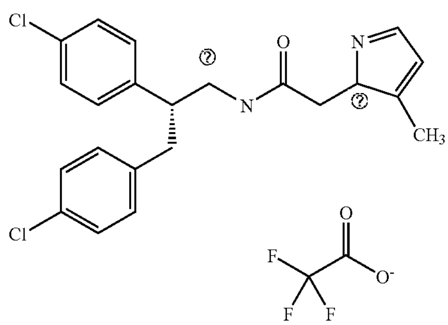 | 1.294 | 416.1 |
| 36. | N-[2,3-bis(4-chlorophenyl)-1-methyl-propyl]-2-(4-methyl-1,2,4-triazol-3-yl-thio)acetamide, trifluoroacetic acid salt | 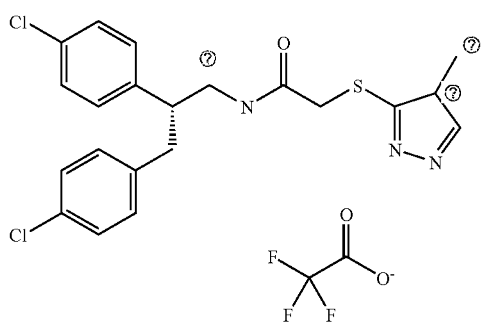 | 1.180 | 449.1 |
| 37. | N-[2,3-bis(4-chlorophenyl)-1-methyl-propyl]-2-(2,3,4,5-tetrahydro-1,4-benzoxazepin-4-yl)acetamide, trifluoroacetic acid salt | 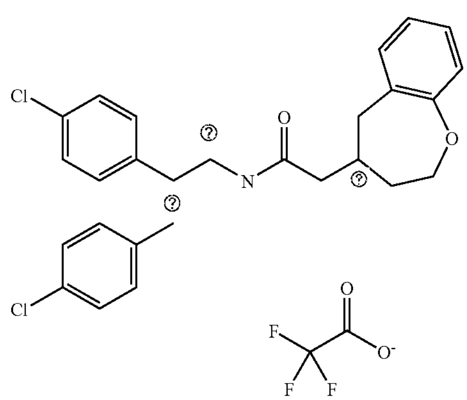 | 1.190 | 483.1 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 38. | N-[2,3-bis(4-chlorophenyl)-1-methyl-propyl]-6-(t-butyloxycarbonylamino)hexanamide | 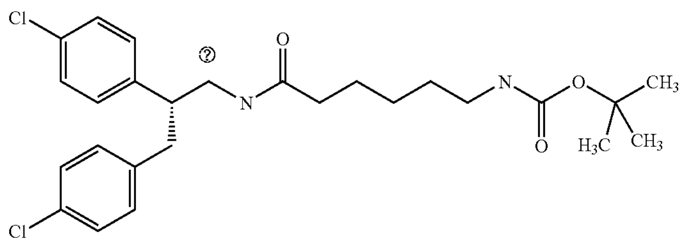 | 1.415 | 407.1 (-BOC) |
| 39. | N-[2,3-bis(4-chlorophenyl)-1-methyl-propyl]-2-(5,6-dihydro-imidazo[2,1-b]thiazol-3-yl)acetamide, trifluoroacetic acid salt | 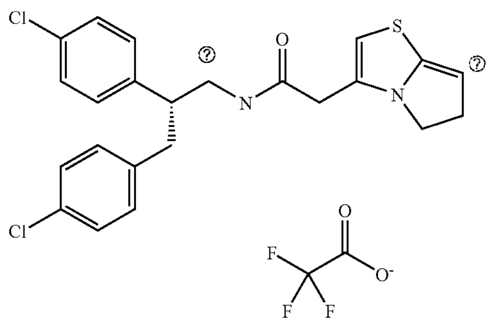 | 1.134 | 460.0 |
| 40. | N-[2,3-bis(4-chlorophenyl)-1-methyl-propyl]-2-(morpholin-4-yl)-2-(3-pyridyl)acetamide, trifluoroacetic acid salt | 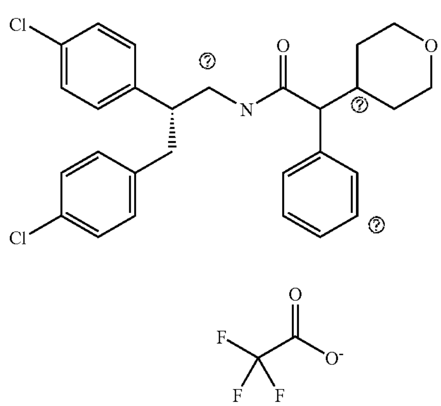 | 1.14 | 498.2 |
| 41. | N-[2,3-bis(4-chlorophenyl)-1-methyl-propyl]-4-(aminosulfonyl)-butanamide | 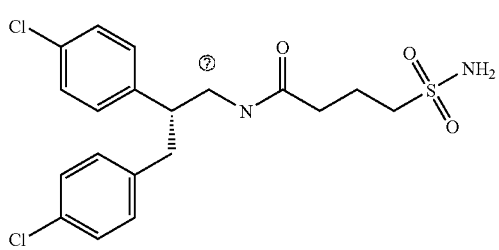 | 1.198 | 443.1 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 42. | N-[2,3-bis(4-chlorophenyl)-1-methyl-propyl]-2-(4-phenyl-piperazin-1-yl)acetamide, trifluoroacetic acid salt | 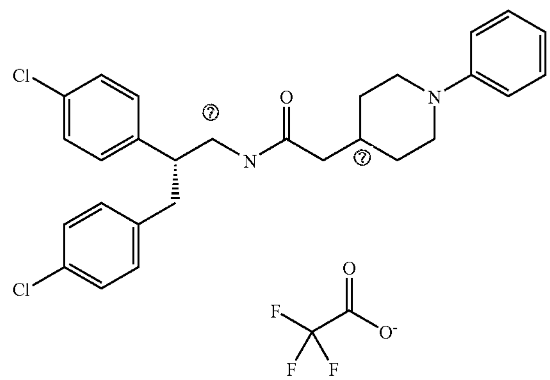 | 1.210 | 496.2 |
| 43. | N-[2,3-bis(4-chlorophenyl)-1-methyl-propyl]-trans-cinnamamide | 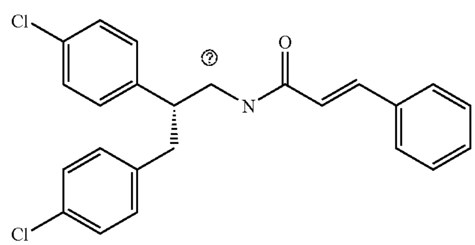 | 1.438 | 424.15 |
| 44. | N-[2,3-bis(4-chlorophenyl)-1-methyl-propyl]-9-phenyl-9-oxo-nonanamide | 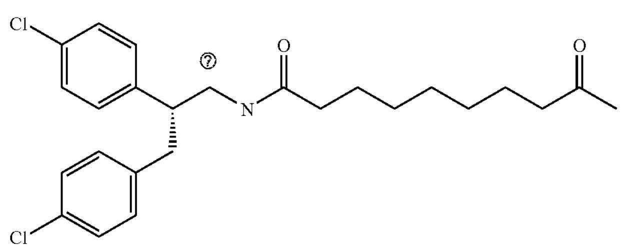 | 1.519 | 524.3 |
| 45. | N-[2,3-bis(4-chlorophenyl)-1-methyl-propyl]-2-phenyl-butanamide | 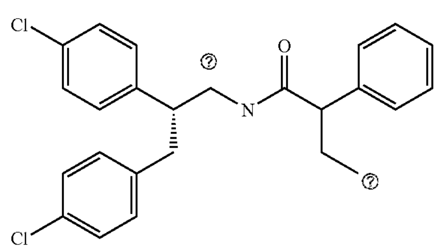 | 1.483 | 440.1 |
| 46. | N-[2,3-bis(4-chlorophenyl)-1-methyl-propyl]-2-cyclopropyl-acetamide | 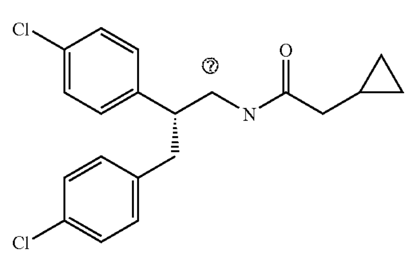 | 1.350 | 376 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 47. | N-[2,3-bis(4-chlorophenyl)-1-methyl-propyl]-2-(1-naphthyl)-acetamide | 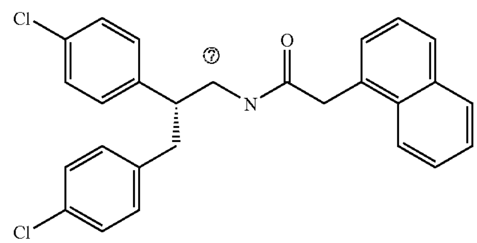 | 0.918 | 459.3 |
| 48. | N-[2,3-bis(4-chlorophenyl)-1-methyl-propyl]-2-(5-methoxy-1-indanon-3-yl)-acetamide | 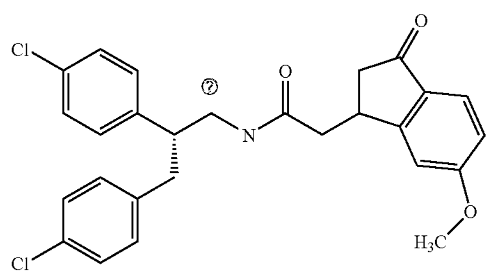 | 1.35 | 496.2 |
| 49. | N-[2,3-bis(4-chlorophenyl)-1-methyl-propyl]-2-phenoxy-acetamide | 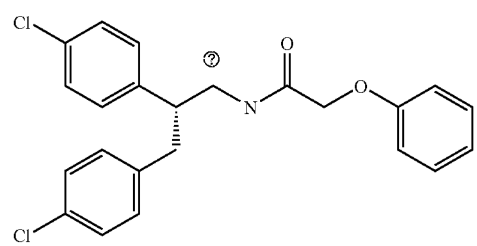 | 1.430 | 428.1 |
| 50. | N-[2,3-bis(4-chlorophenyl)-1-methyl-propyl]-3-(4-hydroxyphenyl)-propanamide | 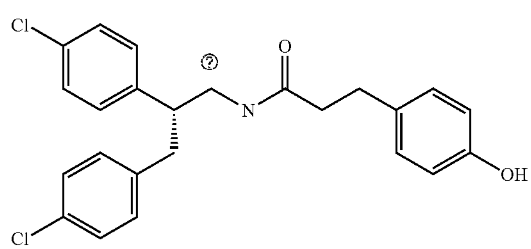 | 1.248 | 442.0 |
| 51. | N-[2,3-bis(4-chlorophenyl)-1-methyl-propyl]-hexanamide | 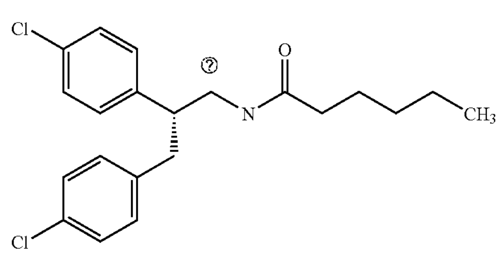 | 1.436 | 392.1 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 52. | N-[2,3-bis(4-chlorophenyl)-1-methyl-propyl]-2-cyclopentyl-acetamide | 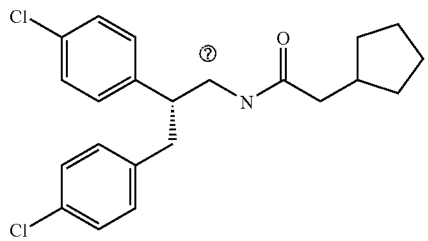 | 1.49 | 404.2 |
| 53. | N-[2,3-bis(4-chlorophenyl)-1-methyl-propyl]-2-ethoxy-acetamide | 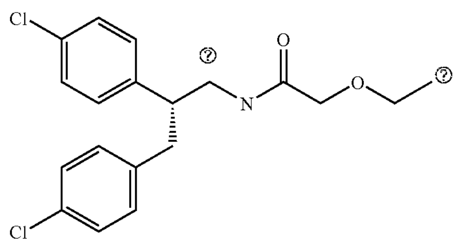 | 1.346 | 380.1 |
| 54. | N-[2,3-bis(4-chlorophenyl)-1-methyl-propyl]-3-methyl-butanamide | 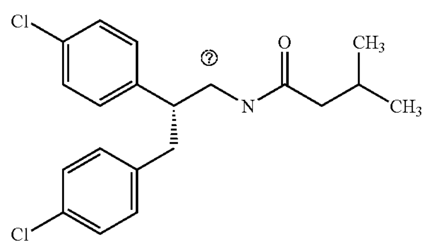 | 1.380 | 378.1 |
| 55. | N-[2,3-bis(4-chlorophenyl)-1-methyl-propyl]-3-(1-t-butoxycarbonyl-piperidin-4-yl)-propanamide | 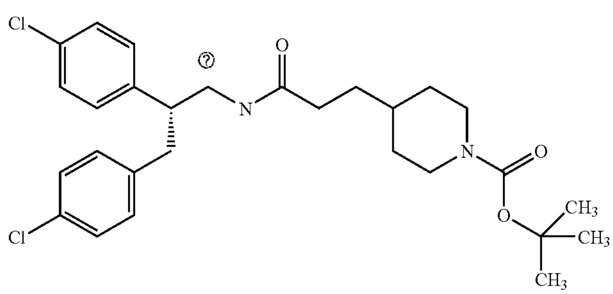 | 1.52 | 433.3 (-BOC) |
| 56. | N-[2,3-bis(4-chlorophenyl)-1-methyl-propyl]-2-(3-chlorophenyl)-acetamide | 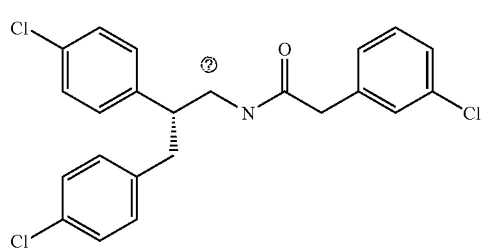 | 0.879 | 445.2 |

TABLE 2-continued

Compounds prepared by automated synthesis (the following compounds are racemic, and the structures imply relative stereochemistry only).

| Ex. No. | Name | Structure | retention time (min) | HPLC-mass spectrum m/e |
|---|---|---|---|---|
| 57. | N-[2,3-bis(4-chlorophenyl)-1-methyl-propyl]-3-(4-chlorophenyl)-propanamide | 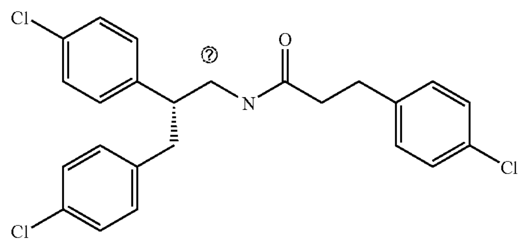 | 1.462 | 462.1 |
| 58. | N-[2,3-bis(4-chlorophenyl)-1-methyl-propyl]-2-hydroxy-2-phenyl-acetamide | 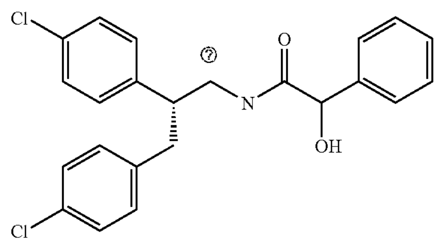 | 1.346 | 428.1 |
| 59. | N-[2,3-bis(4-chlorophenyl)-1-methyl-propyl]-2-hydroxy-2-(4-methoxy-phenyl)-acetamide | 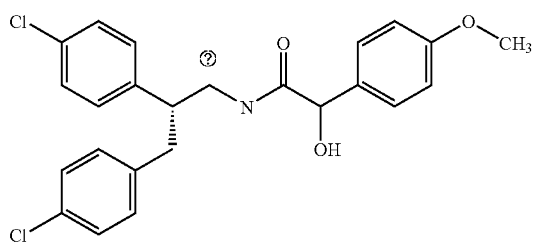 | 1.335 | 458.1 |
| 60. | N-[2,3-bis(4-chlorophenyl)-1-methyl-propyl]-2-methoxy-2-phenyl-acetamide | Chiral | 1.48 | 442.0 |
| 61. | N-[2,3-bis(4-chlorophenyl)-1-methyl-propyl]-2-hydroxy-2,2-diphenyl-acetamide | 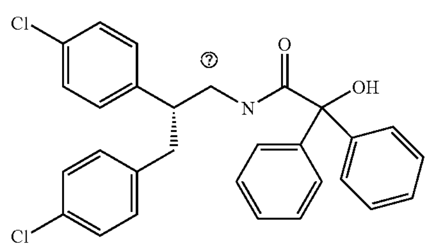 | 1.500 | 504.11 |

Examples 62 and 63

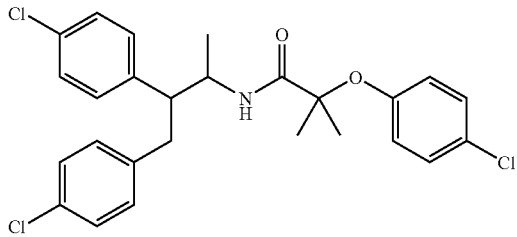

N-[2,3-Bis(4-Chlorophenyl)-1-methylpropyl]-2-(4-chlorophenyloxy)-2-methylpropanamide (Diastereomers α and β)

To a solution of 2-(4-chlorophenyloxy)-2-methylpropionic acid (Aldrich, 0.22 g, 1.0 mmol) in $CH_2Cl_2$ (2 mL) at 0° C. was added a drop of DMF and oxalyl chloride (0.27 mL, 3.0 mmol). After stirring at room temperature for 1 h, the reaction mixture was concentrated on a rotary evaporator and dried under vacuum, and the resulting crude acyl chloride was used without further purification. Thus, the crude acyl chloride was dissolved in 1 mL $CH_2Cl_2$ and was added to a suspension of 2-amino-3,4-bis(4-chlorophenyl)butane hydrochloride salt (Reference Example 1) (diastereomer α contaminated with some diastereomer β, 0.20 g, 0.60 mmol) and N-methylmorpholine (0.27 mL, 2.4 mmol) in 4 mL $CH_2Cl_2$. After stirring at room temperature for 6 h, the reaction mixture was loaded onto a silica gel column, which was eluted with 10% EtOAc to give a pure faster eluting isomer (diastereomer α) and a slower eluting isomer (diastereomer β).

Diastereomer α: $^1$H NMR (500 MHz, $CD_3OD$): δ 7.24 (d, 2H), 7.20 (d, 2H), 7.05 (d, 2H), 7.01 (d, 2H), 6.94 (d, 2H), 6.76 (d, 2H), 4.25 (m, 1H), 3.03 (dd, 1H), 2.88 (ddd, 1H), 2.67 (dd, 1H), 1.59 (s, 3H), 1.53 (s, 3H), 0.88 (d, 3H). LC-MS: m/e 490(M+H)$^+$ (4.7 min).

Diastereomer β: $^1$H NMR (500 MHz, $CD_3OD$): δ 7.16 (d, 2H), 7.14 (d, 2H), 7.09 (d, 2H), 6.99 (d, 2H), 6.88 (d, 2H), 6.64 (d, 2H), 4.33 (m, 1H), 3.12 (dd, 1H), 3.03 (ddd, 1H), 2.74 (dd, 1H), 1.36 (s, 3H), 1.30 (d, 3H), 1.30 (s, 3H). LC-MS: m/e 490(M+H)$^+$ (4.7 min).

Examples 64-148 (Table 3) were prepared following the procedures described in Examples 62 and 63 substituting 2-amino-3,4-bis(4-chlorophenyl)butane hydrochloride salt with the appropriate amines from the Reference Examples and 2-(4-chlorophenyloxy)-2-methylpropionic acid with the appropriate acids from the Reference Examples. In some cases, commercial acids or acyl chlorides were employed, and N-diisopropyl-ethylamine may be used in place of N-methylmorpholine with similar results. The diastereomer designations (α or β) correspond to designations of the starting amines.

TABLE 3

Compounds prepared according to the methods described in Examples 62-63.

| Ex. No. | Name | Structure | HPLC-retention time (min) | mass spectrum m/e | Diastereomer α and/or β |
|---|---|---|---|---|---|
| 64. | N-[2,3-Bis(4-chlorophenyl)-1-methylpropyl]-2-(4-cyclohexyloxy)-2-methylpropanamide$^a$ | 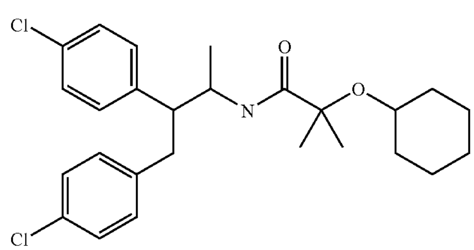 | 4.8 | 462 | α |
| 65. | N-[2,3-Bis(4-chlorophenyl)-1-methylpropyl]-2-(4-cyclohexyloxy)-2-methylpropanamide$^a$ | 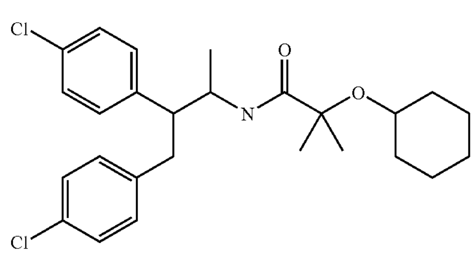 | 4.9 | 462 | β |

TABLE 3-continued

Compounds prepared according to the methods described in Examples 62-63.

| Ex. No. | Name | Structure | HPLC-retention time (min) | mass spectrum m/e | Diastereomer α and/or β |
|---|---|---|---|---|---|
| 66. | N-[2,3-Bis(4-chlorophenyl)-1-methylpropyl]-2-(2-fluorophenyloxy)-2-methylpropanamide | 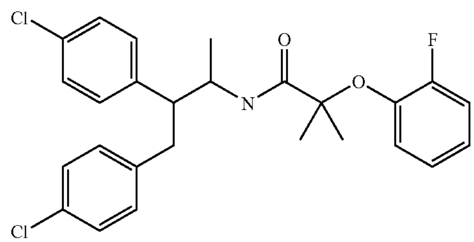 | 4.5 | 474 | α |
| 67. | N-[2,3-Bis(4-chlorophenyl)-1-methylpropyl]-2-(3-fluorophenyloxy)-2-methylpropanamide | 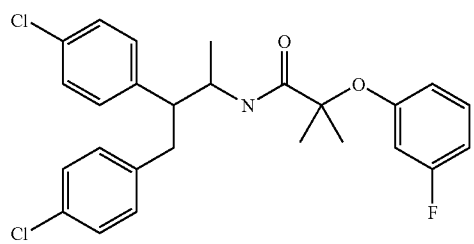 | 4.5 | 474 | α |
| 68. | N-[2,3-Bis(4-chlorophenyl)-1-methylpropyl]-2-(3,4-difluorophenyloxy)-2-methylpropanamide | 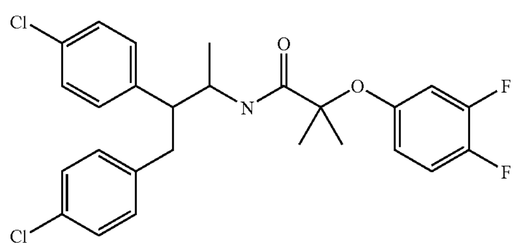 | 4.5 | 492 | α |
| 69. | N-[2,3-Bis(4-chlorophenyl)-1-methylpropyl]-2-(3-chlorophenyloxy)-2-methylpropanamide | 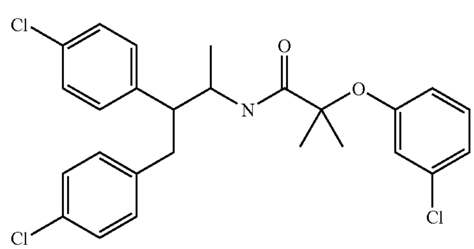 | 4.7 | 490 | α |
| 70. | N-[2,3-Bis(4-chlorophenyl)-1-methylpropyl]-2-(2-chlorophenyloxy)-2-methylpropanamide | 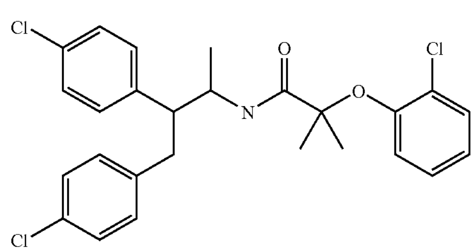 | 4.7 | 490 | α |

TABLE 3-continued

Compounds prepared according to the methods described in Examples 62-63.

| Ex. No. | Name | Structure | HPLC-retention time (min) | mass spectrum m/e | Diastereomer α and/or β |
|---|---|---|---|---|---|
| 71. | N-[2,3-Bis(4-chlorophenyl)-1-methylpropyl]-2-(3,5-difluorophenyloxy)-2-methylpropanamide | 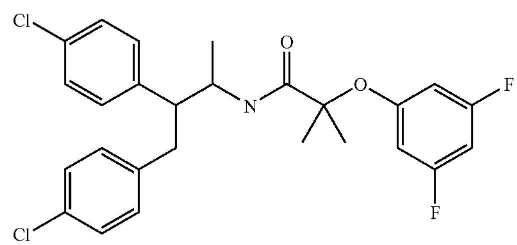 | 4.5 | 492 | α |
| 72. | N-[2,3-Bis(4-chlorophenyl)-1-methylpropyl]-2-(3-cyanophenyloxy)-2-methylpropanamide | 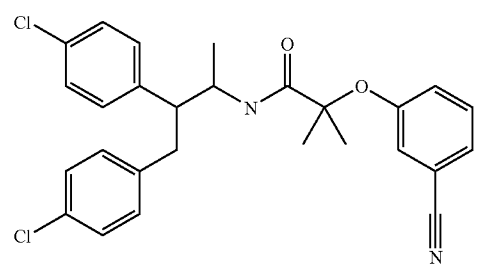 | 4.2 | 481 | α |
| 73. | N-[3-(4-Chlorophenyl)-2-(2,4-dichlorophenyl)-1-methylpropyl]-2-(4-chlorophenyloxy)-2-methylpropanamide | 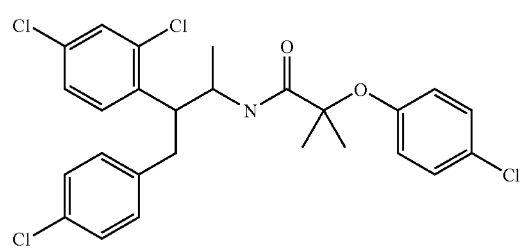 | 4.9 | 524 | α |
| 74. | N-[3-(4-Chlorophenyl)-2-(2,4-dichlorophenyl)-1-methylpropyl]-2-(4-chlorophenyloxy)-2-methylpropanamide | 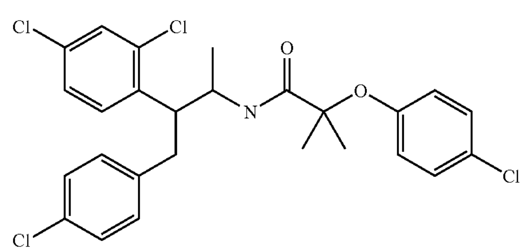 | 4.9 | 524 | β |
| 75. | N-[2,3-Bis(4-chlorophenyl)-1-methylpropyl]-2-phenyloxy-2-methylpropanamide | 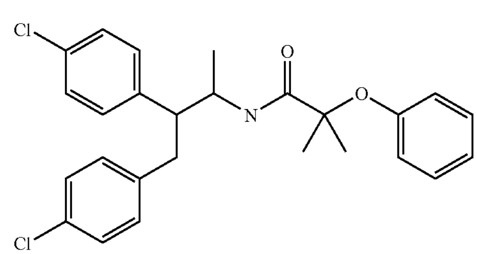 | 4.5 | 456 | α |

TABLE 3-continued

Compounds prepared according to the methods described in Examples 62-63.

| Ex. No. | Name | Structure | HPLC-retention time (min) | mass spectrum m/e | Diastereomer α and/or β |
|---|---|---|---|---|---|
| 76. | N-[2,3-Bis(4-chlorophenyl)-1-methylpropyl]-2-(4-fluorophenyloxy)-2-methylpropanamide | 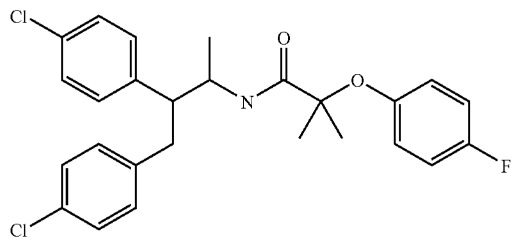 | 4.5 | 474 | α |
| 77. | N-[2,3-Bis(4-chlorophenyl)-1-methylpropyl]-2,2-dimethylpropanamide | 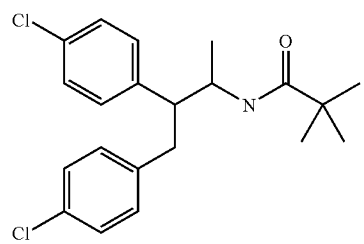 | 4.0 | 378 | α |
| 78. | N-[2,3-Bis(4-chlorophenyl)-1-methylpropyl]-4-chlorophenyl-carbamate | 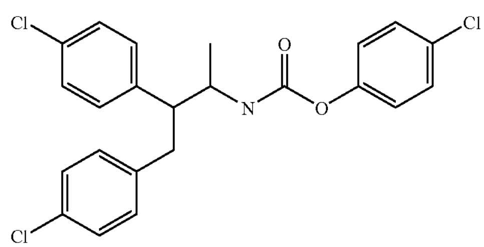 | 4.8 | 448 | α |
| 79. | N-[2,3-Bis(4-chlorophenyl)-1-methylpropyl]-N'-(4-chlorophenyl)urea[b] | 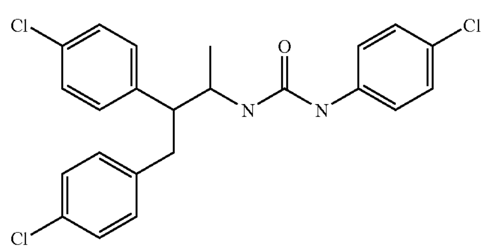 | 4.3 | 447 | α |
| 80. | N-[2,3-Bis(4-chlorophenyl)-1-methylpropyl]benzyl carbamate | 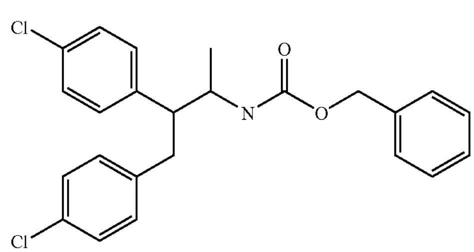 | 4.3 | 428 | α |

TABLE 3-continued

Compounds prepared according to the methods described in Examples 62-63.

| Ex. No. | Name | Structure | re-tention time (min) | HPLC-mass spec-trum m/e | Dias-tere-omer α and/ or β |
|---|---|---|---|---|---|
| 81. | N-[2,3-Bis(4-chlorophenyl)-1-methylpropyl]-tert-butylcarbamate[c] | 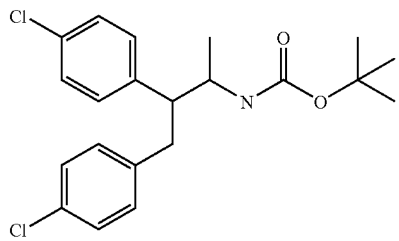 | 4.5 | 394 | α |
| 82. | N-[2,3-Bis(4-chlorophenyl)-1-methylpropyl]-2-(3-pyridyloxy)-2-methylpropanamide | 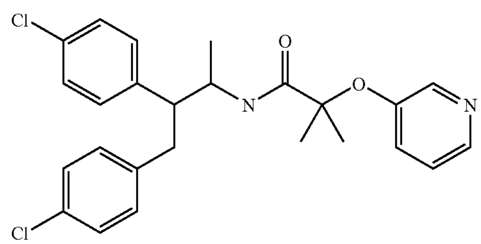 | 3.0 | 457 | α |
| 83. | N-[2,3-Bis(4-chlorophenyl)-1-methylpropyl]-2-(2-pyridylox)-2-methylbutanamide | 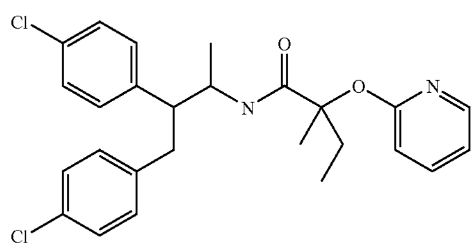 | 4.3 | 471 | α |
| 84. | N-[2,3-Bis(4-chlorophenyl)-1-methylpropyl]-2-(2-pyridyloxy)-2-methylpropanamide | 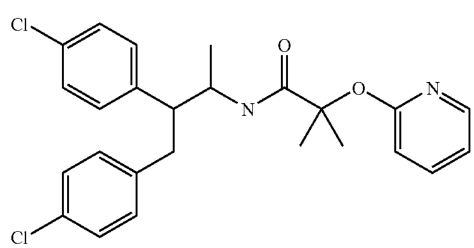 | 4.1 | 457 | α |
| 85. | N-[2,3-Bis(4-chlorophenyl)-1-methylpropyl]-2-(4-pyridyloxy)-2-methylpropanamide | 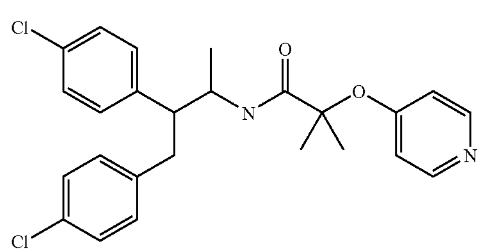 | 3.0 | 457 | α |

TABLE 3-continued

Compounds prepared according to the methods described in Examples 62-63.

| Ex. No. | Name | Structure | HPLC-retention time (min) | mass spectrum m/e | Diastereomer α and/or β |
|---|---|---|---|---|---|
| 86. | N-[3,4-Bis(4-Chlorophenyl)-1-methylpropyl]-2-(2-methoxyphenyloxy)-propenamide | 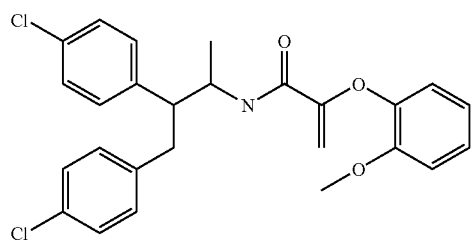 | 4.3 | 470 | α |
| 87. | N-[3,4-Bis(4-Chlorophenyl)-1-methylpropyl]-2-(2-methoxyphenyloxy)-propenamide | 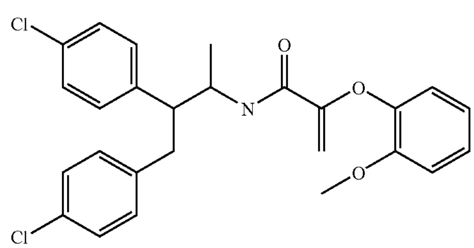 | 4.3 | 470 | β |
| 88. | N-[3-(4-Chlorophenyl)-1-methyl-2-phenylpropyl]-2-(2-fluorophenyloxy)-2-methylpropanamide | 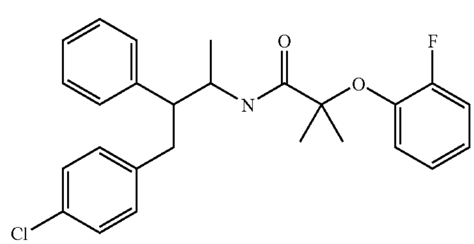 | 4.3 | 440 | α |
| 89. | N-[3-(4-Chlorophenyl)-1-methyl-2-phenylpropyl]-2-(3-fluorophenyloxy)-2-methylpropanamide | 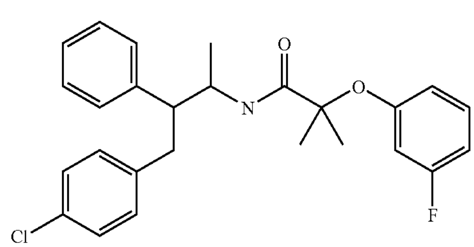 | 4.3 | 440 | α |
| 90. | N-[3-(4-Chlorophenyl)-1-methyl-2-phenylpropyl]-2-(3,4-difluorophenyloxy)-2-methylpropanamide | 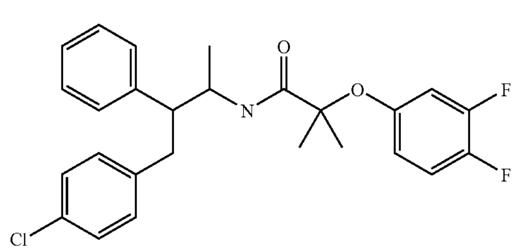 | 4.3 | 458 | α |

TABLE 3-continued

Compounds prepared according to the methods described in Examples 62-63.

| Ex. No. | Name | Structure | retention time (min) | HPLC-mass spectrum m/e | Diastereomer α and/or β |
|---|---|---|---|---|---|
| 91. | N-[3-(4-Chlorophenyl)-1-methyl-2-phenylpropyl]-2-(3-chlorophenyloxy)-2-methylpropanamide | 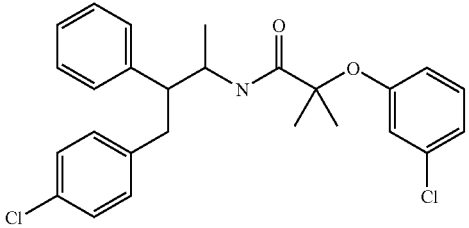 | 4.5 | 456 | α |
| 92. | N-[3-(4-Chlorophenyl)-1-methyl-2-phenylpropyl]-2-(2-chlorophenyloxy)-2-methylpropanamide | 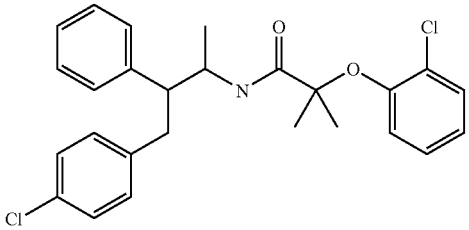 | 4.4 | 456 | α |
| 93. | N-[3-(4-Chlorophenyl)-1-methyl-2-phenylpropyl]-2-(3,5-difluorophenyloxy)-2-methylpropanamide | 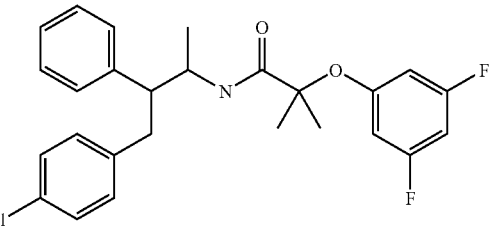 | 4.4 | 458 | α |
| 94. | N-[3-(4-Chlorophenyl)-1-methyl-2-phenylpropyl]-2-cyclohexyloxy-2-methylpropanamide | 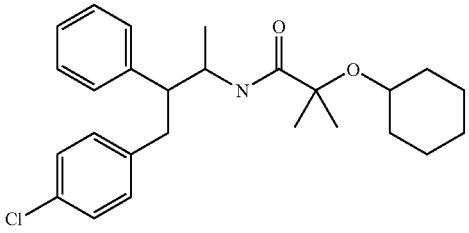 | 4.6 | 428 | α |
| 95. | N-[3-(4-Chlorophenyl)-1-methyl-2-phenylpropyl]-2-(4-fluorophenyloxy)-2-methylpropanamide | 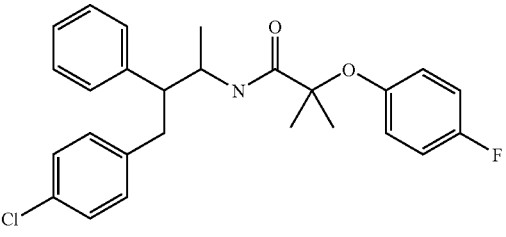 | 4.3 | 440 | β |
| 96. | N-[3-(4-Chlorophenyl)-2-(2-fluorophenyl)-1-methylpropyl]-2-(4-chlorophenyloxy)-2-methylpropanamide | 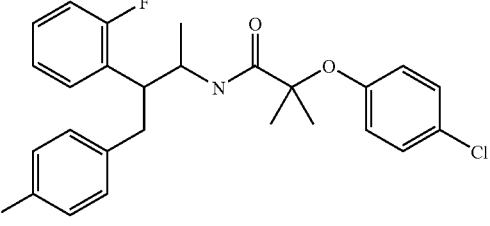 | 4.4 | 474 | α |

TABLE 3-continued

Compounds prepared according to the methods described in Examples 62-63.

| Ex. No. | Name | Structure | retention time (min) | HPLC- mass spectrum m/e | Diastereomer α and/ or β |
|---|---|---|---|---|---|
| 97. | N-[3-(4-Chlorophenyl)-2-(3-fluorophenyl)-1-methylpropyl]-2-(4-chlorophenyloxy)-2-methylpropanamide | 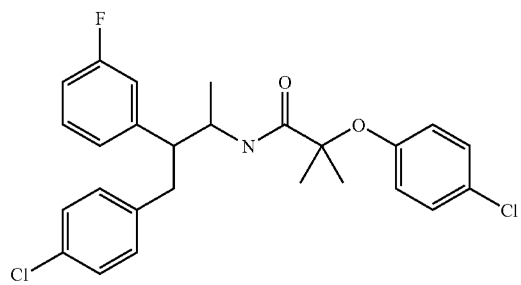 | 4.4 | 474 | α |
| 98. | N-[3-(4-Chlorophenyl)-2-(3-fluorophenyl)-1-methylpropyl]-2-(4-chlorophenyloxy)-2-methylpropanamide | 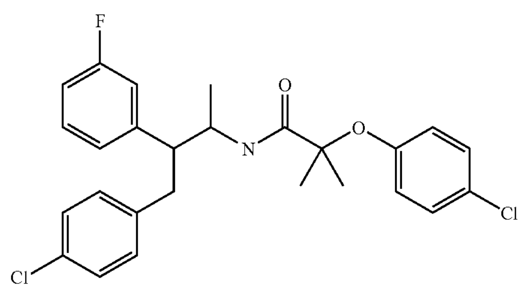 | 4.4 | 474 | α:β 1:10 |
| 99. | N-[3-(4-Chlorophenyl)-2-(2-fluorophenyl)-1-methylpropyl]-2-(4-chlorophenyloxy)-2-methylpropanamide | 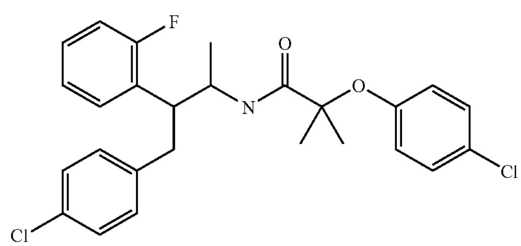 | 4.4 | 474 | α:β 1:3 |
| 100. | N-[3-(4-Chlorophenyl)-1-methyl-2-phenylpropyl)]-2-methyl-2-phenylpropanamide | 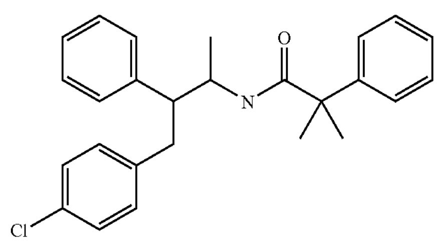 | 4.2 | 406 | α |
| 101. | N-[3-(4-Chlorophenyl)-2-(3-fluorophenyl)-1-methylpropyl]-2-(2-pyridyloxy)-2-methylpropanamide | 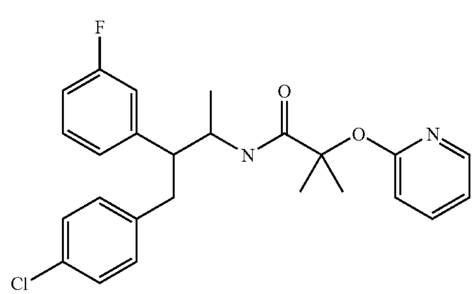 | 3.9 | 440 | α |

TABLE 3-continued

Compounds prepared according to the methods described in Examples 62-63.

| Ex. No. | Name | Structure | retention time (min) | HPLC-mass spectrum m/e | Diastereomer α and/or β |
|---|---|---|---|---|---|
| 102. | N-[3-(4-Chlorophenyl)-2-(3-fluorophenyl)-1-methylpropyl]-2-(3,5-difluorophenyloxy)-2-methylpropanamide | 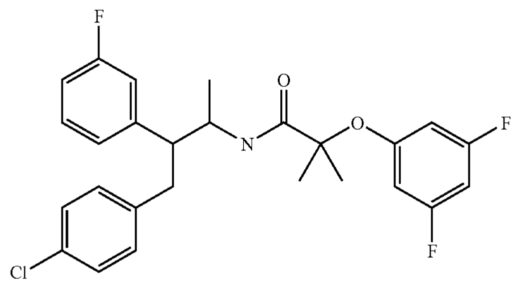 | 4.3 | 476 | α |
| 103. | N-[3-(4-Chlorophenyl)-2-(3-fluorophenyl)-1-methylpropyl]-2-(3,5-difluorophenyloxy)-2-methylpropanamide | 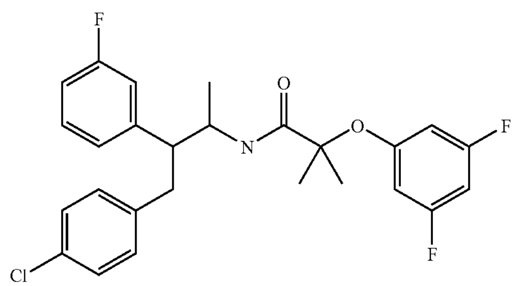 | 4.3 | 476 | β |
| 104. | N-[3-(4-Chlorophenyl)-1-methyl-2-phenylpropyl]-2-(3-pyridyloxy)-2-methylpropanamide | 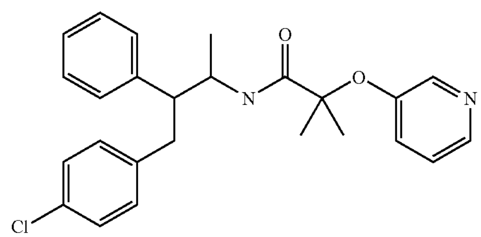 | 2.8 | 423 | α |
| 105. | N-[3-(4-Chlorophenyl)-1-methyl-2-phenylpropyl]-2-(2-pyridyloxy)-2-methylbutanamide | 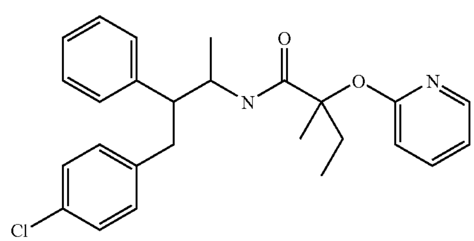 | 4.1 | 437 | α |
| 106. | N-[3-(4-Chlorophenyl)-1-methyl-2-phenylpropyl]-2-(2-pyridyloxy)-2-methylpropanamide | 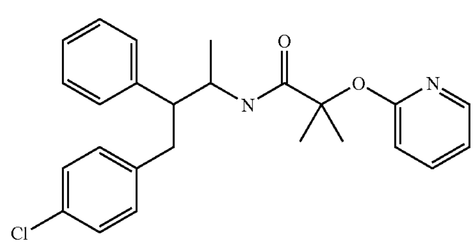 | 3.9 | 423 | α |

TABLE 3-continued

Compounds prepared according to the methods described in Examples 62-63.

| Ex. No. | Name | Structure | HPLC-retention time (min) | mass spectrum m/e | Diastereomer α and/ or β |
|---|---|---|---|---|---|
| 107. | N-[3-(4-Chlorophenyl)-1-methyl-2-phenylpropyl]-2-(4-pyridyloxy)-2-methylpropanamide | 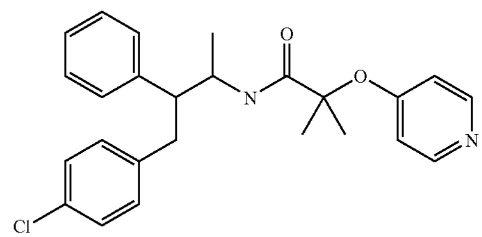 | 2.8 | 423 | α |
| 108. | N-[2-(4-Chlorophenyl)-1-methyl-3-phenylpropyl]-2-(4-chlorophenyloxy)-2-methylpropanamide | 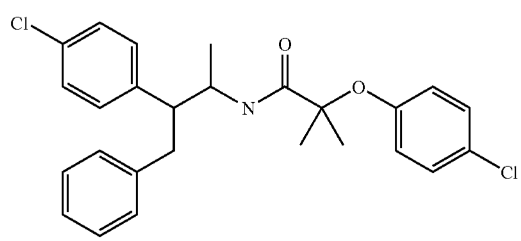 | 4.5 | 456 | α:β 1:1 |
| 109. | N-[2-(4-Chlorophenyl)-1-methyl-3-phenylpropyl]-2-(4-chlorophenyloxy)-2-methylpropanamide | 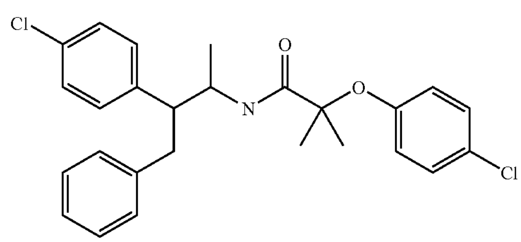 | 4.5 | 456 | β |
| 110. | N-[2-(4-Chlorophenyl)-1-methyl-3-phenylpropyl]-2-(4-fluorophenyloxy)-2-methylpropanamide | 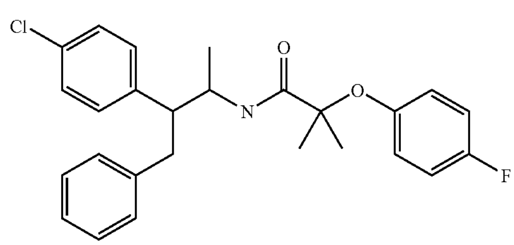 | 4.3 | 440 | α |
| 111. | N-[2-(4-Chlorophenyl)-1-methyl-3-phenylpropyl]-2-(4-chlorophenyloxy)-2-methylpropanamide | 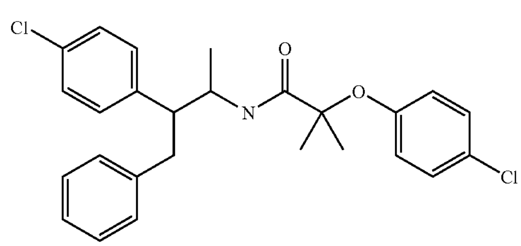 | 4.4 | 456 | α |

TABLE 3-continued

Compounds prepared according to the methods described in Examples 62-63.

| Ex. No. | Name | Structure | retention time (min) | HPLC-mass spectrum m/e | Diastereomer α and/ or β |
|---|---|---|---|---|---|
| 112. | N-[3-(4-Methoxy-carbonylphenyl)-1-methyl-2-phenylpropyl]-2-(4-fluorophenyloxy)-2-methylpropanamide | 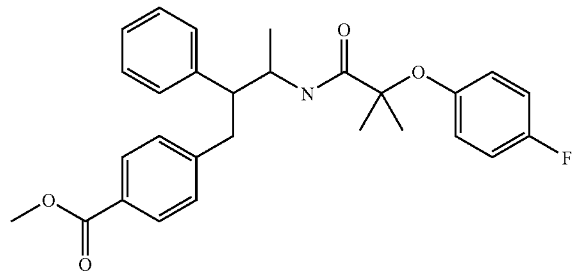 | 4.0 | 464 | α |
| 113. | N-[3-(4-Methoxy-carbonylphenyl)-1-methyl-2-phenylpropyl]-2-(4-fluorophenyloxy)-2-methylpropanamide | 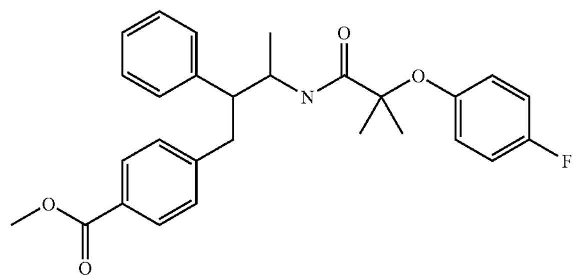 | 4.0 | 464 | β |
| 114. | N-[3-(4-Methoxy-carbonylphenyl)-1-methyl-2-phenylpropyl]-2-(4-fluorophenyloxy)-2-methylpropanamide | 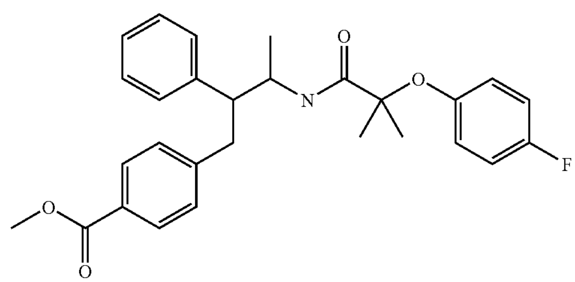 | 4.0 | 464 | α:β 1:2 |
| 115. | N-[3-(4-Methoxy-carbonylphenyl)-1-methyl-2-phenylpropyl]-2-(4-Chlorophenyloxy)-2-methylpropanamide | 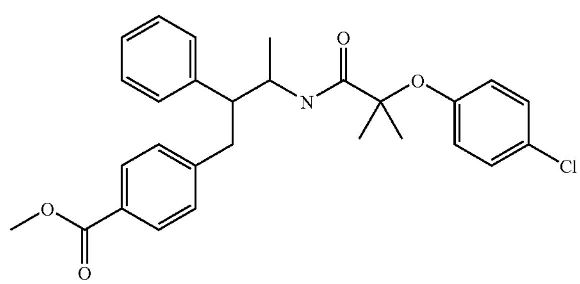 | 4.2 | 480 | α |
| 116. | N-[2-(2-Chlorophenyl)-1-methyl-3-phenylpropyl]-2-(4-fluorophenyloxy)-2-methylpropanamide | 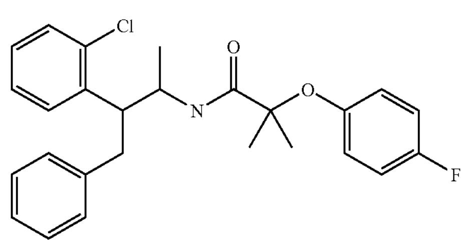 | 4.2 | 440 | α |

TABLE 3-continued

Compounds prepared according to the methods described in Examples 62-63.

| Ex. No. | Name | Structure | HPLC-retention time (min) | mass spectrum m/e | Diastereomer α and/or β |
|---|---|---|---|---|---|
| 117. | N-[2-(2-Chlorophenyl)-1-methyl-3-phenylpropyl]-2-(4-fluorophenyloxy)-2-methylpropanamide | 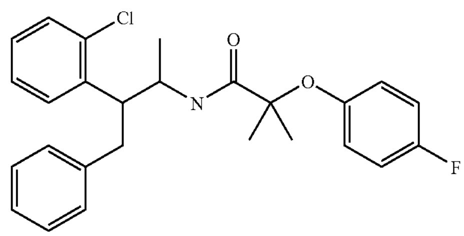 | 4.2 | 440 | β |
| 118. | N-[2-(2-Chlorophenyl)-1-methyl-3-phenylpropyl]-2-(4-chlorophenyloxy)-2-methylpropanamide | 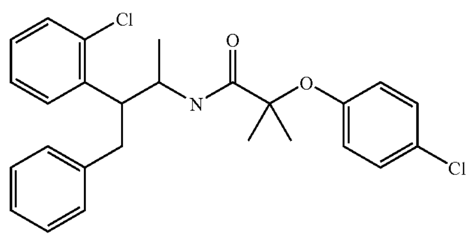 | 4.2 | 440 | α:β 2:5 |
| 119. | N-[2-(2-Chlorophenyl)-1-methyl-3-phenylpropyl]-2-(4-chlorophenyloxy)-2-methylpropanamide | 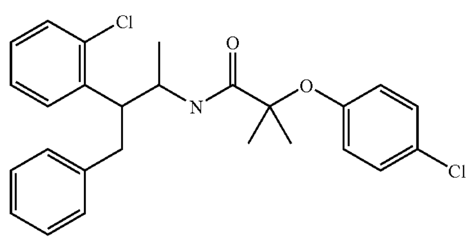 | 4.4 | 456 | β |
| 120. | N-[2-(4-Methoxyphenyl)-1-methyl-3-phenylpropyl]-2-(4-fluorophenyloxy)-2-methylpropanamide | 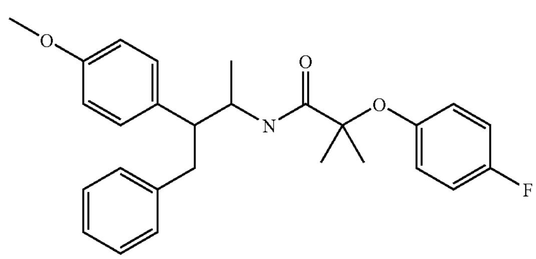 | 4.0 | 436 | α:β 2:5 |
| 121. | N-[2-(4-Methoxyphenyl)-1-methyl-3-phenylpropyl]-2-(4-chlorophenyloxy)-2-methylpropanamide | 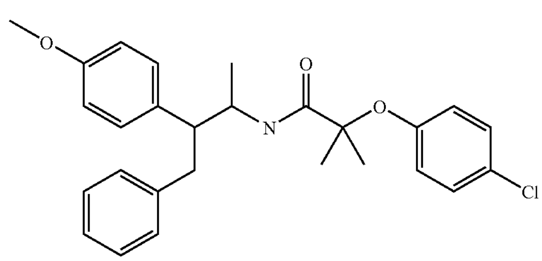 | 4.2 | 452 | α:β 1:2 |

TABLE 3-continued

Compounds prepared according to the methods described in Examples 62-63.

| Ex. No. | Name | Structure | HPLC-retention time (min) | mass spectrum m/e | Diastereomer α and/ or β |
|---|---|---|---|---|---|
| 122. | N-[2-(4-Chlorophenyl)-3-(2,4-dichlorophenyl-1-methyl-propyl]-2-(4-chlorophenyloxy)-2-methylpropanamide | 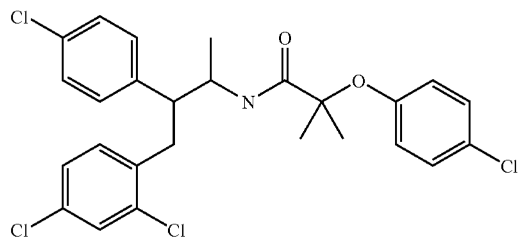 | 4.9 | 524 | isomer 1[d] |
| 123. | N-[2-(4-Chlorophenyl)-3-(2,4-dichlorophenyl)-1-methyl-propyl]-2-(4-chlorophenyloxy)-2-methylpropanamide | 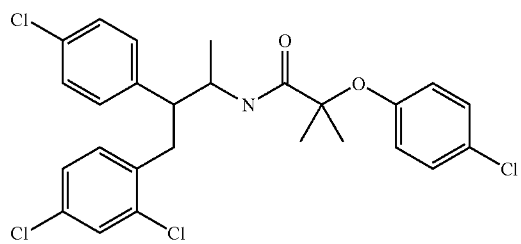 | 4.9 | 524 | isomer 2: isomer 3 1:1[e] |
| 124. | N-[2-(4-Chlorophenyl)-3-(2,4-dichlorophenyl)-1-methyl-propyl]-2,2-dimethylpropanamide | 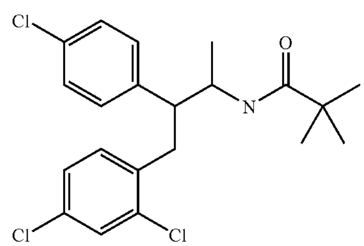 | 4.2 | 412 | isomer 2[e] |
| 125. | N-[2-(4-Chlorophenyl)-3-(2,4-dichlorophenyl)-1-methyl-propyl]-2,2-dimethylpropanamide | 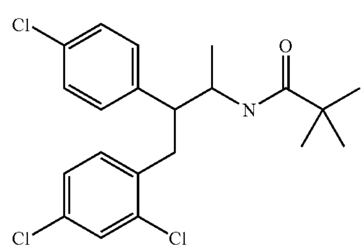 | 4.3 | 412 | isomer 3[e] |
| 126. | N-[2-(4-Chlorophenyl)-3-(2,4-dichlorophenyl)-1-methyl-propyl]-2,2-dimethylpropanamide | 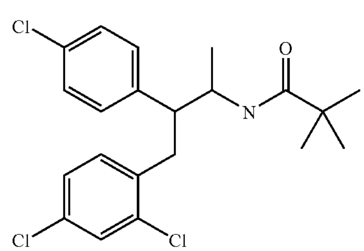 | 4.2/4.3 | 412 | isomer 2: isomer 3 1:1[e] |

TABLE 3-continued

Compounds prepared according to the methods described in Examples 62-63.

| Ex. No. | Name | Structure | HPLC-retention time (min) | mass spectrum m/e | Diastereomer α and/ or β |
|---|---|---|---|---|---|
| 127. | N-[2-(4-Chlorophenyl)-2-(4-chloro-2-fluorophenyl)-1-methyl-propyl]-2-(4-chlorophenyloxy)-2-methylpropanamide | 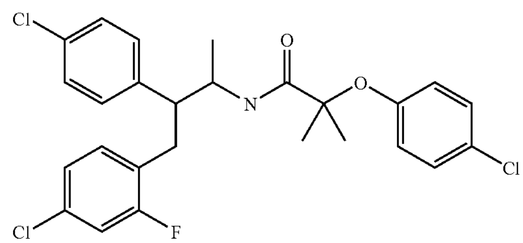 | 4.7 | 508 | isomer 1[d] |
| 128. | N-[2-(4-Chlorophenyl)-2-(4-chloro 2-fluorophenyl)-1-methyl-propyl]-2-(4-chlorophenyloxy)-2-methylpropanamide | 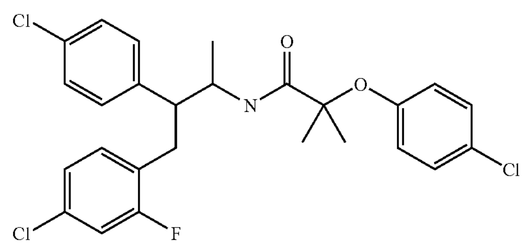 | 4.7 | 508 | isomer 2[e] |
| 129. | N-[2-(4-Chlorophenyl)-2-(4-chloro-2-fluorophenyl)-1-methyl-propyl]-2-(4-chlorophenyloxy)-2-methylpropanamide | 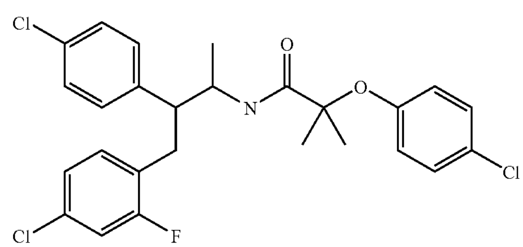 | 4.7 | 508 | isomer 3[e] |
| 130. | N-[2-(4-Chlorophenyl)-2-(4-chloro-2-fluorophenyl)-1-methyl-propyl]-2-(4-fluorophenyloxy)-2-methylpropanamide | 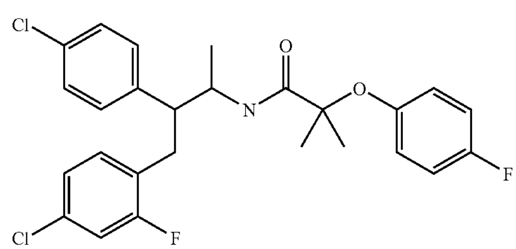 | 4.6 | 492 | isomer 2[e] |
| 131. | N-[2-(4-Chlorophenyl)-2-(4-chloro-2-fluorophenyl)-1-methyl-propyl]-2-(4-fluorophenyloxy)-2-methylpropanamide | 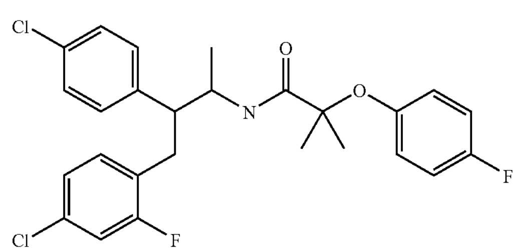 | 4.5 | 492 | isomer 3[e] |

TABLE 3-continued

Compounds prepared according to the methods described in Examples 62-63.

| Ex. No. | Name | Structure | re-tention time (min) | HPLC-mass spectrum m/e | Diastereomer α and/or β |
|---|---|---|---|---|---|
| 132. | N-[3-(4-Chlorophenyl)-2-(4-fluorophenyl)-1-methyl-propyl]-2-(4-chlorophenyloxy)-2-methylpropanamide | 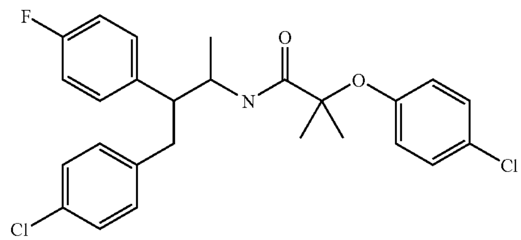 | 4.4 | 474 | α |
| 133. | N-[3-(4-Chlorophenyl)-2-(4-fluorophenyl)-1-methyl-propyl]-2-(4-chlorophenyloxy)-2-methylpropanamide | 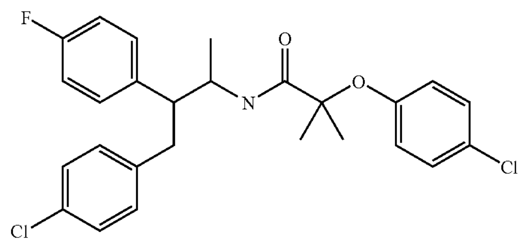 | 4.5 | 474 | α:β 1:4 |
| 134. | N-[3-(4-Chlorophenyl)-1-methyl-2-(2-pyridyl)propyl]-tert-butylcarbamate | 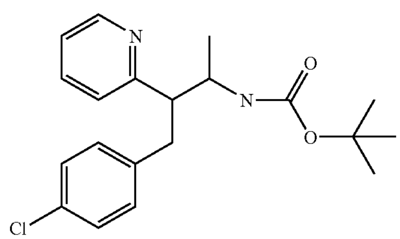 | 2.5 | 361 | α |
| 135. | N-[3-(4-Chlorophenyl)-1-methyl-2-(2-pyridyl)propyl]-2-(4-chlorophenyloxy)-2-methylpropanamide | 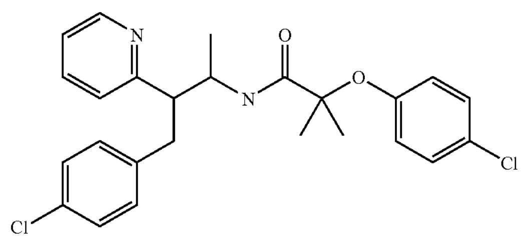 | 3.0 | 457 | α |
| 136. | N-[3-(4-Chlorophenyl)-1-methyl-2-(2-pyridyl)propyl]-2-(4-fluorophenyloxy)-2-methylpropanamide | 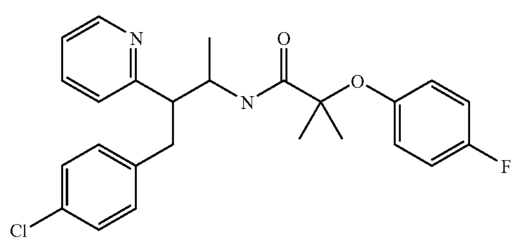 | 2.8 | 441 | α |
| 137. | N-[3-(4-Chlorophenyl)-1-methyl-2-(4-pyridyl)propyl]-2-(4-chlorophenyloxy)-2-methylpropanamide | 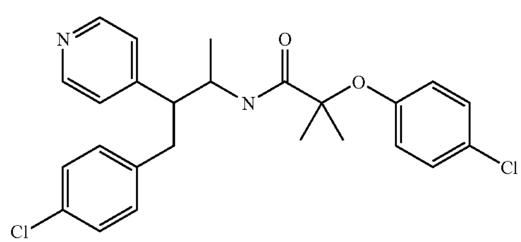 | 2.9 | 457 | α |

TABLE 3-continued

Compounds prepared according to the methods described in Examples 62-63.

| Ex. No. | Name | Structure | HPLC-retention time (min) | mass spectrum m/e | Diastereomer α and/ or β |
|---|---|---|---|---|---|
| 138. | N-[3-(4-Cyanophenyl)-1-methyl-2-phenylpropyl]-2-(3-chlorophenyloxy)-2-methylpropanamide | 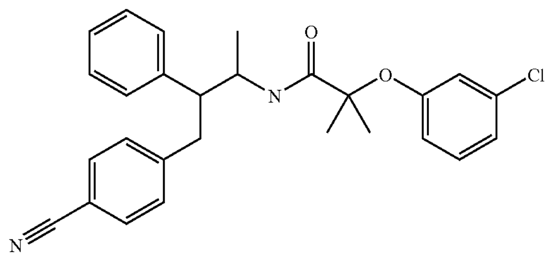 | 4.0 | 447 | α |
| 139. | N-[3-(5-Chloro-2-pyridyl)-1-methyl-2-phenylpropyl]-2-(3,5-difluorophenyloxy)-2-methylpropanamide | 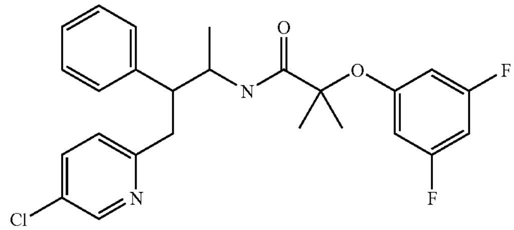 | 3.8 | 459 | α |
| 140. | N-[3-(4-Chlorophenyl)-1-methyl-2-(3-pyridyl)propyl]-tert-butylcarbamate[f] | 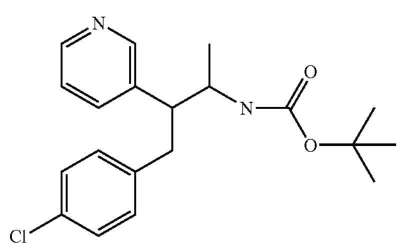 | 2.5 | 361 | α |
| 141. | N-[3-(4-Chlorophenyl)-1-methyl-2-(3-pyridyl)propyl]-2-(4-chlorophenyloxy)-2-methylpropanamide | 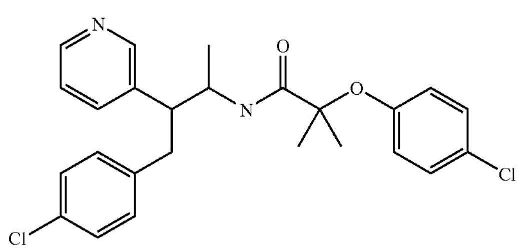 | 3.0 | 457 | α |
| 142. | N-[3-(4-Chlorophenyl)-1-methyl-2-(3-pyridyl)propyl]-2-(3,5-difluorophenyloxy)-2-methylpropanamide | 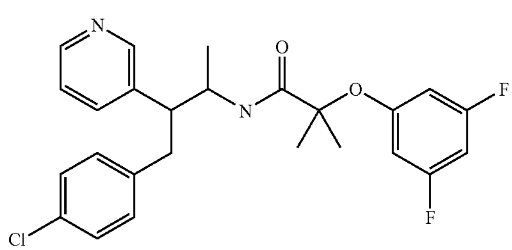 | 2.8 | 459 | α |

TABLE 3-continued

Compounds prepared according to the methods described in Examples 62-63.

| Ex. No. | Name | Structure | HPLC-retention time (min) | mass spectrum m/e | Diastereomer α and/or β |
|---|---|---|---|---|---|
| 143. | N-[3-(4-Chlorophenyl)-1-methyl-2-(3-pyridyl)propyl]-2-(3-fluorophenyloxy)-2-methylpropanamide | 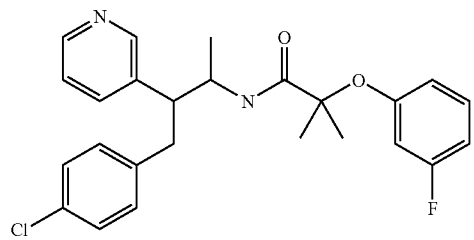 | 2.8 | 441 | α |
| 144. | N-[2-(4-Chlorophenoxy)-2-(4-chlorophenyl)ethyl]-2-(4-chlorophenyloxy)-2-methylpropanamide | 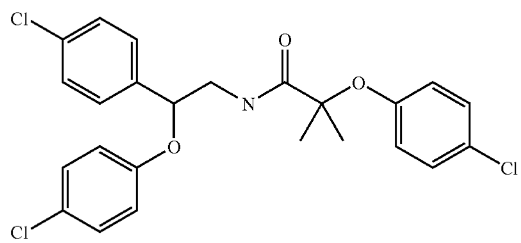 | 4.2 | 479 | — |
| 145. | N-[2,2-Bis(4-chlorophenyl)ethyl] allylcarbamate[f] | 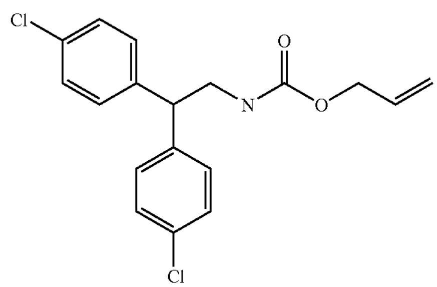 | 3.9 | 350 | — |
| 146. | N-[2,2-Bis(4-chlorophenyl)ethyl]-2-(4-chlorophenyloxy)-2-methylpropanamide[f] | 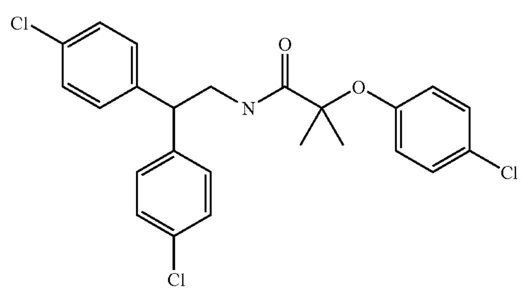 | 4.4 | 462 | — |
| 147. | N-[2-(4-Chlorophenylthio)-2-(4-chlorophenyl)-1-methylpropyl]-2-(4-chlorophenyloxy)-2-methylpropanamide | 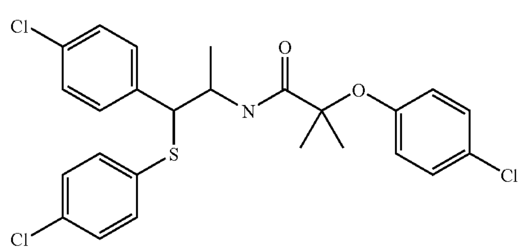 | 4.8 | 508 | α:β 2:3 |

TABLE 3-continued

Compounds prepared according to the methods described in Examples 62-63.

| Ex. No. | Name | Structure | retention time (min) | HPLC-mass spectrum m/e | Diastereomer α and/or β |
|---|---|---|---|---|---|
| 148. | N-[2-(4-Chlorophenylthio)-2-(4-chlorophenyl)-1-methylpropyl]-2-(4-chlorophenyloxy)-2-methylpropanamide | 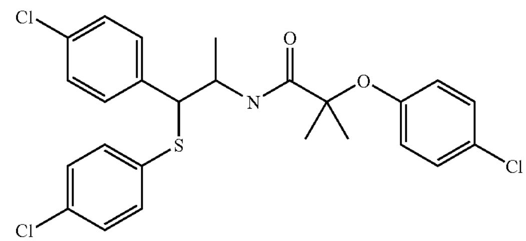 | 4.8 | 508 | β |

[a] For the synthesis of the acid starting material, see Eliel, EL J. Am. Chem. Soc. 1962, 84, 2371.
[b] 4-Chlorophenylisocyanate was used in place of an acyl chloride.
[c] Di(tert-butyl)dicarbonate was used in place of an acyl chloride.
[d] Isomer 1 is derived from Isomer 1 of the amine (Reference Examples 21-22).
[e] Isomers 2 and 3 are derived from Isomers 2 and 3 of the amine (Reference Examples 21-22), and are separated on silica gel.
[f] Intermediates in the synthesis of the corresponding amines.

Examples 149 and 150

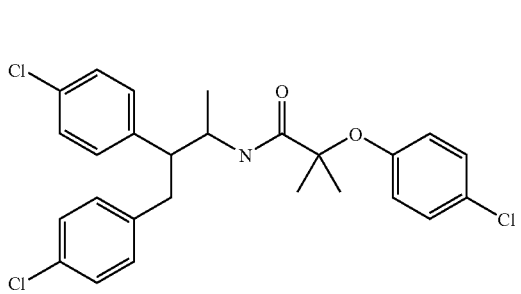

N-[2,3-Bis(4-Chlorophenyl)-1-methylpropyl]-2-(4-chlorophenyloxy)-2-methylpropanamide (Diastereomer α Enantiomers A and B)

Preparative HPLC was performed on a Gilson HPLC system for the separation of enantiomers. Thus, a solution of N-[2,3-bis(4-chlorophenyl)-1-methylpropyl]-2-(4-chlorophenyloxy)-2-methylpropanamide (Diastereomer α) (Example 60, 1.0 g) in hexane (3 mL)/ethanol (7 mL) was loaded onto a Chiralpak AD column (2 cm×25 cm), which was eluted with 5% ethanol in hexane (flow rate 9 mL/min, 500 μL per injection) to give the two pure enantiomers.

Faster eluting enantiomer (Enantiomer A): Analytical HPLC: retention time=7.8 min (Chiralpak AD column, flow rate=0.75 mL/min, 5% ethanol/hexane). LC-MS: m/e 490 (M+H)+ (4.7 min).

Slower eluting enantiomer (Enantiomer B): Analytical HPLC: retention time=9.6 min (Chiralpak AD column, flow rate=0.75 mL/min, 5% ethanol/hexane). LC-MS: m/e 490 (M+H)+ (4.7 min).

Examples 151 and 152

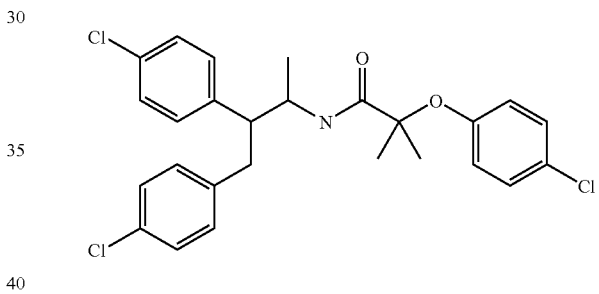

N-[2,3-Bis(4-Chlorophenyl)-1-methylpropyl]-2-(4-chlorophenyloxy)-2-methylpropanamide (Diastereomer A, Enantiomers C and D)

Diastereomer β of N-[2,3-bis(4-Chlorophenyl)-1-methylpropyl]-2-(4-chlorophenyloxy)-2-methylpropanamide from Example 61 was separated on a CHIRALPAK AD column following the procedure described for Examples 149-150 to give the faster eluting enantiomer (Enantiomer C) and the slower eluting enantiomer (Enantiomer D).

Faster eluting enantiomer (Enantiomer C): Analytical HPLC: retention time=8.0 min (Chiralpak AD column, flow rate=0.50 mL/min, 5% ethanol/hexane). LC-MS: m/e 490 (M+H)+ (4.7 min).

Slower eluting enantiomer (Enantiomer D): Analytical HPLC: retention time=12.6 min (Chiralpak AD column, flow rate=0.50 mL/min, 5% ethanol/hexane). LC-MS: m/e 490 (M+H)+ (4.7 min).

Examples 153-188 (Table 4) were isolated as single enantiomers following the procedures described in Examples 149-150 from the corresponding racemic material (Table 3) with appropriate modifications of (1) the eluent composition (4-15% ethanol/hexane), (2) flow rate (6-9 mL/min) and (3) injection volume (200 to 2000 μL).

TABLE 4

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 153. | N-[2,3-Bis(4-chlorophenyl)-1-methylpropyl]-2-phenyloxy)-2-methylpropanamide | 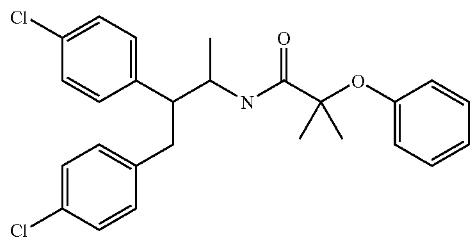 | 4.5 | 456 | A |
| 154. | N-[2,3-Bis(4-chlorophenyl)-1-methylpropyl]-2-phenyloxy-2-methylpropanamide | 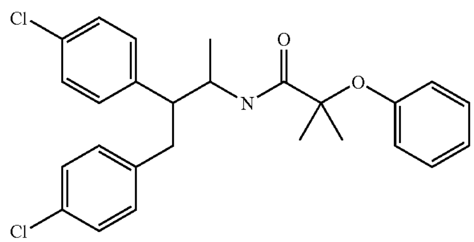 | 4.5 | 456 | B |
| 155. | N-[2,3-Bis(4-chlorophenyl)-1-methylpropyl]-2-(4-fluorophenyloxy)-2-methylpropanamide | 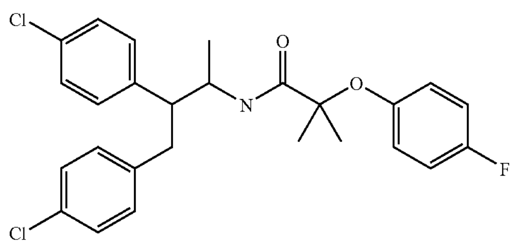 | 4.5 | 474 | A |
| 156. | N-[2,3-Bis(4-chlorophenyl)-1-methylpropyl]-2-(4-fluorophenyloxy)-2-methylpropanamide | 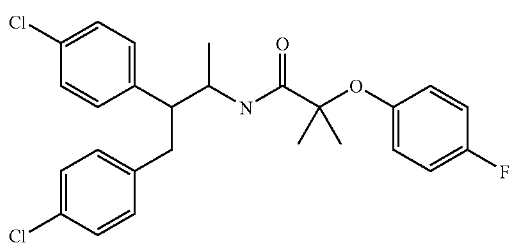 | 4.5 | 474 | B |
| 157. | N-[2,3-Bis(4-chlorophenyl)-1-methylpropyl]-2-(6-methyl-3-pyridyloxy)-2-methylpropanamide | 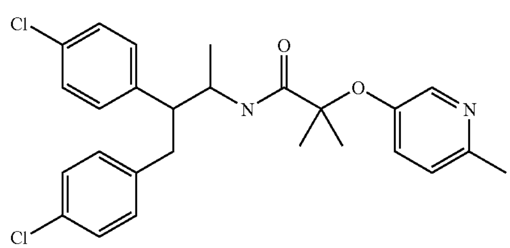 | 3.1 | 471 | A |
| 158. | N-[2,3-Bis(4-chlorophenyl)-1-methylpropyl]-2-(6-methyl-3-pyridyloxy)-2-methylpropanamide | 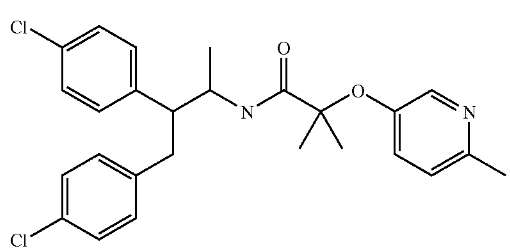 | 3.1 | 471 | B |

TABLE 4-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 159. | N-[3-(4-Chlorophenyl)-1-methyl-2-phenylpropyl]-2-(3-fluorophenyloxy)-2-methylpropanamide | 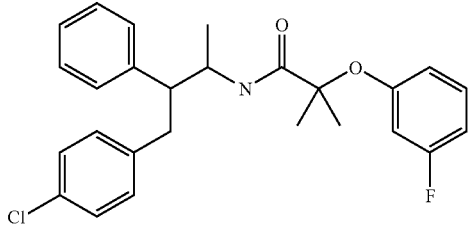 | 4.3 | 440 | A |
| 160. | N-[3-(4-Chlorophenyl)-1-methyl-2-phenylpropyl]-2-(3-fluorophenyloxy)-2-methylpropanamide | 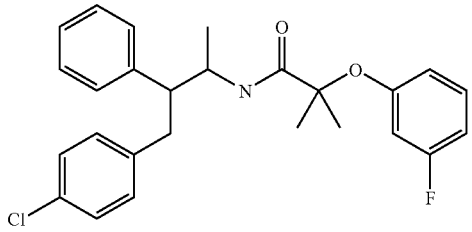 | 4.3 | 440 | B |
| 161. | N-[3-(4-Chlorophenyl)-1-methyl-2-phenylpropyl]-2-(3,4-difluorophenyloxy)-2-methylpropanamide | 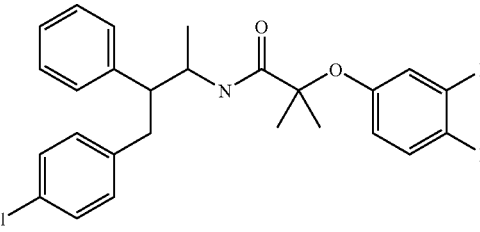 | 4.3 | 458 | A |
| 162. | N-[3-(4-Chlorophenyl)-1-methyl-2-phenylpropyl]-2-(3,4-difluorophenyloxy)-2-methylpropanamide | 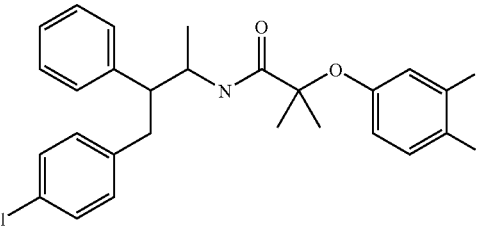 | 4.3 | 458 | B |
| 163. | N-[3-(4-Chlorophenyl)-1-methyl-2-phenylpropyl]-2-(3-chlorophenyloxy)-2-methylpropanamide | 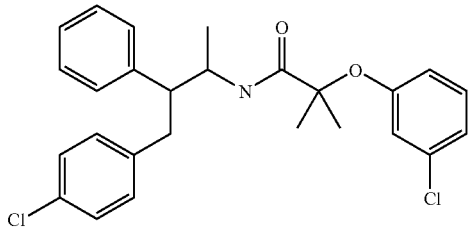 | 4.5 | 456 | A |
| 164. | N-[3-(4-Chlorophenyl)-1-methyl-2-phenylpropyl]-2-(3-chlorophenyloxy)-2-methylpropanamide | 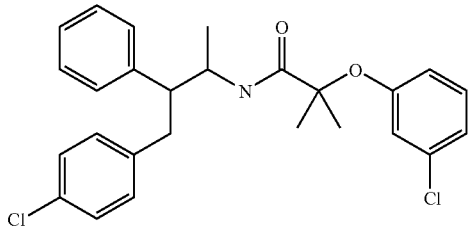 | 4.5 | 456 | B |

TABLE 4-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 165. | N-[3-(4-Chlorophenyl)-1-methyl-2-phenylpropyl]-2-(3,5-difluorophenyloxy)-2-methylpropanamide | 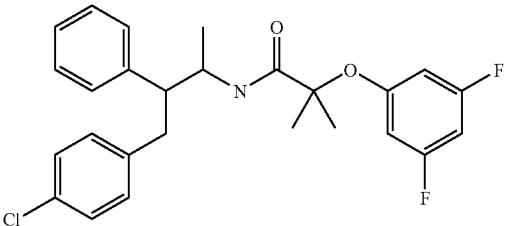 | 4.3 | 458 | A |
| 166. | N-[3-(4-Chlorophenyl)-1-methyl-2-phenylpropyl]-2-(3,5-difluorophenyloxy)-2-methylpropanamide | 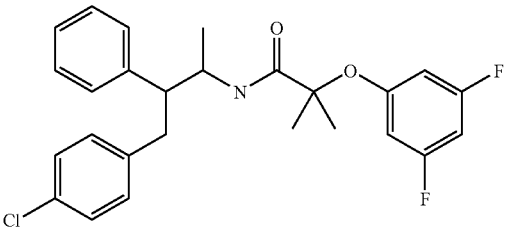 | 4.3 | 458 | B |
| 167. | N-[3-(4-Chlorophenyl)-1-methyl-2-phenylpropyl]-2-(4-fluorophenyloxy)-2-methylpropanamide | 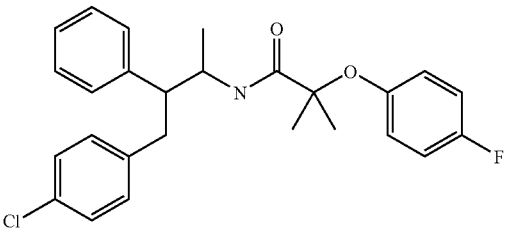 | 4.3 | 440 | A |
| 168. | N-[3-(4-Chlorophenyl)-1-methyl-2-phenylpropyl]-2-(4-fluorophenyloxy)-2-methylpropanamide | 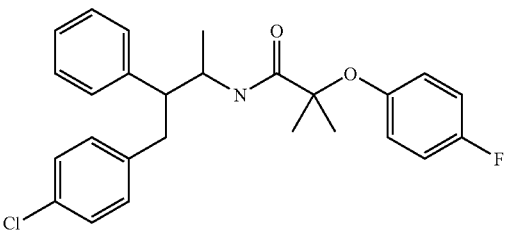 | 4.3 | 440 | B |
| 169. | N-[3-(4-Chlorophenyl)-2-(3-fluorophenyl)-1-methylpropyl]-2-(4-fluorophenyloxy)-2-methylpropanamide | 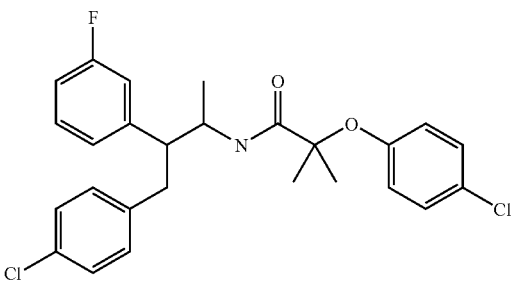 | 4.4 | 474 | A |

TABLE 4-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 170. | N-[3-(4-Chlorophenyl)-2-(3-fluorophenyl)-1-methylpropyl]-2-(4-fluorophenyloxy)-2-methylpropanamide | 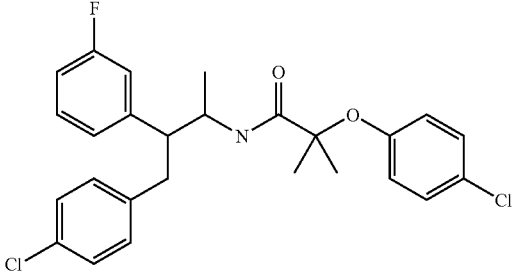 | 4.4 | 474 | B |
| 171. | N-[3-(4-Chlorophenyl)-2-(3-fluorophenyl)-1-methylpropyl]-2-(3,5-difluorophenyloxy)-2-methylpropanamide | 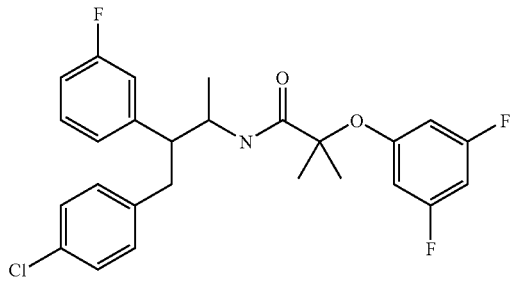 | 4.3 | 476 | A |
| 172. | N-[3-(4-Chlorophenyl)-2-(3-fluorophenyl)-1-methylpropyl]-2-(3,5-difluorophenyloxy)-2-methylpropanamide | 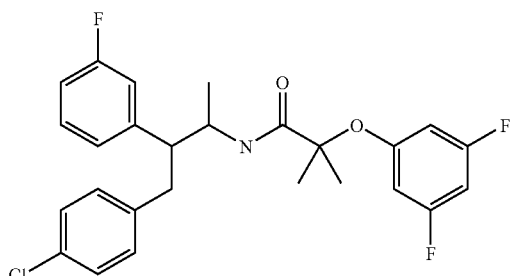 | 4.3 | 476 | B |
| 173. | N-[3-(4-Chlorophenyl)-2-(3-fluorophenyl)-1-methylpropyl]-2-(2-pyridyloxy)-2-methylpropanamide | 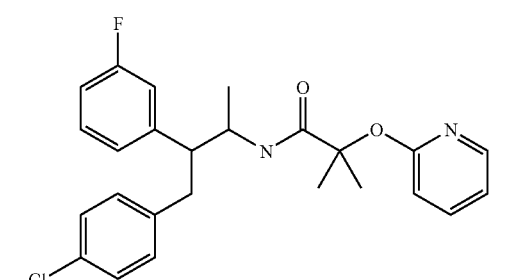 | 3.9 | 440 | A |
| 174. | N-[3-(4-Chlorophenyl)-2-(3-fluorophenyl)-1-methylpropyl]-2-(2-pyridyloxy)-2-methylpropanamide | 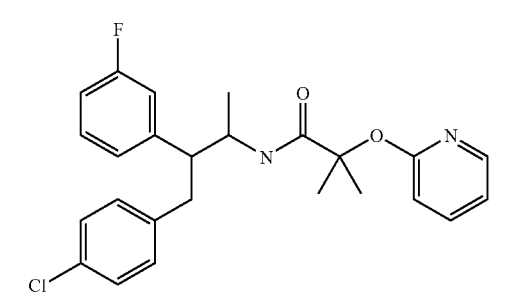 | 3.9 | 440 | B |

TABLE 4-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 175. | N-[3-(4-Chlorophenyl)-1-methyl-2-phenylpropyl]-2-(2-pyridyloxy)-2-methylpropanamide | 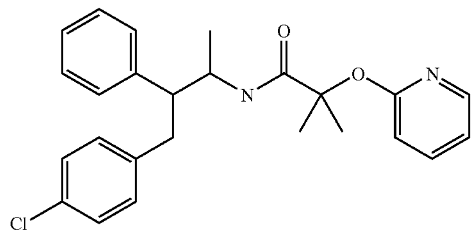 | 3.9 | 423 | A |
| 176. | N-[3-(4-Chlorophenyl)-1-methyl-2-phenylpropyl]-2-(2-pyridyloxy)-2-methylpropanamide | 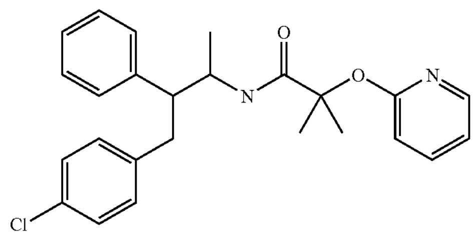 | 3.9 | 423 | B |
| 177. | N-[3-(4-Chlorophenyl)-1-methyl-2-(2-pyridyl)propyl]-2-(4-chlorophenyloxy)-2-methylpropanamide | 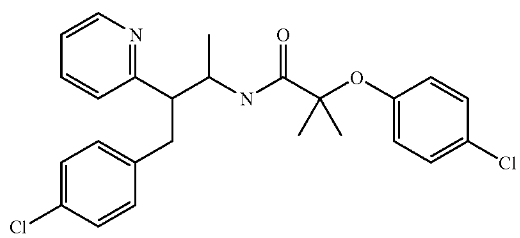 | 3.0 | 457 | A |
| 178. | N-[3-(4-Chlorophenyl)-1-methyl-2-(2-pyridyl)propyl]-2-(4-chlorophenyloxy)-2-methylpropanamide | 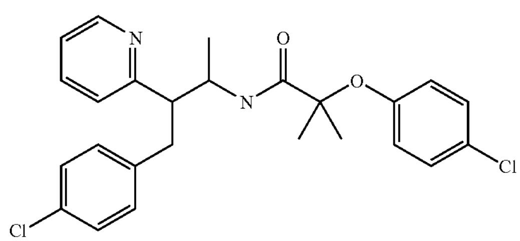 | 3.0 | 457 | B |
| 179. | N-[3-(4-Cyanophenyl)-1-methyl-2-phenylpropyl]-2-(3-chlorophenyloxy)-2-methylpropanamide | 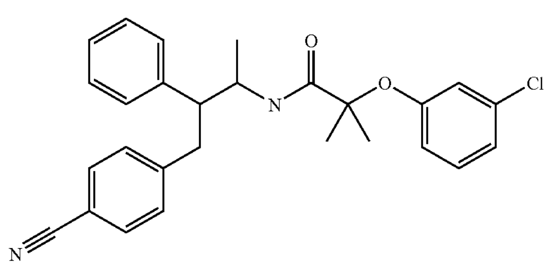 | 4.0 | 447 | A |

TABLE 4-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 180. | N-[3-(4-Cyanophenyl)-1-methyl-2-phenylpropyl]-2-(3-chlorophenyloxy)-2-methylpropanamide | 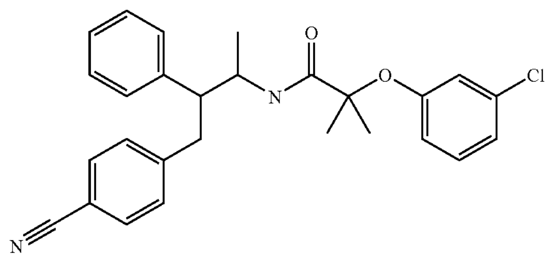 | 4.0 | 447 | B |
| 181. | N-[3-(4-Chlorophenyl)-1-methyl-2-(3-pyridyl)propyl]-2-(4-chlorophenyloxy)-2-methylpropanamide | 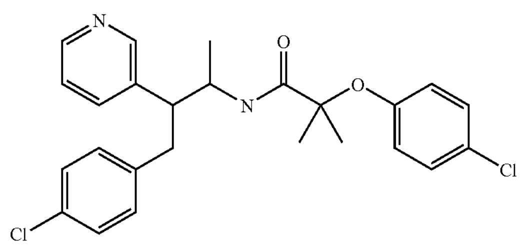 | 3.0 | 457 | A |
| 182. | N-[3-(4-Chlorophenyl)-1-methyl-2-(3-pyridyl)propyl]-2-(4-chlorophenyloxy)-2-methylpropanamide | 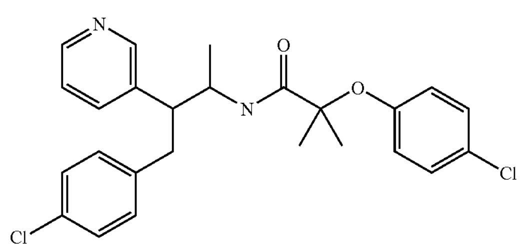 | 3.0 | 457 | B |
| 183. | N-[3-(4-Chlorophenyl)-1-methyl-2-(3-pyridyl)propyl]-2-(3,5-difluorophenyloxy)-2-methylpropanamide | 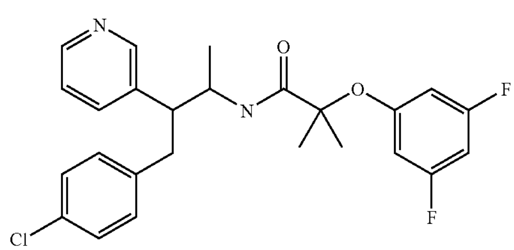 | 2.8 | 459 | A |
| 184. | N-[3-(4-Chlorophenyl)-1-methyl-2-(3-pyridyl)propyl]-2-(3,5-difluorophenyloxy)-2-methylpropanamide | 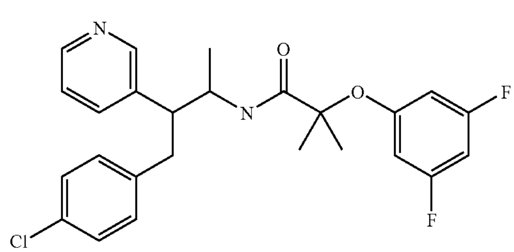 | 2.8 | 459 | B |

TABLE 4-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 185. | N-[3-(4-Chlorophenyl)-1-methyl-2-(3-pyridyl)propyl]-2-(3-fluorophenyloxy)-2-methylpropanamide | 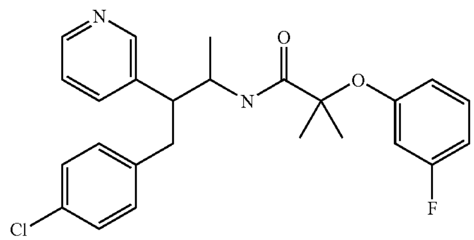 | 2.8 | 441 | A |
| 186. | N-[3-(4-Chlorophenyl)-1-methyl-2-(3-pyridyl)propyl]-2-(3-fluorophenyloxy)-2-methylpropanamide | 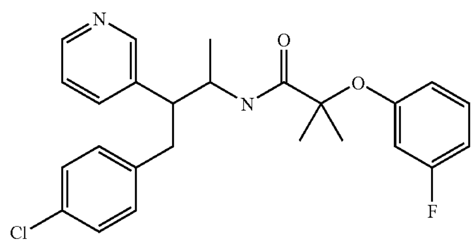 | 2.8 | 441 | B |
| 187. | N-[2-(4-Chlorophenoxy)-2-(4-chlorophenyl)ethyl]-2-(4-chlorophenyloxy)-2-methylpropanamide | 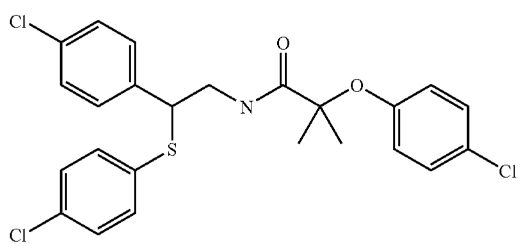 | 4.7 | 494 | A |
| 188. | N-[2-(4-Chlorophenoxy)-2-(4-chlorophenyl)ethyl]-2-(4-chlorophenyloxy)-2-methylpropanamide | | 4.7 | 494 | B |

Example 189

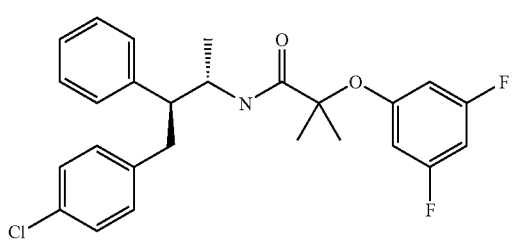

N-[3-(4-chlorophenyl)-2(S)-phenyl-1(S)-methylpropyl]-2-(3,5-difluorophenyloxy)-2-methylpropanamide The title compound was prepared following the procedures described in Examples 62-63 substituting 2-amino-3,4-bis(4-chlorophenyl)butane hydrochloride salt with N-[3-(4-chlorophenyl)-2(S)-phenyl-1(S)-methylpropyl]-amine, hydrochloride (Reference Example 11). $^1$H NMR (500 MHz, CD$_3$OD): δ 7.22 (m, 2H), 7.16 (m, 1H), 7.06-7.02 (m, 4H), 6.76 (d, 2H), 6.62-6.54 (m, 3H), 4.30 (m, 1H), 3.01 (dd, 1H), 2.83 (ddd, 1H), 2.95 (dd, 1H), 1.68 (s, 3H), 1.62 (s, 3H), 0.88 (d, 3H).

LC-MS: m/e 458 (M+H)+ (4.3 min).

Examples 190-194 (Table 5) were prepared following the procedures described in Examples 62-63 employing N-[3-(4-chlorophenyl)-2(S)-phenyl-1(S)-methylpropyl]-amine, hydrochloride from Reference Example 11 coupled to the appropriate carboxylic acid.

TABLE 5

Single enantiomeric compounds prepared with N-[3-(4-chlorophenyl)-2(S)-phenyl-1(S)-methylpropyl]-amine, hydrochloride from Reference Example 11.

| Ex. No. | Name | Structure | HPLC-retention time (min) | mass spectrum m/e |
|---|---|---|---|---|
| 190. | N-[3-(4-chlorophenyl)-2(S)-phenyl-1(S)-methylpropyl]-2-(3,4,5-trifluorophenyloxy)-2-methylpropanamide | 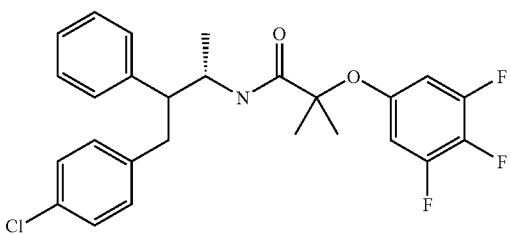 | 4.3 | 476 |
| 191. | N-[3-(4-chlorophenyl)-2(S)-phenyl-1(S)-methylpropyl]-2-(3-chloro-4-fluorophenyloxy)-2-methylpropanamide | 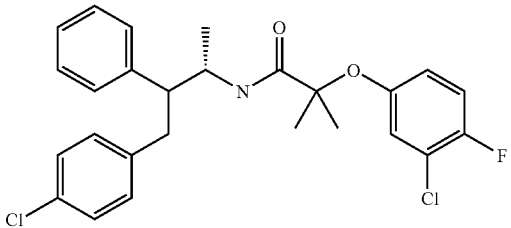 | 4.5 | 474 |
| 192. | N-[3-(4-chlorophenyl)-2(S)-phenyl-1(S)-methylpropyl]-2-(4-chloro-3-fluorophenyloxy)-2-methylpropanamide | 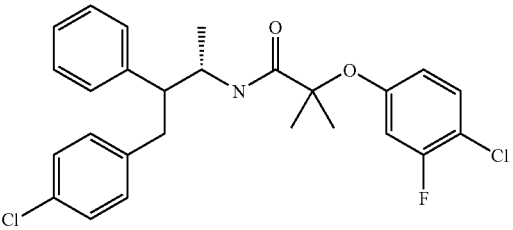 | 4.5 | 474 |
| 193. | N-[3-(4-chlorophenyl)-2(S)-phenyl-1(S)-methylpropyl]-2-(3,4-dichlorophenyloxy)-2-methylpropanamide | 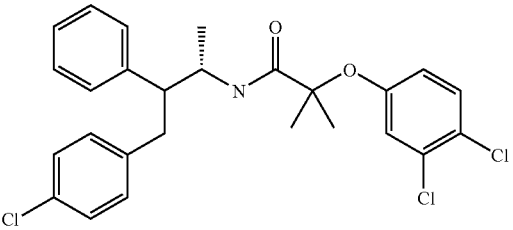 | 4.6 | 490 |
| 194. | N-[3-(4-chlorophenyl)-2(S)-phenyl-1(S)-methylpropyl]-2-(3,5-dichlorophenyloxy)-2-methylpropanamide | 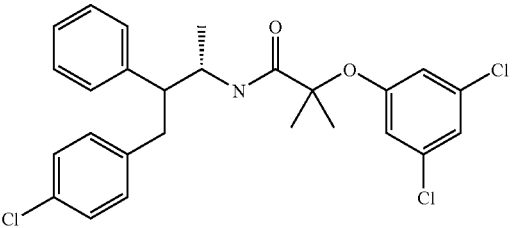 | 4.7 | 490 |

Example 195

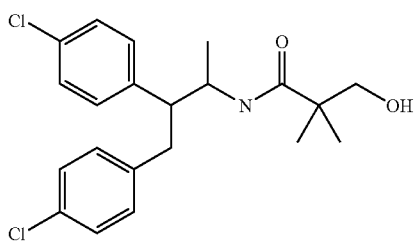

N-[2,3-Bis(4-chlorophenyl)-1-methylpropyl]-3-hydroxy-2,2-dimethylpropanamide

To a mixture of 2-amino-3,4-bis(4-chlorophenyl)butane hydrochloride salt (Reference Example 1, Diastereomer a) (3.7 g, 11 mmol), 3-hydroxy-2,2-dimethylpropionic acid (2.0 g, 17 mmol) in $CH_2Cl_2$ (100 mL) was added 1-hydroxybenzotriazole (2.3 g, 17 mmol), diisopropylethylamine (7.7 mL, 44 mmol) and 1-[3-(dimethylamino)propyl]-3-ethylcarbodiimide hydrochloride (3.2 g, 17 mmol). After stirring at room temperature overnight. The reaction mixture was diluted with EtOAc (200 mL), washed with water and saturated aqueous sodium bicarbonate, and concentrated to dryness, and the residue was purified by flash column chromatography on silica gel eluted with 50% EtOAc in hexane to give the title compound. $^1$H NMR (500 MHz, $CD_3OD$): δ7.24 (d, 2H), 7.12 (d, 2H), 7.10 (d, 2H), 6.92 (d, 2H), 4.25 (m, 1H), 3.68 (ABq, 2H), 3.18 (dd, 1H), 2.93 (ddd, 1H), 2.76 (dd, 1H), 1.20 (s, 3H), 1.19 (s, 3H), 0.96 (d, 3H). LC-MS: m/e 394 (M+H)$^+$ (3.5 min).

Example 196

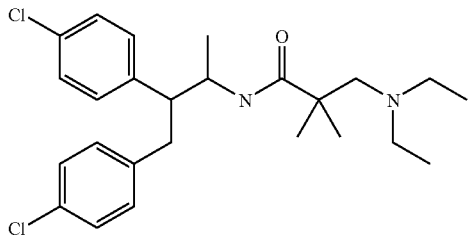

N-[2,3-Bis(4-chlorophenyl)-1-methylpropyl]-3-diethylamino-2,2-dimethylpropanamide

Step A N-[2,3-Bis(4-chlorophenyl)-1-methylpropyl]-2-formyl-2,2-dimethylpropanamide To a solution of N-[2,3-bis(4-chlorophenyl)-1-methylpropyl]-3-hydroxy-2,2-dimethylpropanamide (Example 193, 0.48 g, 1.2 mmol) in 20 mL $CH_2Cl_2$ was added crushed activated molecular sieves (2 g). After stirring at room temperature for 10 min, pyridinium chlorochromate (0.39 g, 1.8 mmol) was added. After stirring at room temperature for 1 h, CELITE diatomaceous earth (4 g) was added followed by 20 mL ether. The resulting mixture was filtered through a silica gel pad, which was washed with ether (2×20 mL). The filtrate was concentrated to dryness to give the title compound, which was used without further purification.

Step B N-[2,3-Bis(4-chlorophenyl)-1-methylpropyl]-3-diethylamino-2,2-dimethylpropanamide To a solution of N-[2,3-bis(4-chlorophenyl)-1-methylpropyl]-2-formyl-2,2-dimethylpropanamide (Step A, 37 mg, 0.094 mmol) and diethylamine (0.010 mL, 0.094 mmol) in 1 mL 1,2-dichloroethane was added sodium triacetoxyborohydride (28 mg, 0.13 mmol). After stirring at room temperature overnight, the reaction mixture was loaded onto a silica gel column eluted with 2% ammonia in MeOH (2 M) in EtOAc/hexane (1:1) to give the title compound. $^1$H NMR (500 MHz, $CD_3OD$): δ 7.24 (d, 2H), 7.12 (d, 2H), 7.10 (d, 2H), 6.96 (d, 2H), 4.24 (m, 1H), 3.17 (dd, 1H), 3.00 (ddd, 1H), 2.80 (dd, 1H), 2.60 (q, 4H), 1.22 (s, 3H), 1.18 (s, 3H), 0.99 (d, 3H), 0.98 (t, 6H). LC-MS: m/e 449 (M+H)$^+$ (3.2 min).

The compounds in Examples 197-199 were prepared following the procedures described in Example 196 substituting diethylamine with the appropriate amine.

Example 197

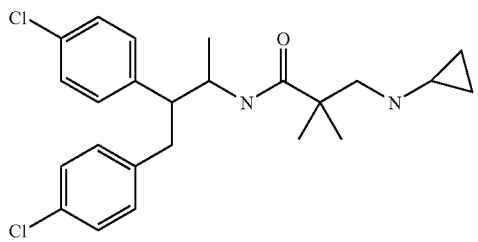

N-[2,3-Bis(4-chlorophenyl)-1-methylpropyl]-3-cyclopropylamino-2,2-dimethylpropanamide LC-MS: m/e 433 (M+H)$^+$ (3.0 min).

Example 198

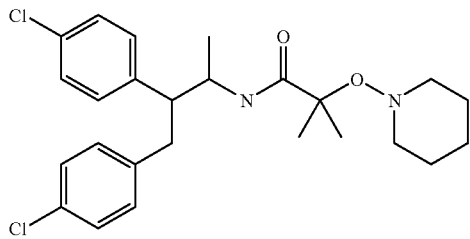

N-[2,3-Bis(4-chlorophenyl)-1-methylpropyl]-2,2-dimethyl-3-piperidinylpropanamide $^1$H NMR (500 MHz, $CD_3OD$): δ 7.24 (d, 2H), 7.14 (d, 2H), 7.12 (d, 2H), 6.96 (d, 2H), 4.24 (m, 1H), 3.14 (dd, 1H), 3.00 (m, 1H), 2.82 (dd, 1H), 2.62-2.40 (m, 4H), 1.62-1.3 (m, 6H), 1.22 (s, 3H), 1.16 (s, 3H), 1.00 (d, 3H). LC-MS: m/e 461 (M+H)+(3.2 min).

Example 199

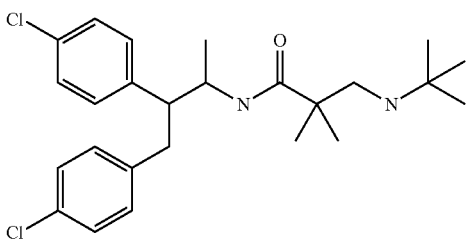

N-[2,3-Bis(4-chlorophenyl)-1-methylpropyl]-3-tert-butylamino-2,2-dimethylpropanamide ¹H NMR (500 MHz, CD₃OD): δ 7.24 (d, 2H), 7.12 (d, 2H), 7.08 (d, 2H), 6.94 (d, 2H), 4.21 (m, 1H), 3.13 (dd, 1H), 2.98 (m, 1H), 2.81 (dd, 1H), 1.22 (s, 3H), 1.20 (s, 3H), 1.12 (s, 9H), 0.98 (d, 3H). LC-MS: m/e 449 (M+H)⁺ (3.2 min).

Example 200

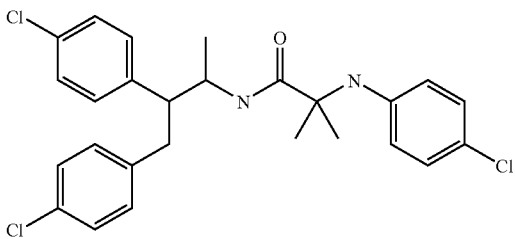

N-[2,3-Bis(4-chlorophenyl)-1-methylpropyl]-2-(4-chlorophenylamino)-2-methylpropanamide To a mixture of 2-amino-3,4-bis(4-chlorophenyl)butane 27hydrochloride salt (Diastereomer α, Section I, Reference Example 1, 0.31 g, 0.94 mmol) and 2-(4-chlorophenylamino)-2-methylpropionic acid (0.20 g, 0.94 mmol) in 5 mL CH₂Cl₂ was added N-methylmorpholine (0.41 mL, 3.5 mmol) and tris(pyrrolindinyl) phosphonium hexafluorophosphate (0.73 g, 1.4 mmol). After stirring at RT overnight, the reaction mixture was loaded onto a silica gel column eluted with 30% EtOAc in hexane to give the title compound. ¹H NMR (400 MHz, CD₃OD): δ 7.18 (d, 2H), 7.04 (d, 2H), 7.02 (d, 2H), 6.97 (d, 2H), 6.70 (d, 2H), 6.56 (d, 2H), 4.20 (m, 1H), 3.02 (dd, 1H), 2.78 (ddd, 1H), 2.64 (dd, 1H), 1.52 (s, 3H), 1.45 (s, 3H), 0.82 (d, 3H). LC-MS: m/e 489 (M+H)⁺ (4.3 min).

Example 201

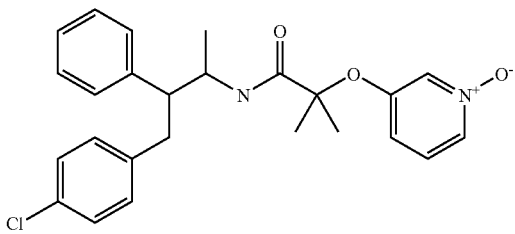

N-[3-(4-Chlorophenyl)-1-methyl-2-phenylpropyl]-2-(3-pyridyloxy-N-oxide)-2-methylpropanamide To a solution N-[3-(4-chlorophenyl)-1-methyl-2-phenylpropyl]-2-(3-pyridyloxy)-2-methylpropanamide (Example 102, 83 mg, 0.20 mmol) in 1 mL CH₂Cl₂ was added m-chloroperbenzoic acid (50%, 0.10 g, 0.30 mmol). After stirring at room temperature for 1 h, the reaction mixture was concentrated to dryness, and the residue was dissolved in DMSO, acetonitrile and water (2:2:1, 2 mL) and loaded onto a reverse-phase semi-preparative HPLC column eluted with 75% water/acetonitrile (0.1% trifluoroacetic acid) to 100% acetonitrile (0.1% trifluoroacetic acid) to give the title compound. ¹H NMR (500 MHz, CD₃OD): δ 8.16 (m, 1H), 8.05 (dd, 1H), 7.47 (dd, 1H), 7.28 (dd, 1H), 7.22 (m, 2H), 7.15 (m, 1H), 7.04 (d, 4H), 6.78 (d, 2H), 4.30 (m, 1H), 2.99 (dd, 1H), 2.88 (ddd, 1H), 2.74 (dd, 1H), 1.71 (s, 3H), 1.66 (s, 3H), 0.88 (d, 3H). LC-MS: m/e 439 (M+H)⁺ (3.0 min).

Example 202

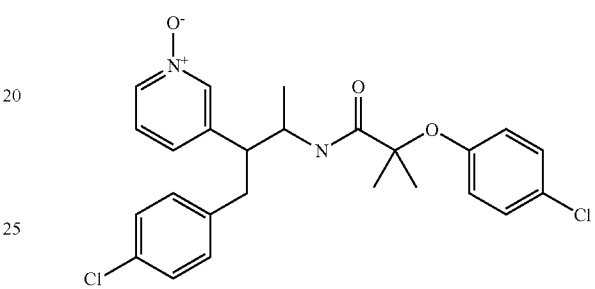

N-[3-(4-Chlorophenyl)-1-methyl-2-(3-pyridyl-N-oxide)propyl]-2-(4-chlorophenyloxy)-2-methylpropanamide (Diastereomer α, Enantiomer B)

N-[3-(4-Chlorophenyl)-1-methyl-2-(3-pyridyl)propyl]-2-(4-chlorophenyloxy)-2-methylpropanamide (Example 182) was converted to the title compound following the procedure described in Example 201. LC-MS: m/e 473 (M+H)⁺ (3.2 min).

Example 203

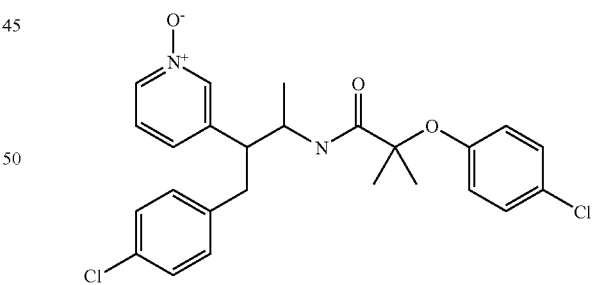

N-[3-(4-Chlorophenyl)-1-methyl-2-(3-pyridyl-N-oxide)propyl]-2-(3,5-difluorophenyloxy)-2-methylpropanamide (Diastereomer α, Enantiomer A)

N-[3-(4-Chlorophenyl)-1-methyl-2-(3-pyridyl)propyl]-2-(4-chlorophenyloxy)-2-methylpropanamide (Example 181) was converted to the title compound following the procedure described in Example 201. LC-MS: m/e 475 (M+H)⁺ (3.1 min).

Example 204

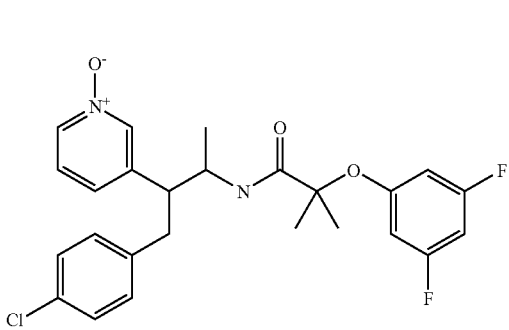

N-[3-(4-Chlorophenyl)-1-methyl-2-(3-pyridyl-N-oxide)propyl]-2-(3,5-difluorophenyloxy)-2-methyl-propanamide (Diastereomer α, Enantiomer B)

N-[3-(4-Chlorophenyl)-1-methyl-2-(3-pyridyl)propyl]-2-(4-chlorophenyloxy)-2-methylpropanamide (Example 184) was converted to the title compound following the procedure described in Example 201. LC-MS: m/e 475 (M+H)$^+$ (3.1 min).

Example 205

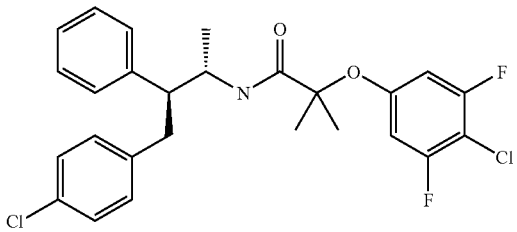

N-[3-(4-Chlorophenyl)-1(S)-methyl-2(S)-phenylpropyl]-2-(4-chloro-3,5-difluorophenyloxy)-2-methyl-propanamide A solution of N-[(3-(4-chlorophenyl)-1(S)-methyl-2(S)-phenylpropyl]-2-(3,5-difluorophenyloxy)-2-methylpropanamide (Example 189, 0.20 g, 0.43 mmol) in anhydrous THF (1 mL) was added dropwise to a solution of sec-butyl lithium (1.3 M in cyclohexane, 0.84 mL, 1.1 mmol) and N,N,N'N'-tetramethylethylenediamine (0.16 mL, 1.1 mmol) in 1 mLTHF at −78° C. After stirring at −78° C. under nitrogen for 1 h, a solution of N-chlorosuccinimide (0.13 g, 0.86 mmol) in 4 mLTHF was added at −7° C. After stirring at −78° C. for another hour, the reaction mixture was poured into saturated aqueous ammonium chloride (50 mL), and the product was extracted with EtOAc (3×50 mL). The combined extracts were dried over anhydrous sodium sulfate, filtered and concentrated to dryness, and the residue was purified by flash column chromatography eluted with 10% EtOAc in hexane to give the title compound. $^1$H NMR (500 MHz, CD$_3$OD): δ 7.3-6.5 (m, 11H), 4.29 (m, 1H), 2.97 (dd, 1H), 2.84 (m, 1H), 2.70 (dd, 1H), 1.67 (s, 3H), 1.62 (s, 3H), 0.88 (d, 3H). LC-MS: m/e 492 (M+H)$^+$ (4.5 min).

Example 206

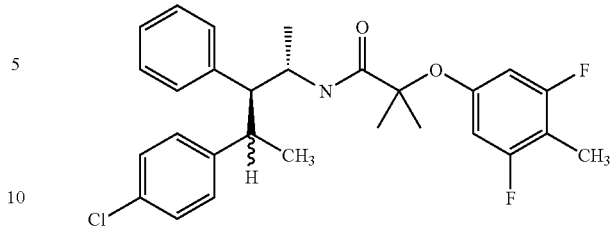

N-[3(R)-(4-Chlorophenyl)-1(S),3-dimethyl-2(S)-phenylbutyl]-2-(3,5-difluoro-4-methylphenyloxy)-2-methylpropanamide and N-[3(S)-(4-Chlorophenyl)-1(S), 3-dimethyl-2(S)-phenylbutyl]-2-(3,5-difluoro-4-methylphenyloxy)-2-methylpropanamide (2 isomers).

A solution of N-[(2S,3S)-3-(4-chlorophenyl)-1-methyl-2-phenylpropyl]-2-(3,5-difluorophenyloxy)-2-methylpropanamide (Example 187, 0.20 g, 0.43 mmol) in anhydrous THF (1 mL) was added dropwise to a solution of sec-butyl lithium (1.3 M in cyclohexane, 0.84 mL, 1.1 mmol) and N,N,N'N'-tetramethylethylenediamine (0.16 mL, 1.1 mmol) in 1 mLTHF at −78° C. After stirring at −78° C. under nitrogen for 1 h, methyl iodide (0.11 mL, 1.7 mmol) was added at −78° C. After stirring at −78° C. for another hour, the reaction mixture was poured into saturated aqueous ammonium chloride (50 mL), and the product was extracted with EtOAc (3×50 mL). The combined extracts were dried over anhydrous sodium sulfate, filtered and concentrated to dryness, and the residue was purified by flash column chromatography on silica gel eluted with 10% EtOAc in hexane to give the title compound as a 1:1 mixture of diastereomers. Further purification by reverse-phase HPLC afforded the pure diastereomers.

Faster eluting diastereomer: $^1$H NMR (500 MHz, CD$_3$OD): δ 7.3-6.5 (m, 11H), 4.46 (m, 1H), 3.26 (m, 1H), 3.03 (dd, 1H), 2.09 (s, 3H), 1.62 (s, 3H), 1.55 (s, 3H), 1.29 (d, 3H), 0.97 (d, 3H). LC-MS: m/e 486 (M+H)$^+$ (4.7 min).

Slower eluting diastereomer (14 mg): $^1$H NMR (500 MHz, CD$_3$OD): δ 7.28-7.18 (m, 5H), 7.02-6.94 (m, 4H), 6.48 (d, 2H), 4.27 (m, 1H), 3.13 (m, 1H), 2.98 (dd, 1H), 2.03 (s, 3H), 1.57 (s, 3H), 1.51 (s, 3H), 1.04 (d, 3H), 0.93 (d, 3H). LC-MS: m/e 486 (M+H)$^+$ (4.8 min).

Example 207

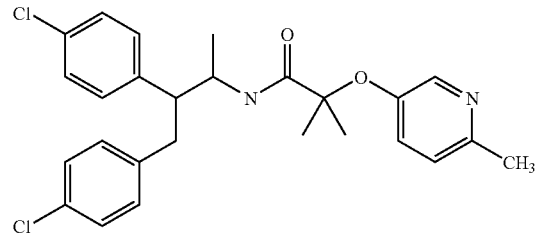

N-[2,3-Bis(4-Chlorophenyl)-1-methylpropyl]-2-(6-methyl-3-pyridyloxy)-2-methylpropanamide (Diastereomer α)

Step A Ethyl 2-(4-Methyl-3-pyridyloxy)-2-methylpropionate

To a solution of ethyl 2-(6-methyl-3-pyridyloxy)acetate (5.0 g, 26 mmol) and methyl iodide (6.3 mL, 0.10 mol) in 100 mLanhydrous THF at −78° C. was added potassium tertbutoxide (1 M in THF, 50 mL, 50 mmol), and the reaction was allowed to warm to room temperature overnight. The reaction mixture was poured into saturated ammonium chloride (200 mL), and the product was extracted with EtOAc (2×150 mL). The combined extracts were dried over anhydrous MgSO$_4$, filtered and concentrated to dryness, and the residue was purified by flash column chromatography eluted with 4:1 to 2:1 hexane/EtOAc to give the title compound. $^1$H NMR (500 MHz, CD$_3$OD): δ 8.04-8.00 (m, 1H), 7.28-7.18 (m, 2H), 4.77 (q, 2H), 2.45 (s, 3H), 1.44 (s, 6H), 1.24 (t, 3H).

Step B
2-(6-Methyl-3-pyridyloxy)-2-methylpropionic Acid

To a solution of ethyl 2-(6-methyl-3-pyridyloxy)-2-methylpropionate (Step A, 2.0 g, 8.9 mmol) in DMSO (20 mL) was added potasium hydroxide (1.0 g, 20 mmol) in 2 mL water. After stirring at room temperature for 2 h, the reaction was quenched by addition of formic acid (85%, 10 mmol) and poured into water (200 mL). The product was extracted with EtOAc (2×100 mL), and the combined extracts were dried over anhydrous sodium sulfate, filtered and concentrated to dryness to give the title compound contaminated with DMSO (molar ratio 1:5, determined by NMR). $^1$H NMR (500 MHz, CD$_3$OD): δ 8.06 (d, 1H), 7.38-7.22 (m, 2H), 2.47 (s, 3H), 1.58 (s, 6H).

Step C N-[2,3-Bis(4-Chlorophenyl)-1-methylpropyl]-2-(6-methyl-3-pyridyloxy)-2-methylpropanamide (Diastereomer α)

The title compound was prepared by reacting 2-(6-methyl-3-pyridyloxy)-2-methylpropionic acid (Step B, 75 mg, 0.63 mmol) with 2-amino-3,4-bis(4-chlorophenyl)butane hydrochloride salt (Diastereomer α, Reference Example 1) (0.23 g, 0.63 mmol) following the procedure described in Example 62-63. LC-MS: m/e 471 (M+H)$^+$ (3.1 min).

Example 208

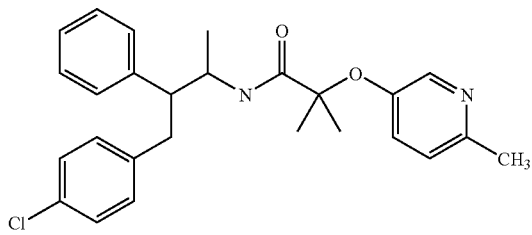

N-[3-(4-Chlorophenyl)-2-phenyl-1-methylpropyl]-2-(6-methyl-3-pyridyloxy)-2-methylpropanamide (Diastereomer β)

The title compound was prepared following the procedures described in Example 207 substituting 2-amino-3,4-bis(4-chlorophenyl)butane hydrochloride salt with 2-amino-3-(4-chlorophenyl)-2-phenylbutane hydrochloride salt (Diastereomer β, Reference Example 5)) at Step C. LC-MS: m/e 437 (M+H)$^+$ (2.8 min).

Example 209

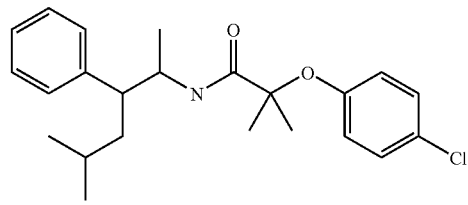

N-(1,4-dimethyl-2-phenylpentyl)-2-(4-chlorophenoxy)-2-methylpropanamide

2-Amino-5-methyl-3-phenylhexane hydrochloride salt from Reference Example 26 (30 mg) was reacted with the acid chloride prepared from of 2-(4-chlorophenoxy)-2-methyl-propionic acid (37 mg) according to the procedure described in Example 62-63 to afford the title compound after purification by preparative TLC on silica gel eluted with 20% EtOAC-hexane. $^1$H NMR: (500 MHz, CDCl$_3$): δ 0.83 and 0.85 (2d, 6H), 0.96 (d, 3H), 1.34 (m, 1H), 1.45 (m, 1H), 1.53 (s, 3H), 1.59 (s, 3H), 2.73 (m, 1H), 4.24 (m, 1H), 6.41 (d, 1H), 6.8-7.4 (m, 9H).

LC-MS: R$_t$=4.5 min. m/e=388.3 (M+1).

The following compounds in Table 6 were prepared following the procedure of Example 209 substituting appropriate amine for 2-amino-5-methyl-3-phenylhexane and appropriate carboxylic acid for 2-(4-chlorophenoxy)-2-methyl-propionic acid.

TABLE 6

| Ex. No. | Name | Structure | retention time (min) | HPLC-mass spectrum m/e |
|---|---|---|---|---|
| 210. | N-(1-methyl-2-phenylpentyl)-2-(4-chlorophenoxy)-acetamide | 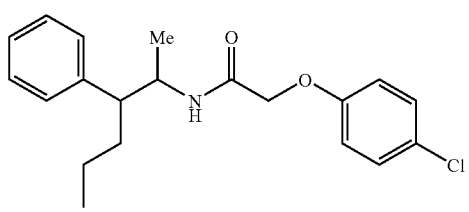 | 4.4 | 374.1 |

TABLE 6-continued

| Ex. No. | Name | Structure | retention time (min) | HPLC-mass spectrum m/e |
|---|---|---|---|---|
| 211. | N-(1-methyl-2,5-diphenylpentyl)-2-(4-chlorophenoxy)-acetamide | 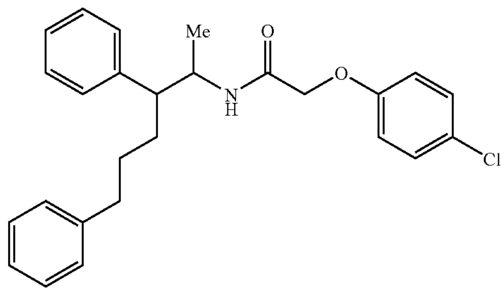 | 4.7 | 450.3 |
| 212. | N-(1,3-dimethyl-2-phenylbutyl)-2-(4-chlorophenoxy)-propanamide | 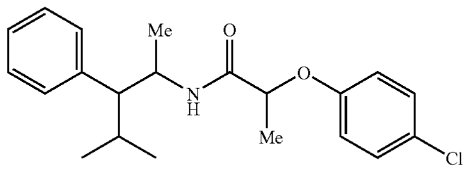 | 4.4 | 374.2 |

Example 213

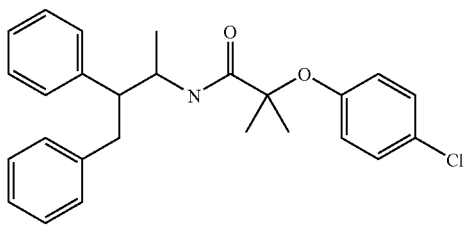

N-(2,3-Diphenyl-1-methylpropyl)-2-(4-chlorophenoxy)-2-methylpropanamide (Diastereomer β)

A solution of 2-(4-chlorophenoxy)-2-methylpropionic acid (20 mg, 0.095 mmol) in $CH_2Cl_2$ (1 mL) and DMF (10 μL) was treated with oxalyl chloride (11 μL). After 30 min the reaction was concentrated and the residue was dissolved in 1 mL $CH_2Cl_2$. This solution was added to a mixture of 16 mg N-(2,3-diphenyl-1-methylpropylamine (β isomer from Reference Example 2) and 1 mL saturated $NaHCO_3$. The reaction was stirred overnight and the organic layer was removed with a pipet. Purification of this solution by preparative TLC eluted with 30% EtOAc/hexane afforded the title compound. $^1$H NMR: (500 MHz, $CDCl_3$): δ 1.17 (d, 3H), 1.36 (s, 3H), 1.46 (s, 3H), 2.85-3.05 (m, 3H), 4.44 (m, 1H), 6.37 (d, 1H), 6.75-7.4 (m, 14H). LC-MS: $R_t$=4.4 min. m/e=422.2 (M+1).

Example 214

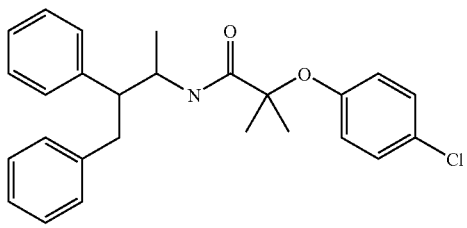

N-(2,3-Diphenyl-1-methylpropyl)-2-(4-chlorophenoxy)-2-methylpropanamide (Diastereomer α)

Reaction of 16 mg N-(2,3-diphenyl)-1-methylpropylamine (α isomer, Reference Example 2) with the acid chloride prepared from 20 mg 2-(4-chlorophenoxy)-2-methylpropionic acid as described in example 213 gave the title compound. $^1$H NMR: (500 MHz, $CDCl_3$): δ 1.02 (d, 3H), 1.51 (s, 3H), 1.57 (s, 3H), 2.9-3.2 (m, 3H), 4.37 (m, 1H), 6.51 (d, 1H), 6.8-7.4 (m, 14H). LC-MS: $R_t$=4.3 min. m/e=422.3 (M+1).

Examples 215 and 216

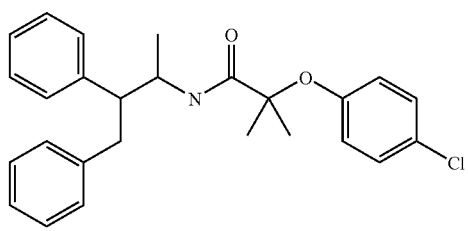

N-(2,3-Diphenyl-1-methylpropyl)-2-(4-chlorophenoxy)-2-methylpropanamide (Diastereomer β, Enantiomers A and B)

The racemic N-(2,3-diphenyl-1-methylpropyl)-2-(4-chlorophenoxy)-2-methylpropanamide (Diastereomer β, Example 213) was resolved on a Chiralcel OD column using 5% EtOH/hexane as an eluant at a flow rate of 7 mL/min on HPLC. The respective enantiomers of the title compound had retention times of 9.85 min and 13.17 min on an analytical Chiralcel OD (4.6×250 mm) column using 5% EtOH/hexane at 0.5 mL/min.

Faster eluting isomer A: $^1$H NMR: (500 MHz, $CDCl_3$): δ 1.16 (d, 3H), 1.36 (s, 3H), 1.46 (s, 3H), 2.89 (m, 1H), 2.97 (m, 1H), 3.09 (m, 1H), 4.44 (m, 1H), 6.36 (d, 1H), 6.75 (m, 2H), 7.0-7.4 (m, 12H).

Slower eluting isomer B: ¹H NMR: (500 MHz, CDCl₃): δ 1.16 (d, 3H), 1.36 (s, 3H), 1.46 (s, 3H), 2.89 (m, 1H), 2.97 (m, 1H), 3.09 (m, 1H), 4.44 (m, 1H), 6.36 (d, 1H), 6.75 (m, 2H), 7.0-7.4 (m, 12H).

Examples 217 and 218

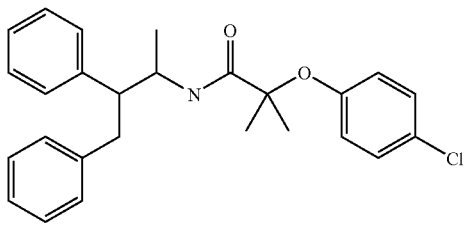

N-(2,3-Diphenyl-1-methylpropyl)-2-(4-chlorophenoxy)-2-methylpropanamide (Diastereomer α, Enantiomers A and B)

Resolution of N-(2,3-diphenyl-1-methylpropyl)-2-(4-chlorophenoxy)-2-methylpropanamide (Diastereomer α, Example 214) was carried out on a Chiralcel OD column as detailed in Example 215-216 to afford the respective enantiomers.

Faster eluting enantiomer A (Rt=13.8 min): ¹H NMR: (500 MHz, CDCl₃): δ 1.01 (d, 3H), 1.51 (s, 3H), 1.57 (s, 3H), 2.97 (m, 2H), 3.1 (m, 1H), 4.37 (m, 1H), 6.5 (d, 1H), 6.8-7.4 (m, 14H).

Slower eluting enantiomer B (R$_t$=21.6 min): ¹H NMR: (500 MHz, CDCl₃): δ 1.01 (d, 3H), 1.51 (s, 3H), 1.57 (s, 3H), 2.97 (m, 2H), 3.1 (m, 1H), 4.37 (m, 1H), 6.5 (d, 1H), 6.8-7.4 (m, 14H).

Example 219

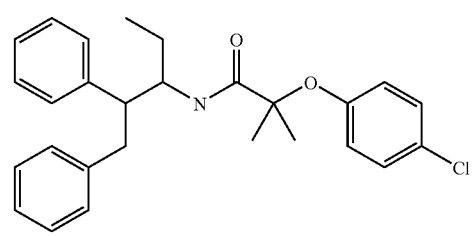

N-(2,3-Diphenyl-1-ethylpropyl)-2-(4-chlorophenoxy)-2-methylpropanamide

N-(2,3-diphenyl)-1-ethylpropylamine (Reference Example 3) was reacted with the acid chloride derived from 2-(4-chlorophenoxy)-2-methylpropionic acid according to the procedures described in Example 213 to afford the title compound as a mixture of diastereomers. ¹H NMR: (500 MHz, CDCl₃): δ 0.82 (t, 3H), 1.16 (m, 1H), 1.57 (s, 3H), 1.60 (s, 3H), 2.95 (m, 2H), 3.14 (m, 1H), 4.25 (m, 1H), 6.5 (d, 1H), 6.8-7.4 (m, 14H). LC-MS: R$_t$=4.5 min. m/e=436.2 (M+1).

The following compounds in Table 7 were prepared following the procedures of Example 213 substituting an appropriate amine for N-(2,3-diphenyl-1-methylpropylamine and appropriate carboxylic acid for 2-(4-chlorophenoxy)-2-methyl-propionic acid.

TABLE 7

| Ex. No. | Name | Structure | HPLC-retention time (min) | mass spectrum m/e |
|---|---|---|---|---|
| 220. | N-(3-(4-chlorophenyl)-2-phenyl-1-methylpropyl)-2-(4-chlorophenoxy)-acetamide | 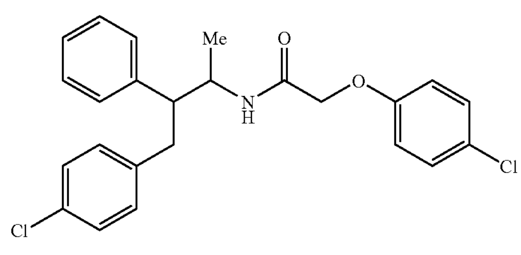 | 4.2 | 428.0 |
| 221. | N-(2,3-diphenyl-1-methylpropyl)-2-(4-chlorophenoxy)-acetamide | 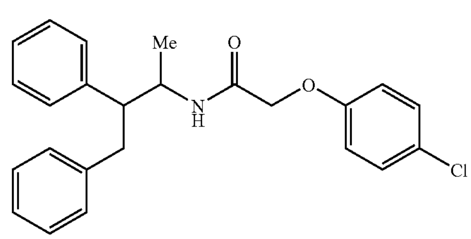 | 4.0 | 394.1 |

TABLE 7-continued

| Ex. No. | Name | Structure | retention time (min) | HPLC-mass spectrum m/e |
|---|---|---|---|---|
| 222. | N-(3-(4-chlorophenyl)-2-phenyl-1-methylpropyl)-2-(4-chlorophenoxy)-propanamide | 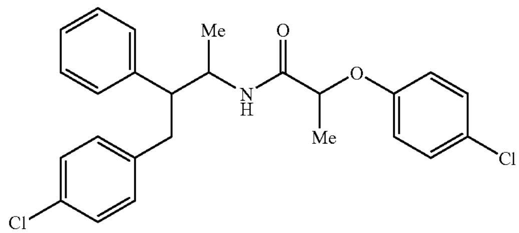 | 4.2 | 442.1 |
| 223. | N-(2,3-diphenyl-1-methylpropyl)-2-(4-chlorophenoxy)-propanamide | 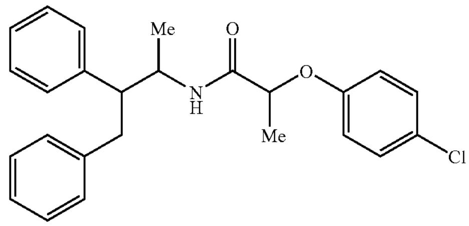 | 4.0 | 408.2 |
| 224. | N-(2,3-bis(4-chlorophenyl)-1-methylpropyl)-2-methyl-3-phenyl-propanamide (Isomer A) | 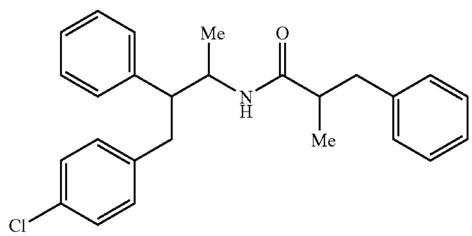 | 4.2 | 440.2 |
| 225. | N-(2,3-bis(4-chlorophenyl)-1-methylpropyl)-2-methyl-3-phenyl-propanamide (Isomer B) | 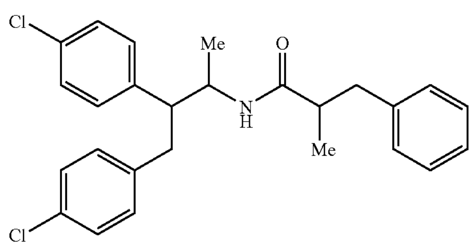 | 4.3 | 440.3 |
| 226. | N-(2,3-bis(4-chlorophenyl)-1-methylpropyl)-2-methyl-3-(4-chlorophenyl)-propanamide (Isomer A) | 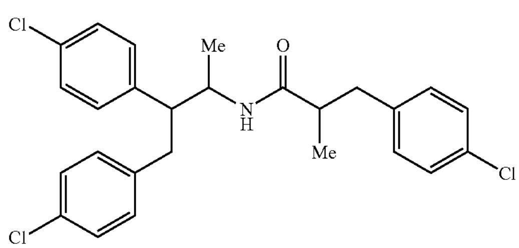 | 4.3<br>4.4 | 476.1 |
| 227. | N-(2,3-bis(4-chlorophenyl)-1-methylpropyl)-2-methyl-3-(4-chlorophenyl)-propanamide (Isomer B) | 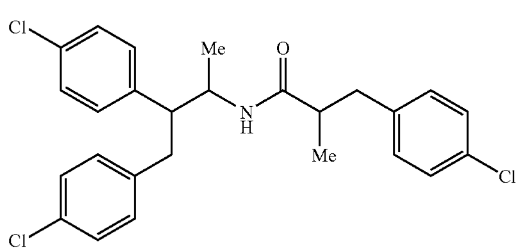 | 4.3<br>4.5 | 474.2 |

TABLE 7-continued

| Ex. No. | Name | Structure | retention time (min) | HPLC-mass spectrum m/e |
|---|---|---|---|---|
| 228. | N-(3-(4-chlorophenyl)-2-phenyl-1-methylpropyl)-2-(4-chloro-anilino)-acetamide | 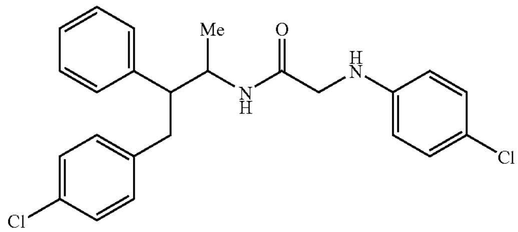 | 3.8 | 393.1 |
| 229. | N-(2,3-diphenyl-1-methylpropyl)-2-(4-chloro-anilino)-acetamide | 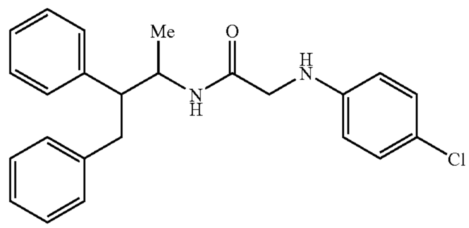 | 3.5 | 359.2 |
| 230. | N-(2,3-bis(4-chlorophenyl)-1-methylpropyl)-2,2-dimethyl-3-phenyl-propanamide | 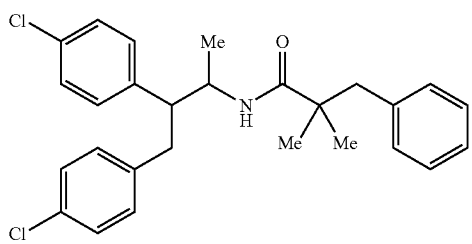 | 4.5 | 454.2 |
| 231. | N-(3-(4-chlorophenyl)-2-phenyl-1-methylpropyl)-2-methyl-2-(4-chlorophenoxy)-propanamide | 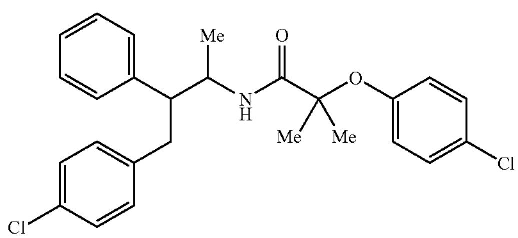 | 4.5 | 456.0 |
| 232. | N-(3-(2-chlorophenyl)-2-phenyl-1-methylpropyl)-2-methyl-2-(4-chlorophenoxy)-propanamide | 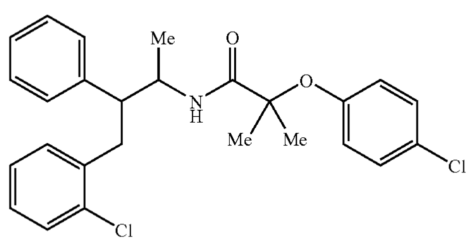 | 4.5 | 456.2 |
| 233. | N-(3-(4-trifluoromethylphenyl)-2-phenyl-1-methylpropyl)-2-methyl-2-(4-chlorophenoxy)-propanamide | 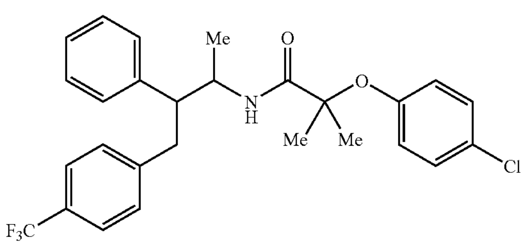 | 4.5 | 490.1 |

TABLE 7-continued

| Ex. No. | Name | Structure | retention time (min) | HPLC- mass spectrum m/e |
|---|---|---|---|---|
| 234. | N-(3-(4-fluorophenyl)-2-phenyl-1-methylpropyl)-2-methyl-2-(4-chlorophenoxy)-propanamide | 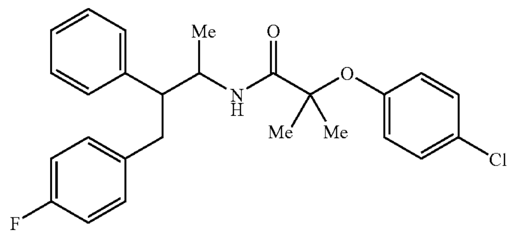 | 4.3 | 440.2 |
| 235. | N-(3-(4-chlorophenyl)-2-phenyl-1-methylpropyl)-2-methyl-2-phenoxy-propanamide | 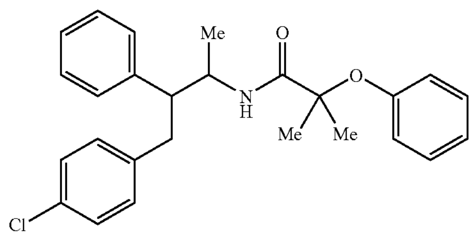 | 4.3 | 422.2 |
| 236. | N-(3-(4-chlorophenyl)-2-phenyl-1-methylpropyl)-2-methyl-2-(4-fluorophenoxy)-propanamide | 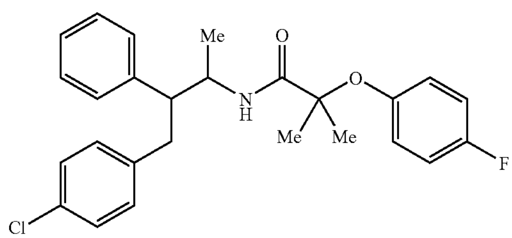 | 4.2 | 440.1 |
| 237. | N-(2,3-diphenyl-1-methylpropyl)-2-methyl-2-(4-fluorophenoxy)-propanamide | 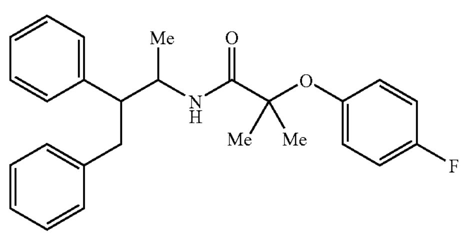 | 4.1 | 406.2 |
| 238. | N-(3-phenyl-2-benzyl-1-methylpropyl)-2-methyl-2-(4-chlorophenoxy)-propanamide | 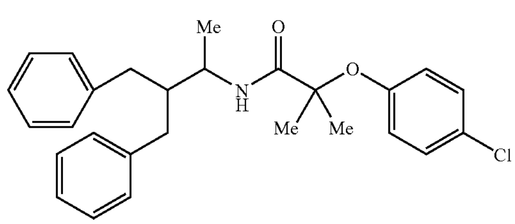 | 4.6 | 436.2 |

The following compounds in Table 8 were prepared following the procedures of Examples 62-63 substituting an appropriate amine for N-(2,3-diphenyl-1-methylpropylamine and appropriate carboxylic acid for 2-(4-chlorophenoxy)-2-methyl-propionic acid.

TABLE 8

Compounds prepared according to the methods described in Examples 62-63.

| Ex. No. | Name | Structure | retention time (min) | HPLC-mass spectrum m/e | Diastereomer α and/or β |
|---|---|---|---|---|---|
| 239. | N-[3-(4-Chlorophenyl)-2-(3,5-difluorophenyl)-1-methylpropyl]-2-(3,5-difluorophenyloxy)-2-methylpropanamide | 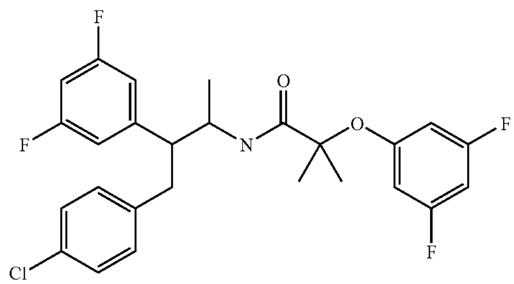 | 4.3 | 494 | α |
| 240. | N-[3-(4-Chlorophenyl)-2-(3,5-difluorophenyl)-1-methylpropyl]-2-methyl-2-(3,4,5-trifluorophenyloxy)propanamide | 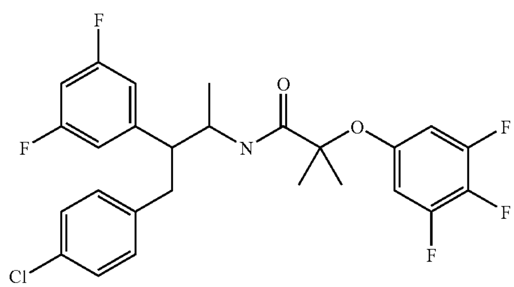 | 4.4 | 512 | α |
| 241. | N-[3-(4-Chlorophenyl)-2-(3,5-difluorophenyl)-1-methylpropyl]-2-methyl-2-(2-pyridyloxy)propanamide | 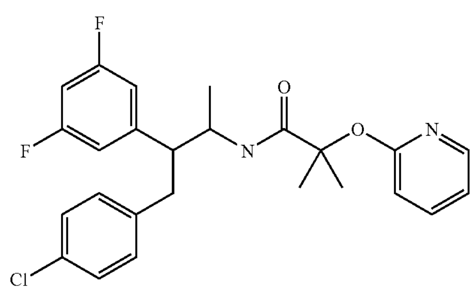 | 3.9 | 459 | α |
| 242. | N-[3-(4-Chlorophenyl)-2-(3,5-difluorophenyl)-1-methylpropyl]-2-(4-chlorophenyloxy)-2-methylpropanamide | 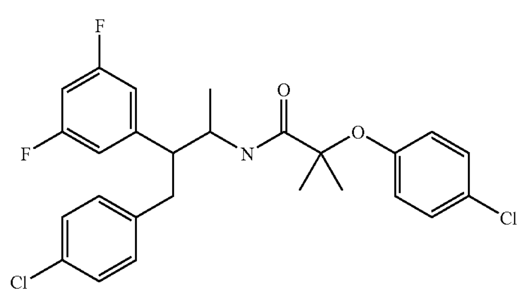 | 4.4 | 492 | α |

TABLE 8-continued

Compounds prepared according to the methods described in Examples 62-63.

| Ex. No. | Name | Structure | retention time (min) | HPLC-mass spectrum m/e | Diastereomer α and/or β |
|---|---|---|---|---|---|
| 243. | N-[3-(4-Chlorophenyl)-2-(3-pyridyl)-1-methylpropyl]-2-(3,5-dichlorophenyloxy)-2-methylpropanamide | 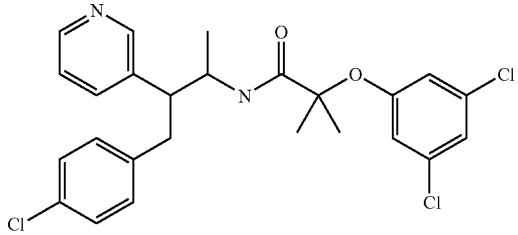 | 3.0 | 491 | α |
| 244. | N-[3-(4-Chlorophenyl)-2-(3-pyridyl)-1-methylpropyl]-2-(3-chlorophenyloxy)-2-methylpropanamide | 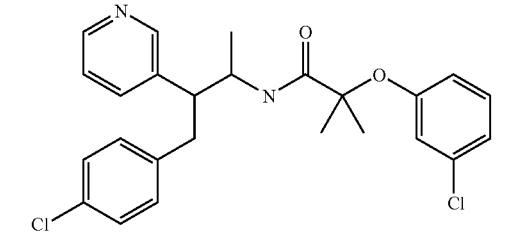 | 2.9 | 457 | α |
| 245. | N-[3-(4-Chlorophenyl)-2-(3-pyridyl)-1-methylpropyl]-2-(3-chloro-5-fluorophenyloxy)-2-methylpropanamide | 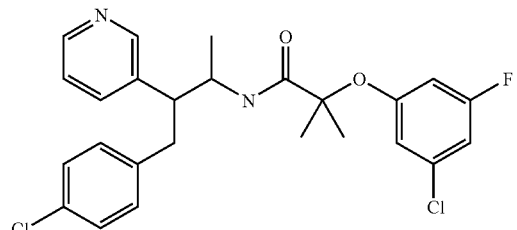 | 3.0 | 475 | α |
| 246. | N-[3-(4-Chlorophenyl)-2-(3-pyridyl)-1-methylpropyl]-2-methyl-2-(2-pyridyloxy)propanamide | 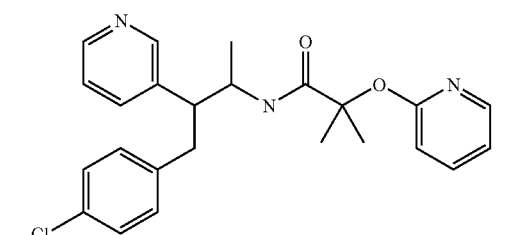 | 2.4 | 424 | α |
| 247. | N-[3-(4-Chlorophenyl)-2-(3-fluorophenyl)-1-methylpropyl]-2-(3-chloro-5-fluorophenyloxy)-2-methylpropanamide | 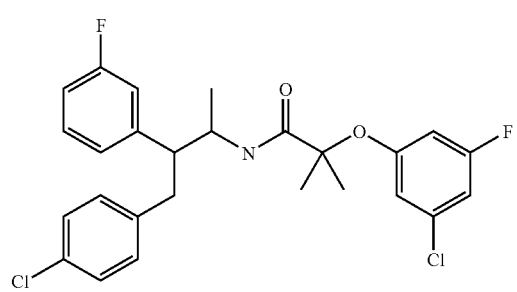 | 4.5 | 492 | α |

TABLE 8-continued

Compounds prepared according to the methods described in Examples 62-63.

| Ex. No. | Name | Structure | retention time (min) | HPLC-mass spectrum m/e | Diastereomer α and/or β |
|---|---|---|---|---|---|
| 248. | N-[3-(4-Chlorophenyl)-2-(3-fluorophenyl)-1-methylpropyl]-2-(3-chlorophenyloxy)-2-methylpropanamide | 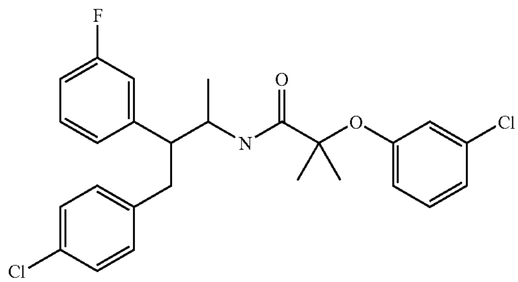 | 4.4 | 474 | α |
| 249. | N-[3-(4-Chlorophenyl)-2-(3-cyanophenyl)-1-methylpropyl]-2-(3-chlorophenyloxy)-2-methylpropanamide | 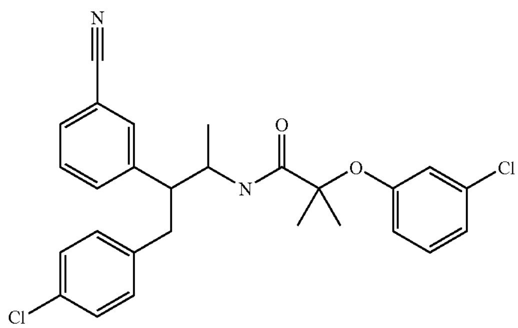 | 4.1 | 481 | α |
| 250. | N-[3-(4-Chlorophenyl)-2-(3-cyanophenyl)-1-methylpropyl]-2-methyl-2-(2-pyridyloxy)propanamide | 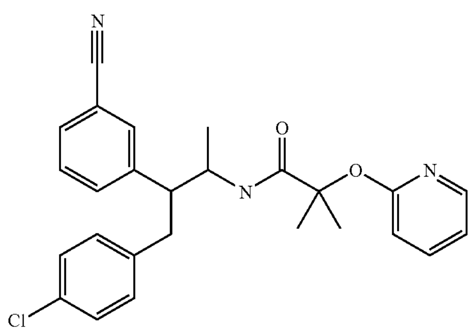 | 3.6 | 448 | α |
| 251. | N-[2-(3-Chlorophenyl)-3-(4-chlorophenyl)-1-methylpropyl]-2-methyl-2-(2-pyridyloxy)propanamide | 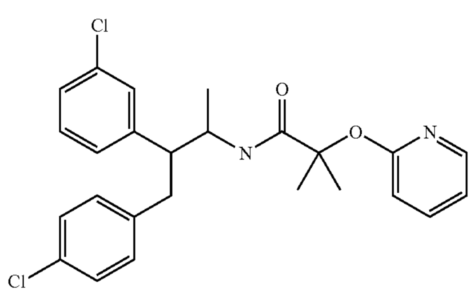 | 4.2 | 457 | α |

The following compounds in Table 9 were isolated according to the procedures for separating enantiomers described in Examples 149-150.

TABLE 9

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 251. | N-[3-(4-Chlorophenyl)-2-(3,5-difluorophenyl)-1-methylpropyl]-2-(3,5-difluorophenyloxy)-2-methylpropanamide | 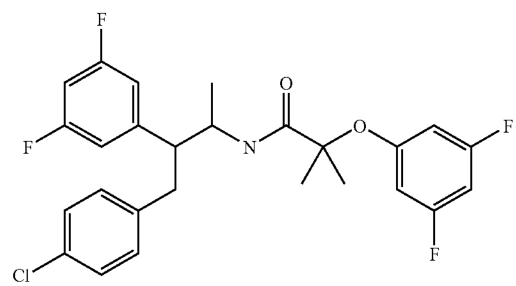 | 4.3 | 494 | A |
| 252. | N-[3-(4-Chlorophenyl)-2-(3,5-difluorophenyl)-1-methylpropyl]-2-(3,5-difluorophenyloxy)-2-methylpropanamide | 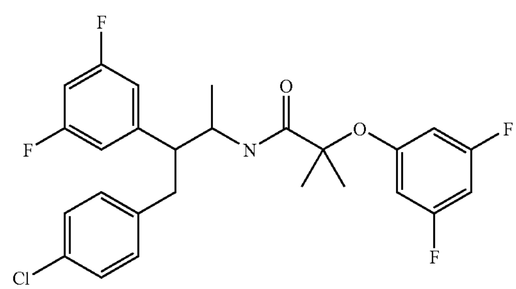 | 4.4 | 494 | B |
| 253. | N-[3-(4-Chlorophenyl)-2-(3,5-difluorophenyl)-1-methylpropyl]-2-methyl-2-(3,4,5-trifluorophenyloxy)propanamide | 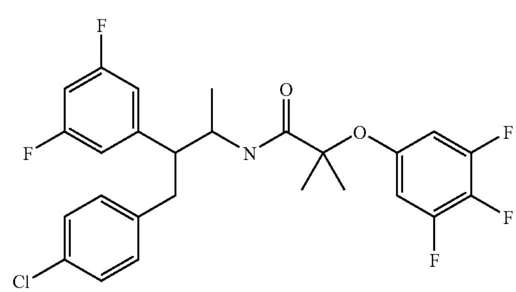 | 4.4 | 512 | A |
| 254. | N-[3-(4-Chlorophenyl)-1-(3,5-difluorophenyl)-1-methylpropyl]-2-methyl-2-(3,4,5-trifluorophenyloxy)propanamide | 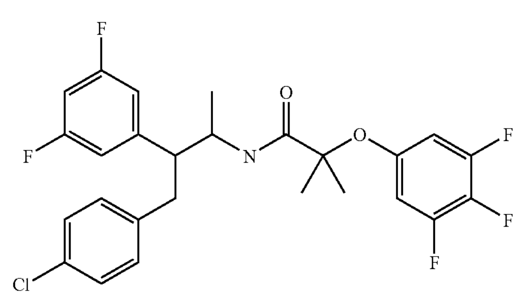 | 4.4 | 512 | A |

TABLE 9-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 255. | N-[3-(4-Chlorophenyl)-2-(3,5-difluorophenyl)-1-methylpropyl]-2-(4-chlorophenyloxy)-2-methylpropanamide | 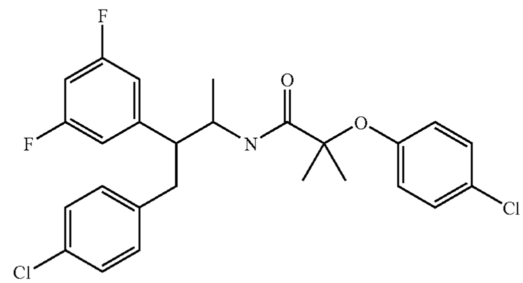 | 4.5 | 492 | A |
| 256. | N-[3-(4-Chlorophenyl)-2-(3,5-difluorophenyl)-1-methylpropyl]-2-(4-chlorophenyloxy)-2-methylpropanamide | 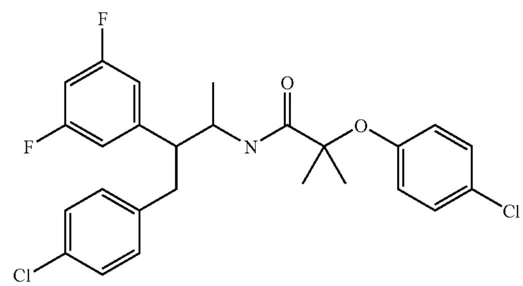 | 4.5 | 492 | B |
| 257. | N-[3-(4-Chlorophenyl)-2-(3,5-difluorophenyl)-1-methylpropyl]-2-methyl-2-(2-pyridyloxy)propanamide | 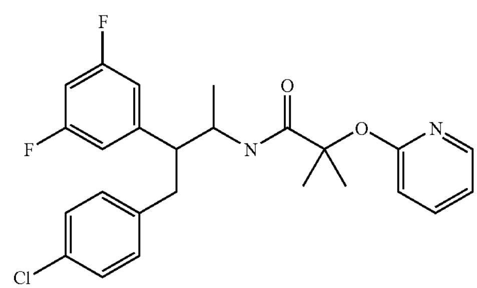 | 3.9 | 459 | A |
| 258. | N-[3-(4-Chlorophenyl)-2-(3,5-difluorophenyl)-1-methylpropyl]-2-methyl-2-(2-pyridyloxy)propanamide | 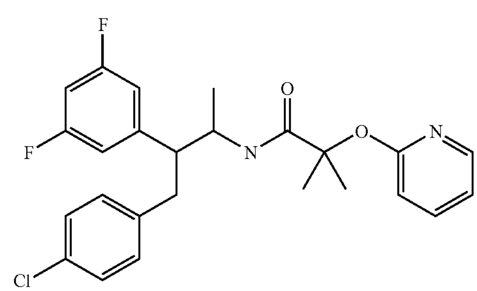 | 3.2 | 491 | A |
| 259. | N-[3-(4-Chlorophenyl)-2-(3-pyridyl)-1-methylpropyl]-2-(3,5-dichlorophenyloxy)-2-methylpropanamide | 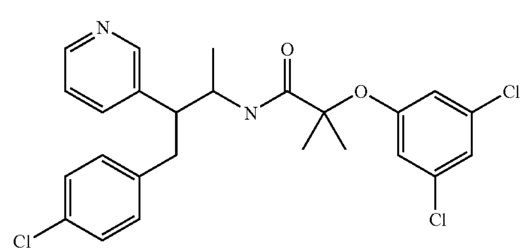 | 3.2 | 491 | A |

TABLE 9-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 260. | N-[3-(4-Chlorophenyl)-2-(3-pyridyl)-1-methylpropyl]-2-(3,5-dichlorophenyloxy)-2-methylpropanamide | 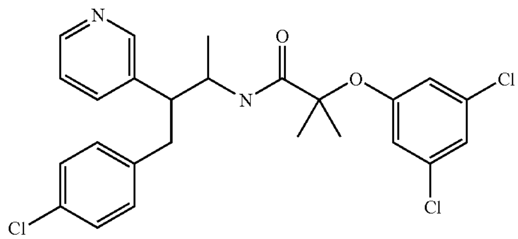 | 3.2 | 491 | B |
| 261. | N-[3-(4-Chlorophenyl)-2-(3-pyridyl)-1-methylpropyl]-2-(3-chlorophenyloxy)-2-methylpropanamide | 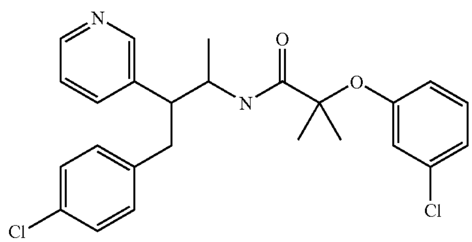 | 2.9 | 457 | A |
| 262. | N-[3-(4-Chlorophenyl)-2-(3-pyridyl)-1-methylpropyl]-2-(3-chlorophenyloxy)-2-methylpropanamide | 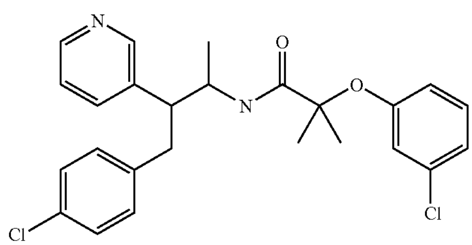 | 2.9 | 457 | B |
| 263. | N-[2-(3-Bromophenyl)-3-(4-chlorophenyl)-1-methylpropyl]-2-methyl-2-(2-pyridyloxy)propanamide | 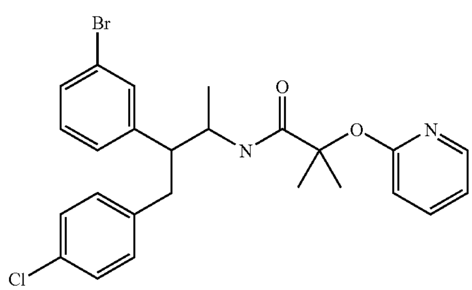 | 4.09 | 501 | A |
| 264. | N-[2-(3-Bromophenyl)-3-(4-chlorophenyl)-1-methylpropyl]-2-methyl-2-(2-pyridyloxy)propanamide | 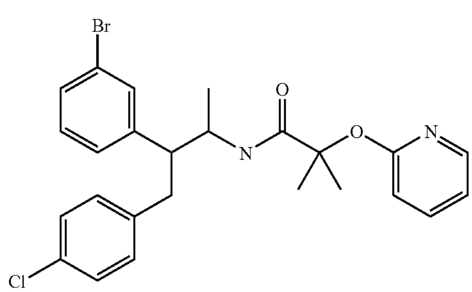 | 4.09 | 501 | B |

TABLE 9-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 265. | N-[2-(3-Bromophenyl)-3-(4-chlorophenyl)-1-methylpropyl]-2-methyl-2-(2-pyridyloxy)propanamide and N-[3-(4-chlorophenyl)-2-(3-iodophenyl)-1-methylpropyl]-2-methyl-2-(2-pyridyloxy)propanamide (1:1 mixture) | | 4.2 | 501/549 | A |
| 266. | N-[2-(3-Bromophenyl)-3-(4-chlorophenyl)-1-methylpropyl]-2-methyl-2-(2-pyridyloxy)propanamide and N-[3-(4-chlorophenyl)-2-(3-iodophenyl)-1-methylpropyl]-2-methyl-2-(2-pyridyloxy)propanamide (1:1 mixture) | | 4.2 | 501/549 | B |
| 267. | N-[2-(3-Bromophenyl)-3-(4-chlorophenyl)-1-methylpropyl]-2-methyl-2-(2-phenyloxy)propanamide | 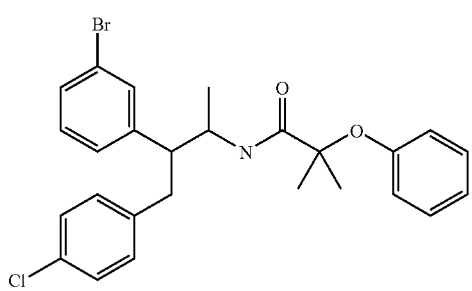 | 4.4 | 500 | A |

TABLE 9-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 268. | N-[2-(3-Bromophenyl)-3-(4-chlorophenyl)-1-methylpropyl]-2-methyl-2-(2-phenyloxy)propanamide | 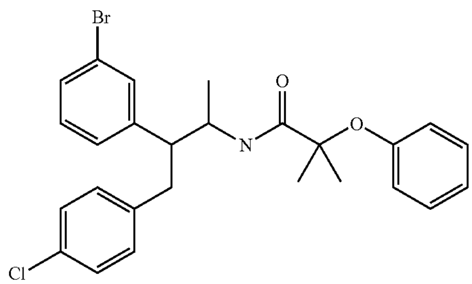 | 4.4 | 500 | B |
| 269. | N-[3-(4-Chlorophenyl)-2-(3-pyridyl)-1-methylpropyl]-2-methyl-2-(2-pyridyloxy)propanamide | 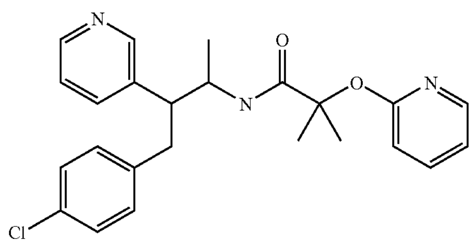 | 2.5 | 424 | A |
| 270. | N-[3-(4-Chlorophenyl)-2-(3-pyridyl)-1-methylpropyl]-2-methyl-2-(2-pyridyloxy)propanamide | 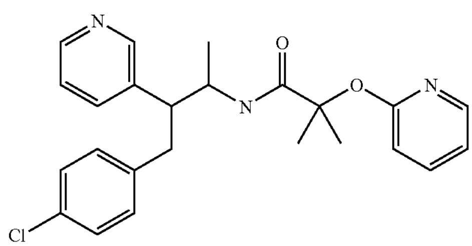 | 2.5 | 424 | B |
| 271. | N-[3-(4-Chlorophenyl)-2-(3-fluorophenyl)-1-methylpropyl]-2-(3-chloro-5-fluorophenyloxy)-2-methylpropanamide | 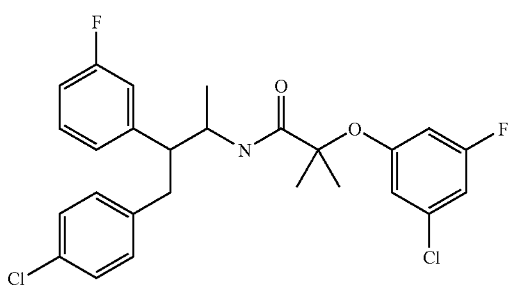 | 4.6 | 492 | A |
| 272. | N-[3-(4-Chlorophenyl)-2-(3-fluorophenyl)-1-methylpropyl]-2-(3-chloro-5-fluorophenyloxy)-2-methylpropanamide | 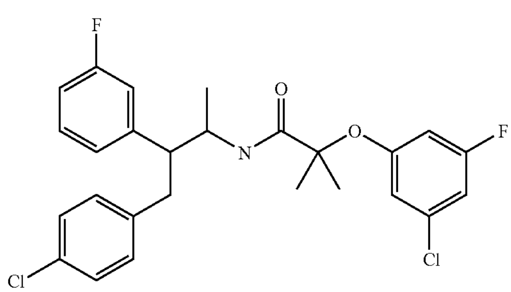 | 4.6 | 492 | B |

TABLE 9-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 273. | N-[3-(4-Chlorophenyl)-2-(3-fluorophenyl)-1-methylpropyl]-2-(3-chlorophenyloxy)-2-methylpropanamide | 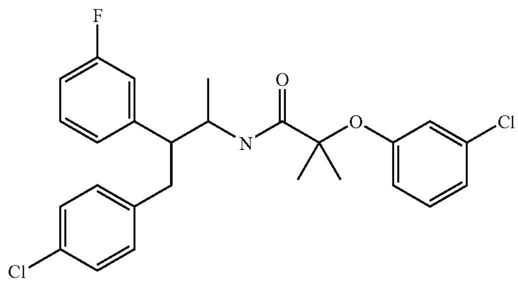 | 4.4 | 474 | A |
| 274. | N-[3-(4-Chlorophenyl)-2-(3-fluorophenyl)-1-methylpropyl]-2-(3-chlorophenyloxy)-2-methylpropanamide | 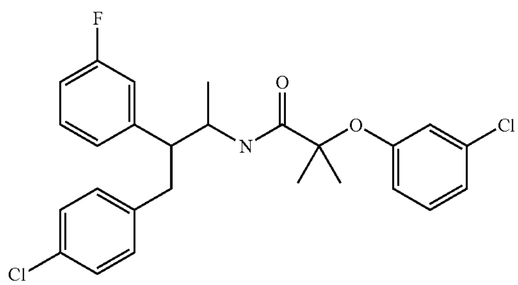 | 4.4 | 474 | B |
| 275. | N-[3-(4-Chlorophenyl)-2-(3-cyanophenyl)-1-methylpropyl]-2-(3-chlorophenyloxy)-2-methylpropanamide | 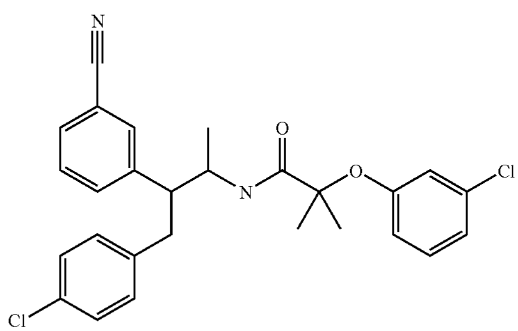 | 4.3 | 481 | A |
| 276. | N-[3-(4-Chlorophenyl)-2-(3-cyanophenyl)-1-methylpropyl]-2-(3-chlorophenyloxy)-2-methylpropanamide | 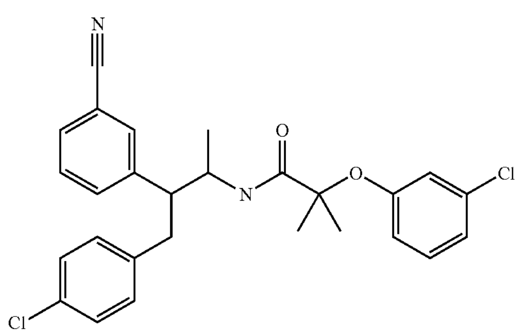 | 4.3 | 481 | B |

TABLE 9-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 277. | N-[3-(4-Chlorophenyl)-2-(3-cyanophenyl)-1-methylpropyl]-2-methyl-2-(2-pyridyloxy)propanamide | 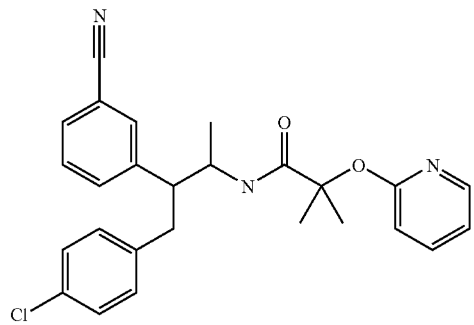 | 3.8 | 448 | A |
| 278. | N-[3-(4-Chlorophenyl)-2-(3-cyanophenyl)-1-methylpropyl]-2-methyl-2-(2-pyridyloxy)propanamide | 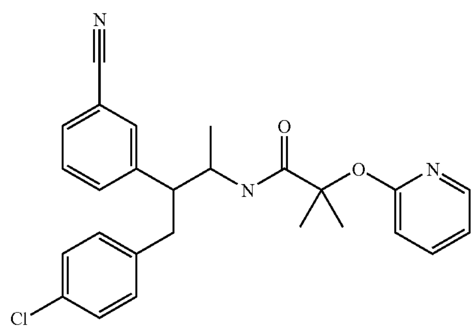 | 3.8 | 448 | B |
| 279. | N-[2-(3-Chlorophenyl)-3-(4-chlorophenyl)-1-methylpropyl]-2-methyl-2-(2-pyridyloxy)propanamide | 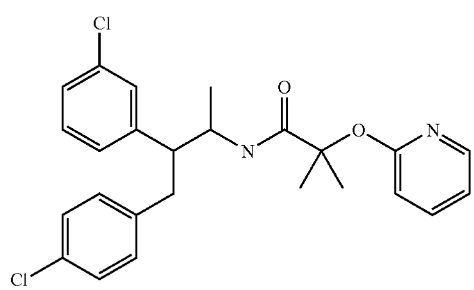 | 4.0 | 457 | A |
| 280. | N-[2-(3-Chlorophenyl)-3-(4-chlorophenyl)-1-methylpropyl]-2-methyl-2-(2-pyridyloxy)propanamide | 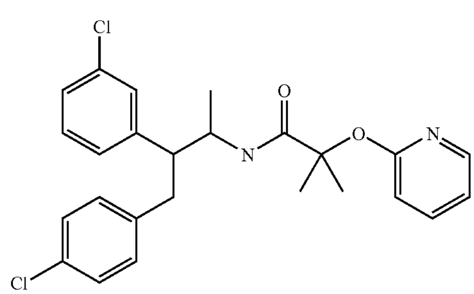 | 4.0 | 457 | BA |

The following compounds in Table 10 were prepared with N-[3-(4-chlorophenyl)-2(S)-phenyl-1(S)-methylpropyl]-amine, hydrochloride from Reference Example 11 and the appropriate acid to afford a single enantiomer.

TABLE 10

Single enantiomeric compounds prepared with N-[3-(4-chlorophenyl)-2(S)-phenyl-1(S)-methylpropyl]-amine, hydrochloride.

| Ex. No. | Name | Structure | HPLC-retention time (min) | mass spectrum m/e |
|---|---|---|---|---|
| 281. | N-[(2S,3S)-3-(4-Chlorophenyl)-1-methyl-2-phenylpropyl]-2-(5-chloropyridyloxy)-2-methylpropanamide | 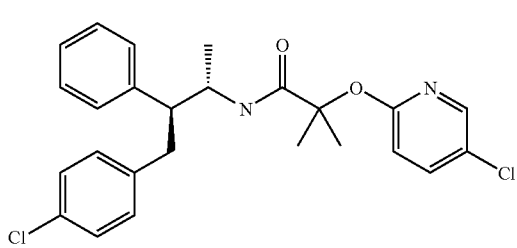 | 4.2 | 457 |
| 282. | N-[(2S,3S)-3-(4-Chlorophenyl)-1-methyl-2-phenylpropyl]-2-(6-methylpyridyloxy)-2-methylpropanamide | 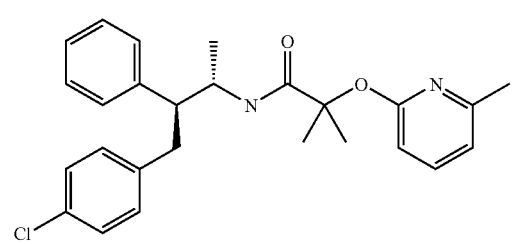 | 3.8 | 437 |
| 283. | N-[(2S,3S)-3-(4-Chlorophenyl)-1-methyl-2-phenylpropyl]-2-(3-chloro-5-fluorophenyloxy)-2-methylpropanamide | 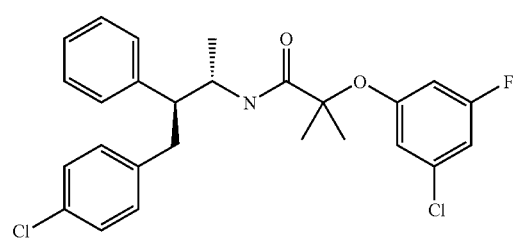 | 4.6 | 474 |
| 284. | N-[(2S,3S)-3-(4-Chlorophenyl)-1-methyl-2-phenylpropyl]-2-(3-pyridazinyloxy)-2-methylpropanamide | 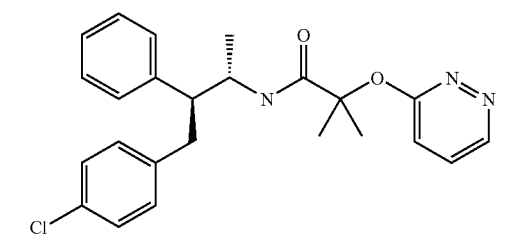 | 3.4 | 424 |
| 285. | N-[(2S,3S)-3-(4-Chlorophenyl)-1-methyl-2-phenylpropyl]-2-(4-trifluoromethylphenyloxy)-2-methylpropanamide | 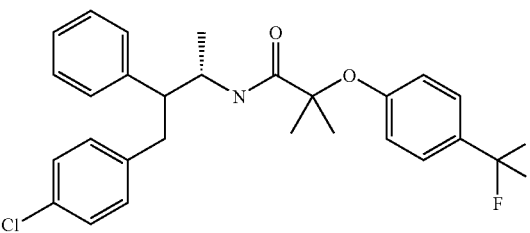 | 4.5 | 490 |

TABLE 10-continued

Single enantiomeric compounds prepared with N-[3-(4-chlorophenyl)-2(S)-phenyl-1(S)-methylpropyl]-amine, hydrochloride.

| Ex. No. | Name | Structure | retention time (min) | HPLC-mass spectrum m/e |
|---|---|---|---|---|
| 286. | N-[(2S,3S)-3-(4-Chlorophenyl)-1-methyl-2-phenylpropyl]-2-(5-trifluoromethylpyridyloxy)-2-methylpropanamide | 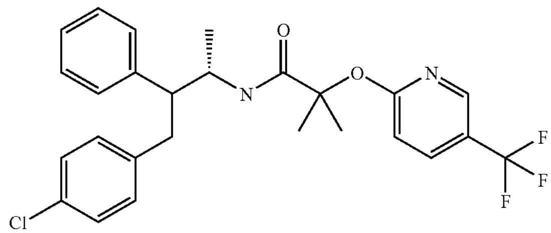 | 4.3 | 491 |
| 287. | N-[(2S,3S)-3-(4-Chlorophenyl)-1-methyl-2-phenylpropyl]-2-(4,6-dimethylpyridyloxy)-2-methylpropanamide | 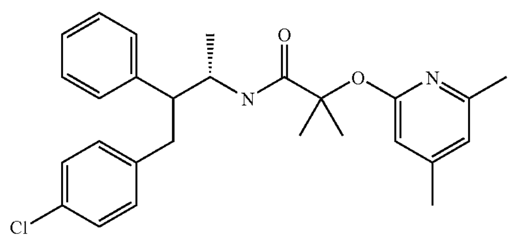 | 3.8 | 451 |

The following compounds in Table 11 were prepared according to the procedures of Example 200 substituting an appropriate amine for N-(2,3-diphenyl-1-methylpropylamine and an appropriate carboxylic acid for 2-(4-chlorophenoxy)-2-methyl-propionic acid.

TABLE 11

| Ex. No. | Name | Structure | retention time (min) | HPLC-mass spectrum m/e |
|---|---|---|---|---|
| 288. | N-(3-(4-chlorophenyl)-2-cyclopentyl-1-methyl)propyl-2-(3,5-dichlorophenoxy)-2-methylpropanamide (Diastereomer A) | 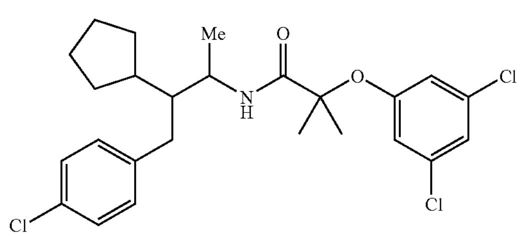 | 5.3[a] | 484.0 |
| 289. | N-(3-(4-chlorophenyl)-2-cyclopentyl-1-methyl)propyl-2-(3,5-dichlorophenoxy)-2-methylpropanamide (Diastereomer B) | 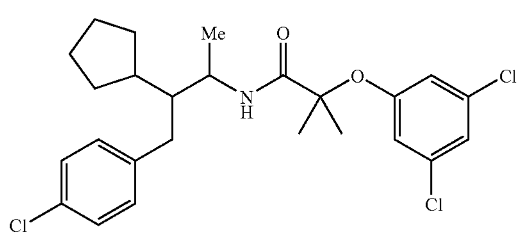 | 5.3[b] | 484.0 |

TABLE 11-continued

| Ex. No. | Name | Structure | retention time (min) | HPLC-mass spectrum m/e |
|---|---|---|---|---|
| 290. | N-(3-(4-chlorophenyl)-2-cyclopentyl-1-methyl)propyl-2-(3,5-difluorophenoxy)-2-methylpropanamide (Diastereomer A) | 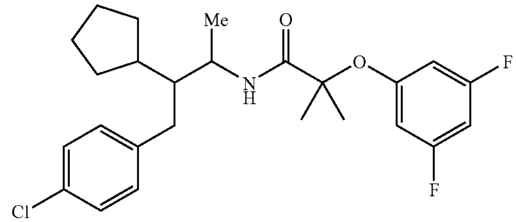 | 4.9[a] | 450.1 |
| 291. | N-(3-(4-chlorophenyl)-2-cyclopentyl-1-methyl)propyl-2-(3,5-difluorophenoxy)-2-methylpropanamide (Diastereomer B) | 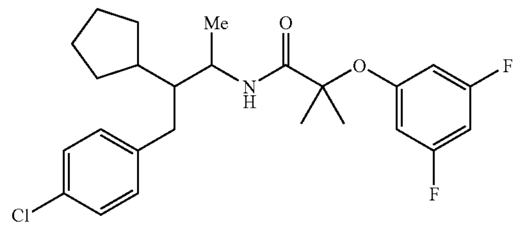 | 4.9[b] | 450.1 |
| 292. | N-(3-(4-chlorophenyl)-2-ethoxy-1-methyl)propyl-2-(3,5-dichlorophenoxy)-2-methylpropanamide (Diastereomer A) | 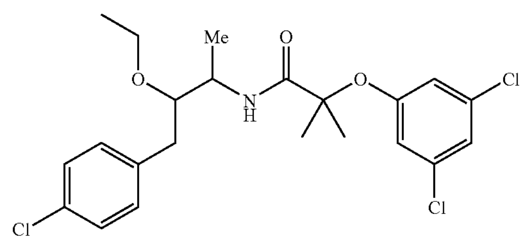 | 4.7 | 460.0 |
| 293. | N-(3-(4-chlorophenyl)-2-ethoxy-1-methyl)propyl-2-(3,5-dichlorophenoxy)-2-methylpropanamide (Diastereomer B) | 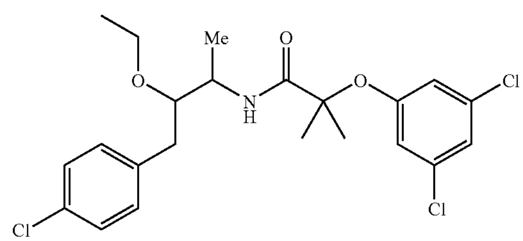 | 4.6 | 460.0 |
| 294. | N-(3-(4-chlorophenyl)-2-isopropyl-1-methyl)propyl-2-(3,5-dichlorophenoxy)-2-methylpropanamide | 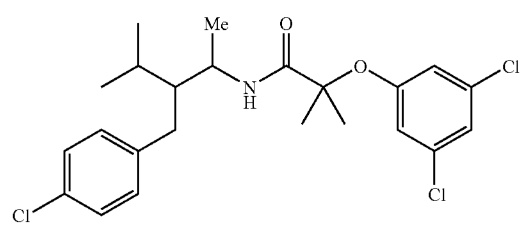 | 4.9 | 458.0 |
| 295. | N-(3-(4-chlorophenyl)-1-methyl-2-propoxy)propyl-2-(3,5-dichlorophenoxy)-2-methylpropanamide (Diastereomer A) | 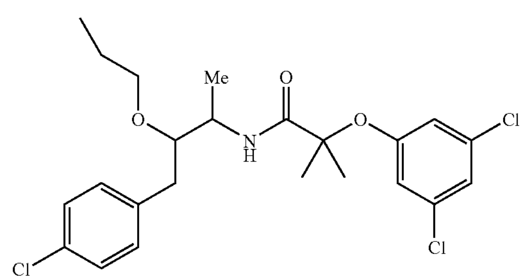 | 4.9 | 474.0 |

TABLE 11-continued

| Ex. No. | Name | Structure | retention time (min) | HPLC-mass spectrum m/e |
|---|---|---|---|---|
| 296. | N-(3-(4-chlorophenyl)-1-methyl-2-propoxy)propyl-2-(3,5-dichlorophenoxy)-2-methylpropanamide (Diastereomer B) | 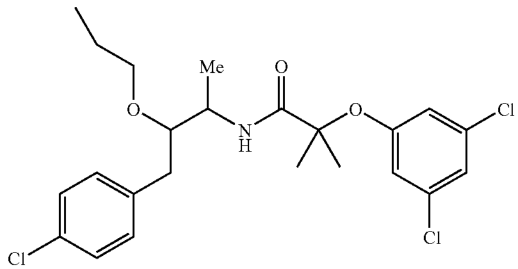 | 4.8 | 474.0 |
| 297. | N-(3-(4-chlorophenyl)-1-methyl-2-pentoxy)propyl-2-(3,5-dichlorophenoxy)-2-methylpropanamide (Diastereomer A) | 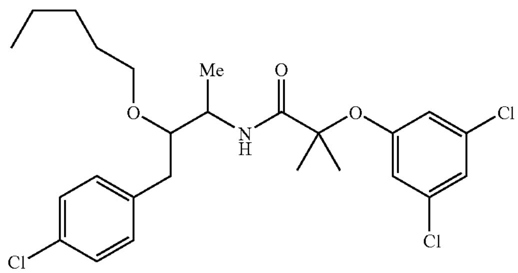 | 5.3 | 502.0 |
| 298. | N-(3-(4-chlorophenyl)-1-methyl-2-pentoxy)propyl-2-(3,5-dichlorophenoxy)-2-methylpropanamide (Diastereomer B) | 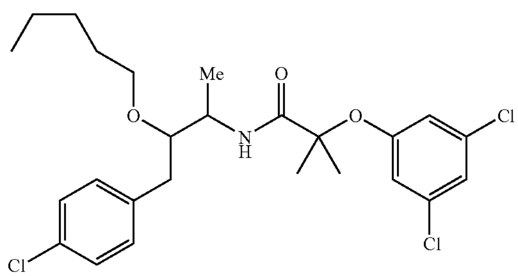 | 5.1 | 502.0 |
| 299. | N-(3-(4-chlorophenyl)-2-cyclopentylmethoxy-1-methyl)propyl-2-(3,5-dichlorophenoxy)-2-methylpropanamide (Diastereomer A) | 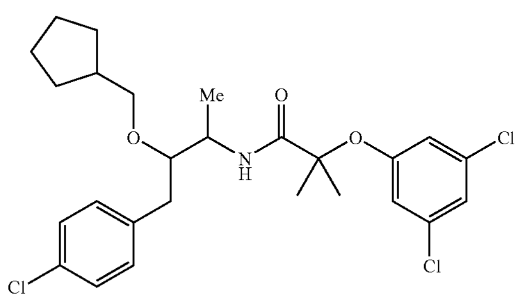 | 5.3 | 514.0 |
| 300. | N-(3-(4-chlorophenyl)-2-cyclopentylmethoxy-1-methyl)propyl-2-(3,5-dichlorophenoxy)-2-methylpropanamide (Diastereomer B) | 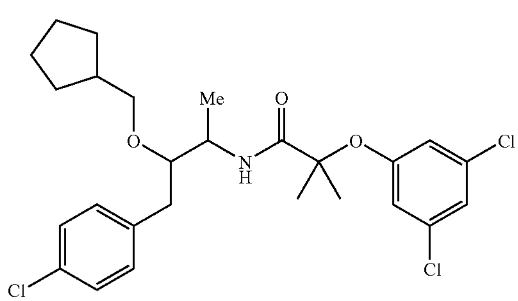 | 5.2 | 514.0 |

TABLE 11-continued

| Ex. No. | Name | Structure | retention time (min) | HPLC-mass spectrum m/e |
|---|---|---|---|---|
| 301. | N-(3-(4-chlorophenyl)-2-cyclobutylmethoxy-1-methyl)propyl-2-(3,5-dichlorophenoxy)-2-methylpropanamide (Diastereomer A) | 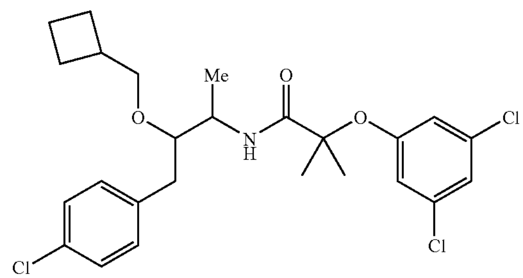 | 5.1[a] | 500.0 |
| 302. | N-(3-(4-chlorophenyl)-2-cyclobutylmethoxy-1-methyl)propyl-2-(3,5-dichlorophenoxy)-2-methylpropanamide (Diastereomer B) | 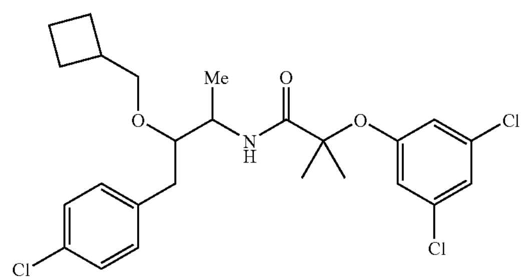 | 5.1[b] | 500.0 |
| 303. | N-(3-(4-chlorophenyl)-2-ethyl-1-methyl)propyl-2-(3,5-dichlorophenoxy)-2-methylpropanamide | 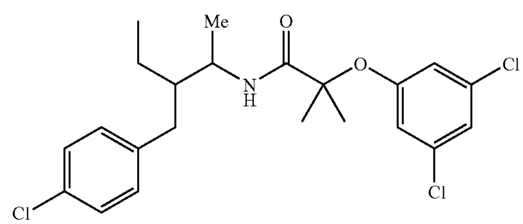 | 4.8 | 443.8 |
| 304. | N-(3-(4-chlorophenyl)-2-ethyl-1-methyl)propyl-2-(3,5-difluorophenoxy)-2-methylpropanamide | 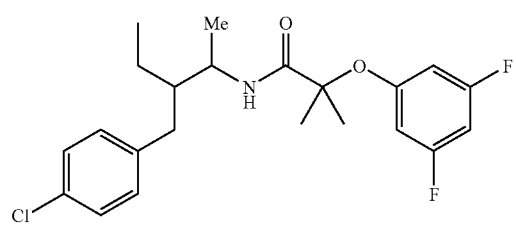 | 4.4 | 410.8 |
| 305. | N-(3-(4-chlorophenyl)-2-methoxy-1-methyl)propyl-2-(3,5-dichlorophenoxy)-2-methylpropanamide (Diastereomer A) | 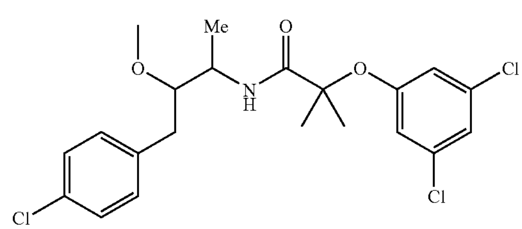 | 4.6 | 445.8 |
| 306. | N-(3-(4-chlorophenyl)-2-methoxy-1-methyl)propyl-2-(3,5-dichlorophenoxy)-2-methylpropanamide (Diastereomer B) | 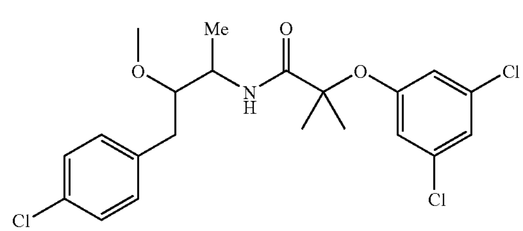 | 4.5 | 445.8 |

TABLE 11-continued

| Ex. No. | Name | Structure | retention time (min) | HPLC-mass spectrum m/e |
|---|---|---|---|---|
| 307. | N-(3-(4-chlorophenyl)-2-pyrrolidin-N-yl-1-methyl)propyl-2-(3,5-dichlorophenoxy)-2-methylpropanamide | 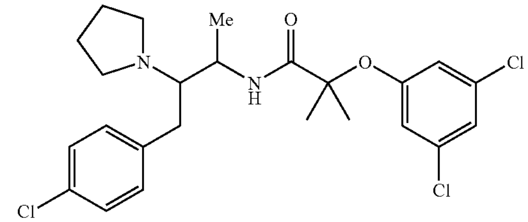 | 3.3 3.5 | 484.9 |
| 308. | N-(3-(4-chlorophenyl)-2-benzyloxycarbonyl-1-methyl)propyl-2-(3,5-dichlorophenoxy)-2-methylpropanamide | 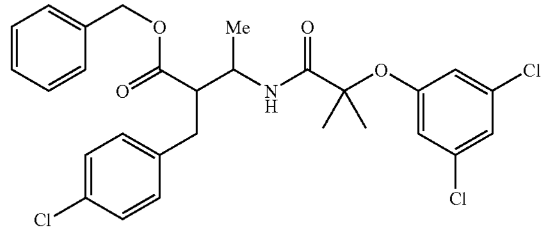 | 4.6 4.7 | 548.0 |

[a] The less polar pair of diastereomers.
[b] The more polar pair of diastereomers.

Example 309

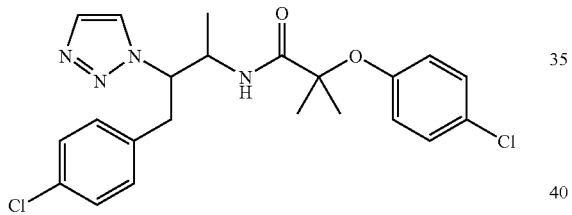

N-(2-(1-(1,2,3-triazolyl))-3-(4-chlorophenyl)-1-methylpropyl)-2-(4-chlorophenyloxy)-2-methylpropanamide A mixture of 2-amino-3-(1-(1,2,3-triazolyl)-4-(4-chlorophenyl)butane (Reference Example 62) 50 mg (0.2 mmol), 2-methyl-2-(4-chlorophenoxy)-propanoic acid (44 mg, 0.2 mmol), disiopropylethylamine (0.102 mL, 0.6 mmol), and PYBOP (117 mg, 0.22 mmol) in 2 mL CH$_2$Cl$_2$ was stirred overnight at room temperature. The mixture was then purified by TLC eluted with ether 3 times. UV active areas were scraped and stirred in EtOAc containing 5% MeOH. The solid was filtered and washed with EtOAc. The filtrate was concentrated. The faster moving band gave diastereomer A of the title compound as oil. $^1$H NMR (400 MHz, CDCl$_3$): δ 1.26 (d, 3H), 1.47 (s, 3H), 1.49 (s, 3H), 3.185-3.232 (m, 1H), 3.404-3.466 (m, 1H), 4.44-4.49 (m, 1H), 4.941-4.992 (m, 1H), 6.796-7.256 (d's, 8H), 7.215 (s, 1H), 7.622 (s, 1H). MS: m/e 447.1; retention time 3.5 min.

The slower moving band gave Diastereomer B of the title compound as oil. $^1$H NMR (400 MHz, CDCl$_3$): δ 1.068 (d, 3H), 1.527 (s, 3H), 1.58 (s, 3H), 3.14-3.256 (m, 2H), 4.54-4.586 (m, 1H), 4.658-4.710 (m, 1H), 6.779-7.263 (d's, 8H), 7.167 (s, 1H), 7.597 (s, 1H). MS: m/e 447.1; retention time 3.5 min

Example 310

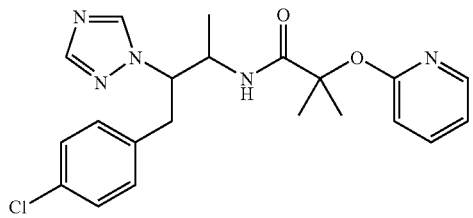

N-(2-(1-(1,2,4-triazolyl))-3-(4-chlorophenyl)-1-methylpropyl)-2-(2-pyridyloxy)-2-methylpropanamide The individual diastereomers were independently prepared from the amines from Reference Example 63 (which were derived from the reduction of the two separated diastereomeric azides) and 2-pyridyloxy-2-methylpropanoic acid instead of 2-methyl-2-(4-chlorophenoxy)-propanoic acid according to the procedures described in Example 309.

The Diastereomer A of the title compound from the faster moving azide: LC-MS: m/e 447.1; retention time 2.9 min. $^1$H NMR (400 MHz, CDCl$_3$): δ 1.095 (d, 3H), 1.659 (s, 3H), 1.668 (s, 3H), 3.14-3.186 (m, 1H), 3.256-3.318 (m, 1H), 4.376-4.427 (m, 1H), 4.554-4.603 (m, 1H), 6.22 (d, 1H), 6.763 (d, 1H), 6.858 (d, 2H), 6.908-6.939 (m, 1H), 7.161 (d, 2H), 7.50 (s, 1H), 7.605-7.649 (m, 1H), 7.911 (s, 1H).

The title diastereomeric amide derived from the slower moving azide on silica gel: LC-MS: m/e 447.1; retention time 3.0 min. $^1$H NMR (400 MHz, CDCl$_3$): δ 0.881 (d, 3H), 1.719 (s, 3H), 1.818 (s, 3H), 2.94-3.025 (m, 2H), 4.225-4.27 (m, 1H), 4.551-4.60 (m, 1H), 6.694 (d, 2H), 6.822-6.852 (m, 1H), 6.895 (d, 1H), 7.151 (d, 2H), 7.553 (s, 1H), 7.604-7.648 (m, 1H), 7.856 (s, 1H), 8.042-8.058 (m, 1H).

Examples 311-323 (Table 12) were prepared from N-[3-(4-chlorophenyl)-2(S)-phenyl-1(S)-methylpropyl]amine, hydrochloride (Reference Example 11) or N-[3-(5-chloro-2-pyridyl)-2(S)-phenyl-1(S)-methylpropyl]amine, hydrochloride (Reference Example 66) and the appropriate carboxylic acid following the procedures described in Examples 62-63 (via an acyl chloride intermediate) or Example 200 (with a coupling reagent).

TABLE 12

| Ex. No. | Name | Structure | HPLC-retention time (min) | mass spectrum m/e |
|---|---|---|---|---|
| 311. | N-[3-(5-chloro-2-pyridyl)-2(S)-phenyl-1(S)-methylpropyl]-2-(5-chloro-2-pyridyloxy)-2-methylpropanamide | 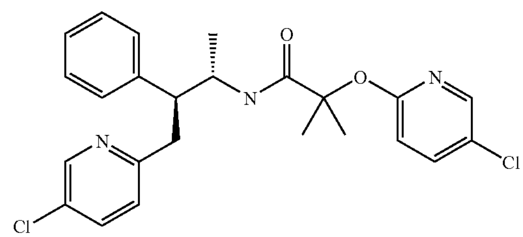 | 3.8 | 458 |
| 312. | N-[3-(4-chlorophenyl)-2(S)-phenyl-1(S)-methylpropyl]-2-(3-trifluoromethylphenyloxy)-2-methylpropanamide | 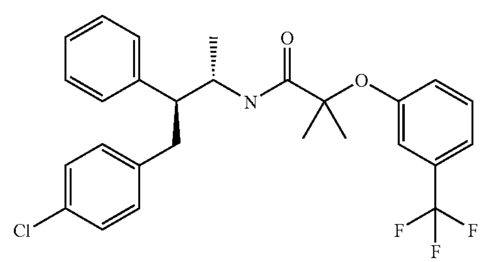 | 4.6 | 490 |
| 313. | N-[3-(4-chlorophenyl)-2(S)-phenyl-1(S)-methylpropyl]-2-(6-chloro-2-pyridyloxy)-2-methylpropanamide | 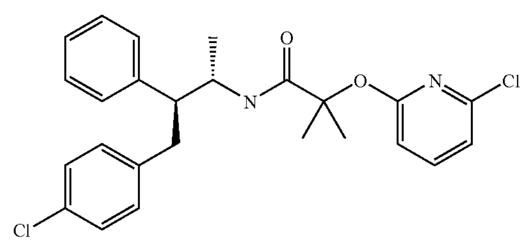 | 4.2 | 457 |
| 314. | N-[3-(4-chlorophenyl)-2(S)-phenyl-1(S)-methylpropyl]-2-(4-cyanophenyloxy)-2-methylpropanamide | 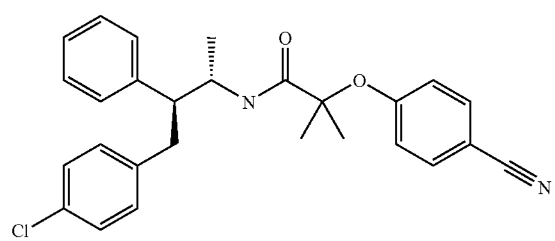 | 4.1 | 447 |
| 315. | N-[3-(4-chlorophenyl)-2(S)-phenyl-1(S)-methylpropyl]-2-(3-cyanophenyloxy)-2-methylpropanamide | 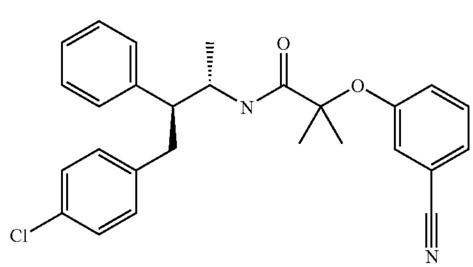 | 4.1 | 447 |

TABLE 12-continued

| Ex. No. | Name | Structure | retention time (min) | HPLC-mass spectrum m/e |
|---|---|---|---|---|
| 316. | N-[3-(5-chloro-2-pyridyl)-2(S)-phenyl-1(S)-methylpropyl]-2-(5-trifluoromethyl-2-pyridyloxy)-2-methylpropanamide | 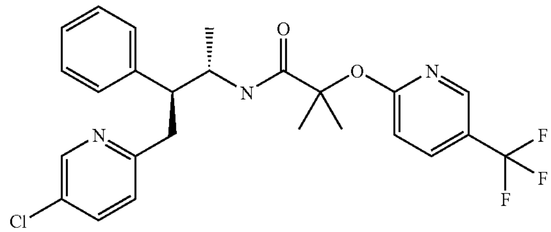 | 3.7 | 492 |
| 317. | N-[3-(4-chlorophenyl)-2(S)-phenyl-1(S)-methylpropyl]-2-(5-chloro-2-pyrimidyloxy)-2-methylpropanamide | 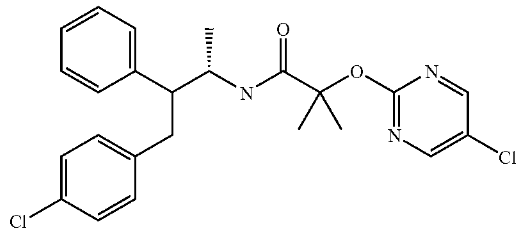 | 3.9 | 458 |
| 318. | N-[3-(4-chlorophenyl)-2(S)-phenyl-1(S)-methylpropyl]-2-(2-pyrimidyloxy)-2-methylpropanamide | 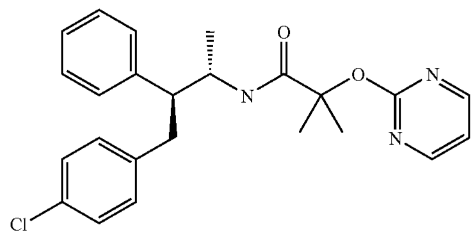 | 3.6 | 424 |
| 319. | N-[3-(4-chlorophenyl)-2(S)-phenyl-1(S)-methylpropyl]-2-(4-trifluoromethyl-2-pyridyloxy)-2-methylpropanamide | 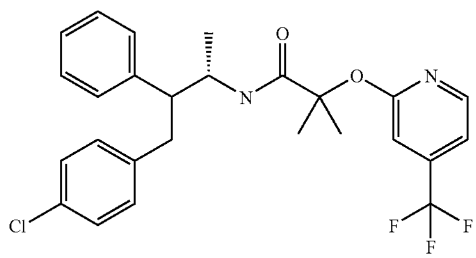 | 4.3 | 491 |
| 320. | N-[3-(4-chlorophenyl)-2(S)-phenyl-1(S)-methylpropyl]-2-(4-trifluoromethyl-2-pyrimidyloxy)-2-methylpropanamide | 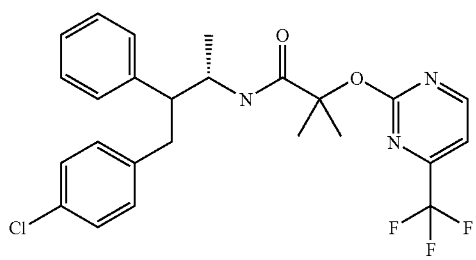 | 3.9 | 492 |
| 321. | N-[3-(4-chlorophenyl)-2(S)-phenyl-1(S)-methylpropyl]-2-(4-pyrimidyloxy)-2-methylpropanamide | 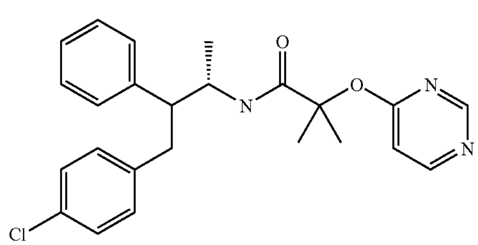 | 3.2 | 424 |

TABLE 12-continued

| Ex. No. | Name | Structure | retention time (min) | HPLC- mass spectrum m/e |
|---|---|---|---|---|
| 322. | N-[3-(4-chlorophenyl)-2(S)-phenyl-1(S)-methylpropyl]-2(R)-(4-trifluoromethyl-2-pyridyloxy)propanamide | 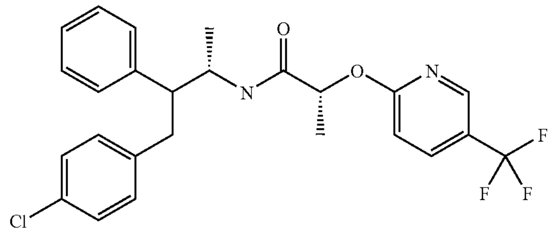 | 3.8 | 477 |
| 323. | N-[3-(4-chlorophenyl)-2(S)-phenyl-1(S)-methylpropyl]-2-(4-trifluoromethyl-4-pyrimidyloxy)-2-methylpropanamide | 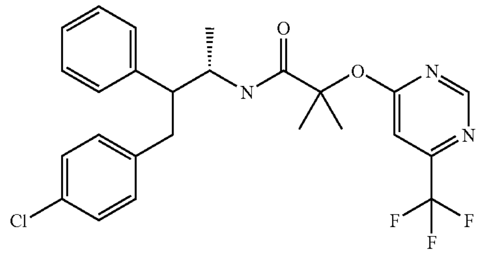 | 4.1 | 492 |

Examples 324-363 (Table 13) were prepared from the appropriate amine and acid of Reference Examples following the procedures described in Examples 62-63 (via an acyl chloride intermediate) or Example 200 (with a coupling reagent).

TABLE 13

| Ex. No. | Name | Structure | retention time (min) | HPLC- mass spectrum m/e | Diastereomer α and/ or β |
|---|---|---|---|---|---|
| 324. | N-[3-(4-Chlorophenyl)-2-(3-fluorophenyl)-1-methylpropyl]-2-(5-chloro-2-pyridyloxy)-2-methylpropanamide | 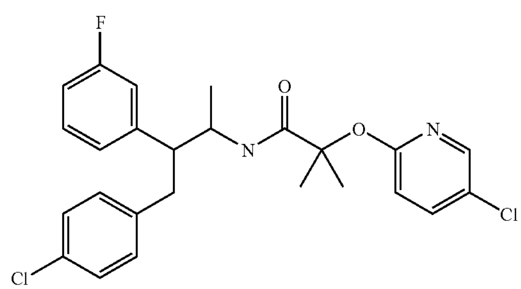 | 4.3 | 475 | α |
| 325. | N-[3-(4-Chlorophenyl)-2-(3-fluorophenyl)-1-methylpropyl]-2-(5-trifluoromethyl-2-pyridyloxy)-2-methylpropanamide | 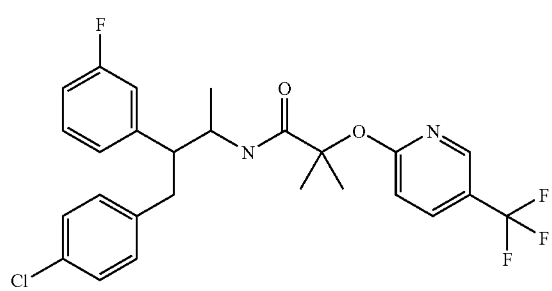 | 4.2 | 509 | α |

TABLE 13-continued

| Ex. No. | Name | Structure | retention time (min) | HPLC-mass spectrum m/e | Diastereomer α and/ or β |
|---|---|---|---|---|---|
| 326. | N-[3-(4-Chlorophenyl)-2-(3-fluorophenyl)-1-methylpropyl]-2-(6-trifluoromethyl-4-pyrimidyloxy)-2-methylpropanamide | 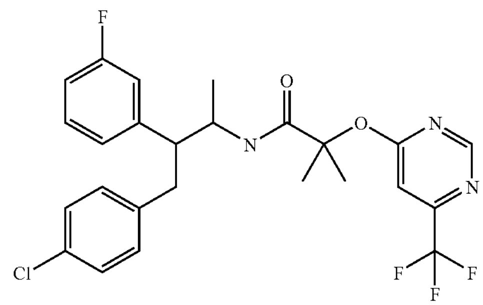 | 4.1 | 510 | α |
| 327. | N-[3-(4-Chlorophenyl)-2-(3-fluorophenyl)-1-methylpropyl]-2-(4-trifluoromethyl-2-pyridyloxy)-2-methylpropanamide | 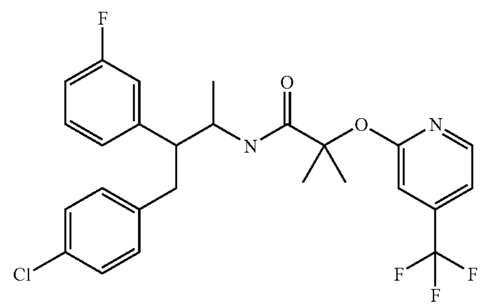 | 4.3 | 509 | α |
| 328. | N-[2-(3-Bromo-5-fluorophenyl)-3-(4-fluorophenyl)-1-methylpropyl]-2-(5-trifluoromethyl-2-pyridyloxy)-2-methylpropanamide | 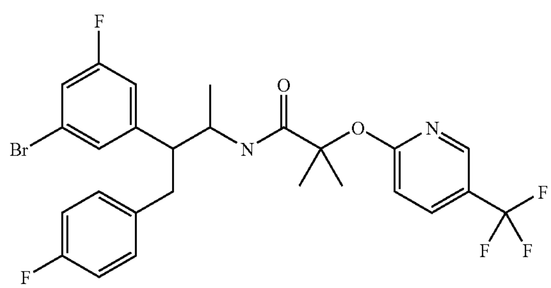 | 4.3 | 571 | α |
| 329. | N-[2-(3-Bromo-5-fluorophenyl)-3-(4-chlorophenyl)-1-methylpropyl]-2-(5-trifluoromethyl-2-pyridyloxy)-2-methylpropanamide | 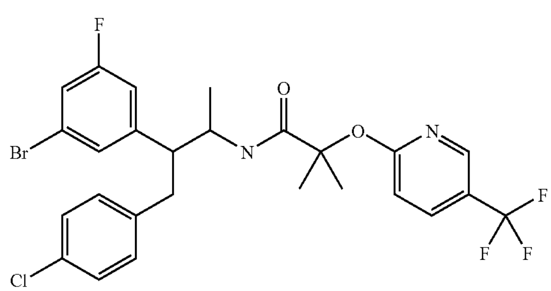 | 4.4 | 587 | α |
| 330. | N-[2-(3-Bromo-5-fluorophenyl)-3-(4-fluorophenyl)-1-methylpropyl]-2-(6-trifluoromethyl-4-pyrimidyloxy)-2-methylpropanamide | 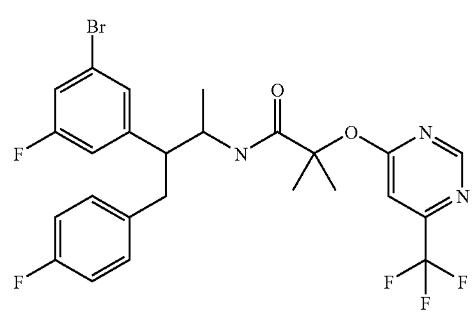 | 4.1 | 572 | α |

TABLE 13-continued

| Ex. No. | Name | Structure | retention time (min) | HPLC-mass spectrum m/e | Diastereomer α and/ or β |
|---|---|---|---|---|---|
| 331. | N-[2-(3-Bromo-5-fluorophenyl)-3-(4-chlorophenyl)-1-methylpropyl]-2-(6-trifluoromethyl-4-pyrimidyloxy)-2-methylpropanamide | 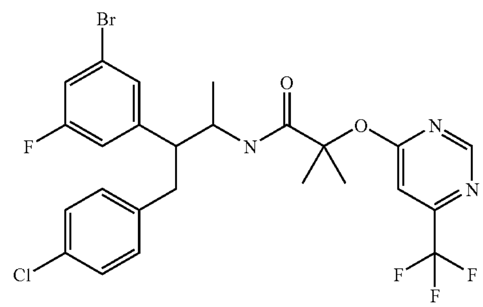 | 4.3 | 588 | α |
| 332. | N-[2-(3-Chlorophenyl)-3-(4-chlorophenyl)-1-methylpropyl]-2-(5-chloro-2-pyridyloxy)-2-methylpropanamide | 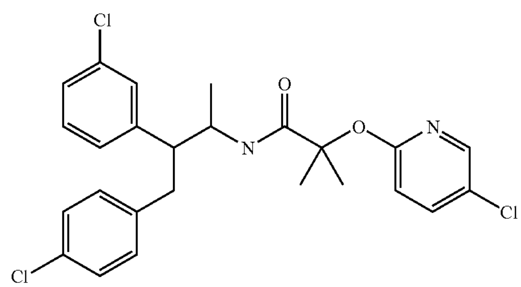 | 4.4 | 491 | α |
| 333. | N-[2-(3-Chlorophenyl)-3-(5-chloro-2-pyridyl)-1-methylpropyl]-2-(5-trifluoromethyl-2-pyridyloxy)-2-methylpropanamide | 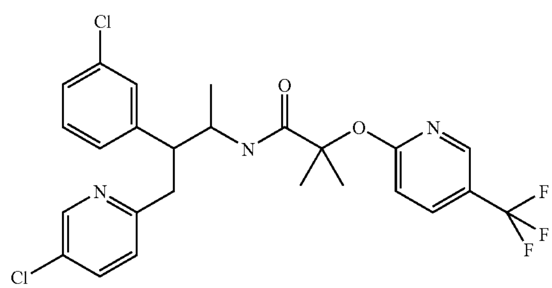 | 4.0 | 526 | α |
| 334. | N-[2-(3-Chlorophenyl)-3-(4-chlorophenyl)-1-methylpropyl]-2-(5-trifluoromethyl-2-pyridyloxy)-2-methylpropanamide | 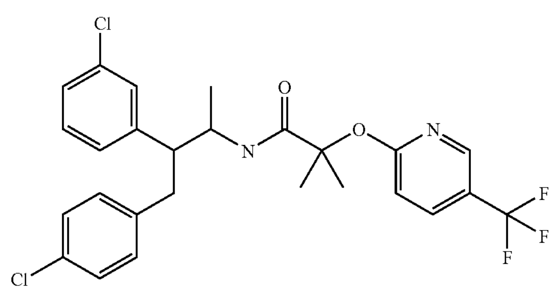 | 4.4 | 525 | α |
| 335. | N-[2-(3-Bromophenyl)-3-(4-chlorophenyl)-1-methylpropyl]-2-(5-trifluoromethyl-2-pyridyloxy)-2-methylpropanamide | 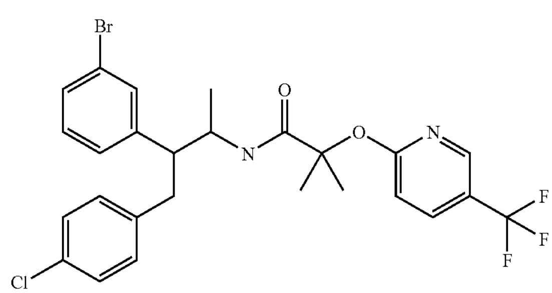 | 4.4 | 569 | α |

TABLE 13-continued

| Ex. No. | Name | Structure | retention time (min) | HPLC-mass spectrum m/e | Diastereomer α and/or β |
|---|---|---|---|---|---|
| 336. | N-[2-(3-Bromophenyl)-3-(5-chloro-2-pyridyl)-1-methylpropyl]-2-(5-trifluoromethyl-2-pyridyloxy)-2-methylpropanamide | 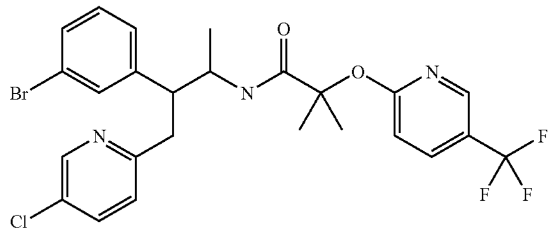 | 3.9 | 570 | α |
| 337. | N-[3-(4-Chlorophenyl)-2-(3-trifluoromethylphenyl)-1-methylpropyl]-2-(5-trifluoromethyl-2-pyridyloxy)-2-methylpropanamide | 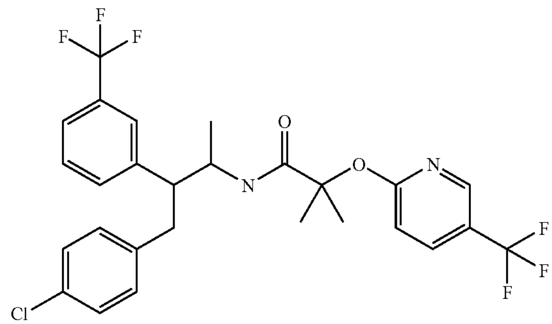 | 4.4 | 559 | α |
| 338. | N-[3-(4-Chlorophenyl)-2-(3-methylphenyl)-1-methylpropyl]-2-(5-trifluoromethyl-2-pyridyloxy)-2-methylpropanamide | 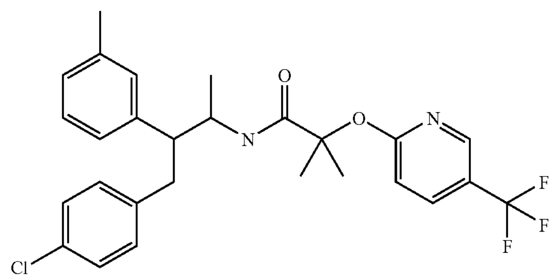 | 4.4 | 505 | α |
| 339. | N-[3-(4-Chlorophenyl)-2-(3-cyanophenyl)-1-methylpropyl]-2-(5-chloro-2-pyridyloxy)-2-methylpropanamide | 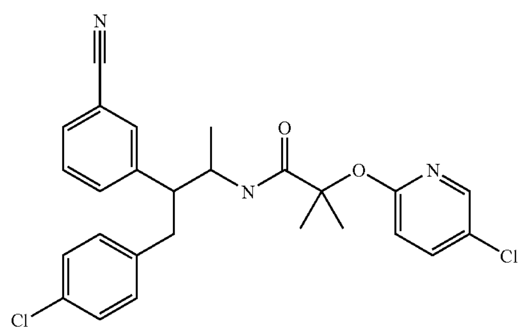 | 4.0 | 482 | α |
| 340. | N-[3-(4-Chlorophenyl)-2-(3-cyanophenyl)-1-methylpropyl]-2-(5-trifluoromethyl-2-pyridyloxy)-2-methylpropanamide | 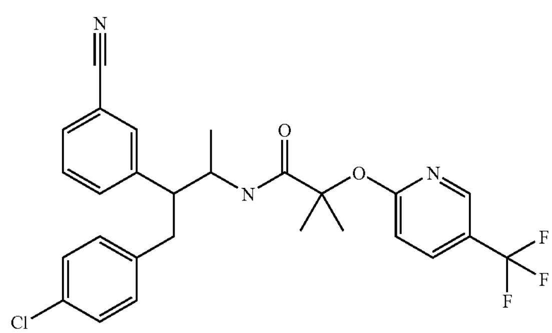 | 4.1 | 516 | α |

TABLE 13-continued

| Ex. No. | Name | Structure | retention time (min) | HPLC-mass spectrum m/e | Diastereomer α and/ or β |
|---|---|---|---|---|---|
| 341. | N-[3-(5-Chloro-2-pyridyl)-2-(3-cyanophenyl)-1-methylpropyl]-2-(5-trifluoromethyl-2-pyridyloxy)-2-methylpropanamide | 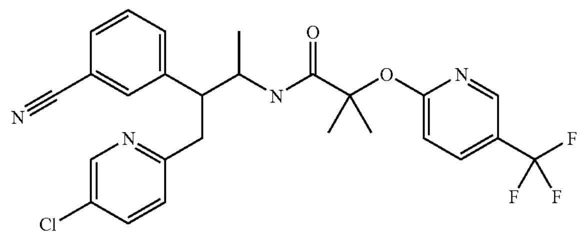 | 3.6 | 517 | α |
| 342. | N-[3-(4-Chlorophenyl)-2-(3-cyanophenyl)-1-methylpropyl]-2-(6-trifluoromethyl-4-pyrimidyloxy)-2-methylpropanamide | 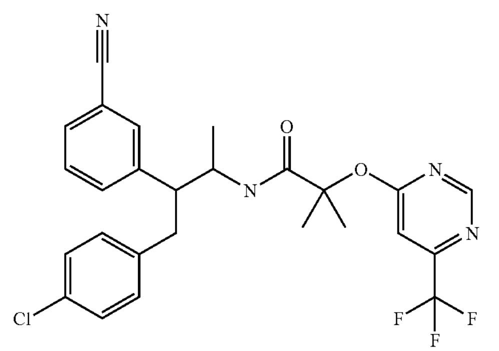 | 4.0 | 517 | α |
| 343. | N-[3-(4-Chlorophenyl)-2-(2-pyridyl)-1-methylpropyl]-2-(5-trifluoromethyl-2-pyridyloxy)-2-methylpropanamide | 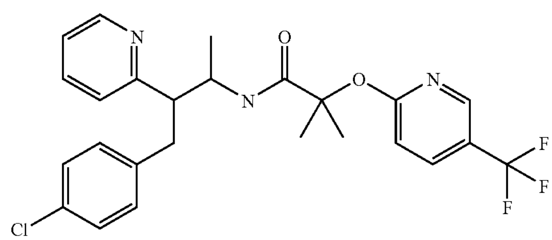 | 2.8 | 492 | α |
| 344. | N-[3-(4-Chlorophenyl)-2-(3-pyridyl)-1-methylpropyl]-2-(5-trifluoromethyl-2-pyridyloxy)-2-methylpropanamide | 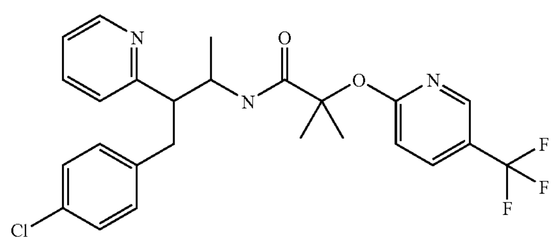 | 2.7 | 492 | α |
| 345. | N-[3-(4-Chlorophenyl)-2-(5-fluoro-3-pyridyl)-1-methylpropyl]-2-(5-trifluoromethyl-2-pyridyloxy)-2-methylpropanamide | 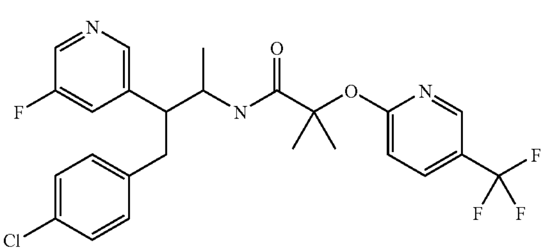 | 3.6 | 510 | α |

TABLE 13-continued

| Ex. No. | Name | Structure | retention time (min) | HPLC-mass spectrum m/e | Diastereomer α and/ or β |
|---|---|---|---|---|---|
| 346. | N-[3-(4-Chlorophenyl)-2-(5-fluoro-3-pyridyl)-1-methylpropyl]-2-(6-trifluoromethyl-4-pyrimidyloxy)-2-methylpropanamide | 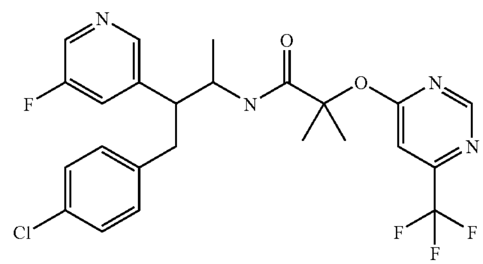 | 3.4 | 511 | α |
| 347. | N-[3-(4-Chlorophenyl)-2-(5-chloro-3-pyridyl)-1-methylpropyl]-2-(5-trifluoromethyl-2-pyridyloxy)-2-methylpropanamide | 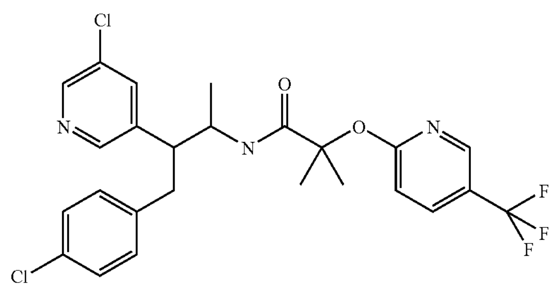 | 3.9 | 526 | α |
| 348. | N-[3-(4-Chlorophenyl)-2-(5-chloro-3-pyridyl)-1-methylpropyl]-2-(4-trifluoromethyl-2-pyridyloxy)-2-methylpropanamide | 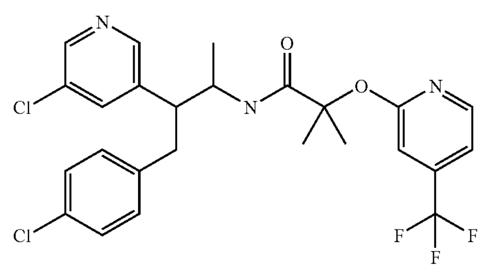 | 3.9 | 526 | α |
| 349. | N-[3-(4-Chlorophenyl)-2-(5-chloro-3-pyridyl)-1-methylpropyl]-2-(4-trifluoromethyl-2-pyrimidyloxy)-2-methylpropanamide | 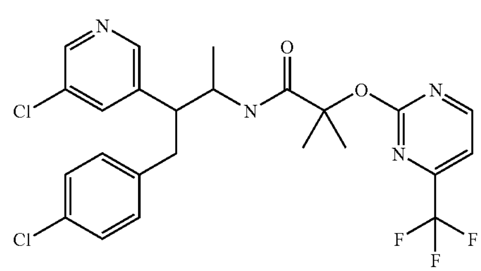 | 3.5 | 527 | α |
| 350. | N-[3-(4-Chlorophenyl)-2-(5-chloro-3-pyridyl)-1-methylpropyl]-2-(6-trifluoromethyl-4-pyrimidyloxy)-2-methylpropanamide | 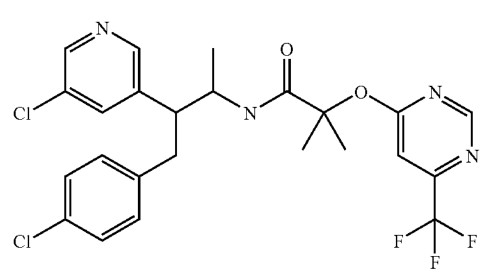 | 3.6 | 527 | α |

TABLE 13-continued

| Ex. No. | Name | Structure | HPLC-retention time (min) | mass spectrum m/e | Diastereomer α and/ or β |
|---|---|---|---|---|---|
| 351. | N-[3-(4-Chlorophenyl)-2-(5-chloro-3-pyridyl)-1-methylpropyl]-2-(6-trifluoromethyl-4-pyridyloxy)-2-methylpropanamide | 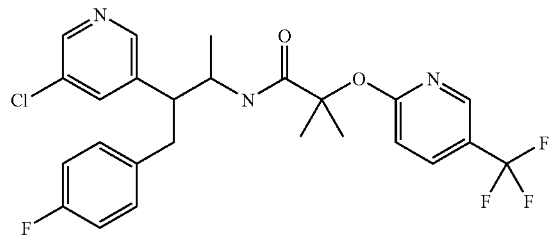 | 3.8 | 510 | α |
| 352. | N-[2-(5-Chloro-3-pyridyl)-3-cyclobutyl-1-methylpropyl]-2-(6-trifluoromethyl-4-pyridyloxy)-2-methylpropanamide | 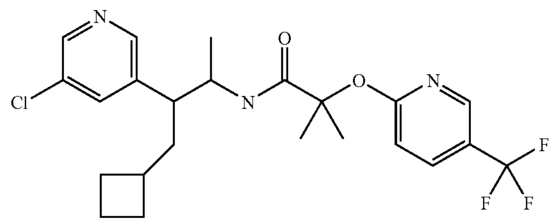 | 4.0 | 470 | α/β 6:1 |
| 353. | N-[2-(5-Chloro-3-pyridyl)-3-cyclobutyl-5-methyl-2-hexyl]-2-(6-trifluoromethyl-4-pyridyloxy)-2-methylpropanamide | 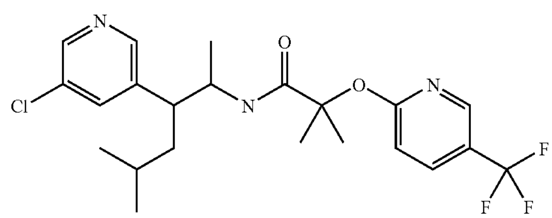 | 3.9 | 458 | α/β 6:1 |
| 354. | N-[3-(4-Chlorophenyl)-2-(5-cyano-3-pyridyl)-1-methylpropyl]-2-(5-trifluoromethyl-2-pyridyloxy)-2-methylpropanamide | 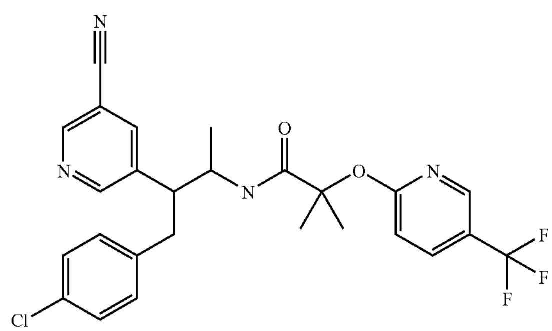 | 3.7 | 517 | α |
| 355. | N-[3-(4-Chlorophenyl)-2-(5-cyano-3-pyridyl)-1-methylpropyl]-2-(6-trifluoromethyl-4-pyrimidyloxy)-2-methylpropanamide | 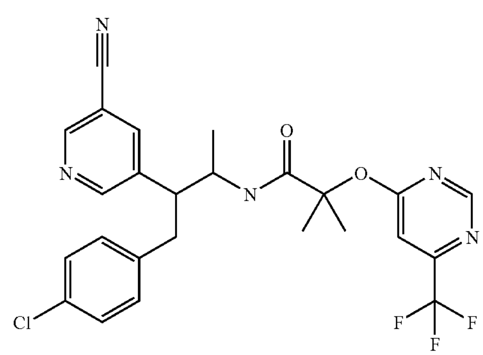 | 3.6 | 518 | α |

TABLE 13-continued

| Ex. No. | Name | Structure | retention time (min) | HPLC-mass spectrum m/e | Diastereomer α and/ or β |
|---|---|---|---|---|---|
| 356. | N-[3-(4-Chlorophenyl)-2-(5-cyano-3-pyridyl)-1-methylpropyl]-2-(4-trifluoromethyl-2-pyridyloxy)-2-methylpropanamide | 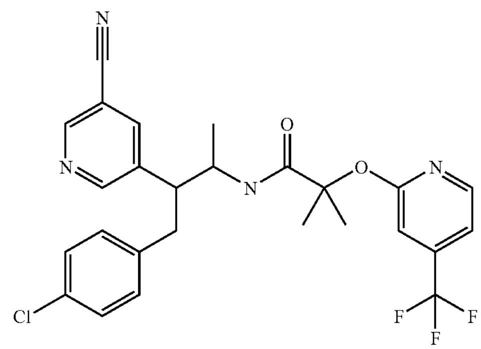 | 3.9 | 517 | α |
| 357. | N-[2-(5-Bromo-3-pyridyl)-3-(4-chlorophenyl)-1-methylpropyl]-2-(5-trifluoromethyl-2-pyridyloxy)-2-methylpropanamide | 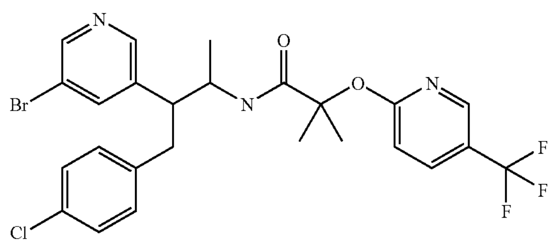 | 4.0 | 570 | α |
| 358. | N-[2-(5-Bromo-3-pyridyl)-3-(4-fluorophenyl)-1-methylpropyl]-2-(5-trifluoromethyl-2-pyridyloxy)-2-methylpropanamide | 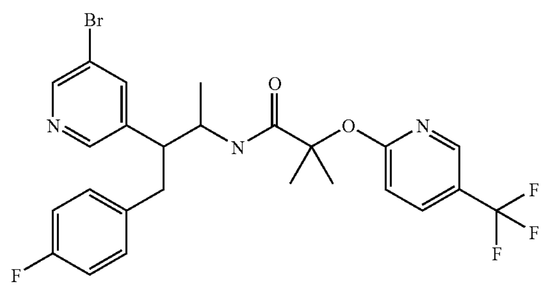 | 3.8 | 554 | α |
| 359. | N-[2-(5-Bromo-3-pyridyl)-3-(4-fluorophenyl)-1-methylpropyl]-2-(4-trifluoromethyl-2-pyridyloxy)-2-methylpropanamide | 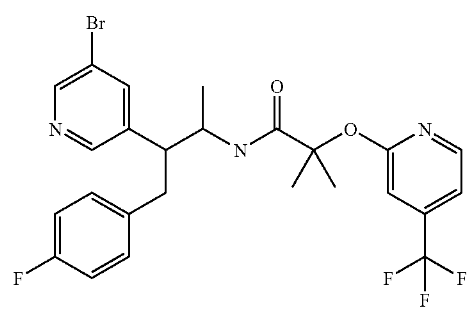 | 3.9 | 554 | α |
| 360. | N-[2-(5-Bromo-3-pyridyl)-3-(4-chlorophenyl)-1-methylpropyl]-2-(4-trifluoromethyl-2-pyridyloxy)-2-methylpropanamide | 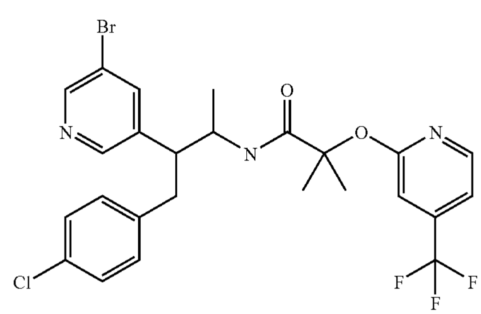 | 4.0 | 570 | α |

TABLE 13-continued

| Ex. No. | Name | Structure | retention time (min) | HPLC-mass spectrum m/e | Diastereomer α and/ or β |
|---|---|---|---|---|---|
| 361. | N-[2-(5-Bromo-3-pyridyl)-3-(4-fluorophenyl)-1-methylpropyl]-2-(6-trifluoromethyl-4-pyrimidyloxy)-2-methylpropanamide | 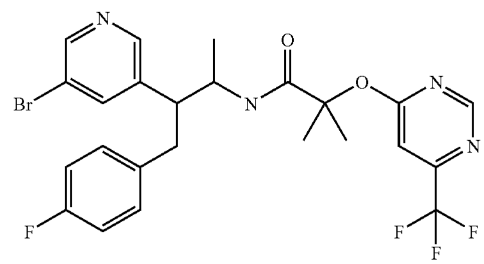 | 3.7 | 555 | α |
| 362. | N-[2-(5-Bromo-3-pyridyl)-3-(4-chlorophenyl)-1-methylpropyl]-2-(6-trifluoromethyl-4-pyrimidyloxy)-2-methylpropanamide | 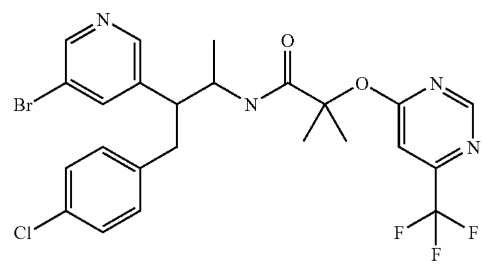 | 3.9 | 571 | α |
| 363. | N-[3-(4-Chlorophenyl)-2-(5-methyl-3-pyridyl)-1-methylpropyl]-2-(5-trifluoromethyl-2-pyridyloxy)-2-methylpropanamide | 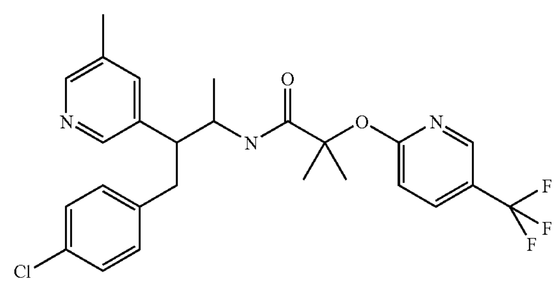 | 2.8 | 506 | α |

Examples 364-436 (Table 14) were isolated as single enantiomers from the corresponding racemic material (Table 13) following the procedures described in Examples 149-150 with appropriate modifications of (1) the eluent composition (4-15% ethanol/hexane), (2) flow rate (6-9 mL/min) and (3) injection volume (200 to 2000 μL).

TABLE 14

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 364. | N-[3-(4-Chlorophenyl)-2-(3-fluorophenyl)-1-methylpropyl]-2-(5-chloro-2-pyridyloxy)-2-methylpropanamide | 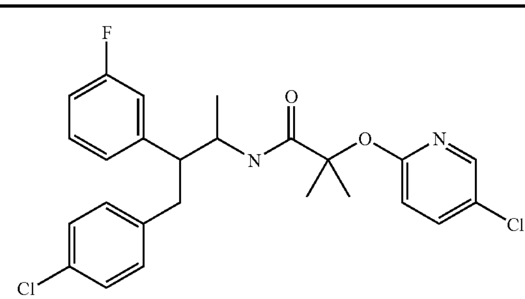 | 4.4 | 475 | A |

TABLE 14-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 365. | N-[3-(4-Chlorophenyl)-2-(3-fluorophenyl)-1-methylpropyl]-2-(5-chloro-2-pyridyloxy)-2-methylpropanamide | 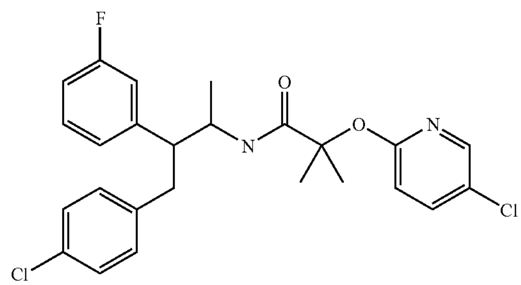 | 4.4 | 475 | B |
| 366. | N-[3-(4-Chlorophenyl)-2-(3-fluorophenyl)-1-methylpropyl]-2-(5-trifluoromethyl-2-pyridyloxy)-2-methylpropanamide | 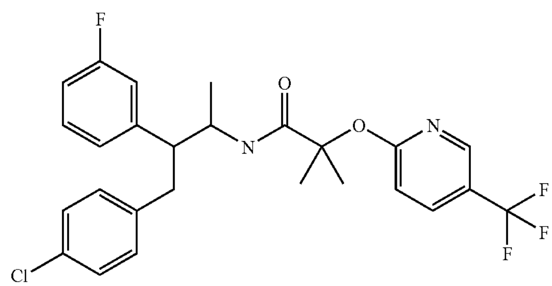 | 4.2 | 509 | A |
| 367. | N-[3-(4-Chlorophenyl)-2-(3-fluorophenyl)-1-methylpropyl]-2-(5-trifluoromethyl-2-pyridyloxy)-2-methylpropanamide | 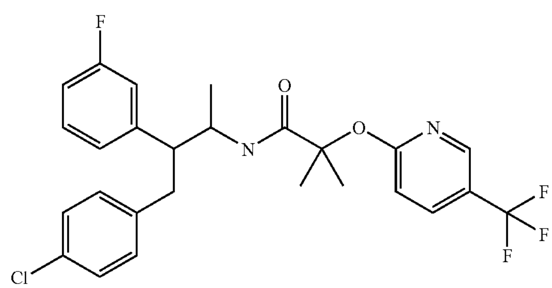 | 4.2 | 509 | B |
| 368. | N-[3-(4-Chlorophenyl)-2-(3-fluorophenyl)-1-methylpropyl]-2-(6-trifluoromethyl-4-pyrimidyloxy)-2-methylpropanamide | 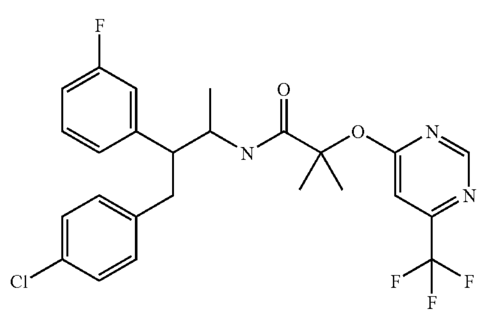 | 4.1 | 510 | A |

TABLE 14-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 369. | N-[3-(4-Chlorophenyl)-2-(3-fluorophenyl)-1-methylpropyl]-2-(6-trifluoromethyl-4-pyrimidyloxy)-2-methylpropanamide | 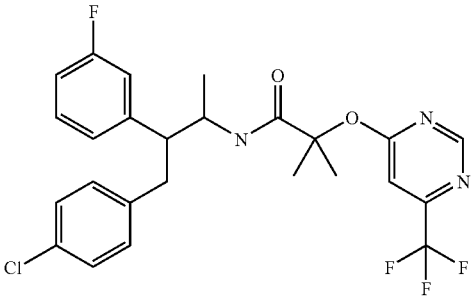 | 4.1 | 510 | B |
| 370. | N-[3-(4-Chlorophenyl)-2-(3-fluorophenyl)-1-methylpropyl]-2-(4-trifluoromethyl-2-pyridyloxy)-2-methylpropanamide | 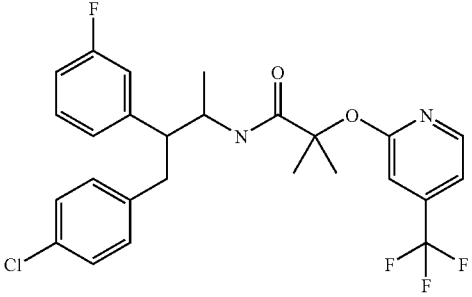 | 4.3 | 509 | A |
| 371. | N-[3-(4-Chlorophenyl)-2-(3-fluorophenyl)-1-methylpropyl]-2-(4-trifluoromethyl-2-pyridyloxy)-2-methylpropanamide | 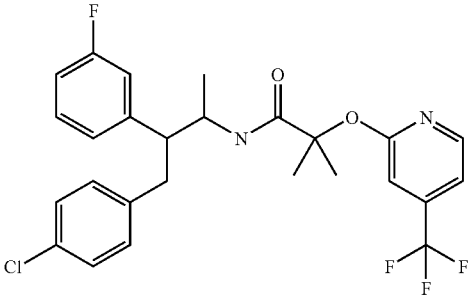 | 4.3 | 509 | B |
| 372. | N-[2-(3-Chlorophenyl)-3-(4-chlorophenyl)-1-methylpropyl]-2-(5-chloro-2-pyridyloxy)-2-methylpropanamide | 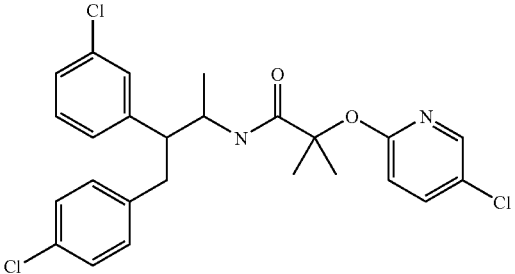 | 4.5 | 491 | A |

TABLE 14-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 373. | N-[2-(3-Chlorophenyl)-3-(4-chlorophenyl)-1-methylpropyl]-2-(5-chloro-2-pyridyloxy)-2-methylpropanamide | 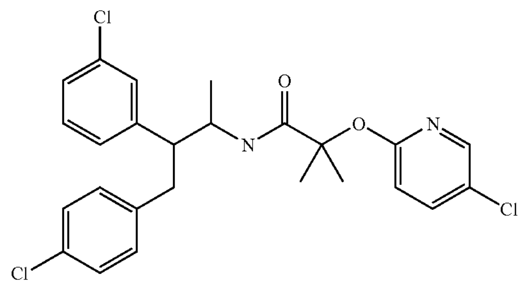 | 4.5 | 491 | B |
| 374. | N-[2-(3-Chlorophenyl)-3-(5-chloro-2-pyridyl)-1-methylpropyl]-2-(5-trifluoromethyl-2-pyridyloxy)-2-methylpropanamide | 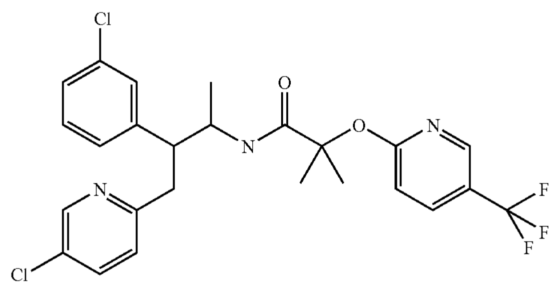 | 3.9 | 526 | B |
| 375. | N-[2-(3-Chlorophenyl)-3-(5-chloro-2-pyridyl)-1-methylpropyl]-2-(5-trifluoromethyl-2-pyridyloxy)-2-methylpropanamide | 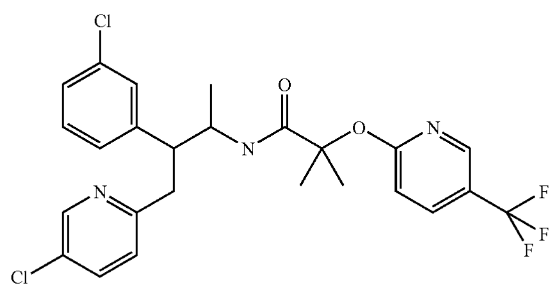 | 3.9 | 526 | A |
| 376. | N-[2-(3-Chlorophenyl)-3-(4-chlorophenyl)-1-methylpropyl]-2-(5-trifluoromethyl-2-pyridyloxy)-2-methylpropanamide | 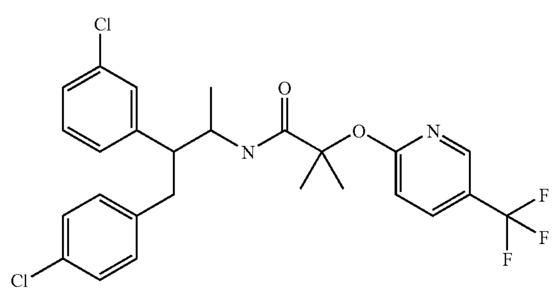 | 4.4 | 525 | A |
| 377. | N-[2-(3-Chlorophenyl)-3-(4-chlorophenyl)-1-methylpropyl]-2-(5-trifluoromethyl-2-pyridyloxy)-2-methylpropanamide | 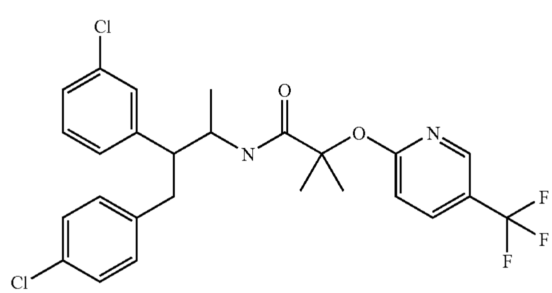 | 4.4 | 525 | B |

TABLE 14-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 378. | N-[2-(3-Bromophenyl)-3-(4-chlorophenyl)-1-methylpropyl]-2-(5-chloro-2-pyridyloxy)-2-methylpropanamide | 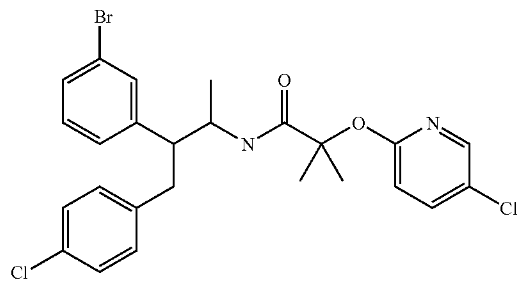 | 4.3 | 579 | A |
| 379. | N-[2-(3-Bromophenyl)-3-(4-chlorophenyl)-1-methylpropyl]-2-(5-chloro-2-pyridyloxy)-2-methylpropanamide | 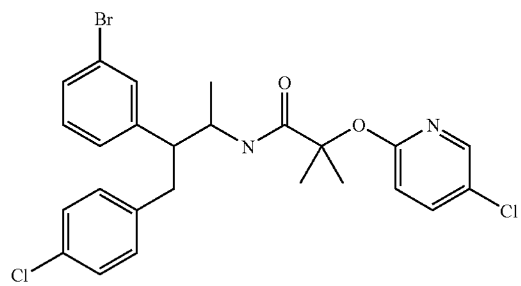 | 4.3 | 579 | B |
| 380. | N-[2-(3-Bromophenyl)-3-(5-chloro-2-pyridyl)-1-methylpropyl]-2-(5-trifluoromethyl-2-pyridyloxy)-2-methylpropanamide | 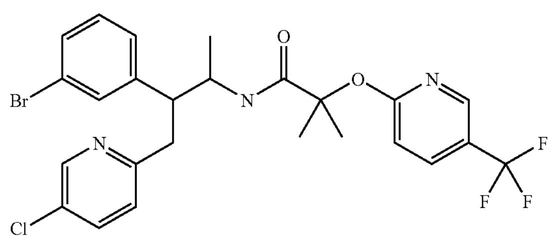 | 3.9 | 570 | A |
| 381. | N-[2-(3-Bromophenyl)-3-(5-chloro-2-pyridyl)-1-methylpropyl]-2-(5-trifluoromethyl-2-pyridyloxy)-2-methylpropanamide | 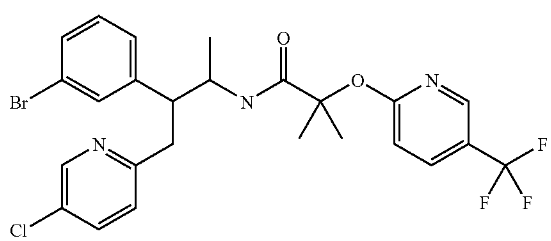 | 3.9 | 570 | B |
| 382. | N-[3-(4-chlorophenyl)-2-(3-trifluoromethylphenyl)-1-methylpropyl]-2-(5-trifluoromethyl-2-pyridyloxy)-2-methylpropanamide | 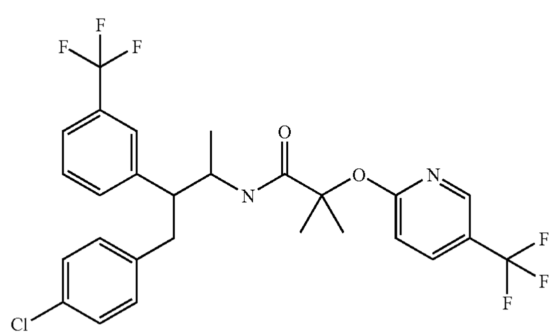 | 4.4 | 559 | A |

TABLE 14-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 383. | N-[3-(4-chlorophenyl)-2-(3-trifluoromethylphenyl)-1-methylpropyl]-2-(5-trifluoromethyl-2-pyridyloxy)-2-methylpropanamide | 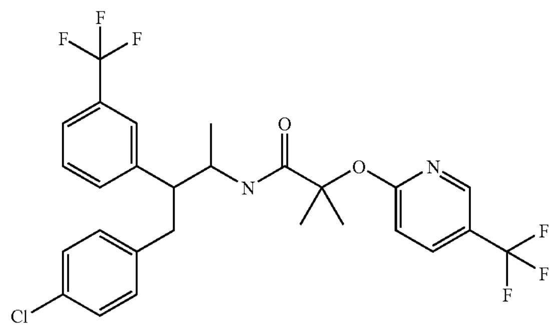 | 4.4 | 559 | B |
| 384. | N-[3-(4-chlorophenyl)-2-(3-methylphenyl)-1-methylpropyl]-2-(5-trifluoromethyl-2-pyridyloxy)-2-methylpropanamide | 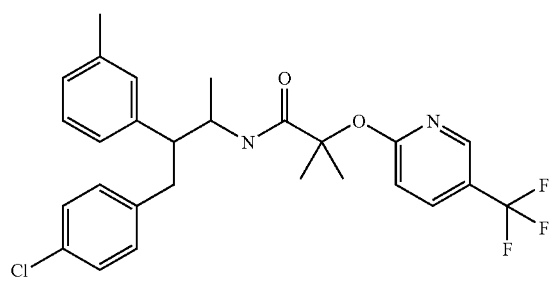 | 4.4 | 505 | A |
| 385. | N-[3-(4-chlorophenyl)-2-(3-methylphenyl)-1-methylpropyl]-2-(5-trifluoromethyl-2-pyridyloxy)-2-methylpropanamide | 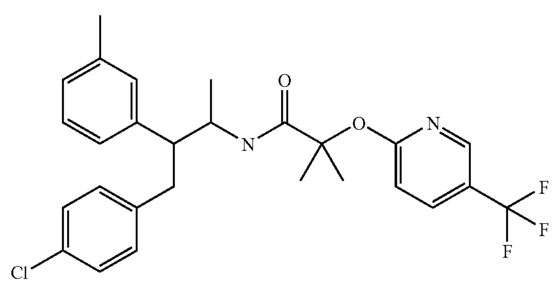 | 4.4 | 505 | B |
| 386. | N-[3-(4-chlorophenyl)-2-(3-cyanophenyl)-1-methylpropyl]-2-(5-chloro-2-pyridyloxy)-2-methylpropanamide | 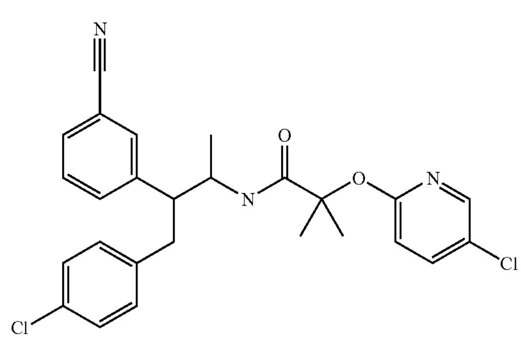 | 4.2 | 482 | A |

TABLE 14-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 387. | N-[3-(4-chlorophenyl)-2-(3-cyanophenyl)-1-methylpropyl]-2-(5-chloro-2-pyridyloxy)-2-methylpropanamide | 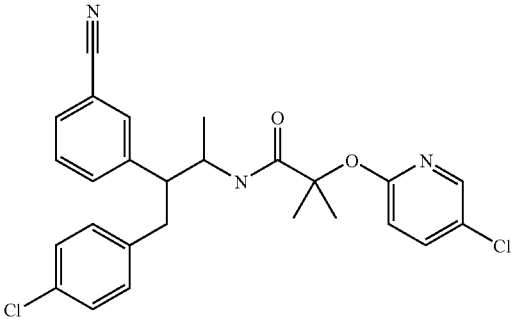 | 4.2 | 482 | B |
| 388. | N-[3-(4-chlorophenyl)-2-(3-cyanophenyl)-1-methylpropyl]-2-(5-trifluoromethyl-2-pyridyloxy)-2-methylpropanamide | 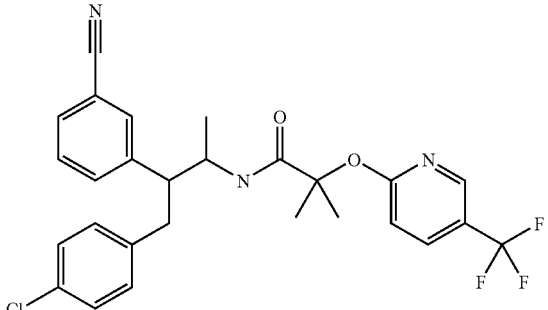 | 3.9 | 516 | A |
| 389. | N-[3-(4-chlorophenyl)-2-(3-cyanophenyl)-1-methylpropyl]-2-(5-trifluoromethyl-2-pyridyloxy)-2-methylpropanamide | 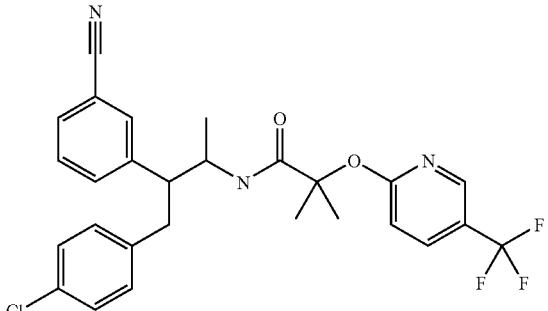 | 3.9 | 516 | B |
| 390. | N-[3-(4-Chlorophenyl)-2-(2-pyridyl)-1-methylpropyl]-2-(5-trifluoromethyl-2-pyridyloxy)-2-methylpropanamide | 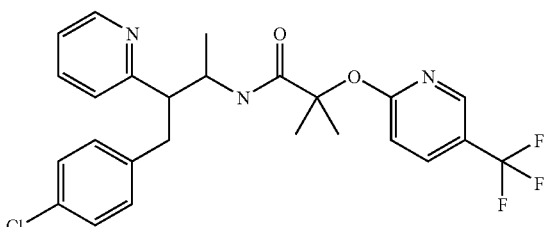 | 2.8 | 492 | A |
| 391. | N-[3-(4-Chlorophenyl)-2-(2-pyridyl)-1-methylpropyl]-2-(5-trifluoromethyl-2-pyridyloxy)-2-methylpropanamide | 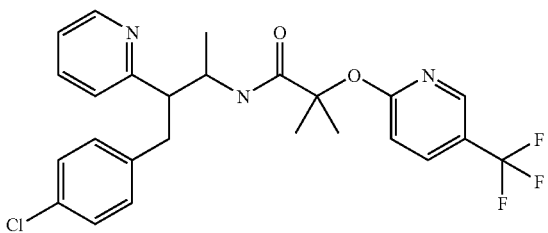 | 2.8 | 492 | B |

TABLE 14-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 392. | N-[3-(4-Chlorophenyl)-2-(3-pyridyl)-1-methylpropyl]-2-(5-trifluoromethyl-2-pyridyloxy)-2-methylpropanamide | 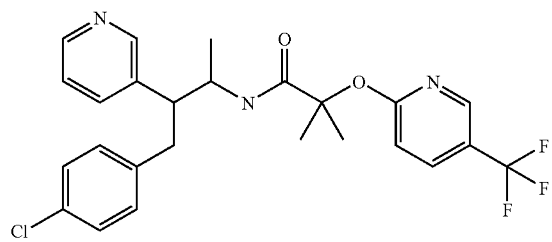 | 2.7 | 492 | B |
| 393. | N-[3-(4-Chlorophenyl)-2-(5-fluoro-3-pyridyl)-1-methylpropyl]-2-(5-trifluoromethyl-2-pyridyloxy)-2-methylpropanamide | 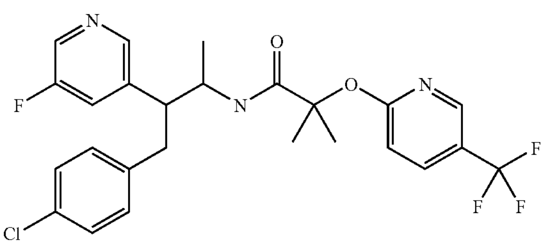 | 3.6 | 510 | A |
| 394. | N-[3-(4-Chlorophenyl)-2-(5-fluoro-3-pyridyl)-1-methylpropyl]-2-(5-trifluoromethyl-2-pyridyloxy)-2-methylpropanamide | 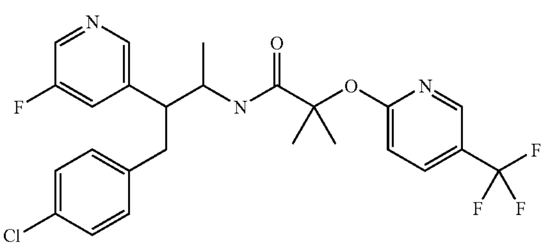 | 3.6 | 510 | B |
| 395. | N-[3-(4-Chlorophenyl)-2-(5-fluoro-3-pyridyl)-1-methylpropyl]-2-(6-trifluoromethyl-4-pyrimidyloxy)-2-methylpropanamide | 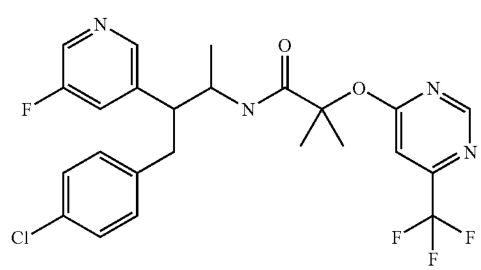 | 3.4 | 511 | A |
| 396. | N-[3-(4-Chlorophenyl)-2-(5-fluoro-3-pyridyl)-1-methylpropyl]-2-(6-trifluoromethyl-2-pyrimidyloxy)-2-methylpropanamide | 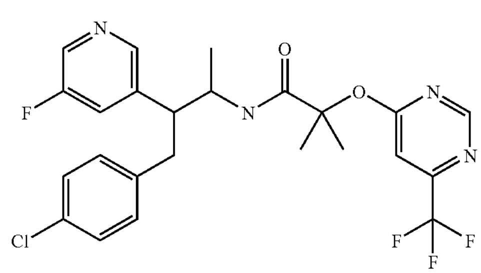 | 3.4 | 511 | B |

TABLE 14-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 397. | N-[3-(4-Chlorophenyl)-2-(5-chloro-3-pyridyl)-1-methylpropyl]-2-(5-trifluoromethyl-2-pyridyloxy)-2-methylpropanamide | 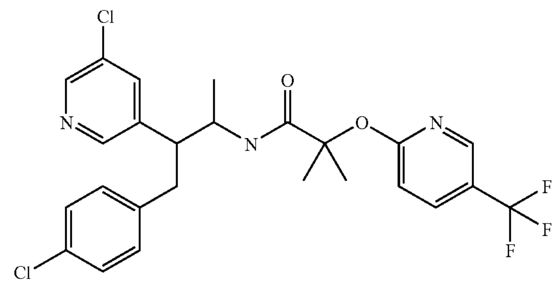 | 3.8 | 526 | A |
| 398. | N-[3-(4-Chlorophenyl)-2-(5-chloro-3-pyridyl)-1-methylpropyl]-2-(5-trifluoromethyl-2-pyridyloxy)-2-methylpropanamide | 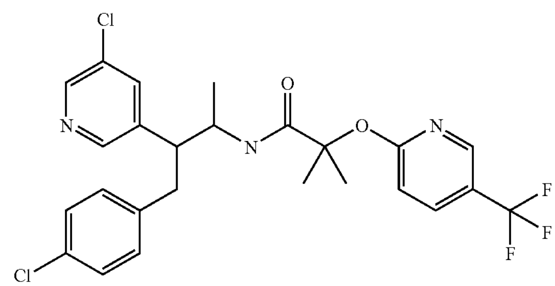 | 3.8 | 526 | B |
| 399. | N-[3-(4-Chlorophenyl)-2-(5-chloro-3-pyridyl)-1-methylpropyl]-2-(4-trifluoromethyl-2-pyridyloxy)-2-methylpropanamide | 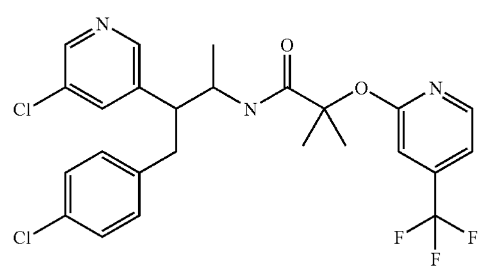 | 3.9 | 526 | A |
| 400. | N-[3-(4-Chlorophenyl)-2-(5-chloro-3-pyridyl)-1-methylpropyl]-2-(4-trifluoromethyl-2-pyridyloxy)-2-methylpropanamide | 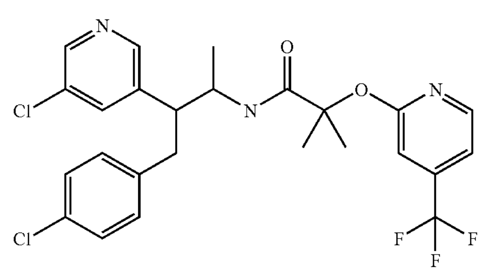 | 3.9 | 526 | B |
| 401. | N-[3-(4-Chlorophenyl)-2-(5-chloro-3-pyridyl)-1-methylpropyl]-2-(4-trifluoromethyl-2-pyrimidyloxy)-2-methylpropanamide | 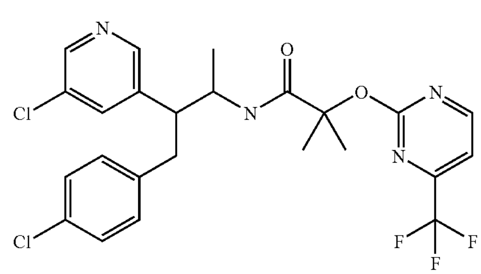 | 3.5 | 527 | A |

TABLE 14-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 402. | N-[3-(4-Chlorophenyl)-2-(5-chloro-3-pyridyl)-1-methylpropyl]-2-(4-trifluoromethyl-2-pyrimidyloxy)-2-methylpropanamide | 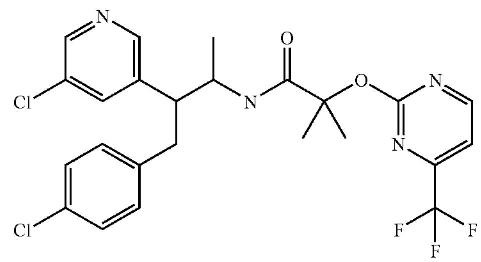 | 3.5 | 527 | B |
| 403. | N-[3-(4-Chlorophenyl)-2-(5-chloro-3-pyridyl)-1-methylpropyl]-2-(6-trifluoromethyl-4-pyrimidyloxy)-2-methylpropanamide | 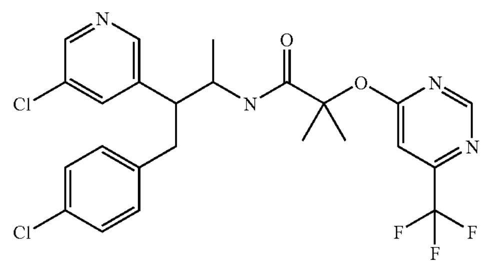 | 3.6 | 527 | A |
| 404. | N-[3-(4-Chlorophenyl)-2-(5-chloro-3-pyridyl)-1-methylpropyl]-2-(6-trifluoromethyl-4-pyrimidyloxy)-2-methylpropanamide | 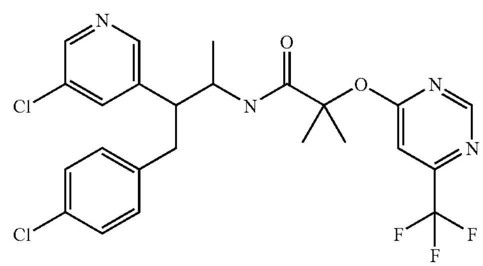 | 3.6 | 527 | B |
| 405. | N-[2-(5-chloro-3-pyridyl)-3-(4-fluorophenyl)-1-methylpropyl]-2-(5-trifluoromethyl-4-pyridyloxy)-2-methylpropanamide | 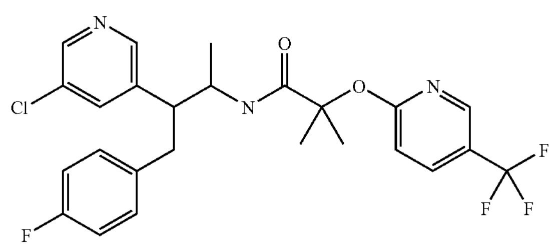 | 3.8 | 510 | A |
| 406. | N-[2-(5-chloro-3-pyridyl)-3-(4-fluorophenyl)-1-methylpropyl]-2-(5-trifluoromethyl-4-pyridyloxy)-2-methylpropanamide | 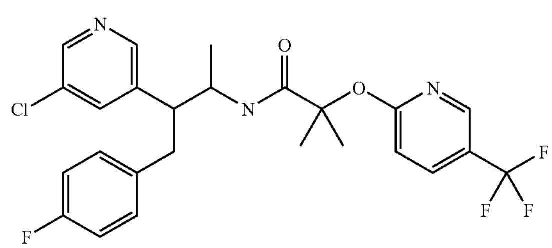 | 3.8 | 510 | B |

TABLE 14-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 407. | N-[2-(5-chloro-3-pyridyl)-3-cyclobutyl-1-methylpropyl]-2-(5-trifluoromethyl-4-pyridyloxy)-2-methylpropanamide | 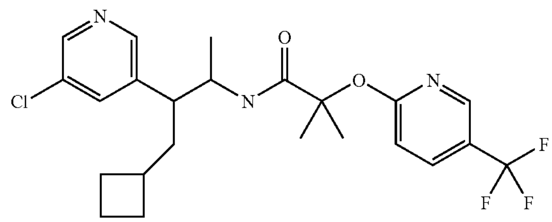 | 4.0 | 470 | A |
| 408. | N-[2-(5-chloro-3-pyridyl)-3-cyclobutyl-1-methylpropyl]-2-(5-trifluoromethyl-4-pyridyloxy)-2-methylpropanamide | 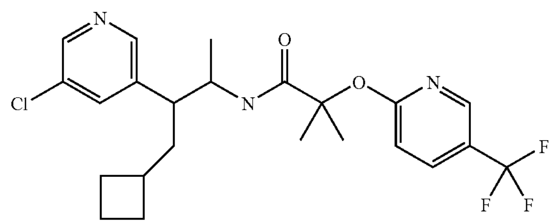 | 4.0 | 470 | B |
| 409. | N-[2-(5-chloro-3-pyridyl)-3-cyclobutyl-1-methylpropyl]-2-(5-trifluoromethyl-4-pyridyloxy)-2-methylpropanamide | 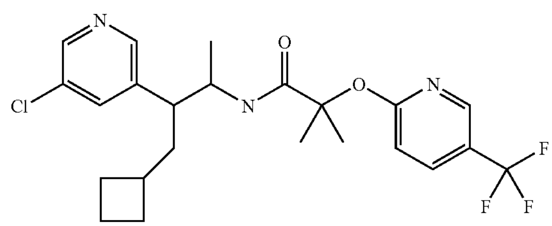 | 4.9 | 470 | C |
| 410. | N-[2-(5-chloro-3-pyridyl)-3-cyclobutyl-1-methylpropyl]-2-(5-trifluoromethyl-4-pyridyloxy)-2-methylpropanamide | 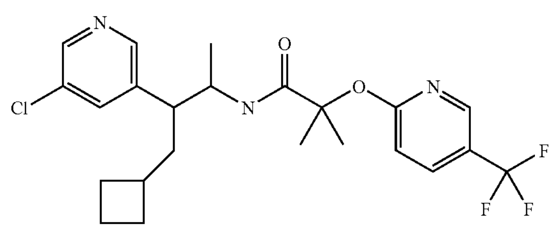 | 4.0 | 470 | D |
| 411. | N-[2-(5-chloro-3-pyridyl)-1,4-dimethylpentyl]-2-(5-trifluoromethyl-4-pyridyloxy)-2-methylpropanamide | 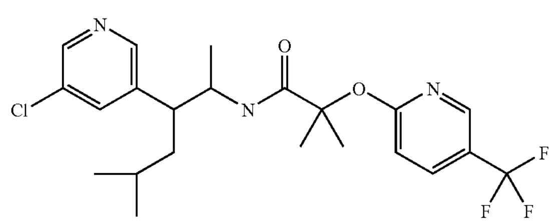 | 3.9 | 458 | A |
| 412. | N-[2-(5-chloro-3-pyridyl)-1,4-dimethylpentyl]-2-(5-trifluoromethyl-4-pyridyloxy)-2-methylpropanamide | 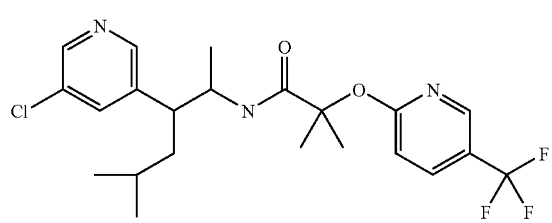 | 3.9 | 458 | B |

TABLE 14-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 413. | N-[2-(5-chloro-3-pyridyl)-1,4-dimethylpentyl]-2-(5-trifluoromethyl-4-pyridyloxy)-2-methylpropanamide | 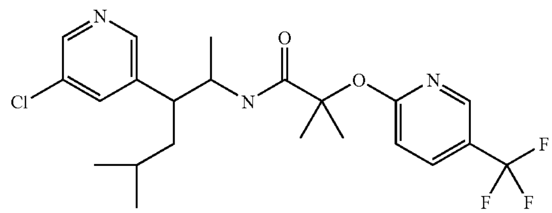 | 3.9 | 458 | C |
| 414. | N-[2-(5-chloro-3-pyridyl)-1,4-dimethylpentyl]-2-(5-trifluoromethyl-4-pyridyloxy)-2-methylpropanamide | 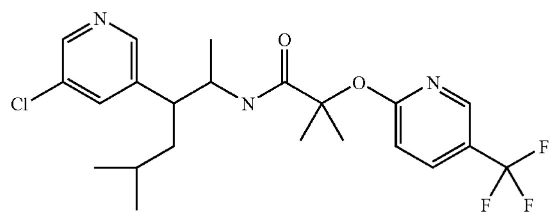 | 3.9 | 458 | D |
| 415. | N-[3-(4-Chlorophenyl)-2-(5-cyano-3-pyridyl)-1-methylpropyl]-2-(5-trifluoromethyl-2-pyridyloxy)-2-methylpropanamide | 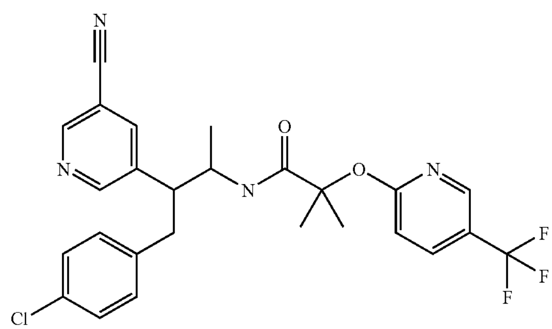 | 3.7 | 517 | A |
| 416. | N-[3-(4-Chlorophenyl)-2-(5-cyano-3-pyridyl)-1-methylpropyl]-2-(5-trifluoromethyl-2-pyridyloxy)-2-methylpropanamide | 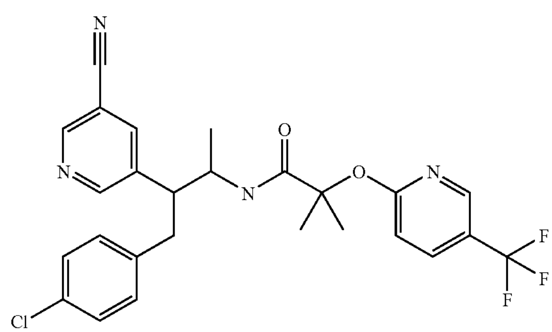 | 3.7 | 517 | B |
| 417. | N-[3-(4-Chlorophenyl)-2-(5-cyano-3-pyridyl)-1-methylpropyl]-2-(6-trifluoromethyl-4-pyrimidyloxy)-2-methylpropanamide | 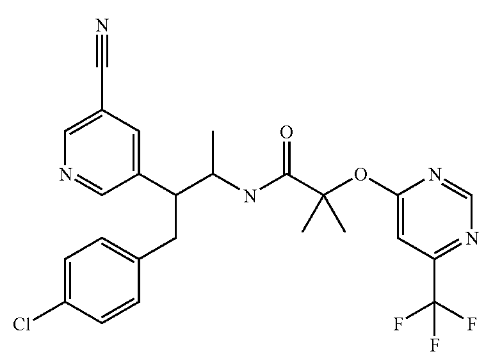 | 3.6 | 518 | A |

TABLE 14-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 418. | N-[3-(4-Chlorophenyl)-2-(5-cyano-3-pyridyl)-1-methylpropyl]-2-(6-trifluoromethyl-4-pyrimidyloxy)-2-methylpropanamide | 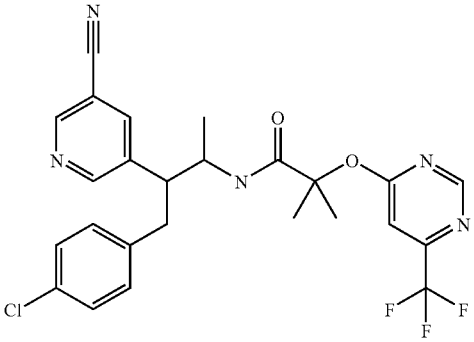 | 3.6 | 518 | B |
| 419. | N-[2-(5-cyano-3-pyridyl)-3-(3,4-difluorophenyl)-1-methylpropyl]-2-(6-trifluoromethyl-4-pyrimidyloxy)-2-methylpropanamide | 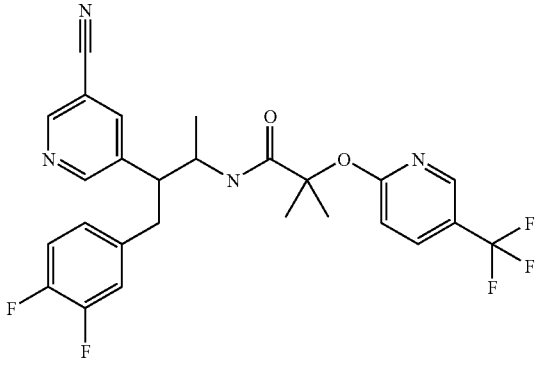 | 3.7 | 519 | A |
| 420. | N-[2-(5-cyano-3-pyridyl)-3-(3,4-difluorophenyl)-1-methylpropyl]-2-(6-trifluoromethyl-4-pyrimidyloxy)-2-methylpropanamide | 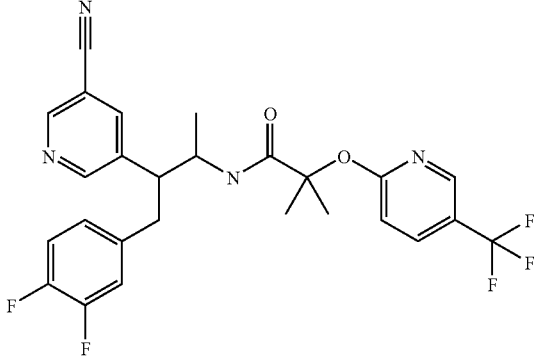 | 3.7 | 519 | B |
| 421. | N-[3-(3-Chlorophenyl)-2-(5-cyano-3-pyridyl)-1-methylpropyl]-2-(5-trifluoromethyl-2-pyridyloxy)-2-methylpropanamide | 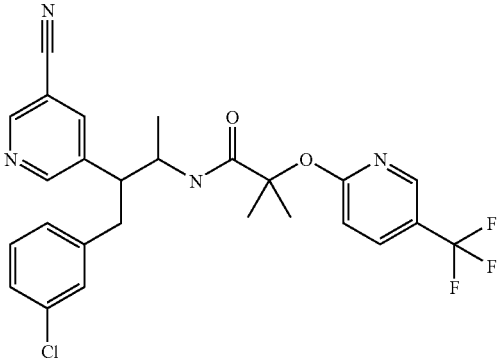 | 3.8 | 517 | A |

TABLE 14-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 422. | N-[3-(3-Chlorophenyl)-2-(5-cyano-3-pyridyl)-1-methylpropyl]-2-(5-trifluoromethyl-2-pyridyloxy)-2-methylpropanamide | 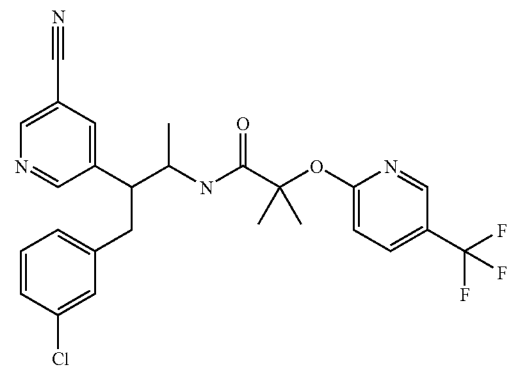 | 3.8 | 517 | B |
| 423. | N-[2-(5-cyano-3-pyridyl)-3-(4-fluorophenyl)-1-methylpropyl]-2-(5-trifluoromethyl-2-pyridyloxy)-2-methylpropanamide | 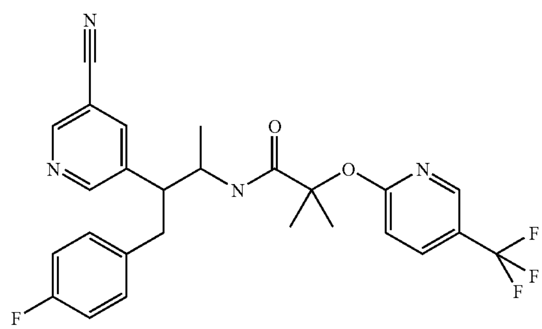 | 3.7 | 501 | A |
| 424. | N-[2-(5-cyano-3-pyridyl)-3-(4-fluorophenyl)-1-methylpropyl]-2-(5-trifluoromethyl-2-pyridyloxy)-2-methylpropanamide | 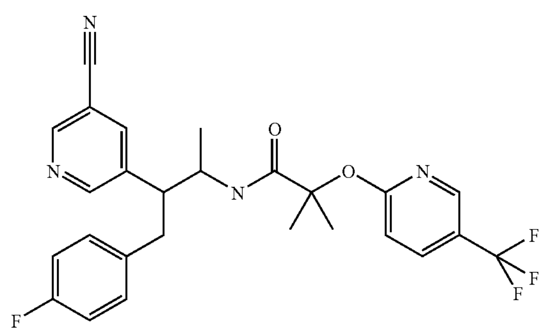 | 3.7 | 501 | B |
| 425. | N-[2-(5-Bromo-3-pyridyl)-3-(4-chlorophenyl)-1-methylpropyl]-2-(5-trifluoromethyl-2-pyridyloxy)-2-methylpropanamide | 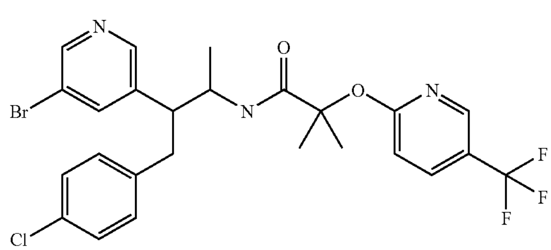 | 4.0 | 570 | A |

TABLE 14-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 426. | N-[2-(5-Bromo-3-pyridyl)-3-(4-chlorophenyl)-1-methylpropyl]-2-(5-trifluoromethyl-2-pyridyloxy)-2-methylpropanamide | 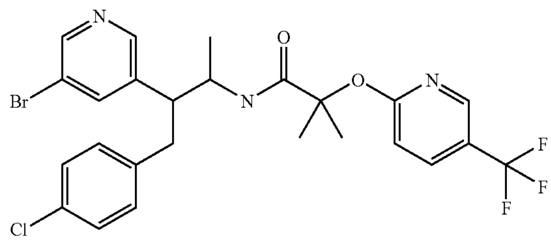 | 4.0 | 570 | B |
| 427. | N-[2-(5-Bromo-3-pyridyl)-3-(4-fluorophenyl)-1-methylpropyl]-2-(5-trifluoromethyl-2-pyridyloxy)-2-methlypropanamide | 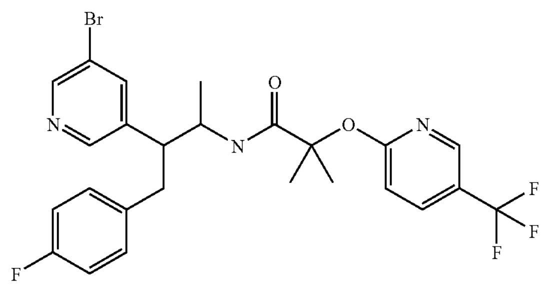 | 3.8 | 554 | A |
| 428. | N-[2-(5-Bromo-3-pyridyl)-3-(4-fluorophenyl)-1-methylpropyl]-2-(5-trifluoromethyl-2-pyridyloxy)-2-methylpropanamide | 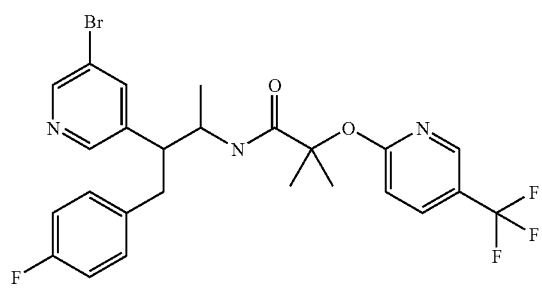 | 3.8 | 554 | B |
| 429. | N-[2-(5-Bromo-3-pyridyl)-3-(4-fluorophenyl)-1-methylpropyl]-2-(6-trifluoromethyl-4-pyrimidyloxy)-2-methylpropanamide | 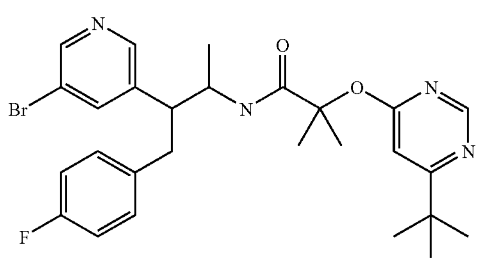 | 3.7 | 555 | A |
| 430. | N-[2-(5-Bromo-3-pyridyl)-3-(4-fluorophenyl)-1-methylpropyl]-2-(6-trifluoromethyl-4-pyrimidyloxy)-2-methylpropanamide | 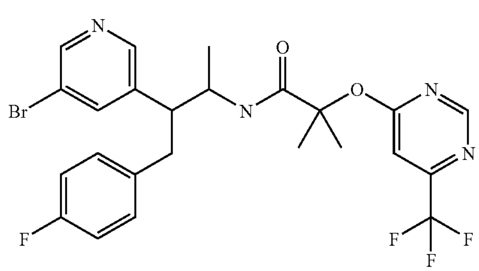 | 3.7 | 555 | B |

TABLE 14-continued

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 431. | N-[2-(5-Bromo-3-pyridyl)-3-(4-chlorophenyl)-1-methylpropyl]-2-(6-trifluoromethyl-4-pyrimidyloxy)-2-methylpropanamide | 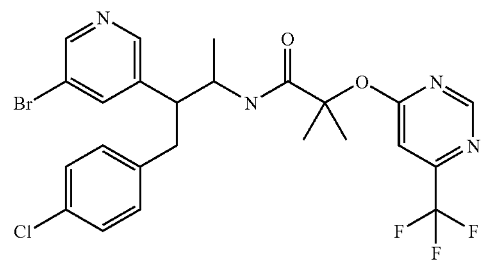 | 3.8 | 571 | A |
| 432. | N-[2-(5-Bromo-3-pyridyl)-3-(4-chlorophenyl)-1-methylpropyl]-2-(6-trifluoromethyl-4-pyrimidyloxy)-2-methylpropanamide | 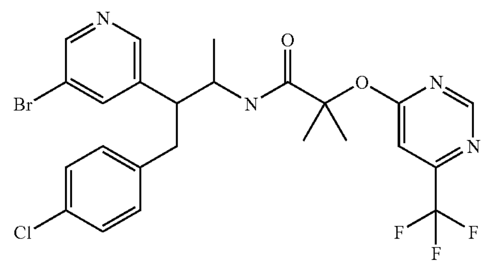 | 3.8 | 571 | B |
| 433. | N-[3-(4-Chlorophenyl)-2-(5-methyl-3-pyridyl)-1-methylpropyl]-2-(5-trifluoromethyl-2-pyridyloxy)-2-methylpropanamide | 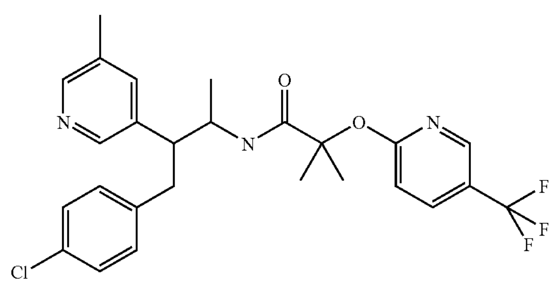 | 2.8 | 506 | A |
| 434. | N-[3-(4-Chlorophenyl)-2-(5-methyl-3-pyridyl)-1-methylpropyl]-2-(5-trifluoromethyl-2-pyridyloxy)-2-methylpropanamide | 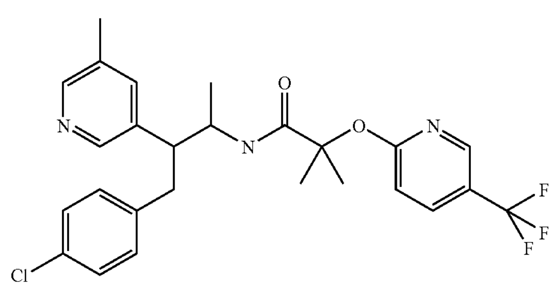 | 2.8 | 506 | B |
| 435. | N-[2-(5-Bromophenyl)-3-(4-chlorophenyl)-1-methylpropyl]-2-(5-chloro-3-pyridyloxy)-2-methylpropanamide | 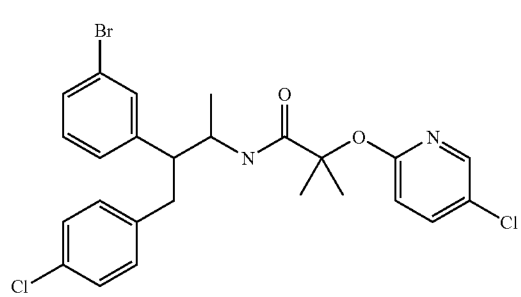 | 4.5 | 535 | A |

TABLE 14-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 436. | N-[2-(3-Bromophenyl)-3-(4-chlorophenyl)-1-methylpropyl]-2-(5-chloro-2-pyridyloxy)-2-methylpropanamide | 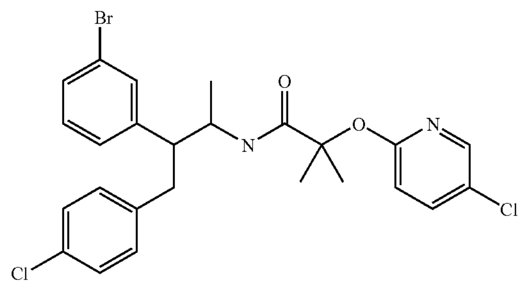 | 4.5 | 535 | B |

Example 437

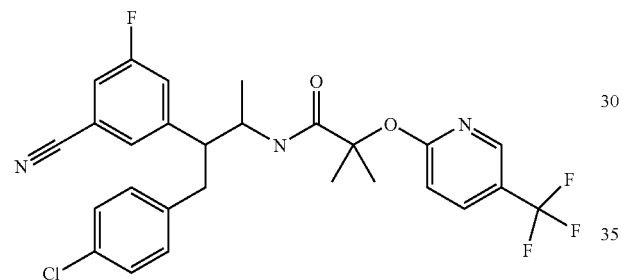

N-[3-(4-Chlorophenyl)-2-(3-cyano-5-fluorophenyl)-1-methylpropyl]-2-(5-trifluoromethyl-2-pyridyloxy)-2-methylpropanamide (Diastereomer α and Enantiomer A and B)

A mixture of N-[2-(3-bromo-5-fluorophenyl)-3-(4-chlorophenyl)-1-methylpropyl]-2-(5-trifluoromethyl-2-pyridyloxy)-2-methylpropanamide (Example 330, 92 mg, 0.16 mmol), sodium cyanide (12 mg, 0.24 mmol), 18-crown-6 (63 mg, 0.24 mmol) and tetrakis(triphenylphosphine)palladium (92 mg, 0.08 mmol) in 2 mL dioxane was heated under nitrogen at 100° C. for 14 h. After cooling to room temperature, the resulting mixture was partitioned between water (50 mL) and EtOAc (50 mL). The organic layer was separated, washed with water, dried over anhydrous sodium sulfate, filtered and concentrated, and the residue was purified by flash column chromatography on silica gel eluting with 30% EtOAc in hexane to afford the title compound as a racemic mixture. $^1$H NMR (500 MHz, CD$_3$OD): δ 8.26 (br s, 1H), 7.96 (d, 1H), 7.93 (dd, 1H), 7.30 (br d, 1H), 7.22 (s, 1H), 7.15 (br d, 1H), 7.06 (d, 2H), 7.05 (m, 1H), 6.74 (d, 2H), 4.24 (m, 1H), 3.05 (dd, 1H), 2.91 (m, 1H), 2.63 (dd, 1H), 1.74 (s, 3H), 1.72 (s, 3H), 0.83 (d, 3H). LC-MS: m/e 534 (M+H)$^+$ (4.2 min).

The racemic mixture obtained above was separated into Enantiomer A and Enantiomer B by preparative HPLC eluting on a Chiralpak AD column (2 cm×25 cm), with 8% ethanol in hexane (flow rate 9 mL/min, 500 μL per injection).

Faster eluting enantiomer (Enantiomer A): Analytical HPLC: retention time=8.2 min (Chiralpak AD column, flow rate=0.75 mL/min, 8% ethanol/hexane). LC-MS: m/e 534 (M+H)$^+$ (4.2 min).

Slower eluting enantiomer (Enantiomer B): Analytical HPLC: retention time=11.0 min (Chiralpak AD column, flow rate=0.75 mL/min, 8% ethanol/hexane). LC-MS: m/e 534 (M+H)$^+$ (4.2 min).

Example 438

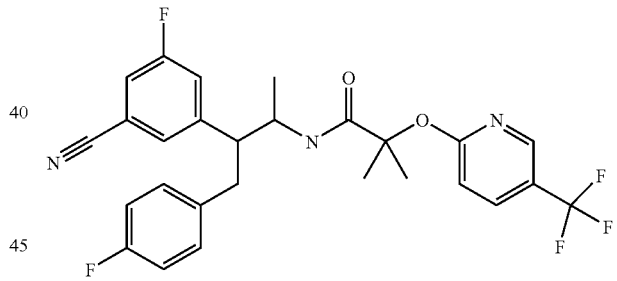

N-[2-(3-Cyano-5-fluorophenyl)-3-(4-fluorophenyl)-1-methylpropyl]-2-(5-trifluoromethyl-2-pyridyloxy)-2-methylpropanamide (Diastereomer α and Enantiomer A and B)

The title compounds were prepared from N-[2-(3-bromo-5-fluorophenyl)-3-(4-fluorophenyl)-1-methylpropyl]-2-(5-trifluoromethyl-2-pyridyloxy)-2-methylpropanamide (Example 329) following the procedure described in Example 437. LC-MS: m/e 518 (M+H)$^+$ (4.1 min).

Faster eluting enantiomer (Enantiomer A): Analytical HPLC: retention time=8.2 min (Chiralpak AD column, flow rate=0.75 mL/min, 8% ethanol/hexane). LC-MS: m/e 518 (M+H)$^+$ (4.1 min).

Slower eluting enantiomer (Enantiomer B): Analytical HPLC: retention time=11.2 min (Chiralpak AD column, flow rate=0.75 mL/min, 8% ethanol/hexane). LC-MS: m/e 518 (M+H)$^+$ (4.1 min).

Example 439

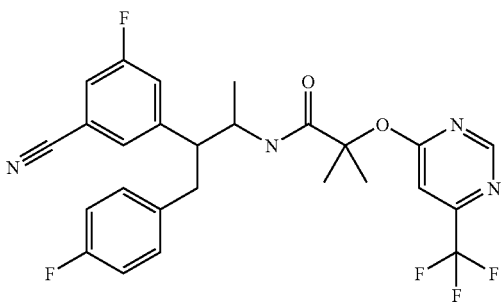

N-[2-(3-Cyano-5-fluorophenyl)-3-(4-fluorophenyl)-1-methylpropyl]-2-(6-trifluoromethyl-4-pyrimidyloxy)-2-methylpropanamide (Diastereomer α)

The title compound was prepared from N-[2-(3-bromo-5-fluorophenyl)-3-(4-fluorophenyl)-1-methylpropyl]-2-(6-trifluoromethyl-4-pyrimidyloxy)-2-methylpropanamide (Example 331) following the procedure described in Example 437. LC-MS: m/e 519 (M+H)$^+$ (3.8 min).

Example 440

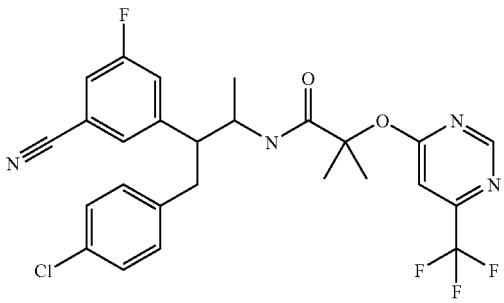

N-[3-(4-Chlorophenyl)-2-(3-cyano-5-fluorophenyl)-1-methylpropyl]-2-(6-trifluoromethyl-4-pyrimidyloxy)-2-methylpropanamide (Diastereomer α)

The title compound was prepared from N-[2-(3-bromo-5-fluorophenyl)-3-(4-chlorophenyl)-1-methylpropyl]-2-(6-trifluoromethyl-4-pyrimidyloxy)-2-methylpropanamide (Example 332) following the procedure described in Example 4370. LC-MS: m/e 535 (M+H)$^+$ (4.1 min).

Example 441

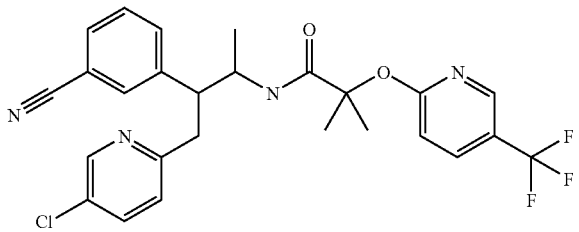

N-[3-(5-Chloro-2-pyridyl)-2-(3-cyanophenyl)-1-methylpropyl]-2-(5-trifluoromethyl-2-pyridyloxy)-2-methylpropanamide (Enantiomer A and B)

The title compounds were prepared from N-[2-(3-bromophenyl)-3-(5-chloro-2-pyridyl)-1-methylpropyl]-2-(5-trifluoromethyl-2-pyridyloxy)-2-methylpropanamide (Example 382) following the procedure described in Example 437.

Faster eluting enantiomer (Enantiomer A): Analytical HPLC: retention time=8.9 min (Chiralpak AD column, flow rate=0.75 mL/min, 10% ethanol/hexane). LC-MS: m/e 517 (M+H)$^+$ (3.6 min).

Slower eluting enantiomer (Enantiomer B): Analytical HPLC: retention time=11.1 min (Chiralpak AD column, flow rate=0.75 mL/min, 10% ethanol/hexane). LC-MS: m/e 517 (M+H)$^+$ (3.6 min).

Example 442

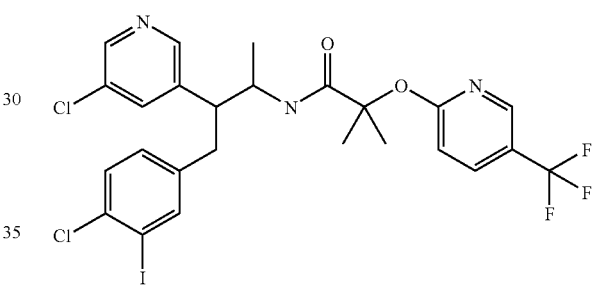

N-[2-(5-Chloro-3-pyridyl)-3-(4-chloro-3-iodophenyl)-1-methylpropyl]-2-(5-trifluoromethyl-2-pyridyloxy)-2-methylpropanamide (Enantiomer B)

The procedure of Barluenga (J Org Chem 1990, 55, 3104) was used. Thus, to a solution of N-[3-(4-chlorophenyl)-2-(5-chloro-3-pyridyl)-1-methylpropyl]-2-(5-trifluoromethyl-2-pyridyloxy)-2-methylpropanamide (Example 398, 22 mg, 0.041 mmol) and bis(pyridine)iodonium tetrafluoroborate (30 mg, 0.082 mmol) in 0.3 mL anhydrous $CH_2Cl_2$ was added triflic acid (18 µL, 0.20 mmol). After stirring at room temperature for 50 min, the reaction mixture was poured into a mixture of ice (20 g) and sodium bisulfite (1 g) and was extracted with EtOAc. The organic extracts were dried over anhydrous sodium sulfate, filtered and concentrated to dryness to give the crude product, which was purified by preparative HPLC eluting on a reverse-phase HPLC column with 75 to 100% water in acetonitrile (containing 0.1% trifluoroacetic acid) to give the title compound. $^1$H NMR (500 MHz, $CD_3OD$): δ 8.43 (d, 1H), 8.32 (s, 1H), 8.10 (s, 1H), 8.04 (d, 1H), 7.99 (dd, 1H), 7.82 (m, 1H), 7.36 d, 1H), 7.22 (d, 1H), 7.08 (d, 1H), 6.78 (dd, 1H), 4.29 (m, 1H), 3.03 (dd, 1H), 2.94 (m, 1H), 2.64 (dd, 1H), 1.78 (s, 3H), 1.75 (s, 3H), 0.88 (d, 3H). LC-MS: m/e 652 (M+H)$^+$ (4.1 min).

Example 443

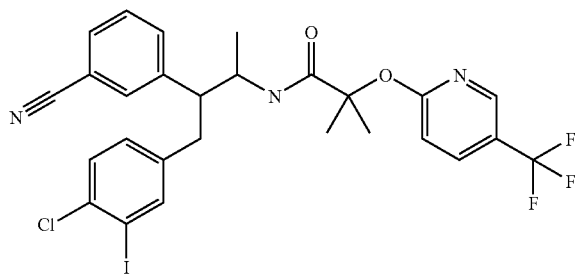

N-[3-(4-Chloro-3-iodophenyl)-2-(3-cyanophenyl)-1-methylpropyl]-2-(5-trifluoromethyl-2-pyridyloxy)-2-methylpropanamide (Enantiomer B)

The title compound was prepared from N-[3-(4-chlorophenyl)-2-(3-cyanophenyl)-1-methylpropyl]-2-(5-trifluoromethyl-2-pyridyloxy)-2-methyl propanamide (Enantiomer B) (Example 389) following the procedure described in Example 442. $^1$H NMR (500 MHz, CD$_3$OD): δ 8.31 (s, 1H), 8.02 (d, 1H), 7.98 (dd, 1H), 7.54 (d, 1H), 7.5-7.4 (m, 2H), 7.35 (d, 1H), 7.27 (d, 1H), 7.17 (d, 1H), 7.08 (d, 1H), 6.70 (dd, 1H), 4.27 (m, 1H), 2.98 (dd, 1H), 2.84 (m, 1H), 2.61 (dd, 1H), 1.78 (s, 3H), 1.75 (s, 3H), 0.83 (d, 3H). LC-MS: m/e 642 (M+H)$^+$ (4.2 min).

Examples 444-451 (Table 15) were isolated as diastereomers as indicated (Isomer A or B) on silica gel chromatography columns. The single enantiomers noted were separated on the chiral AD column noted above.

TABLE 15

| Ex. No. | Name | Structure | HPLC-retention time (min) | mass spectrum m/e | Diastereomer A or B |
|---|---|---|---|---|---|
| 444. | N-(3-(4-chlorophenyl)-2-benzisoxazol-3-yl)-1-methyl)propyl-2-(5-chloro-2-oxypyridine-2-yl)-2-methylpropanamide | 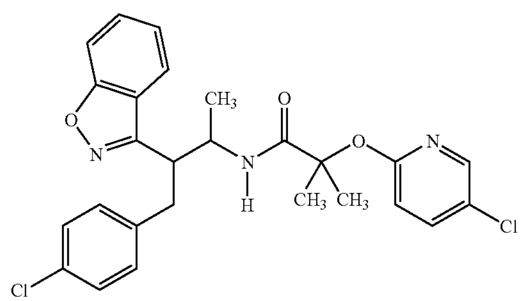 | 4.1, 4.3 | 498.1 | A and B |
| 445. | N-(3-(4-chlorophenyl)-2-(benzisoxazol-3-yl)-1-methyl)propyl-2-(3,5-dichlorophenoxy)-2-methylpropanamide | 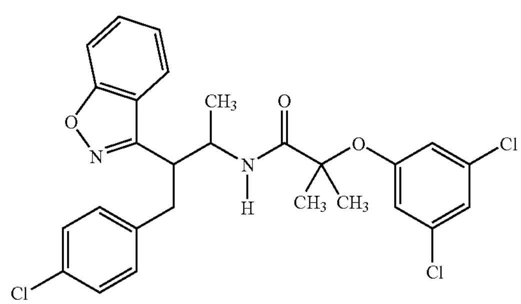 | 4.7, 4.8 | 532.8 | A and B |
| 446. | N-(3-(4-chlorophenyl)-2-(benzisoxazol-3-yl)-1-methyl)propyl-2-(5-trifluoromethyl-2-oxypyridine-2-yl)2-methylpropanamide | 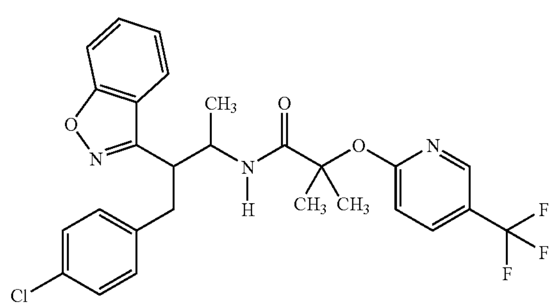 | 4.2 | 532.1 | B |

TABLE 15-continued

| Ex. No. | Name | Structure | retention time (min) | HPLC-mass spectrum m/e | Diastereomer A or B |
|---|---|---|---|---|---|
| 447. | N-(3-(4-chlorophenyl)-2-(7-azaindol-N-yl)-1-methyl)propyl-2-(5-trifluoromethyl-2-oxypyridine-2-yl)-2-methylpropanamide | 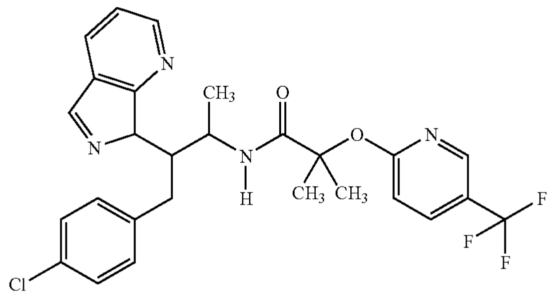 | 3.89 | 532.1 | B |
| 448. | N-(3-(4-chlorophenyl)-2-(N-methyl-N-phenyl)amino-1-methyl)propyl-2-(5-trifluoromethyl-2-oxypyridine-2-yl)-2-methylpropanamide | 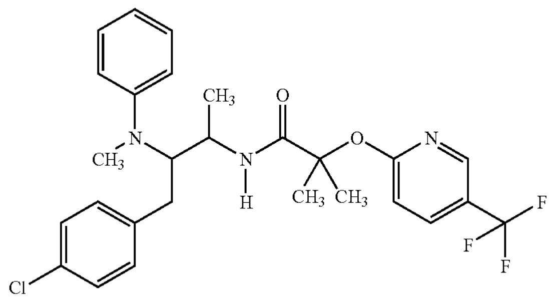 | 4.40 | 521 | Single enantiomer derived from Isomer B |
| 449. | N-(3-(4-chlorophenyl)-2-(indol-N-yl)-1-methyl)propyl-2-(5-trifluoromethyl-2-oxypyridine-2-yl)-2-methylpropanamide | 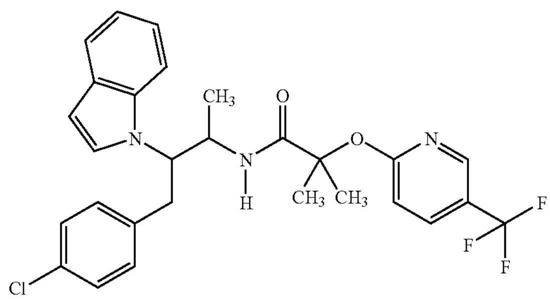 | 4.32[b,c] | 531 | Single enantiomer derived from Isomer B |
| 450. | N-(3-(4-chlorophenyl)-2-(indolin-N-yl)-1-methyl)propyl-2(4-trifluoromethyl-2-oxypyridine-2-yl)-2-methylpropanamide | 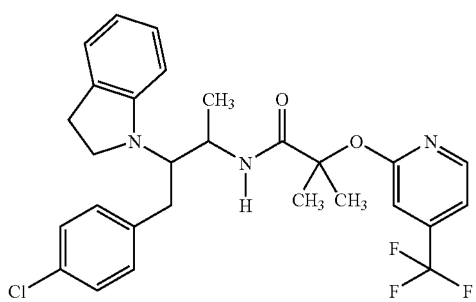 | 4.32[b] | 531 | B |
| 451. | N-(3-(4-chlorophenyl)-2-(indolin-N-yl)-1-methyl)propyl-2(5-trifluoromethyl-2-oxypyridine-2-yl)-2-methylpropanamide | 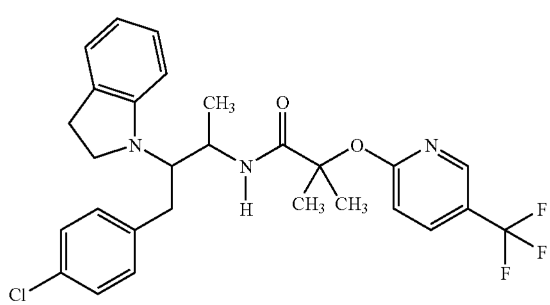 | 4.40[b] | 532 | B |

Example 452

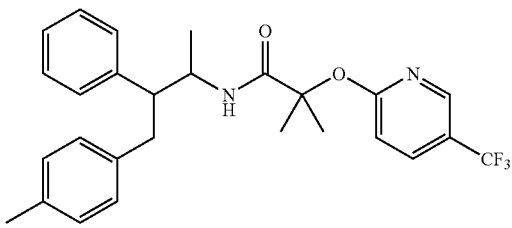

2-Methyl-N-[1-methyl-3-(4-methylphenyl)-2-phenylpropyl]-2-{[5-(trifluoromethyl)pyridin-2-yl]oxy}propanamide

To a solution of 2-methyl-2-{[5-(trifluoromethyl)pyridin-2-yl]oxy}propanoic acid (Reference example 55, 250 mg, 1.04 mmol) and 4-(4-methylphenyl)-3-phenylbutan-2-amine (Reference example 102, 260 mg, 1.04 mmol, mixture of 4 isomers) in $CH_2Cl_2$ (5.5 mL) at RT was added diisopropyl-ethylamine (272 μl, 1.56 mmol) followed by PyBOP (649 mg, 1.25 mmol) and the reaction mixture stirred overnight. The reaction was purified by loading the reaction mixture directly onto a silica gel column and eluting from 0-30% EtOAc/hexane to give the title compound as a mixture of 4 isomers. The diastereomers were separated by HPLC on a ZORBAX RxSi column eluting 97% hexane: 3% ethanol at 20 mL/min with retention times of:

less polar diastereomer eluted at 4.73 minutes; more polar diasteromer eluted at 5.87 minutes. The more polar diastereomer was additionally separated into enantiomers on a ChiralPak AD column eluting with 95% hexane: 5% ethanol at 8 mL/min with retention times of:

less polar enantiomer eluted at 6.84 minutes; more polar diastereomer eluted at 8.36 minutes.

Less polar diastereomer: $^1$H NMR (500 MHz, $CDCl_3$): δ 8.44 (s, 1H), 7.86 (dd, J=8.6, 2.5 Hz, 1H), 7.19 (t, J=3.2 Hz, 3H), 7.00 (dd, J=21.3, 8.0 Hz, 4H), 6.91 (m, 2H), 6.83 (d, J=8.7 Hz, 1H), 5.70 (d, J=9.4 Hz, 1H), 4.43 (m, 1H), 3.02 (dd, J=13.3, 6.7 Hz, 1H), 2.84 (dt, J=7.3, 4.3 Hz, 1H), 2.84 (dd, J=13.2, 7.7 Hz, 1H), 2.29 (s, 3H), 1.69 (s, 3H), 1.66 (s, 3H), 1.03 (d, J=6.8 Hz, 3H). LC-MS: m/e 471 (M+H)$^+$ (4.22 min)

More polar diastereomer: $^1$H NMR (500 MHz, $CDCl_3$): δ 8.40 (s, 1H), 7.83 (dd, J=8.7, 2.6 Hz, 1H), 7.21 (m, 3H), 7.00 (dd, J=30.4, 6.2 Hz, 4H), 6.82 (t, J=9.2 Hz, 3H), 5.84 (d, J=9.2 Hz, 1H), 4.36 (ddt, J=9.1, 6.7, 6.6 Hz, 1H), 3.06 (dd, J=12.8, 4.1 Hz, 1H), 2.88 (m, 1H), 2.26 (s, 3H), 1.78 (s, 3H), 1.73 (s, 3H), 0.92 (d, J=6.6 Hz, 3H). LC-MS: m/e 471 (M+H)$^+$ (4.17 min).

Example 453

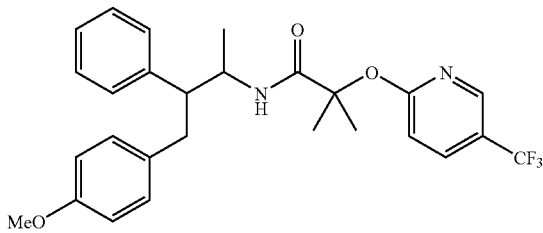

N-[3-(4-Methoxyphenyl)-1-methyl-2-phenylpropyl]-2-methyl-2-{[5-(trifluoromethyl)pyridin-2-yl]oxy}propanamide

Prepared as in Example 452 using 4-(4-methoxyphenyl)-3-phenylbutan-2-amine (Reference example 103) as the amine component to give the title compound as a mixture of 4 isomers. The diastereomers were separated by HPLC on a ZORBAX RxSi column eluting 97% hexane: 3% ethanol at 20 mL/min with retention times of: less polar diastereomer eluted at 6.12 minutes; more polar diasteromer eluted at 7.74 minutes. The more polar diastereomer was additionally separated into enantiomers on a ChiralPak AD column eluting with 90% hexane: 10% ethanol at 8 mL/min with retention times of: less polar enantiomer eluted at 6.19 minutes; more polar diastereomer eluted at 7.22 minutes.

Less polar diastereomer: $^1$H NMR (500 MHz, $CDCl_3$): δ 8.44 (s, 1H), 7.86 (dd, J=8.7, 2.5 Hz, 1H), 7.19 (t, J=2.8 Hz, 3H), 7.01 (d, J=8.5 Hz, 2H), 6.90 (m, 2H), 6.83 (d, J=8.7 Hz, 1H), 6.77 (d, J=8.5 Hz), 5.70 (d, J=9.6 Hz, 1H), 4.42 (m, 1H), 3.77 (s, 3H), 2.99 (dd, J=13.5, 6.6 Hz, 1H), 2.89 (m, 1H), 2.80 (dd, J=13.3, 7.6 Hz, 1H), 1.69 (s, 3H), 1.67 (s, 3H), 1.03 (d, J=6.6 Hz, 3H). LC-MS: m/e 471 (M+H)$^+$ (3.96 min)

More polar diastereomer: $^1$H NMR (500 MHz, $CDCl_3$): δ 8.41 (s, 1H), 7.83 (dd, J=8.7, 2.6 Hz, 1H), 7.21 (m, 3H), 7.01 (m, 2H), 6.82 (m, 3H), 6.70 (m, 2H) 5.84 (d, J=9.2 Hz, 1H), 4.36 (ddt, J=9.1, 6.7, 6.6 Hz, 1H), 3.75 (s, 3H), 3.06 (dd, J=13.3, 4.6 Hz, 1H), 2.85 (m, 2H), 1.78 (s, 3H), 1.73 (s, 3H), 0.92 (d, J=6.8 Hz, 3H). LC-MS: m/e 471 (M+H)$^+$ (4.02 min).

Example 454

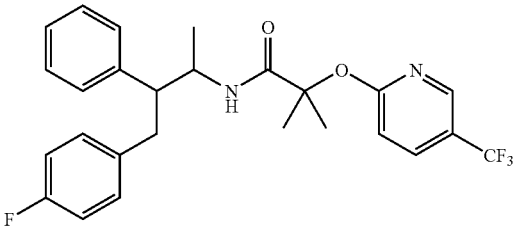

N-[3-(4-Fluorophenyl)-1-methyl-2-phenylpropyl]-2-methyl-2-{[5-(trifluoromethyl)pyridin-2-yl]oxy}propanamide

Prepared as in Example 452 using 4-(4-fluorophenyl)-3-phenylbutan-2-amine (Reference example 105) as the amine component to give the title compound as a mixture of 4 isomers. The diastereomers were separated by HPLC on a ZORBAX RxSi column eluting 96% hexane: 4% ethanol at 20 mL/min with retention times of: less polar diastereomer was not isolated, very little present; more polar diasteromer eluted at 6.65 minutes. The more polar diastereomer was additionally separated into enantiomers on a ChiralPak AD column eluting with 92% hexane: 8% ethanol at 8 mL/min with retention times of: less polar enantiomer eluted at 6.06 minutes; more polar diastereomer eluted at 7.02 minutes. More polar diastereomer: $^1$H NMR (500 MHz, $CDCl_3$): δ 8.42 (s, 1H), 7.85 (dd, J=8.7, 2.5 Hz, 1H), 7.22 (m, 3H), 7.01 (m, 2H), 7.00 (m, 2H), 6.84 (m, 5H) 5.85 (d, J=9.1 Hz, 1H), 4.39 (ddt, J=9.1, 6.7, 6.6 Hz, 1H), 2.89 (dd, J=13.7, 10.3 Hz, 1H), 2.80 (ddd, J=10.3, 7.8, 4.8 Hz, 1H), 1.80 (s, 3H), 1.75 (s, 3H), 0.93 (d, J=6.7 Hz, 3H). LC-MS: m/e 475 (M+H)$^+$ (4.11 min).

Example 455

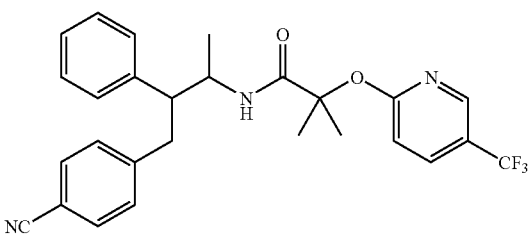

329
N-[3-(4-Cyanophenyl)-1-methyl-2-phenylpropyl]-2-methyl-2-{[5-(trifluoromethyl)pyridin-2-yl]oxy}propanamide Prepared as in Reference example 452 using 4-(4-cyanophenyl)-3-phenylbutan-2-amine (Reference example 17) as the amine component to give the title compound as a mixture of 4 isomers. The diastereomers were separated by HPLC on a Zorbax RxSi column eluting 90% hexane: 10% ethanol at 20 mL/min with retention times of: less polar diastereomer was not isolated, very little present; more polar diasteromer eluted at 6.44 minutes. The more polar diastereomer was additionally separated into enantiomers on a ChiralPak AD column eluting with 92% hexane: 8% ethanol at 8 mL/min with retention times of: less polar enantiomer eluted at 8.83 minutes; more polar diastereomer eluted at 10.83 minutes.

More polar diastereomer: $^1$H NMR (500 MHz, CDCl$_3$): δ 8.42 (s, 1H), 7.86 (dd, J=8.6, 2.2 Hz, 1H), 7.40 (d, J=8.2 Hz, 2H), 7.01 (m, 2H), 7.20 (m, 3H), 6.97 (m, 2H), 6.93 (d, J=8.2 Hz, 2H), 6.87 (d, J=8.7 Hz, 1H), 5.85 (d, J=9.2 Hz, 1H), 4.38 (dq, J=15.5, 8.4 Hz, 1H), 3.17 (dd, J=13.9, 4.5 Hz, 1H), 2.95 (dd, J=13.7, 10.7 Hz, 1H), 2.78 (m, 1H), 1.79 (s, 3H), 1.74 (s, 3H), 0.92 (d, J=6.8 Hz, 3H). LC-MS: m/e 482 (M+H)$^+$ (4.27 min).

Example 456

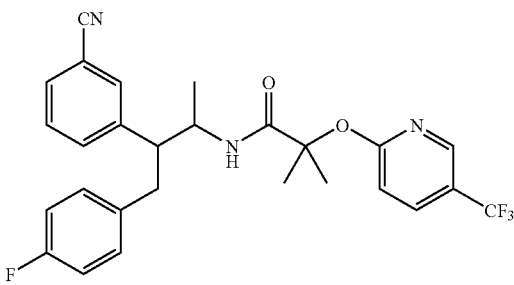

330
N-[2-(3-Cyanophenyl)-3-(4-fluorophenyl)-1-methylpropyl]-2-methyl-2-{[5-(trifluoromethyl)pyridin-2-yl]oxy}propanamide Prepared as in Example 452 only using 3-[2-amino-1-(4-fluorobenzyl)propyl]benzonitrile (Reference example 104) as the amine component to give the title compound as a mixture of 4 isomers. The diastereomers were separated by HPLC on a Zorbax RxSi column eluting 96% hexane: 4% ethanol at 20 mL/min with retention times of: less polar diastereomer eluted at 11.75 minutes;

more polar diasteromer eluted at 15.17 minutes. The more polar diastereomer was additionally separated into enantiomers on a ChiralPak AD column eluting with 92% hexane: 8% ethanol at 8 mL/min with retention times of: less polar enantiomer eluted at 9.65 minutes; more polar diastereomer eluted at 11.78 minutes.

Less polar diastereomer: $^1$H NMR (500 MHz, CD$_3$OD): δ 8.29 (s, 1H), 7.93 (dd, J=8.7, 2.5 Hz, 1H), 7.50 (m, 1H), 7.42 (m, 1H), 7.27 (m, 2H), 6.96-6.78 (m, 5H 5.70 (d, J=9.6 Hz, 1H), 4.33 (m, 1H), 3.18-3.04 (m, 2H), 2.7 (dd, J=13.5, 6.6 Hz, 1H), 1.52 (s, 3H), 1.35 (s, 3H), 1.17 (d, J=6.6 Hz, 3H). LC-MS: m/e 500 (M+H)$^+$ (4.33 min)

More polar diastereomer: $^1$H NMR (500 MHz, CD$_3$OD): δ 8.28 (s, 1H), 7.95 (dd, J=8.7, 2.5 Hz, 1H), 7.50 (d, J=7.5 Hz, 1H), 7.36 (m, 3H), 7.05 (d, J=8.9 Hz, 3H), 6.78 (m, 2H), 6.72 (m, 2H) 4.26 (dq, J=10, 6.6 Hz, 1H), 3.04 (dd, J=13.7, 3.4 Hz, 1H), 2.85 (ddt J=11.2, 3.7 Hz, 1H), 2.63 (dd, J=13.7, 11.4 Hz, 1H), 1.77 (s, 3H), 1.74 (s, 3H), 0.81 (d, J=6.8 Hz, 3H). LC-MS: m/e 500 (M+H)$^+$ (4.25 min).

The compounds of Table 16 were prepared from the appropriate amine and acid of the Reference Examples following the procedures described in Examples 62-63 (via an acyl chloride intermediate) or Examples 195 or 200 (with a coupling reagent.)

TABLE 16

| Ex. No. | Name | Structure | HPLC-retention time (min) | mass spectrum m/e |
|---|---|---|---|---|
| 457. | N-(2-(1H-1,2,3-Benzotriazol-1-yl)-3-(4-chlorophenyl)-1-methylpropyl)-2-methyl-2-(5-chloropyridin-2-yl)oxy)-2-methylpropanamide | 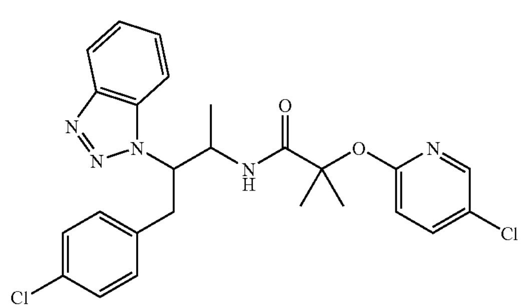 | 3.8 | 498 |

TABLE 16-continued

| Ex. No. | Name | Structure | retention time (min) | HPLC-mass spectrum m/e |
|---|---|---|---|---|
| 458. | N-(2-(1H-1,2,3-Benzotriazol-1-yl)-3-(4-chlorophenyl)-1-methylpropyl)-2-methyl-2-(5-trifluoromethylpyridin-2-yl)oxy)-2-methylpropanamide | 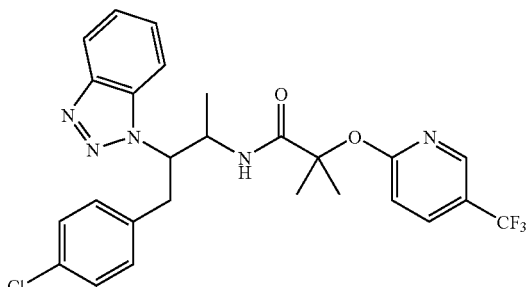 | 3.9 | 532 |
| 459. | N-(2-(1H-1,2,3-Benzotriazol-1-yl)-3-(4-chlorophenyl)-1-methylpropyl)-2-methyl-2-(4-chlorophenoxy)-2-methylpropanamide | 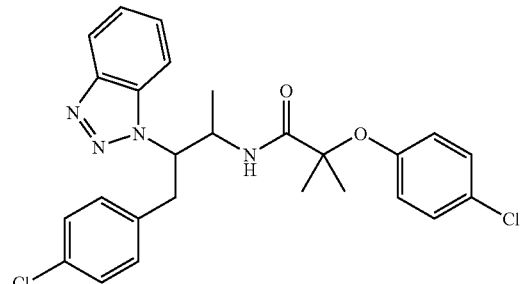 | 4.1 | 497 |
| 460. | N-(3-(4-chlorophenyl)-1-methyl-2-(1H-indazol-1-yl)propyl)-2-methyl-2-(5-trifluoromethylpyridin-2-yl)oxy)-2-methylpropanamide | 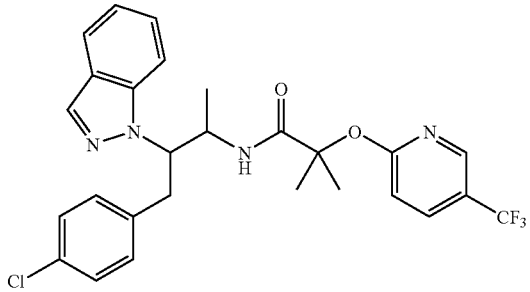 | 4.1 | 531 |
| 461. | N-(3-(4-chlorophenyl)-1-methyl-2-(1-methyl-1H-indol-3-yl)propyl)-2-methyl-2-(5-chloropyridin-2-yl)oxy)-2-methylpropanamide | 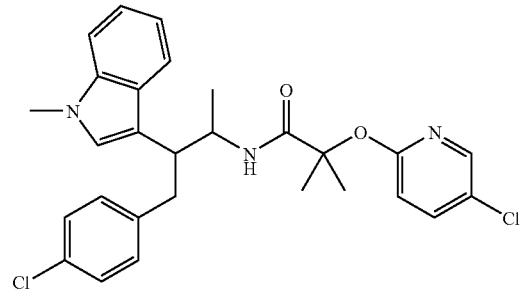 | 4.34 | 510 |
| 462. | N-(3-(4-chlorophenyl)-1-methyl-2-(1-methyl-1H-indol-3-yl)propyl)-2-methyl-2-(5-trifluoromethylpyridin-2-yl)oxy)-2-methylpropanamide | 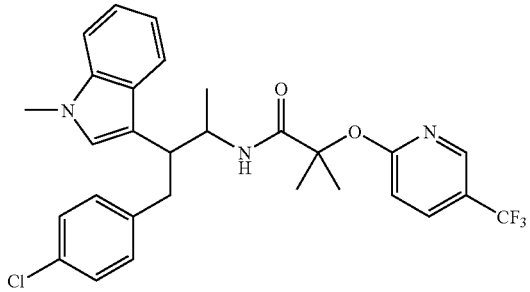 | 4.4 | 544 |

TABLE 16-continued

| Ex. No. | Name | Structure | retention time (min) | HPLC-mass spectrum m/e |
|---|---|---|---|---|
| 463. | N-(3-(4-chlorophenyl)-1-methyl-2-(1-methyl-1H-indol-3-yl)propyl)-2-methyl-2-(4-chlorophenoxy)-2-methylpropanamide | 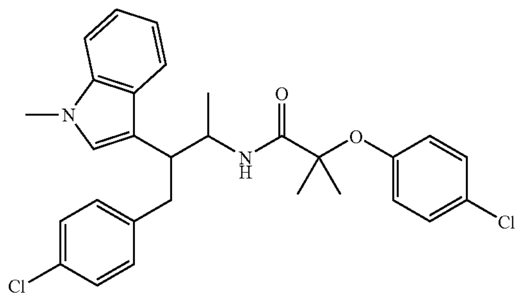 | 4.6 | 409 |
| 464. | N-(3-(4-chlorophenyl)-1-methyl-2-(1-methyl-1H-indol-4-yl)propyl)-2-methyl-2-(5-trifluoromethylpyridin-2-yl)oxy)-2-methylpropanamide | 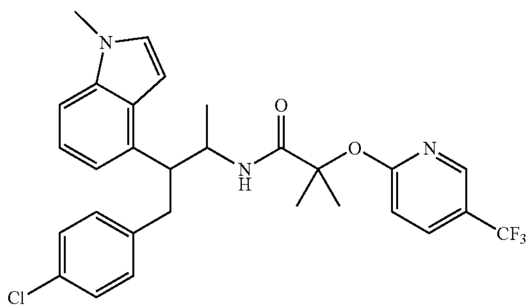 | 4.29 | 544 |
| 465. | N-(3-(4-chlorophenyl)-1-methyl-2-(thiophen-2-yl)propyl)-2-methyl-2-(5-chloropyridin-2-yl)oxy)-2-methylprpoanamide | 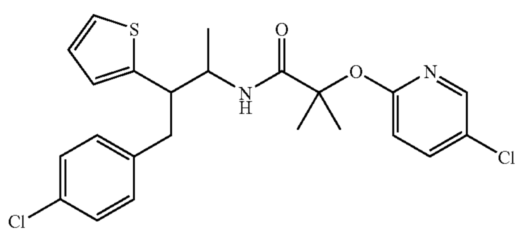 | 4.2 | 463 |
| 466. | N-(3-(4-chlorophenyl)-1-methyl-2-(thiophen-3-yl)propyl)-2-methyl-2-(5-chloropyridin-2-yl)oxy)-2-methylprpoanamide | 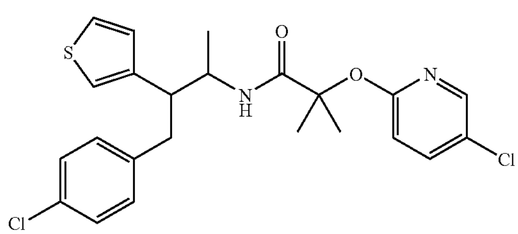 | 4.21 | 463 |
| 467. | N-(3-(4-chlorophenyl)-1-methyl-2-(pyrimidin-5-yl)propyl)-2-methyl-2-(5-chloropyridin-2-yl)oxy)-2-methylprpoanamide | 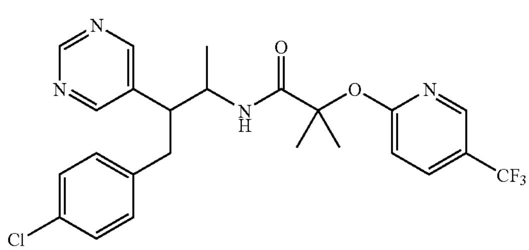 | 3.39 | 493 |

TABLE 16-continued

| Ex. No. | Name | Structure | HPLC-retention time (min) | mass spectrum m/e |
|---|---|---|---|---|
| 468. | N-(3-(4-chlorophenyl)-1-methyl-2-(pyradizin-3-yl)propyl)-2-methyl-2-(5-chloropyridin-2-yl)oxy)-2-methylprpoanamide | 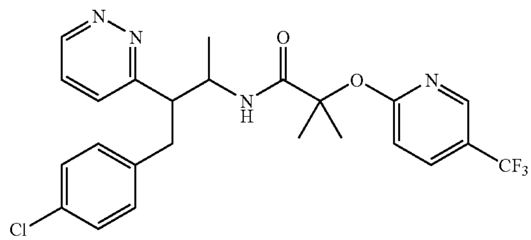 | 3.57 | 493 |
| 469. | N-(2-(3-cyanophenyl)-3-cyclopropyl-1-methylpropyl)-2-methyl-2((5-(trifluoromethyl)pyridin-2-yl)oxy)-propanamide | 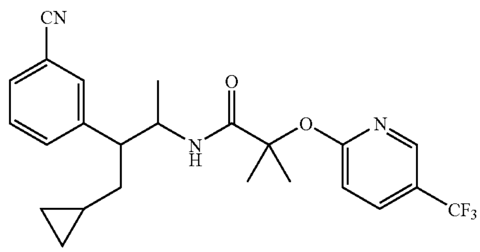 | 3.96 | 446 |
| 470. | N-(2-(3-cyanophenyl)-1,4-dimethylpentyl)-2-methyl-2((5-(trifluoromethyl)pyridin-2-yl)oxy)-propanamide | 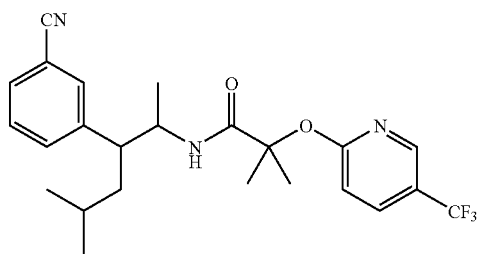 | 4.0 | 448 |
| 471. | N-(2-(3-cyanophenyl)-3-cyclobutyl-1-methylpropyl)-2-methyl-2((5-(trifluoromethyl)pyridin-2-yl)oxy)-propanamide | 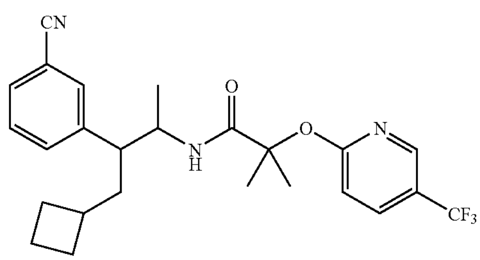 | 4.1 | 460 |
| 472. | N-(2-(3-cyanophenyl)-3-cyclohexyl-1-methylpropyl)-2-methyl-2((5-(trifluoromethyl)pyridin-2-yl)oxy)-propanamide | 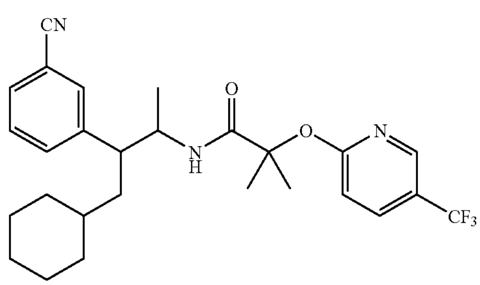 | 4.3 | 488 |

TABLE 16-continued

| Ex. No. | Name | Structure | retention time (min) | HPLC-mass spectrum m/e |
|---|---|---|---|---|
| 473. | N-(2-(3-cyanophenyl)-3-cyclopentyl-1-methylpropyl)-2-methyl-2((5-(trifluoromethyl)pyridin-2-yl)oxy)-propanamide | 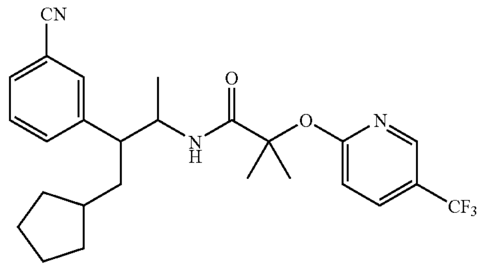 | 4.2 | 474 |
| 474. | N-(2-(3-cyanophenyl)-3-((1-tertbutyloxycarbonyl)piperidin-4-yl)-1-methylpropyl)-2-methyl-2((5-(trifluoromethyl)pyridin-2-yl)oxy)-propanamide | 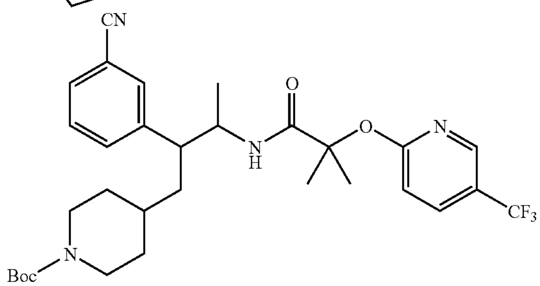 | 4.1 | 589 |

Example 475

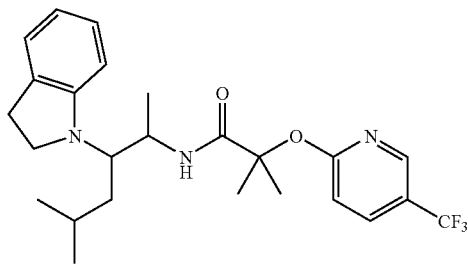

N-(2-(2,3-Dihydro-1H-indol-1-yl)-1,4-dimethylpentyl)-2-methyl-2((5-(trifluoromethyl)pyridin-2-yl)oxy)-propanamide To a solution of 65 mg (0.28 mmol) 2-(2,3-Dihydro-1-H-indol-1-yl)-1,4-dimethylpentylamine in 1 mL CH$_2$Cl$_2$, 65 mg (0.26 mmol) acid, 0.045 mL triethylamine and 0.15 g (0.29 mmol) PyBop were added. After stirring for 3 h, the reaction was quenched by adding 1 mL water and the organic layer was removed with a pipet. This solution was purified by prep-TLC using 20% EtOAc-hexane to isolate the lower band: $^1$H NMR: (500 MHz, CDCl$_3$): δ 0.79 (d, 3H), 0.88 (d, 3H), 1.08 (d, 3H), 1.21 (m, 1H), 1.63 (m, 2H), 1.74 (s, 6H), 3.01 (m, 2H), 3.44 (m, 3H), 4.17 (m, 1H), 6.15 (br d, 1H), 6.2-8.5 (m, 7H); LC-MS, Rt=4.37 min, m/e=464 and 20 mg of the higher band: $^1$H NMR: (500 MHz, CDCl$_3$): δ 0.88 (d, 3H), 0.90 (d, 3H), 1.16 (d, 3H), 1.3 (m, 1H), 1.6 (s, 6H), 1.62 (m, 2H), 2.8-3.5 (m, 5H), 4.13 (m, 1H), 5.98 (br d, 1H), 6.3-8.4 (m, 7H); LC-MS, Rt=4.53 min, m/e=464.

The following compounds in Table 17 were prepared from the appropriate amine and acid of the Reference Examples following the procedures described in Examples 62-63 (via an acyl chloride intermediate) or Examples 195 or 200 (with a coupling reagent.)

TABLE 17

| Ex. No. | Name | Structure | retention time (min) | HPLC-mass spectrum m/e |
|---|---|---|---|---|
| 476. | N-(3-Cyclobutyl-2-(3,4-dihydroquinolin-1(2H)-yl)-1-methylpropyl)-2-methyl-2((5-(trifluoromethyl)pyridin-2-yl)oxy)-propanamide | 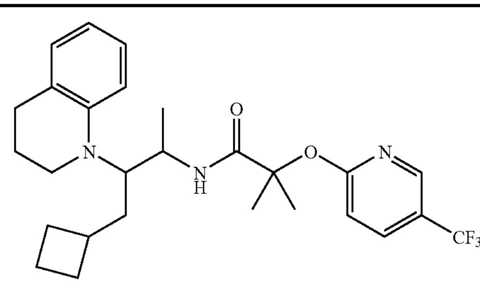 | 4.43 | 490 |

TABLE 17-continued

| Ex. No. | Name | Structure | retention time (min) | HPLC-mass spectrum m/e |
|---|---|---|---|---|
| 477. | N-(2-(3,4-dihydroquinolin-1(2H)-yl)-1,4-dimethylpentyl)-2-methyl-2((5-(trifluoromethyl)pyridin-2-yl)oxy)-propanamide | 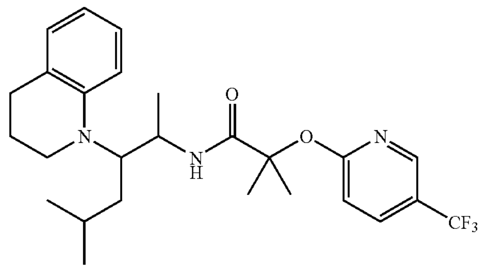 | 4.37 | 478 |

The compounds in Table 18 were isolated according to the procedure for separating enantiomers described in Examples 149-150.

TABLE 18

Enantiomeric compounds isolated according to the methods described in Examples 149-150.

| Ex. No. | Name | Structure | retention time (min) | HPLC-mass spectrum m/e | Enantiomer A or B |
|---|---|---|---|---|---|
| 478. | N-(2-(3-cyanophenyl)-1,4-dimethylpentyl)-2-methyl-2((5-(trifluoromethyl)pyridin-2-yl)oxy)-propanamide | 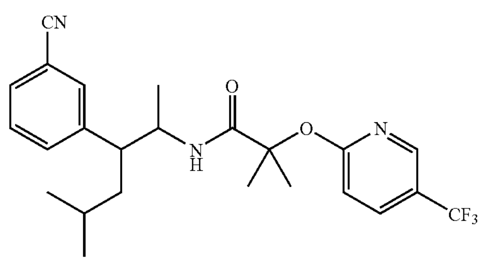 | 4.0 | 448 | B |
| 479. | N-(2-(3-cyanophenyl)-3-cyclobutyl-1-methylpropyl)-2-methyl-2((5-(trifluoromethyl)pyridin-2-yl)oxy)-propanamide | 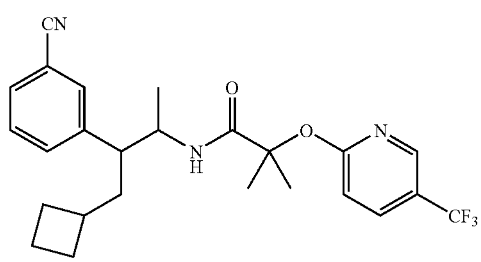 | 4.1 | 460 | B |
| 480. | N-(2-(3-cyanophenyl)-3-cyclopentyl-1-methylpropyl)-2-methyl-2((5-(trifluoromethyl)pyridin-2-yl)oxy)-propanamide | 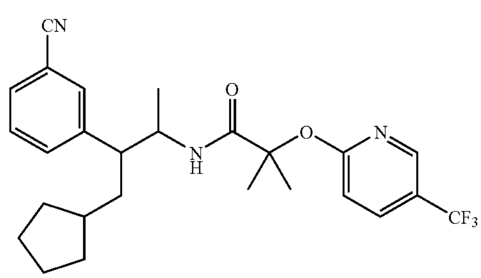 | 4.18 | 474 | B |

TABLE 18-continued

Enantiomeric compounds isolated according to the methods described in Examples 149-150.

| Ex. No. | Name | Structure | HPLC-retention time (min) | mass spectrum m/e | Enantiomer A or B |
|---|---|---|---|---|---|
| 481. | N-(2-(3-cyanophenyl)-3-cyclohexyl-1-methylpropyl)-2-methyl-2((5-(trifluoromethyl)pyridin-2-yl)oxy)-propanamide | 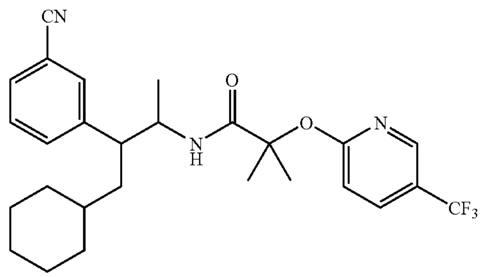 | 4.29 | 488 | B |

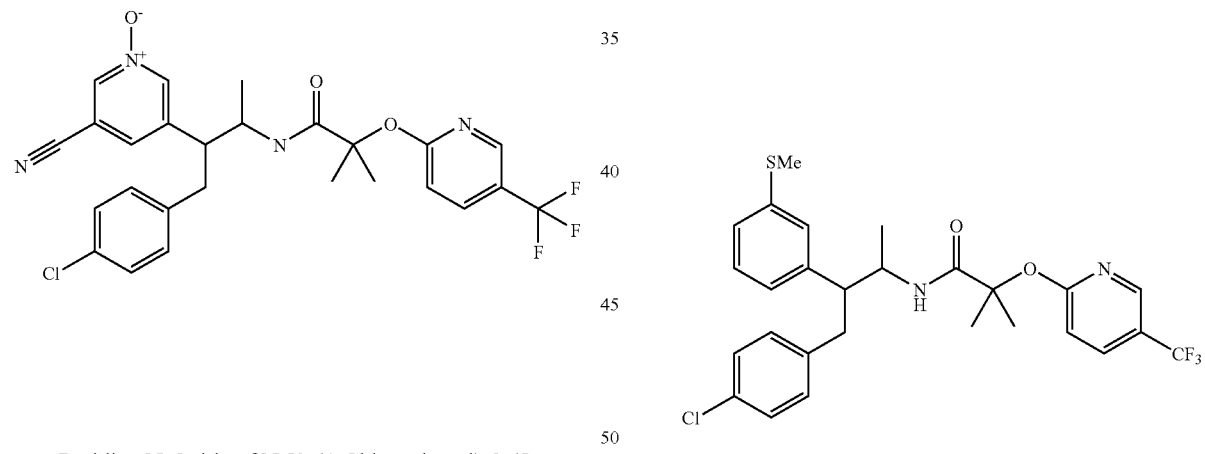

Example 482

Pyridine N-Oxide of N-[3-(4-Chlorophenyl)-2-(5-cyano-3-pyridyl)-1-methylpropyl]-2-(5-trifluoromethyl-2-pyridyloxy)-2-methylpropanamide (Enantiomer B)

A mixture of N-[3-(4-chlorophenyl)-2-(5-cyano-3-pyridyl)-1-methylpropyl]-2-(5-trifluoromethyl-2-pyridyloxy)-2-methylpropanamide (Enantiomer B, Example 416, 0.10 g, 0.19 mmol) and m-chloroperbenzoic acid (77%, 0.15 g, 0.67 mmol) in 2 mL of methylene chloride was stirred at room temperature for 14 h. The reaction mixture was concentrated and the residue was purified by HPLC eluting on a reverse phase C18 column with 30 to 100% acetonitrile in water (contains 0.1% trifluoroacetic acid) to give the title compound (0.10 g). $^1$H NMR (500 MHz, CD$_3$OD): δ 8.58 (s, 1H), 8.32 (br s, 1H), 8.17 (s, 1H), 7.99 (br d, 1H), 7.97 (dd, 1H), 7.81 (s, 1H), 7.16 (d, 2H), 7.06 (d, 1H), 6.87 (d, 2H), 4.28 (m, 1H), 3.11 (dd, 1H), 3.01 (m, 1H), 2.71 (dd, 1H), 1.75 (s, 3H), 1.74 (s, 3H), 0.94 (d, 3H). LC-MS: m/e 533 (M+H)$^+$ (4.1 min).

Example 483

N-[3-(4-chlorophenyl)-2-(3-methylthiophenyl)-1-methylpropyl]-2-methyl-2-(5-trifluoromethylpyridin-2-oxy)propanamide The title compound was prepared following the procedure described in Example 200. $^1$H NMR (500 MHz, CDCl$_3$): δ 8.28 (s, 1H), 7.94 (dd, 1H), 7.33 (t, 1H), 7.07-7.00 (m, 4H), 6.85 (s, 1H), 6.80 (d, 1H), 6.67 (d, 2H), 4.24 (m, 1H), 2.98 (dd, 1H), 2.70 (m, 1H), 2.58 (dd, 1H), 2.36 (s, 3H), 1.77 (s, 3H), 1.74 (s, 3H), 0.82 (d, 3H). LC-MS: m/e 537 (M+H)$^+$ (4.36 min).

Example 484

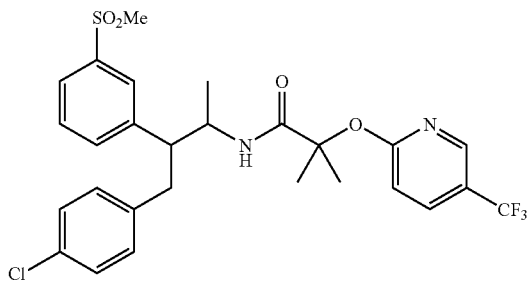

N-[3-(4-chlorophenyl)-2-(3-methylsulfonylphenyl)-1-methylpropyl]-2-methyl-2-(5-trifluoromethylpyridin-2-oxy)propanamide To a solution of N-[3-(4-chlorophenyl)-2-(3-methylthiophenyl)-1-methylpropyl]-2-methyl-2-(5-trifluoromethylpyridinyl-2-oxy)propanamide (Example 483, 0.20 g, 0.37 mmol) in 40 mL of methylene chloride was added m-chloroperbenzoic acid (0.10 g, 0.60 mmol), and the mixture was stirred at room temperature overnight. The reaction was quenched by addition of saturated sodium bisulfite (5 mL) and saturated sodium bicarbonate (5 mL). After stirring at room temperature for 10 min, the reaction mixture was extracted with ether (2×20 mL). The organic extracts were dried over anhydrous sodium sulfate, filtered, and concentrated to dryness, and the residue was purified by flash column chromatography eluting with 0 to 100% ethyl acetate in hexane to give the title compound. $^1$H NMR (500 MHz, CDCl$_3$): δ 8.30 (s, 1H), 7.96 (dd, 1H), 7.74 (d, 1H), 7.52 (s, 1H), 7.49 (t, 1H), 7.41 (d, 1H), 7.08-7.00 (m, 3H), 6.70 (d, 2H), 4.34 (m, 1H), 3.07 (dd, 1H), 2.98 (s, 3H), 2.95 (m, 1H), 2.64 (dd, 1H), 1.78 (s, 3H), 1.75 (s, 3H), 0.85 (d, 3H). LC-MS: m/e 569 (M+H)$^+$ (5.21 min).

Examples 485-489 (Table 19) were isolated as single enantiomers following the procedures described in Example 189 or Examples 149-150 from the corresponding racemic material with appropriate modifications of (1) the eluent composition (4-15% ethanol/hexane), (2) flow rate (6-9 mL/min) and (3) injection volume (200 to 2000 μL).

TABLE 19

Enantiomeric compounds isolated according to the methods described in Examples 485-489.

| Ex. No. | Name | Structure | retention time (min) | HPLC-mass spectrum m/e | Enantiomer A or B |
|---|---|---|---|---|---|
| 485. | N-[3-(4-chlorophenyl)-2-(3-methylsulfonylphenyl)-1-methylpropyl]-2-methyl-2-(5-trifluoromethylpyridin-2-oxy)propanamide | 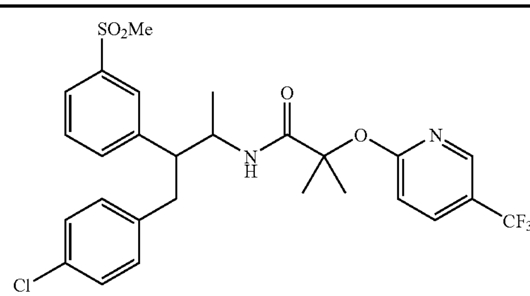 | 3.9 | 568 | A |
| 486. | N-[3-(4-chlorophenyl)-2-(3-methylsulfonylphenyl)-1-methylpropyl]-2-methyl-2-(5-trifluoromethylpyridin-2-oxy)propanamide | 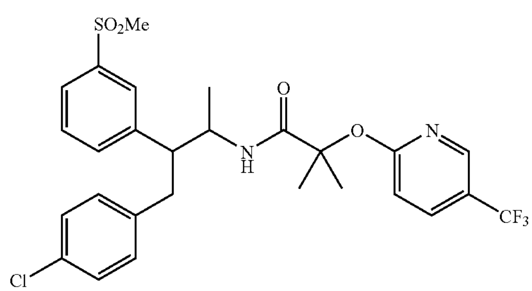 | 3.9 | 568 | B |
| 487. | N-[3-(4-chlorophenyl)-2-(3-cyanophenyl)-1-methylpropyl]-2-methyl-2-(5-methylsulfonylpyridin-2-oxy)propanamide | 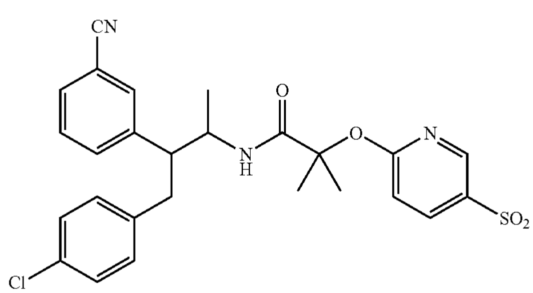 | 3.3 | 525 | B |

TABLE 19-continued

Enantiomeric compounds isolated according to the methods described in Examples 485-489.

| Ex. No. | Name | Structure | retention time (min) | HPLC-mass spectrum m/e | Enantiomer A or B |
|---|---|---|---|---|---|
| 488. | N-[3-(4-chlorophenyl)-2-(3-methylthiophenyl)-1-methylpropyl]-2-methyl-2-(5-trifluoromethylpyridin-2-oxy)propanamide | 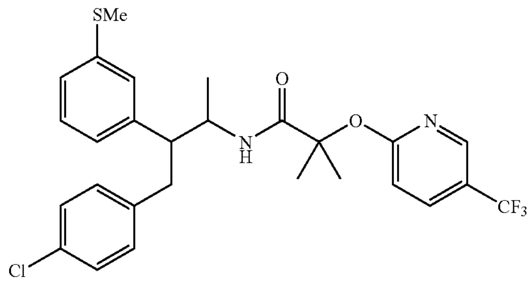 | 4.3 | 534 | A |
| 489. | N-[3-(4-chlorophenyl)-2-(3-methylthiophenyl)-1-methylpropyl]-2-methyl-2-(5-trifluoromethylpyridin-2-oxy)propanamide | 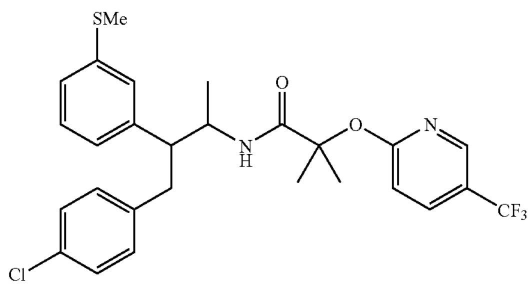 | 4.3 | 534 | B |

Example 490

Cannabinoid Receptor-1 (CB1) Binding Assay

Binding affinity determination is based on recombinant human CB1 receptor expressed in Chinese Hamster Ovary (CHO) cells (Felder et al, Mol. Pharmacol. 48: 443-450, 1995). Total assay volume is 250 μl (240 μl CB1 receptor membrane solution plus 5 μl test compound solution plus 5 μl [3H]CP-55940 solution). Final concentration of [3H]CP-55940 is 0.6 nM. Binding buffer contains 50 mM Tris-HCl, pH7.4, 2.5 mM EDTA, 5 mM MgCl$_2$, 0.5 mg/mL fatty acid free bovine serum albumin and protease inhibitors (Cat#P8340, from Sigma). To initiate the binding reaction, 5 μl of radioligand solution is added, the mixture is incubated with gentle shaking on a shaker for 1.5 h at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from IC50 values (DeBlasi et al., Trends Pharmacol Sci 10: 227-229, 1989).

The binding assay for CB2 receptor is done similarly with recombinant human CB2 receptor expressed in CHO cells.

Example 491

Cannabinoid Receptor-1 (CB1) Functional Activity Assay

The functional activation of CB1 receptor is based on recombinant human CB1 receptor expressed in CHO cells (Felder et al, Mol. Pharmacol. 48: 443-450, 1995). To determine the agonist activity or inverse agonist activity of any test compound, 50 ul of CB1-CHO cell suspension are mixed with test compound and 70 ul assay buffer containing 0.34 mM 3-isobutyl-1-methylxanthine and 5.1 uM of forskolin in 96-well plates. The assay buffer is comprised of Earle's Balanced Salt Solution supplemented with 5 mM MgCl$_2$, 1 mM glutamine, 10 mM HEPES, and 1 mg/mL bovine serum albumin. The mixture is incubated at room temperature for 30 minutes, and terminated by adding 30 ul/well of 0.5M HCl. The total intracellular cAMP level is quantitated using the New England Nuclear Flashplate and cAMP radioimmunoassay kit.

To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

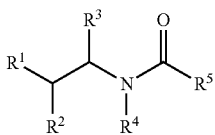

or a pharmaceutically acceptable salt thereof, wherein;

$R^1$ is selected from:
(1) cycloheteroalkyl, and
(2) heteroaryl,
wherein each cycloheteroalkyl, and heteroaryl is optionally substituted with one to four substituents independently selected from $R^b$;

$R^2$ is aryl-$C_{1-4}$alkyl,
wherein each alkyl is optionally substituted with one to four substituents independently selected from $R^a$, and each aryl is optionally substituted with one to four substituents independently selected from $R^b$;

$R^3$ is selected from:
(1) hydrogen, and
(2) $C_{1-4}$alkyl,
wherein each alkyl is optionally substituted with one to four substituents independently selected from $R^a$;

$R^4$ is selected from:
(1) hydrogen, and
(2) $C_{1-4}$alkyl,
wherein each alkyl is optionally substituted with one to four substituents independently selected from $R^a$;

$R^5$ is $C_{1-8}$alkyl substituted with —$OR^d$, wherein $R^d$ is heteroaryl and wherein heteroaryl is unsubstituted or substituted with one to three substituents selected from $R^h$;

each $R^a$ is independently selected from:
(1) —$OR^d$,
(2) —$NR^cS(O)_mR^d$,
(3) halogen,
(4) —$SR^d$,
(5) —$S(O)_mNR^cR^d$,
(6) —$NR^cR^d$,
(7) —$C(O)R^d$,
(8) —$CO_2R^d$,
(9) —CN,
(10) —$C(O)NR^cR^d$,
(11) —$NR^cC(O)R^d$,
(12) —$NR^cC(O)OR^d$,
(3) —$NR^cC(O)NR^cR^d$,
(14) —$CF_3$,
(15) —$OCF_3$, and
(16) cycloheteroalkyl;

each $R^b$ is independently selected from:
(1) —$OR^d$,
(2) halogen,
(3) —CN,
(4) —$CF_3$,
(5) —$OCF_3$,
(6) cycloheteroalkyl;
(7) $C_{1-4}$alkyl,
(8) oxo,
(9) phenyl,
(10) benzyl, and
(11) heteroaryl;

each $R^c$ is independently selected from:
(1) hydrogen, and
(2) $C_{1-4}$alkyl, and each $R^d$ is independently selected from:
(1) hydrogen,
(2) $C_{1-4}$alkyl,
(3) $C_{2-6}$alkenyl,
(4) cycloalkyl,
(5) cycloalkyl-$C_{1-4}$alkyl,
(6) cycloheteroalkyl,
(7) cycloheteroalkyl-$C_{1-4}$ alkyl,
(8) phenyl,
(9) heteroaryl,
(10) phenyl-$C_{1-4}$alkyl, and
(11) heteroaryl-$C_{1-4}$alkyl, or $R^c$ and $R^d$ together with the atom(s) to which they are attached form a heterocyclic ring of 4 to 7 members containing 0-2 additional heteroatoms independently selected from oxygen, sulfur and N—$R^g$,
each $R^c$ and $R^d$ may be unsubstituted or substituted with one to three substituents selected from $R^h$;

each $R^g$ is independently selected from:
(1) $C_{1-4}$alkyl, and
(2) —$C(O)C_{1-4}$alkyl;

each $R^h$ is independently selected from:
(1) halogen,
(2) $C_{1-10}$alkyl,
(3) —O $C_{1-4}$alkyl,
(4) —S $C_{1-4}$alkyl,
(5) —CN,
(6) —$CF_3$, and
(7) —$OCF_3$, m is selected from 1 and 2.

2. The compound according to claim 1, wherein $R^4$ is selected from:
(1) hydrogen, and
(2) methyl;
and pharmaceutically acceptable salts thereof.

3. The compound according to claim 2, wherein $R^3$ is selected from hydrogen, methyl and ethyl;
and pharmaceutically acceptable salts thereof.

4. The compound according to claim 3, selected from:
(1) N-[3-(4-chlorophenyl)-2-(3-pyridyl)-1-methylpropyl]-2-methyl-2-(2-pyridyloxy)propanamide;
(2) N-[3-(4-chlorophenyl)-2-(3-pyridyl)-1-methylpropyl]-methyl-2-(2-pyridyloxy)propanamide;
(3) N-(2-(1-(1,2,4-triazolyl))-3-(4-chlorophenyl)-1-methylpropyl)-2-(2-pyridyloxy)-2-methylpropanamide;
(4) N-[3-(4-chlorophenyl)-2-(2-pyridyl)-1-methylpropyl]-2-(5-trifluoromethyl-2-pyridyloxy)-2-methylpropanamide;
(5) N-[3-(4-chlorophenyl)-2-(3-pyridyl)-1-methylpropyl]-2-(5-trifluoromethyl-2-pyridyloxy)-2-methylpropanamide;
(6) N-[3 (4-chlorophenyl)-2-(5-fluoro-3-pyridyl)-1-methylpropyl]-2-(5-trifluoromethyl-2-pyridyloxy)-2-methylpropanamide;
(7) N-[3-(4-chlorophenyl)-2-(5-fluoro-3-pyridyl)-1-methylpropyl]-2-(6-trifluoromethyl-4-pyrimidyloxy)-2-methylpropanamide;

(8) N-[3 (4-chlorophenyl)-2-(5-chloro-3-pyridyl)-1-methylpropyl]-2-(5-trifluoromethyl-2-pyridyloxy)-2-methylpropanamide;
(9) N-[3 (4-chlorophenyl)-2-(5-chloro-3-pyridyl)-1-methylpropyl]-2-(4-trifluoromethyl-2-pyrimidyloxy)-2-methylpropanamide;
(10) N-[3 (4-chlorophenyl)-2-(5-chloro-3-pyridyl)-1-methylpropyl]-2-(6-trifluoromethyl-4-pyrimidyloxy)-2-methylpropanamide;
(11) N-[3 (4-chlorophenyl)-2-(5-chloro-3-pyridyl-1-methylpropyl]-2-(6-trifluoromethyl-4-pyridyloxy)-2-methylpropanamide;
(12) N-[3-(4-chlorophenyl)-2-(5-cyano-3-pyridyl)-1-methylpropyl]-2-(5-trifluoromethyl-2-pyridyloxy)-2-methylpropanamide;
(13) N-[3-(4-chlorophenyl)-2-(5-cyano-3-pyridyl)-1-methylpropyl]-2-(6-trifluoromethyl-4-pyrimidyloxy)-2-methylpropanamide;
(14) N-[3-(4-chlorophenyl)-2-(5-cyano-3-pyridyl)-1-methylpropyl]-2-(4-trifluoromethyl-2-pyridyloxy)-2-methylpropanamide;
(15) N-[2 (5 bromo-3-pyridyl)-3-(4-chlorophenyl)-1-methylpropyl]-2-(5-trifluoromethyl-2-pyridyloxy)-2-methylpropanamide;
(16) N-[2-(5-bromo-3-pyridyl)-3-(4-fluorophenyl)-1-methylpropyl]-2-(4-trifluoromethyl-2-pyridyloxy)-2-methylpropanamide;
(17) N-[2 (5 bromo-3-pyridyl)-3-(4-chlorophenyl)-1-methylpropyl]-2-(4-trifluoromethyl-2-pyridyloxy)-2-methylpropanamide;
(18) N-[2-(5-bromo-3-pyridyl)-3-(4-fluorophenyl)-1-methylpropyl]-2-(6-trifluoromethyl-4-pyrimidyloxy)-2-methylpropanamide;
(19) N-[2-(5-bromo-3-pyridyl)-3-(4-chlorophenyl)-1-methylpropyl]-2-(6-trifluoromethyl-4-pyrimidyloxy)-2-methylpropanamide;
(20) N-[3-(4-chlorophenyl)-2-(5-methyl-3-pyridyl)-1-methylpropyl]-2-(5-trifluoromethyl-2-pyridyloxy)-2-methylpropanamide;
(21) N-[3-(4 chlorophenyl)-2-(2-pyridyl)-1-methylpropyl]-2-(5-trifluoromethyl-2-pyridyloxy)-2-methylpropanamide;
(22) N-[3-(4-chlorophenyl)-2-(3-pyridyl)-1-methylpropyl]-2-(5-trifluoromethyl-2-pyridyloxy)-2-methylpropanamide;
(23) N-[3-(4-chlorophenyl)-2-(5-fluoro-3-pyridyl)-1-methylpropyl]-2-(5-trifluoromethyl-2-pyridyloxy)-2-methylpropanamide;
(24) N-[3 (4-chlorophenyl)-2-(5-fluoro-3-pyridyl)-1-methylpropyl]-2-(6-trifluoromethyl-4-pyrimidyloxy)-2-methylpropanamide;
(25) N-[3-(4-chlorophenyl)-2-(5-chloro-3-pyridyl)-1-methylpropyl]-2-(5-trifluoromethyl-2-pyridyloxy)-2-methylpropanamide;
(26) N-[3-(4-chlorophenyl)-2-(5-chloro-3-pyridyl)-1-methylpropyl]-2-(4-trifluoromethyl-2-pyridyloxy)-2-methylpropanamide;
(27) N-[3-(4-chlorophenyl)-2-(5-chloro-3-pyridyl)-1-methylpropyl]-2-(4-trifluoromethyl-2-pyrimidyloxy)-2-methylpropanamide;
(28) N-[3-(4-chlorophenyl)-2-(5-chloro-3-pyridyl)-1-methylpropyl]-2-(6-trifluoromethyl-4-pyrimidyloxy)-2-methylpropanamide;
(29) N-[2-(5-chloro-3-pyridyl)-3-(4-fluorophenyl)-1-methylpropyl]-2-(5-trifluoromethyl-4-pyridyloxy)-2-methylpropanamide;
(30) N-[3-(4-chlorophenyl)-2-(5-cyano-3-pyridyl)-1-methylpropyl]-2-(5-trifluoromethyl-2-pyridyloxy)-2-methylpropanamide;
(31) N-[3-(4-chlorophenyl)-2-(5-cyano-3-pyridyl)-1-methylpropyl]-2-(6-trifluoromethyl-4-pyrimidyloxy)-2-methylpropanamide;
(32) N-[2-(5-cyano-3-pyridyl)-3-(3,4-difluorophenyl)-1-methylpropyl]-2-(6-trifluoromethyl-4-pyrimidyloxy)-2-methylpropanamide;
(33) N-[3-(3-chlorophenyl)-2-(5-cyano-3-pyridyl)-1-methylpropyl]-2-(5-trifluoromethyl-2-pyridyloxy)-2-methylpropanamide;
(34) N-[2-(5-cyano-3-pyridyl)-3-(4-fluorophenyl)-1-methylpropyl]-2-(5-trifluoromethyl-2-pyridyloxy)-2-methylpropanamide;
(35) N-[2-(5-bromo-3-pyridyl)-3-(4-chlorophenyl)-1-methylpropyl]-2-(5-trifluoromethyl-2-pyridyloxy)-2-methylpropanamide;
(36) N-[2-(5-bromo-3-pyridyl)-3-(4-fluorophenyl)-1-methylpropyl]-2-(5-trifluoromethyl-2-pyridyloxy)-2-methylpropanamide;
(37) N-[2 (5 bromo-3-pyridyl)-3-(4-fluorophenyl)-1-methylpropyl]-2-(6-trifluoromethyl-4-pyrimidyloxy)-2-methylpropanamide;
(38) N-[2 (5 bromo-3-pyridyl)-3-(4-chlorophenyl)-1-methylpropyl]-2-(6-trifluoromethyl-4-pyrimidyloxy)-2-methylpropanamide;
(39) N-[3-(4-chlorophenyl)-2-(5-methyl-3-pyridyl)-1-methylpropyl]-2-(5-trifluoromethyl-2-pyridyloxy)-2-methylpropanamide;
(40) N-[2 (5-chloro-3-pyridyl)-3-(4-chloro-3-iodophenyl)-1-methylpropyl]-2-(5-trifluoromethyl-2-pyridyloxy)-2-methylpropanamide;
(41) N-(3-(4 chlorophenyl)-2-benzisoxazol-3-yl)-1-methyl)propyl-2-(5-chloro-2-oxypyridine-2-yl)-2-methylpropanamide;
(42) N-(3-(4 chlorophenyl)-2-(benzisoxazol-3-yl)-1-methyl)propyl-2-(5-trifluoromethyl-2-oxypyridine-2-yl)-2-methylpropanamide;
(43) N-(3-(4-chlorophenyl)-2-(7-azaindol-N-yl)-1-methyl)propyl-2-(5-trifluoromethyl-2-oxypyridine-2-yl)-2-methylpropanamide;
(44) N-(3-(4-chlorophenyl)-2-(indol-N-yl)-1-methyl)propyl-2-(5-trifluoromethyl-2-oxypyridine-2-yl)-2-methylpropanamide;
(45) N-(3 (4-chlorophenyl)-2-(indolin-N-yl)-1-methyl)propyl-2(4-trifluoromethyl-2-oxypyridine-2-yl)-2-methylpropanamide;
(46) N-(3-(4-chlorophenyl)-2-(indolin-N-yl)-1-methyl)propyl-2(5-trifluoromethyl-2-oxypyridine-2-yl)-2-methylpropanamide;
(47) N-(2-(1H-1,2,3-benzotriazol-1-yl)-3-(4-chlorophenyl)-1-methylpropyl)-2-methyl-2-(5-chloropyridin-2-yl)oxy)-2-methylpropanamide;
(48) N-(2-(1H-1,2,3-benzotriazol-1-yl)-3-(4-chlorophenyl)-1-methylpropyl)-2-methyl-2-(5-trifluoromethylpyridin-2-yl)oxy)-2-methylpropanamide;
(49) N-(3-(4 chlorophenyl)-1-methyl-2-(1H-indazol-1-yl)propyl)-2-methyl-2-(5-trifluoromethylpyridin-2-yl)oxy)-2-methylpropanamide;
(50) N-(3-(4-chlorophenyl)-1-methyl-2-(1-methyl-1H-indol-3-yl)propyl)-2-methyl-2-(5-chloropyridin-2-yl)oxy)-2-methylpropanamide;
(51) N-(3-(4-chlorophenyl)-1-methyl-2-(1-methyl-1H-indol-3-yl)propyl)-2-methyl-2-(5-trifluoromethylpyridin-2-yl)oxy)-2-methylpropanamide;

351

(52) N-(3-(4-chlorophenyl)-1-methyl-2-(1-methyl-1H-indol-4-yl)propyl)-2-methyl-2-(5-trifluoromethylpyridin-2-yl)oxy)-2-methylpropanamide;
(53) N-(3-(4-chlorophenyl)-1-methyl-2-(thiophen-2-yl)propyl)-2-methyl-2-(5-chloropyridin-2-yl)oxy)-2-methylprpoanamide;
(54) N-(3-(4-chlorophenyl)-1-methyl-2-(thiophen-3-yl)propyl)-2-methyl-2-(5-chloropyridin-2-yl)oxy)-2-methylprpoanamide;
(55) N-(3-(4-chlorophenyl)-1-methyl-2-(pyrimidin-5-yl)propyl)-2-methyl-2-(5-chloropyridin-2-yl)oxy)-2-methylprpoanamide; and
(56) N-(3-(4-chlorophenyl)-1-methyl-2-(pyradizin-3-yl)propyl)-2-methyl-2-(5-chloropyridin-2-yl)oxy)-2-methylprpoanamide;
and pharmaceutically acceptable salts thereof.

5. The compound according to claim 3, selected from:
(1) N-[3 (4-chlorophenyl)-2-(3-pyridyl)-1-methylpropyl]-2-methyl-2-(2-pyridyloxy)propanamide;
(2) N-[3 (4-chlorophenyl)-2-(3-pyridyl)-1-methylpropyl]-2-methyl-2-(2-pyridyloxy)propanamide; and
(3) N-(2-(1-(1,2,4-triazolyl))-3-(4-chlorophenyl)-1-methylpropyl)-2-(2-pyridyloxy)-2-methylpropanamide;
and pharmaceutically acceptable salts thereof.

6. The compound according to claim 1, wherein:
$R^1$ is selected from:
(1) pyrrolidinyl,
(2) pyridyl, and
(3) triazolyl,
wherein each pyridyl is optionally substituted with one or two substituents selected from halogen, methyl, trifluoromethyl, cyano and methoxy, and each pyridyl is optionally present as the N-oxide,
$R^2$ is selected from:
(1) benzyl,
(2) phenylethyl,
(3) 3-phenylpropyl, and
(4) 2-phenylpropyl,
wherein each aryl is optionally substituted with one or two $R^b$ substituents selected from halogen, trifluoromethyl, cyano, methoxycarbonyl, and methoxy;
$R^3$ is selected from:
(1) hydrogen,
(2) methyl, and
(3) ethyl;
$R^4$ is hydrogen;
$R^5$ is $C_{1-8}$alkyl substituted with —$OR^d$, wherein $R^d$ is heteroaryl and wherein heteroaryl is unsubstituted or substituted with one to three substituents selected from $R^h$;
$R^d$ is selected from:
(1) hydrogen,
(2) $C_{1-4}$alkyl,
(3) $C_{2-6}$ alkenyl,
(4) cycloalkyl,
(5) cycloalkyl-$C_{1-4}$alkyl,
(6) cycloheteroalkyl,
(7) cycloheteroalkyl-$C_{1-4}$ alkyl,
(8) phenyl,
(9) heteroaryl,
(10) phenyl-$C_{1-4}$alkyl, and
(11) heteroaryl-$C_{1-4}$alkyl,
wherein each $R^d$ may be unsubstituted or substituted with one to three substituents selected from $R^h$;
each $R^h$ is independently selected from:
(1) halogen,
(2) $C_{1-4}$alkyl,
(3) —O—$C_{1-4}$alkyl,

352

(4) —S—$C_{1-4}$alkyl,
(5) —CN,
(6) —$CF_3$, and
(7) —$OCF_3$;
and pharmaceutically acceptable salts thereof.

7. The compound according to claim 3, wherein:
$R^1$ is
heteroaryl
wherein heteroaryl is optionally substituted with one to three substituents independently selected from $R^b$;
$R^2$ is
(3) aryl-$C_{1-4}$allyl,
wherein each aryl is optionally substituted with one to three substituents independently selected from $R^b$;
$R^3$ is methyl;
$R^4$ is hydrogen;
$R^5$ is

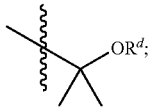

wherein $R^d$ is heteroaryl and wherein heteroaryl is unsubstituted or substituted with one to three substituents selected from $R^h$;
each $R^b$ is independently selected from:
(1) halogen,
(2) cyano,
(3) trifluoromethyl,
(4) trifluoromethoxy,
(5) $C_{1-3}$alkyloxy, and
(6) $C_{1-3}$alkyl;
each $R^c$ is independently selected from
(1) hydrogen,
(2) methyl, and
(3) trifluoromethyl;
$R^d$ is independently selected from:
(1) hydrogen,
(2) $C_{1-6}$alkyl,
(3) cycloalkyl,
(4) aryl,
(5) heteroaryl,
(6) arylmethyl, and
(7) heteroarylmethyl,
each $R^d$ may be unsubstituted or substituted with one to three substituents selected from $R^h$;
each $R^h$ is independently selected from:
(1) halogen,
(2) $C_{1-3}$alkyl,
(3) —CN, and
(4) —$CF_3$;
wherein when pyridyl groups are unsubstituted on the nitrogen, they are may optionally be present as the N-oxide;
and pharmaceutically acceptable salts thereof.

8. The compound according to claim 7, wherein:
$R^1$ is selected from:
(1) pyridyl,
(2) indolyl,
(3) 7-aza-indolyl, and
(4) thiophenyl;

wherein each heteroaryl is optionally substituted with one or two substituents independently selected from $R^b$, and each pyridyl may be optionally present as the N-oxide;

$R^2$ is
phenylmethyl,
wherein each aryl is optionally substituted with one to three substituents independently selected from $R^b$;

each $R^b$ is independently selected from:
(1) halogen,
(2) cyano,
(3) $C_{1-3}$alkyloxy, and
(4) $C_{1-3}$alkyl;

$R^d$ is selected from:
(1) pyridyl, and
(2) pyrimidinyl,
wherein $R^d$ may be unsubstituted or substituted with one or two substituents selected from $R^h$;

each $R^h$ is independently selected from:
(1) fluoro,
(2) chloro,
(3) methyl,
(4) —CN, and
(5) —$CF_3$;
and pharmaceutically acceptable salts thereof.

9. The compound according to claim 8, selected from:
(1) N-[3-(4-chlorophenyl)-2-(3-pyridyl)-1-methylpropyl]-2-(5-trifluoromethyl-2-pyridyloxy)-2-methylpropanamide;
(2) N-[3-(4-chlorophenyl)-2-(5-chloro-3-pyridyl)-1-methylpropyl]-2-(5-trifluoromethyl-2-pyridyloxy)-2-methylpropanamide;
(3) N-[3-(4-chlorophenyl)-2-(5-methyl-3-pyridyl)-1-methylpropyl]-2-(5-trifluoromethyl-2-pyridyloxy)-2-methylpropanamide;
(4) N-[3-(4-chlorophenyl)-2-(5-cyano-3-pyridyl)-1-methylpropyl]-2-(5-trifluoromethyl-2-pyridyloxy)-2-methylpropanamide;
(5) N-[3-(4-chlorophenyl)-1-methyl-2-(thiophen-3-yl)propyl]-2-(5-chloro-2-pyridyloxy)-2-methylpropanamide;
(6) N-[3-(4-chlorophenyl)-2-(1-indolyl)-1-methyl)propyl]-2-(5-trifluoromethyl-2-oxypyridine-2-yl)-2-methylpropanamide;
(8) N-[3-(4-chlorophenyl)-2-(7-azaindol-N-yl)-1-methyl)propyl]-2-(5-trifluoromethyl-2-pyridyloxy)-2-methylpropanamide;
(8) N-[3-(4-chloro-phenyl)-2-(1-indolinyl)-1-methylpropyl]-2-(5-trifluoromethyl-2-pyridyloxy)-2-methylpropanamide; and
(9) N-[3-(4-chlorophenyl)-2-(1-oxido-5-cyano-3-pyridyl)-1-methylpropyl]-2-(5-trifluoromethyl-2-pyridyloxy)-2-methylpropanamide;
and pharmaceutically acceptable salts thereof.

10. The compound according to claim 8, wherein $R^d$ is 5-trifluoromethyl-2-pyridyl; and pharmaceutically acceptable salts thereof.

11. The compound according to claim 10 selected from:
(1) N-[3-(4-chlorophenyl)-2-(3-pyridyl)-1-methylpropyl]-2-(5-trifluoromethyl-2-pyridyloxy)-2-methylpropanamide;
(2) N-[3-(4-chlorophenyl)-2-(5-chloro-3-pyridyl)-1-methylpropyl]-2-(5-trifluoromethyl-2-pyridyloxy)-2-methylpropanamide;
(3) N-[3-(4-chlorophenyl)-2-(5-methyl-3-pyridyl)-1-methylpropyl]-2-(5-trifluoromethyl-2-pyridyloxy)-2-methylpropanamide;
(4) N-[3-(4-chlorophenyl)-2-(5-cyano-3-pyridyl)-1-methylpropyl]-2-(5-trifluoromethyl-2-pyridyloxy)-2-methylpropanamide;
(5) N-[3-(4-chlorophenyl)-2-(1-indolyl)-1-methyl]propyl]-2-(5-trifluoromethyl-2-oxypyridine-2-yl)-2-methylpropanamide;
(6) N-[3-(4-chlorophenyl)-2-(7-azaindol-N-yl)-1-methyl]propyl]-2-(5-trifluoromethyl-2-pyridyloxy)-2-methylpropanamide;
(7) N-[3-(4-chloro-phenyl)-2-(1-indolinyl)-1-methylpropyl]-2-(5-trifluoromethyl-2-pyridyloxy)-2-methylpropanamide;
(8) N-[3-(4-chlorophenyl)-2-(1-oxido-5-cyano-3-pyridyl)-1-methylpropyl]-2-(5-trifluoromethyl-2-pyridyloxy)-2-methylpropanamide;
and pharmaceutically acceptable salts thereof.

12. A composition comprising a compound according to claim 1 and a pharmaceutically acceptable carrier.

13. A compound of structural formula I:

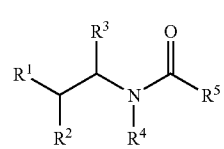

(I)

or a pharmaceutically acceptable salt thereof, wherein;

$R^1$ is selected from:
(1) cycloheteroalkyl, and
(2) heteroaryl,
wherein each is optionally substituted with one to four substituents independently selected from $R^b$;

$R^2$ is
aryl-$C_{1-4}$alkyl,
wherein each alkyl is optionally substituted with one to four substituents independently selected from $R^a$, and each aryl is optionally substituted with one to four substituents independently selected from $R^b$;

$R^3$ is selected from:
(1) hydrogen, and
(2) $C_{1-4}$alkyl,
wherein each alkyl is optionally substituted with one to four substituents independently selected from $R^a$;

$R^4$ is selected from:
(1) hydrogen, and
(2) $C_{1-4}$alkyl,
wherein each alkyl is optionally substituted with one to four substituents independently selected from $R^a$;

$R^5$ is $C_{1-8}$alkyl substituted with —$OR^d$, wherein $R^d$ is heteroaryl and wherein heteroaryl is unsubstituted or substituted with one to three substituents selected from $R^h$;

each $R^a$ is independently selected from:
(1) —$OR^d$,
(2) —$NR^cS(O)_mR^d$,
(3) halogen,
(4) —$S(O)_mR^d$,
(5) —$S(O)_mNR^cR^d$,
(6) —$NR^cR^d$,
(7) —$C(O)R^d$,
(8) —$CO_2R^d$,
(9) —$CN$,
(10) —$C(O)NR^cR^d$,
(11) —$NR^cC(O)R^d$,
(12) —$NR^cC(O)OR^d$,
(13) —$NR^cC(O)NR^cR^d$,
(14) —$CF_3$,
(15) —$OCF_3$, and
(16) cycloheteroalkyl;

each $R^b$ is independently selected from:
(1) halogen,
(2) cyano,
(3) $C_{1-3}$alkyloxy and
(4) $C_{1-3}$alkyl;
each $R^c$ is independently selected from:
(1) hydrogen,
(2) methyl, and
(3) trifluoromethyl;
$R^d$ is selected from:
(1) phenyl,
(2) pyridyl, and
(3) pyrimidinyl,
wherein $R^d$ may be unsubstituted or substituted with one or two substituents selected from $R^h$;
each $R^g$ is independently selected from:
(1) $C_{1-4}$alkyl, and
(2) —C(O)$C_{1-4}$alkyl;
each $R^h$ is independently selected from:
(1) halogen,
(2) $C_{1-3}$alkyl,
(3) —CN, and
(4) —CF$_3$;
m is selected from 0, 1 and 2.

* * * * *